(12) United States Patent
Wlodarski et al.

(10) Patent No.: US 10,076,342 B2
(45) Date of Patent: Sep. 18, 2018

(54) TISSUE DISPLACEMENT TOOLS AND METHODS

(71) Applicant: Conventus Orthopaedics, Inc., Maple Grove, MN (US)

(72) Inventors: Grace Wlodarski, Andover, MN (US); Alex A. Peterson, Maple Grove, MN (US); Todd A. Krinke, Buffalo, MN (US); Michael P. Brenzel, St. Paul, MN (US); Steve D. Kruse, St. Michael, MN (US); Troy Michael Siemers, Becker, MN (US); Kyle Taylor, Brooklyn Park, MN (US)

(73) Assignee: Conventus Orthopaedics, Inc., Maple Grove, MN (US)

( * ) Notice: Subject to any disclaimer, the term of this patent is extended or adjusted under 35 U.S.C. 154(b) by 0 days.

(21) Appl. No.: 15/001,443

(22) Filed: Jan. 20, 2016

(65) Prior Publication Data

US 2016/0128703 A1    May 12, 2016

Related U.S. Application Data

(62) Division of application No. 14/568,301, filed on Dec. 12, 2014, now Pat. No. 10,022,132.

(60) Provisional application No. 61/978,239, filed on Apr. 11, 2014, provisional application No. 61/915,428, filed on Dec. 12, 2013.

(51) Int. Cl.
*A61B 17/00* (2006.01)
*A61B 17/16* (2006.01)
*A61B 17/70* (2006.01)

(52) U.S. Cl.
CPC ........ *A61B 17/164* (2013.01); *A61B 17/1617* (2013.01); *A61B 17/7094* (2013.01); *A61B 2017/00526* (2013.01); *Y10T 29/49826* (2015.01)

(58) Field of Classification Search
CPC ... A61B 17/16–17/17; A61B 17/32002; A61B 17/7094
See application file for complete search history.

(56) References Cited

U.S. PATENT DOCUMENTS

| | | | |
|---|---|---|---|
| 1,362,513 | A | 12/1919 | Skinner |
| 1,344,327 | A | 6/1920 | Wilson |
| 1,493,240 | A | 5/1924 | Bohn |
| 1,685,380 | A | 9/1928 | Shultz |

(Continued)

FOREIGN PATENT DOCUMENTS

| | | |
|---|---|---|
| CA | 2007210 A1 | 11/1990 |
| CA | 2452508 A1 | 1/2003 |

(Continued)

OTHER PUBLICATIONS

US 7,063,700, 06/2006, Michelson (withdrawn)

(Continued)

*Primary Examiner* — Jan Christopher Merene
*Assistant Examiner* — Steven Cotroneo
(74) *Attorney, Agent, or Firm* — Weiss & Arons, LLP

(57) ABSTRACT

Apparatus and methods for bone cavity preparation. Formed broaching members may be supported inside a bone by a rotator. The broaching members may be bowed out inside the bone to create a cavity having a shape determined by the broaching members and bone anatomy.

56 Claims, 87 Drawing Sheets

(56) References Cited

U.S. PATENT DOCUMENTS

| | | |
|---|---|---|
| 2,137,710 A | 12/1937 | Anderson |
| 2,485,531 A | 1/1948 | Dzus et al. |
| 2,493,598 A | 1/1950 | Rozek |
| 2,537,070 A | 1/1951 | Longfellow |
| 2,580,821 A | 1/1952 | Nicola |
| 2,730,101 A | 1/1956 | Hoffman |
| 2,780,223 A | 2/1957 | Haggland |
| 2,898,963 A | 8/1959 | Courtot |
| 3,143,915 A | 8/1964 | Tendler |
| 3,143,916 A | 8/1964 | Rice |
| 3,146,892 A | 9/1964 | White |
| 3,181,533 A | 5/1965 | Heath |
| 3,386,169 A | 6/1968 | Scialom |
| 3,495,586 A | 2/1970 | Regenbogen |
| 3,517,128 A * | 6/1970 | Hines .................. A61M 29/02 606/197 |
| 3,593,342 A | 7/1971 | Niebauer et al. |
| 3,602,218 A | 8/1971 | Riordan |
| 3,623,164 A | 10/1971 | Bokros |
| 3,640,280 A | 2/1972 | Slanker et al. |
| 3,702,611 A | 10/1972 | Fishbein |
| 3,710,789 A | 1/1973 | Ersek |
| 3,744,488 A | 7/1973 | Cox |
| 3,745,590 A | 7/1973 | Stubstad |
| 3,759,257 A | 9/1973 | Fischer et al. |
| 3,760,802 A | 9/1973 | Fischer et al. |
| 3,779,239 A | 12/1973 | Fischer et al. |
| 3,805,775 A | 4/1974 | Fischer et al. |
| 3,828,790 A | 8/1974 | Curtiss et al. |
| 3,835,859 A | 9/1974 | Roberts et al. |
| 3,886,600 A | 6/1975 | Kahn et al. |
| 3,909,853 A | 10/1975 | Lennox |
| 3,917,249 A | 11/1975 | Constantine |
| 3,946,445 A | 3/1976 | Bentley et al. |
| 3,970,075 A | 7/1976 | Sindelar et al. |
| 3,986,504 A | 10/1976 | Avila |
| 3,992,726 A | 11/1976 | Freeman et al. |
| 4,036,107 A | 7/1977 | Constantine |
| 4,091,806 A | 5/1978 | Aginsky |
| 4,124,026 A | 11/1978 | Berner et al. |
| 4,156,296 A | 5/1979 | Johnson et al. |
| 4,180,871 A | 1/1980 | Hamas |
| 4,190,044 A | 2/1980 | Wood |
| 4,193,139 A | 3/1980 | Walker |
| 4,194,250 A | 3/1980 | Walker |
| 4,203,444 A | 5/1980 | Bonnell et al. |
| 4,204,531 A | 5/1980 | Aginsky |
| 4,213,208 A | 7/1980 | Marne |
| 4,227,518 A | 10/1980 | Aginsky |
| 4,229,840 A | 10/1980 | Gristina |
| 4,231,121 A | 11/1980 | Lewis |
| 4,262,665 A | 4/1981 | Roalstad et al. |
| 4,273,128 A | 6/1981 | Lary |
| 4,274,398 A | 6/1981 | Scott et al. |
| 4,275,717 A | 6/1981 | Bolesky |
| 4,293,962 A | 10/1981 | Fuson |
| 4,313,434 A | 2/1982 | Segal |
| 4,349,922 A | 9/1982 | Agee |
| 4,352,212 A | 10/1982 | Greene et al. |
| 4,430,991 A | 2/1984 | Darnell |
| 4,438,762 A | 3/1984 | Kyle |
| 4,453,539 A | 6/1984 | Raftopoulos et al. |
| 4,473,070 A | 9/1984 | Matthews et al. |
| 4,485,816 A | 12/1984 | Krumme |
| 4,502,554 A | 3/1985 | Jones |
| 4,519,100 A | 5/1985 | Wills et al. |
| 4,522,200 A | 6/1985 | Stednitz |
| 4,530,114 A | 7/1985 | Tepic |
| 4,548,199 A | 10/1985 | Agee |
| 4,572,186 A | 2/1986 | Gould et al. |
| 4,573,448 A | 3/1986 | Kambin |
| 4,585,000 A | 4/1986 | Hershenson |
| 4,590,930 A | 5/1986 | Kurth et al. |
| 4,601,290 A | 7/1986 | Effron et al. |
| 4,608,965 A | 9/1986 | Anspach, Jr. et al. |
| 4,611,594 A | 9/1986 | Grayhack et al. |
| 4,619,122 A | 10/1986 | Simpson |
| 4,627,434 A | 12/1986 | Murray |
| 4,634,445 A | 1/1987 | Helal |
| 4,643,177 A | 2/1987 | Sheppard et al. |
| 4,644,951 A | 2/1987 | Bays |
| 4,646,738 A | 3/1987 | Trott |
| 4,655,203 A | 4/1987 | Tormala et al. |
| 4,660,557 A | 4/1987 | Collis |
| 4,662,371 A | 5/1987 | Whipple et al. |
| 4,665,906 A | 5/1987 | Jervis |
| 4,669,237 A | 6/1987 | Constantine |
| 4,674,488 A | 6/1987 | Nashef et al. |
| 4,705,027 A | 11/1987 | Klaue |
| 4,721,103 A | 1/1988 | Freedland |
| 4,730,608 A | 3/1988 | Schlein |
| 4,731,087 A | 3/1988 | Sculco et al. |
| 4,751,922 A | 6/1988 | DiPietropolo |
| 4,772,261 A | 9/1988 | Von Hoff et al. |
| 4,777,942 A | 10/1988 | Frey et al. |
| 4,782,833 A | 11/1988 | Einhorn et al. |
| 4,790,302 A | 12/1988 | Colwill et al. |
| 4,809,793 A | 3/1989 | Hailey |
| 4,820,305 A | 4/1989 | Harms et al. |
| 4,875,474 A | 10/1989 | Border |
| 4,886,062 A | 12/1989 | Wiktor |
| 4,914,818 A | 4/1990 | Hall et al. |
| 4,921,478 A | 5/1990 | Solano et al. |
| 4,941,466 A | 7/1990 | Romano |
| 4,946,459 A | 8/1990 | Bradshaw et al. |
| 4,954,126 A | 9/1990 | Wallsten |
| 4,955,916 A | 9/1990 | Carignan et al. |
| 4,969,888 A | 11/1990 | Scholten et al. |
| 4,973,257 A | 11/1990 | Lhotak |
| 4,978,349 A | 12/1990 | Frigg |
| 4,998,539 A | 3/1991 | Delsanti |
| 5,002,546 A | 3/1991 | Romano |
| 5,015,255 A | 5/1991 | Kuslich |
| 5,030,201 A | 7/1991 | Palestrant |
| 5,035,714 A | 7/1991 | Willert et al. |
| 5,053,036 A | 10/1991 | Perren et al. |
| 5,057,103 A | 10/1991 | Davis |
| 5,059,193 A * | 10/1991 | Kuslich .................. F16B 13/061 606/247 |
| 5,059,206 A | 10/1991 | Winters |
| 5,062,845 A | 11/1991 | Kuslich et al. |
| 5,066,296 A | 11/1991 | Chapman et al. |
| 5,067,957 A | 11/1991 | Jervis |
| 5,071,407 A | 12/1991 | Termin et al. |
| 5,084,050 A | 1/1992 | Draenert |
| 5,100,423 A | 3/1992 | Fearnot |
| 5,102,413 A | 4/1992 | Poddar |
| 5,108,404 A | 4/1992 | Scholten et al. |
| 5,108,435 A | 4/1992 | Gustavson et al. |
| 5,112,333 A | 5/1992 | Fixel |
| 5,113,846 A | 5/1992 | Hiltebrandt et al. |
| 5,116,335 A | 5/1992 | Hannon et al. |
| 5,122,134 A | 6/1992 | Borzone et al. |
| 5,129,906 A | 7/1992 | Ross et al. |
| 5,135,527 A | 8/1992 | Ender |
| 5,139,497 A | 8/1992 | Tilghman et al. |
| 5,151,103 A | 9/1992 | Tepic et al. |
| 5,169,402 A | 12/1992 | Elloy |
| 5,171,284 A | 12/1992 | Branemark |
| 5,174,374 A | 12/1992 | Hailey |
| 5,180,382 A | 1/1993 | Frigg et al. |
| 5,190,545 A | 3/1993 | Corsi et al. |
| 5,190,546 A | 3/1993 | Jervis |
| 5,190,548 A | 3/1993 | Davis |
| 5,197,966 A | 3/1993 | Sommerkamp |
| 5,197,967 A | 3/1993 | Wilson |
| 5,197,971 A | 3/1993 | Bonutti |
| 5,201,741 A | 4/1993 | Dulebohn |
| 5,203,773 A | 4/1993 | Green |
| 5,221,261 A | 6/1993 | Termin et al. |
| 5,236,431 A | 8/1993 | Gogolewski et al. |
| 5,242,017 A | 9/1993 | Hailey |
| 5,242,461 A | 9/1993 | Kortenbach et al. |
| 5,250,048 A | 10/1993 | Gundolf |

(56) References Cited

U.S. PATENT DOCUMENTS

| | | | |
|---|---|---|---|
| 5,263,955 | A | 11/1993 | Baumgart et al. |
| 5,269,785 | A | 12/1993 | Bonutti |
| 5,275,602 | A | 1/1994 | Shimizu et al. |
| 5,275,608 | A | 1/1994 | Forman et al. |
| 5,281,225 | A | 1/1994 | Vicenzi |
| 5,281,226 | A | 1/1994 | Davydov et al. |
| 5,286,249 | A | 2/1994 | Thibodaux |
| 5,307,790 | A | 5/1994 | Byrne |
| 5,314,486 | A | 5/1994 | Zang et al. |
| 5,326,205 | A | 7/1994 | Anspach et al. |
| 5,334,184 | A | 8/1994 | Bimman |
| 5,358,405 | A | 10/1994 | Imai |
| 5,376,097 | A | 12/1994 | Phillips |
| 5,376,100 | A * | 12/1994 | Lefebvre ........ A61B 17/320725 604/22 |
| 5,378,239 | A | 1/1995 | Termin et al. |
| 5,380,328 | A | 1/1995 | Morgan |
| 5,397,320 | A | 3/1995 | Essig et al. |
| 5,415,660 | A | 5/1995 | Campbell et al. |
| 5,423,823 | A | 6/1995 | Schmieding |
| 5,431,671 | A | 7/1995 | Nallakrishnan |
| 5,437,665 | A | 8/1995 | Munro |
| 5,437,674 | A | 8/1995 | Worcel et al. |
| 5,439,464 | A | 8/1995 | Shapiro |
| 5,445,639 | A | 8/1995 | Kuslich et al. |
| 5,454,365 | A * | 10/1995 | Bonutti .............. A61B 17/0218 600/204 |
| 5,458,599 | A | 10/1995 | Adobbati |
| 5,458,648 | A | 10/1995 | Berman et al. |
| 5,462,547 | A | 10/1995 | Weigum |
| 5,467,763 | A | 11/1995 | McMahon et al. |
| D365,634 | S | 12/1995 | Morgan |
| 5,474,557 | A | 12/1995 | Mai |
| 5,480,447 | A | 1/1996 | Skiba |
| 5,496,277 | A | 3/1996 | Termin et al. |
| 5,496,330 | A | 3/1996 | Bates et al. |
| 5,499,981 | A | 3/1996 | Kordis |
| 5,501,695 | A | 3/1996 | Anspach et al. |
| 5,505,734 | A | 4/1996 | Caniggia et al. |
| 5,509,919 | A | 4/1996 | Young |
| 5,512,037 | A | 4/1996 | Russell et al. |
| 5,527,316 | A | 6/1996 | Stone et al. |
| 5,531,792 | A | 7/1996 | Huene |
| 5,536,267 | A | 7/1996 | Edwards et al. |
| 5,540,693 | A | 7/1996 | Fisher |
| 5,545,162 | A | 8/1996 | Huebner |
| 5,554,163 | A | 9/1996 | Shturman |
| 5,556,408 | A | 9/1996 | Farhat |
| 5,571,098 | A | 11/1996 | Domankevitz et al. |
| 5,571,189 | A | 11/1996 | Kuslich |
| 5,578,035 | A | 11/1996 | Lin |
| 5,582,577 | A | 12/1996 | Lund et al. |
| 5,582,618 | A | 12/1996 | Chin et al. |
| 5,586,983 | A | 12/1996 | Sanders et al. |
| 5,586,985 | A | 12/1996 | Putnam et al. |
| 5,586,990 | A | 12/1996 | Hahnen et al. |
| 5,591,169 | A | 1/1997 | Benoist |
| 5,591,170 | A | 1/1997 | Spievack et al. |
| 5,597,378 | A | 1/1997 | Jervis |
| 5,602,935 | A | 2/1997 | Yoshida et al. |
| 5,620,414 | A | 4/1997 | Campbell |
| 5,620,445 | A | 4/1997 | Brosnahan et al. |
| 5,624,440 | A | 4/1997 | Huebner |
| 5,624,447 | A | 4/1997 | Myers |
| 5,626,580 | A | 5/1997 | Brosnahan |
| 5,628,747 | A | 5/1997 | Richelsoph |
| 5,645,589 | A | 7/1997 | Li |
| 5,658,280 | A | 8/1997 | Issa |
| 5,658,283 | A | 8/1997 | Huebner |
| 5,660,188 | A | 8/1997 | Groiso |
| 5,662,649 | A | 9/1997 | Huebner |
| 5,667,509 | A | 9/1997 | Westin |
| 5,676,545 | A | 10/1997 | Jones |
| 5,676,699 | A | 10/1997 | Gogolewski et al. |
| 5,681,310 | A | 10/1997 | Yuan et al. |
| 5,683,389 | A | 11/1997 | Orsak |
| 5,685,826 | A | 11/1997 | Bonutti |
| 5,693,011 | A | 12/1997 | Onik |
| 5,697,981 | A | 12/1997 | Ison et al. |
| 5,707,374 | A | 1/1998 | Schmidt |
| 5,709,697 | A * | 1/1998 | Ratcliff .............. A61B 10/0266 606/167 |
| 5,718,704 | A | 2/1998 | Medoff |
| 5,725,541 | A | 3/1998 | Anspach, III et al. |
| 5,728,047 | A | 3/1998 | Edoga |
| 5,728,098 | A | 3/1998 | Sherman et al. |
| 5,730,704 | A | 3/1998 | Avitall |
| 5,741,266 | A | 4/1998 | Moran et al. |
| 5,741,282 | A | 4/1998 | Anspach et al. |
| 5,758,713 | A | 6/1998 | Fallet |
| 5,779,703 | A | 7/1998 | Benoist |
| 5,792,106 | A | 8/1998 | Mische |
| 5,810,721 | A | 9/1998 | Mueller et al. |
| 5,814,044 | A | 9/1998 | Hooven |
| 5,817,098 | A | 10/1998 | Albrektsson et al. |
| 5,824,095 | A | 10/1998 | Di Maio, Jr. et al. |
| 5,827,289 | A | 10/1998 | Reiley et al. |
| 5,827,312 | A | 10/1998 | Brown et al. |
| D403,069 | S | 12/1998 | Drewry et al. |
| 5,853,054 | A | 12/1998 | McGarian et al. |
| 5,876,399 | A | 3/1999 | Chia et al. |
| 5,879,352 | A | 3/1999 | Filoso et al. |
| 5,879,355 | A | 3/1999 | Ullmark |
| 5,885,258 | A | 3/1999 | Sachdeva et al. |
| 5,885,282 | A | 3/1999 | Szabo |
| 5,888,196 | A | 3/1999 | Bonutti |
| 5,891,147 | A | 4/1999 | Moskovitz et al. |
| 5,893,850 | A | 4/1999 | Cachia |
| 5,897,556 | A | 4/1999 | Drewry et al. |
| 5,908,423 | A | 6/1999 | Kashuba et al. |
| 5,915,036 | A | 6/1999 | Grunkin et al. |
| 5,919,195 | A | 7/1999 | Wilson et al. |
| 5,925,039 | A | 7/1999 | Landingham |
| 5,928,239 | A | 7/1999 | Mirza |
| 5,935,127 | A | 8/1999 | Border |
| 5,938,699 | A | 8/1999 | Campbell |
| 5,941,878 | A | 8/1999 | Medoff |
| 5,951,467 | A | 9/1999 | Picha et al. |
| 5,951,556 | A | 9/1999 | Faccioli et al. |
| 5,957,884 | A | 9/1999 | Hooven |
| 5,964,698 | A | 10/1999 | Fowle |
| 5,976,134 | A | 11/1999 | Huebner |
| 5,980,525 | A | 11/1999 | Bryant et al. |
| 5,984,932 | A | 11/1999 | Yoon |
| 5,984,937 | A | 11/1999 | Morse et al. |
| 5,997,538 | A | 12/1999 | Asnis et al. |
| 6,001,099 | A | 12/1999 | Huebner |
| 6,015,406 | A | 1/2000 | Goble et al. |
| 6,019,762 | A | 2/2000 | Cole |
| 6,019,947 | A | 2/2000 | Kucherov |
| 6,030,406 | A | 2/2000 | Davis et al. |
| 6,033,412 | A | 3/2000 | Losken et al. |
| 6,045,564 | A | 4/2000 | Walen |
| 6,048,309 | A | 4/2000 | Flom et al. |
| 6,053,922 | A | 4/2000 | Krause et al. |
| 6,056,750 | A | 5/2000 | Lob |
| 6,068,642 | A | 5/2000 | Johnson et al. |
| 6,068,648 | A | 5/2000 | Cole et al. |
| 6,074,392 | A | 6/2000 | Durham |
| 6,093,162 | A | 7/2000 | Fairleigh et al. |
| 6,096,040 | A | 8/2000 | Esser |
| 6,113,603 | A | 9/2000 | Medoff |
| 6,120,472 | A | 9/2000 | Singer, Jr. |
| 6,120,504 | A | 9/2000 | Brumback et al. |
| 6,123,704 | A | 9/2000 | Hajianpour |
| 6,126,662 | A | 10/2000 | Carmichael et al. |
| 6,127,597 | A | 10/2000 | Beyar et al. |
| 6,129,762 | A | 10/2000 | Li |
| 6,142,935 | A | 11/2000 | Flom et al. |
| 6,143,012 | A | 11/2000 | Gausepohl |
| 6,149,651 | A | 11/2000 | Drewry et al. |
| 6,149,689 | A | 11/2000 | Grundei |
| 6,156,069 | A | 12/2000 | Amstutz |
| 6,162,223 | A | 12/2000 | Orsak et al. |

(56) References Cited

U.S. PATENT DOCUMENTS

| | | |
|---|---|---|
| 6,162,224 A | 12/2000 | Huebner |
| 6,171,309 B1 | 1/2001 | Huebner |
| 6,174,312 B1 | 1/2001 | Laminger |
| 6,197,027 B1 | 3/2001 | Hajianpour |
| 6,200,330 B1 | 3/2001 | Benderev et al. |
| 6,216,573 B1 | 4/2001 | Moutafis et al. |
| 6,221,074 B1 | 4/2001 | Cole et al. |
| 6,221,102 B1 | 4/2001 | Baker et al. |
| 6,224,600 B1 | 5/2001 | Protogirou |
| 6,224,604 B1 | 5/2001 | Suddaby |
| 6,231,576 B1 | 5/2001 | Frigg et al. |
| 6,235,043 B1 | 5/2001 | Reiley et al. |
| 6,238,417 B1 | 5/2001 | Cole |
| 6,241,734 B1 | 6/2001 | Scribner et al. |
| 6,248,110 B1 | 6/2001 | Reiley et al. |
| 6,258,096 B1 | 7/2001 | Seki |
| 6,261,289 B1 * | 7/2001 | Levy ............... A61B 17/7266 606/62 |
| 6,280,474 B1 | 8/2001 | Cassidy et al. |
| 6,296,639 B1 | 10/2001 | Truckai et al. |
| 6,299,642 B1 | 10/2001 | Chan |
| 6,302,915 B1 | 10/2001 | Cooney et al. |
| 6,306,141 B1 | 10/2001 | Jervis |
| 6,312,467 B1 | 11/2001 | Mcgee |
| 6,319,255 B1 | 11/2001 | Grundei et al. |
| 6,322,591 B1 | 11/2001 | Ahrens |
| 6,331,166 B1 * | 12/2001 | Burbank ......... A61B 17/00491 600/567 |
| 6,332,885 B1 | 12/2001 | Martella |
| 6,332,886 B1 | 12/2001 | Green et al. |
| 6,337,142 B2 | 1/2002 | Harder et al. |
| 6,348,053 B1 | 2/2002 | Cachia |
| 6,364,909 B1 | 4/2002 | Mcgee |
| 6,365,555 B1 | 4/2002 | Moser et al. |
| 6,375,666 B1 | 4/2002 | Mische |
| 6,383,188 B2 | 5/2002 | Kuslich et al. |
| 6,402,753 B1 | 6/2002 | Cole et al. |
| 6,411,729 B1 | 6/2002 | Grunkin |
| 6,416,517 B2 | 7/2002 | Harder et al. |
| 6,423,070 B1 | 7/2002 | Zeppelin |
| 6,440,138 B1 | 8/2002 | Reiley et al. |
| 6,447,514 B1 | 9/2002 | Stalcup et al. |
| 6,447,515 B1 | 9/2002 | Meldrum |
| 6,447,518 B1 | 9/2002 | Krause et al. |
| 6,454,810 B1 | 9/2002 | Lob |
| 6,468,207 B1 | 10/2002 | Fowler |
| 6,475,789 B1 | 11/2002 | Cech et al. |
| 6,488,685 B1 | 12/2002 | Manderson |
| 6,491,694 B1 | 12/2002 | Orsak |
| 6,511,481 B2 | 1/2003 | von Hoffmann et al. |
| 6,517,541 B1 | 2/2003 | Sesic |
| 6,527,775 B1 | 3/2003 | Warburton |
| 6,533,788 B1 | 3/2003 | Orbay |
| 6,540,770 B1 | 4/2003 | Tornier et al. |
| 6,544,267 B1 | 4/2003 | Cole et al. |
| 6,551,321 B1 | 4/2003 | Burkinshaw et al. |
| 6,554,833 B2 * | 4/2003 | Levy ............... A61B 17/7258 606/62 |
| 6,575,973 B1 | 6/2003 | Shekalim |
| 6,575,978 B2 | 6/2003 | Peterson |
| 6,582,467 B1 | 6/2003 | Teitelbaum et al. |
| 6,585,736 B2 | 7/2003 | Hajianpour |
| 6,585,770 B1 | 7/2003 | White et al. |
| 6,610,839 B1 | 8/2003 | Morin et al. |
| 6,613,052 B1 | 9/2003 | Kinnett |
| 6,613,054 B2 | 9/2003 | Scribner et al. |
| 6,617,110 B1 | 9/2003 | Cech et al. |
| 6,632,224 B2 | 10/2003 | Cachia et al. |
| 6,641,616 B1 | 11/2003 | Grundei |
| 6,645,210 B2 | 11/2003 | Manderson |
| 6,648,890 B2 | 11/2003 | Culbert et al. |
| 6,652,585 B2 | 11/2003 | Lange |
| 6,656,187 B1 | 12/2003 | Camino |
| 6,656,219 B1 | 12/2003 | Wiktor |
| 6,660,009 B1 | 12/2003 | Azar |
| 6,660,041 B1 | 12/2003 | Grundei |
| 6,676,665 B2 | 1/2004 | Foley et al. |
| 6,679,886 B2 | 1/2004 | Weikel et al. |
| 6,682,565 B1 | 1/2004 | Krishnan |
| 6,685,706 B2 | 2/2004 | Padget et al. |
| 6,689,138 B2 | 2/2004 | Léchot et al. |
| 6,692,496 B1 | 2/2004 | Wardlaw |
| 6,701,174 B1 | 3/2004 | Krause et al. |
| 6,709,433 B1 | 3/2004 | Schoenefeld |
| 6,711,432 B1 | 3/2004 | Krause et al. |
| 6,712,073 B2 | 3/2004 | Manderson |
| 6,712,858 B1 | 3/2004 | Grundei et al. |
| 6,719,761 B1 | 4/2004 | Reiley et al. |
| 6,719,793 B2 | 4/2004 | McGee et al. |
| 6,740,090 B1 | 5/2004 | Cragg et al. |
| 6,746,451 B2 | 6/2004 | Middleton et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,761,722 B2 | 7/2004 | Cole et al. |
| 6,767,350 B1 | 7/2004 | Lob |
| 6,775,401 B2 | 8/2004 | Hwang et al. |
| 6,780,185 B2 * | 8/2004 | Frei ............... A61B 17/746 606/68 |
| 6,783,530 B1 | 8/2004 | Levy et al. |
| 6,783,532 B2 | 8/2004 | Steiner et al. |
| 6,783,533 B2 | 8/2004 | Green et al. |
| 6,793,655 B2 | 9/2004 | Orsak |
| 6,793,659 B2 | 9/2004 | Putnam |
| 6,811,568 B2 | 11/2004 | Minamikawa |
| 6,827,723 B2 | 12/2004 | Carson |
| 6,827,743 B2 | 12/2004 | Eisermann et al. |
| 6,849,051 B2 | 2/2005 | Sramek et al. |
| 6,852,128 B2 | 2/2005 | Lange |
| 6,866,665 B2 | 3/2005 | Orbay |
| 6,887,243 B2 | 5/2005 | Culbert |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,911,046 B2 | 6/2005 | Schulter |
| 6,913,605 B2 | 7/2005 | Fletcher et al. |
| 6,923,813 B2 | 8/2005 | Phillips et al. |
| 6,923,817 B2 | 8/2005 | Carson et al. |
| 6,923,828 B1 | 8/2005 | Wiktor |
| 6,926,720 B2 | 8/2005 | Castañeda |
| 6,932,086 B1 | 8/2005 | Hajianpour |
| 6,942,666 B2 | 9/2005 | Overaker et al. |
| 6,942,668 B2 | 9/2005 | Padget et al. |
| 6,949,101 B2 | 9/2005 | McCleary et al. |
| 6,951,561 B2 | 10/2005 | Warren et al. |
| 6,953,313 B2 | 10/2005 | Tylosky |
| 6,975,894 B2 | 12/2005 | Wehrli et al. |
| 6,984,248 B2 | 1/2006 | Hyde, Jr. |
| 6,986,771 B2 | 1/2006 | Paul et al. |
| 6,989,011 B2 | 1/2006 | Paul et al. |
| 6,991,656 B2 | 1/2006 | Mears |
| 7,008,425 B2 | 3/2006 | Phillips |
| 7,008,428 B2 | 3/2006 | Cachia et al. |
| 7,008,430 B2 | 3/2006 | Dong et al. |
| 7,011,662 B2 | 3/2006 | Lechot et al. |
| 7,018,332 B1 | 3/2006 | Masson et al. |
| 7,018,380 B2 | 3/2006 | Cole |
| 7,022,069 B2 | 4/2006 | Masson et al. |
| 7,025,789 B2 | 4/2006 | Chow et al. |
| 7,041,104 B1 | 5/2006 | Cole et al. |
| 7,041,138 B2 | 5/2006 | Lange |
| 7,048,542 B2 | 5/2006 | Von Arx et al. |
| 7,052,498 B2 | 5/2006 | Levy et al. |
| 7,063,701 B2 | 6/2006 | Michelson |
| 7,070,601 B2 | 7/2006 | Culbert et al. |
| 7,090,676 B2 | 8/2006 | Huebner et al. |
| 7,097,646 B2 | 8/2006 | Schantz |
| 7,097,648 B1 | 8/2006 | Globerman et al. |
| 7,122,033 B2 | 10/2006 | Wood |
| 7,122,043 B2 | 10/2006 | Greenhalgh et al. |
| 7,122,052 B2 | 10/2006 | Greenhalgh |
| 7,131,995 B2 | 11/2006 | Biedermann et al. |
| 7,137,987 B2 | 11/2006 | Patterson et al. |
| 7,141,054 B2 | 11/2006 | Vandewalle |

(56) References Cited

U.S. PATENT DOCUMENTS

| | | | |
|---|---|---|---|
| 7,141,067 B2 | 11/2006 | Jones et al. |
| 7,147,640 B2 | 12/2006 | Huebner et al. |
| 7,153,307 B2 | 12/2006 | Scribner et al. |
| 7,153,309 B2 | 12/2006 | Huebner et al. |
| 7,160,302 B2 | 1/2007 | Warburton |
| 7,160,331 B2 | 1/2007 | Cooney et al. |
| 7,172,595 B1 | 2/2007 | Goble |
| 7,175,625 B2 | 2/2007 | Culbert |
| 7,179,024 B2 | 2/2007 | Greenhalgh |
| 7,189,237 B2 | 3/2007 | Huebner |
| 7,189,240 B1 | 3/2007 | Dekel |
| 7,195,589 B1 | 3/2007 | Masson et al. |
| 7,195,633 B2 | 3/2007 | Medoff et al. |
| 7,214,227 B2 | 5/2007 | Colleran et al. |
| 7,220,282 B2 | 5/2007 | Kuslich et al. |
| 7,229,441 B2 | 6/2007 | Trieu et al. |
| 7,235,079 B2 | 6/2007 | Jensen et al. |
| 7,237,556 B2 | 7/2007 | Smothers et al. |
| 7,255,712 B1 | 8/2007 | Steinberg |
| 7,258,692 B2 | 8/2007 | Thelen et al. |
| 7,264,622 B2 | 9/2007 | Michelson |
| 7,267,678 B2 | 9/2007 | Medoff |
| 7,282,053 B2 | 10/2007 | Orbay |
| 7,294,130 B2 | 11/2007 | Orbay |
| 7,300,449 B2 | 11/2007 | Mische et al. |
| 7,306,603 B2 | 12/2007 | Boehm et al. |
| 7,306,683 B2 | 12/2007 | Cheung et al. |
| 7,311,711 B2 | 12/2007 | Cole |
| D560,128 S | 1/2008 | Diederich et al. |
| 7,322,938 B2 | 1/2008 | Burbank et al. |
| 7,326,249 B2 | 2/2008 | Lange |
| 7,329,228 B2 | 2/2008 | Burbank et al. |
| 7,341,601 B2 | 3/2008 | Eisermann et al. |
| 7,344,539 B2 | 3/2008 | Serhan et al. |
| 7,354,453 B2 | 4/2008 | McAfee |
| 7,422,360 B2 | 9/2008 | Kozyuk |
| 7,465,318 B2 | 12/2008 | Sennett et al. |
| 7,476,226 B2 | 1/2009 | Weikel et al. |
| 7,481,815 B2 | 1/2009 | Fernandez |
| 7,485,119 B2 | 2/2009 | Thelen et al. |
| 7,488,320 B2 | 2/2009 | Middleton |
| 7,488,329 B2 | 2/2009 | Thelen et al. |
| D589,147 S | 3/2009 | Colleran et al. |
| 7,500,977 B2 | 3/2009 | Assell et al. |
| 7,507,241 B2 | 3/2009 | Levy et al. |
| 7,520,879 B2 | 4/2009 | Justis et al. |
| 7,527,632 B2 | 5/2009 | Houghton et al. |
| 7,563,263 B2 | 7/2009 | Orbay et al. |
| 7,569,061 B2 | 8/2009 | Colleran |
| 7,578,824 B2 | 8/2009 | Justin et al. |
| 7,588,575 B2 | 9/2009 | Colleran et al. |
| 7,588,577 B2 | 9/2009 | Fencl et al. |
| 7,588,588 B2 | 9/2009 | Spitler et al. |
| 7,601,152 B2 | 10/2009 | Levy et al. |
| 7,611,515 B2 | 11/2009 | Wolford et al. |
| 7,621,950 B1* | 11/2009 | Globerman | C25F 3/22 411/34 |
| 7,632,277 B2 | 12/2009 | Woll et al. |
| 7,632,310 B2 | 12/2009 | Clifford et al. |
| 7,666,226 B2 | 2/2010 | Schaller |
| 7,670,339 B2 | 3/2010 | Levy et al. |
| 7,670,374 B2 | 3/2010 | Schaller |
| 7,670,375 B2 | 3/2010 | Schaller |
| 7,682,364 B2 | 3/2010 | Reiley et al. |
| 7,695,471 B2 | 4/2010 | Cheung et al. |
| 7,695,502 B2 | 4/2010 | Orbay et al. |
| 7,704,251 B2 | 4/2010 | Huebner et al. |
| 7,708,742 B2 | 5/2010 | Scribner et al. |
| 7,713,271 B2 | 5/2010 | Warburton et al. |
| 7,717,472 B2 | 5/2010 | Johnson |
| 7,722,612 B2 | 5/2010 | Sala et al. |
| 7,722,626 B2 | 5/2010 | Middleman et al. |
| 7,727,264 B2 | 6/2010 | Orbay et al. |
| 7,731,720 B2 | 6/2010 | Sand et al. |
| 7,749,232 B2 | 7/2010 | Salerni |
| 7,758,500 B2 | 7/2010 | Boyd et al. |
| 7,785,368 B2 | 8/2010 | Schaller |
| 7,806,929 B2 | 10/2010 | Brown |
| 7,811,291 B2 | 10/2010 | Liu et al. |
| 7,828,802 B2 | 11/2010 | Levy et al. |
| 7,837,612 B2 | 11/2010 | Gill et al. |
| 7,842,041 B2 | 11/2010 | Liu et al. |
| 7,846,162 B2 | 12/2010 | Nelson et al. |
| 7,879,038 B2 | 2/2011 | Reiley et al. |
| 7,879,103 B2 | 2/2011 | Gertzman et al. |
| 7,905,909 B2 | 3/2011 | Orbay et al. |
| 7,909,825 B2 | 3/2011 | Saravia et al. |
| 7,909,827 B2 | 3/2011 | Reiley et al. |
| 7,909,873 B2 | 3/2011 | Tan-Malecki et al. |
| 7,914,533 B2 | 3/2011 | Nelson et al. |
| 7,931,689 B2 | 4/2011 | Hochschuler et al. |
| 7,942,875 B2 | 5/2011 | Nelson et al. |
| 7,959,634 B2 | 6/2011 | Sennett |
| 7,959,638 B2 | 6/2011 | Osorio et al. |
| 7,959,683 B2 | 6/2011 | Semler et al. |
| 7,967,827 B2 | 6/2011 | Osorio et al. |
| 7,967,865 B2 | 6/2011 | Schaller |
| 7,972,340 B2 | 7/2011 | Sand et al. |
| 7,988,735 B2 | 8/2011 | Yurek et al. |
| 8,007,498 B2 | 8/2011 | Mische |
| RE42,757 E | 9/2011 | Kuslich et al. |
| 8,021,365 B2 | 9/2011 | Phan |
| 8,021,366 B2 | 9/2011 | Phan |
| 8,043,334 B2 | 10/2011 | Fisher et al. |
| 8,057,544 B2 | 11/2011 | Schaller |
| 8,105,236 B2 | 1/2012 | Malandain et al. |
| 8,109,933 B2 | 2/2012 | Truckai et al. |
| 8,114,084 B2 | 2/2012 | Betts |
| 8,118,952 B2 | 2/2012 | Gall et al. |
| 8,128,627 B2 | 3/2012 | Justin et al. |
| 8,152,737 B2 | 4/2012 | Burbank et al. |
| 8,157,804 B2 | 4/2012 | Betts |
| 8,226,719 B2 | 7/2012 | Melsheimer et al. |
| 8,241,335 B2 | 8/2012 | Truckai et al. |
| 8,287,538 B2 | 10/2012 | Brenzel et al. |
| 8,287,539 B2 | 10/2012 | Nelson et al. |
| 8,287,541 B2 | 10/2012 | Nelson et al. |
| 8,317,791 B2 | 11/2012 | Phan |
| 8,353,911 B2 | 1/2013 | Goldin et al. |
| 8,366,773 B2 | 2/2013 | Schaller et al. |
| 8,409,211 B2 | 4/2013 | Baroud |
| 8,430,879 B2 | 4/2013 | Stoneburner et al. |
| 8,439,917 B2 | 5/2013 | Saravia et al. |
| 8,485,798 B2 | 7/2013 | Sheth et al. |
| 8,491,591 B2 | 7/2013 | Fürderer |
| 8,496,394 B2 | 7/2013 | Schneider |
| 8,496,657 B2 | 7/2013 | Bonutti et al. |
| 8,496,658 B2 | 7/2013 | Stoneburner et al. |
| 8,500,357 B2 | 8/2013 | Stahle |
| 8,505,638 B2 | 8/2013 | Ezell |
| 8,505,879 B2 | 8/2013 | Ruan |
| 8,506,199 B2 | 8/2013 | Rump et al. |
| 8,512,398 B2 | 8/2013 | Alkhatib |
| 8,568,413 B2 | 10/2013 | Mazur et al. |
| 8,579,537 B2 | 11/2013 | VanLandingham et al. |
| 8,597,276 B2 | 12/2013 | Vongphakdy et al. |
| 8,840,612 B2* | 9/2014 | Tontz | A61B 17/7258 606/63 |
| 8,906,022 B2 | 11/2014 | Krinke et al. |
| 8,951,251 B2 | 2/2015 | Willard |
| 8,961,518 B2 | 2/2015 | Taylor et al. |
| 9,155,574 B2* | 10/2015 | Saravia | A61B 17/7208 |
| 2001/0018588 A1 | 8/2001 | Harder et al. |
| 2001/0034526 A1 | 10/2001 | Kuslich et al. |
| 2001/0053912 A1 | 12/2001 | Frigg |
| 2002/0013600 A1 | 1/2002 | Scribner et al. |
| 2002/0015517 A1 | 2/2002 | Hwang et al. |
| 2002/0029081 A1 | 3/2002 | Scarborough et al. |
| 2002/0032444 A1 | 3/2002 | Mische |
| 2002/0055742 A1 | 5/2002 | Lieberman |
| 2002/0055785 A1 | 5/2002 | Harris |
| 2002/0065530 A1 | 5/2002 | Mische |
| 2002/0068974 A1 | 6/2002 | Kuslich et al. |
| 2002/0111629 A1 | 8/2002 | Phillips |

(56) References Cited

U.S. PATENT DOCUMENTS

| | | |
|---|---|---|
| 2002/0111690 A1 | 8/2002 | Hyde |
| 2002/0120269 A1 | 8/2002 | Lange |
| 2002/0120270 A1 | 8/2002 | Trieu et al. |
| 2002/0123750 A1 | 9/2002 | Eisermann et al. |
| 2002/0133153 A1 | 9/2002 | Hyde |
| 2002/0133156 A1 | 9/2002 | Cole |
| 2002/0133172 A1 | 9/2002 | Lambrecht et al. |
| 2002/0133175 A1 | 9/2002 | Carson |
| 2002/0138149 A1 | 9/2002 | Hyde |
| 2002/0143329 A1 | 10/2002 | Serhan et al. |
| 2002/0143333 A1 | 10/2002 | von Hoffmann et al. |
| 2002/0143334 A1 | 10/2002 | Hoffmann et al. |
| 2002/0143335 A1 | 10/2002 | von Hoffmann et al. |
| 2002/0147451 A1 | 10/2002 | Mcgee |
| 2002/0147455 A1 | 10/2002 | Carson |
| 2002/0165461 A1 | 11/2002 | Hayzelden et al. |
| 2002/0171208 A1 | 11/2002 | Lechot et al. |
| 2002/0173813 A1 | 11/2002 | Peterson et al. |
| 2002/0183758 A1 | 12/2002 | Middleton et al. |
| 2002/0191823 A1 | 12/2002 | Wehrli et al. |
| 2003/0040805 A1 | 2/2003 | Minamikawa |
| 2003/0055373 A1 | 3/2003 | Sramek et al. |
| 2003/0055425 A1 | 3/2003 | Hajianpour |
| 2003/0069582 A1 | 4/2003 | Culbert |
| 2003/0069645 A1 | 4/2003 | Ball et al. |
| 2003/0074075 A1 | 4/2003 | Thomas, Jr. et al. |
| 2003/0083660 A1 | 5/2003 | Orbay |
| 2003/0083662 A1 | 5/2003 | Middleton |
| 2003/0093076 A1 | 5/2003 | Venturini et al. |
| 2003/0097132 A1 | 5/2003 | Padget et al. |
| 2003/0097133 A1 | 5/2003 | Green et al. |
| 2003/0105461 A1 | 6/2003 | Putnam |
| 2003/0109932 A1 | 6/2003 | Keynan |
| 2003/0120273 A1 | 6/2003 | Cole |
| 2003/0130660 A1 | 7/2003 | Levy et al. |
| 2003/0153918 A1 | 8/2003 | Putnam et al. |
| 2003/0187449 A1 | 10/2003 | McCleary et al. |
| 2003/0216738 A1 | 11/2003 | Azar |
| 2003/0220641 A1 | 11/2003 | Thelen et al. |
| 2003/0220644 A1 | 11/2003 | Thelen et al. |
| 2003/0220646 A1 | 11/2003 | Thelen et al. |
| 2003/0220698 A1 | 11/2003 | Mears et al. |
| 2003/0225407 A1 | 12/2003 | Estrada |
| 2004/0024410 A1 | 2/2004 | Olson, Jr. et al. |
| 2004/0039384 A1 | 2/2004 | Boehm et al. |
| 2004/0044413 A1 | 3/2004 | Schulter |
| 2004/0049192 A1 | 3/2004 | Shimizu |
| 2004/0078082 A1 | 4/2004 | Lange |
| 2004/0087956 A1 | 5/2004 | Weikel et al. |
| 2004/0092946 A1 | 5/2004 | Bagga et al. |
| 2004/0102777 A1 | 5/2004 | Huebner |
| 2004/0102778 A1 | 5/2004 | Huebner et al. |
| 2004/0102788 A1 | 5/2004 | Huebner et al. |
| 2004/0106925 A1 | 6/2004 | Culbert |
| 2004/0138665 A1 | 7/2004 | Padget et al. |
| 2004/0143264 A1 | 7/2004 | McAfee |
| 2004/0153080 A1 | 8/2004 | Dong et al. |
| 2004/0153114 A1 | 8/2004 | Reiley et al. |
| 2004/0153115 A1 | 8/2004 | Reiley et al. |
| 2004/0167528 A1 | 8/2004 | Schantz |
| 2004/0167625 A1 | 8/2004 | Beyar et al. |
| 2004/0181221 A1 | 9/2004 | Huebner et al. |
| 2004/0193163 A1 | 9/2004 | Orbay |
| 2004/0193164 A1 | 9/2004 | Orbay |
| 2004/0193165 A1 | 9/2004 | Orbay |
| 2004/0193251 A1 | 9/2004 | Rudnick et al. |
| 2004/0193267 A1 | 9/2004 | Jones et al. |
| 2004/0208717 A1 | 10/2004 | Greenhalgh |
| 2004/0214311 A1 | 10/2004 | Levy |
| 2004/0220678 A1 | 11/2004 | Chow et al. |
| 2004/0230193 A1 | 11/2004 | Cheung et al. |
| 2004/0236327 A1 | 11/2004 | Paul et al. |
| 2004/0236328 A1 | 11/2004 | Paul et al. |
| 2004/0236339 A1 | 11/2004 | Pepper |
| 2004/0249375 A1 | 12/2004 | Agee et al. |
| 2004/0260289 A1 | 12/2004 | Padget et al. |
| 2004/0260297 A1 | 12/2004 | Padget et al. |
| 2004/0267269 A1 | 12/2004 | Middleton et al. |
| 2005/0010231 A1 | 1/2005 | Myers |
| 2005/0015129 A1 | 1/2005 | Mische |
| 2005/0015154 A1 | 1/2005 | Lindsey et al. |
| 2005/0033366 A1 | 2/2005 | Cole et al. |
| 2005/0043733 A1 | 2/2005 | Eisermann et al. |
| 2005/0065522 A1 | 3/2005 | Orbay |
| 2005/0065523 A1 | 3/2005 | Orbay |
| 2005/0065524 A1 | 3/2005 | Orbay |
| 2005/0065526 A1 | 3/2005 | Drew et al. |
| 2005/0070902 A1 | 3/2005 | Medoff |
| 2005/0085813 A1 | 4/2005 | Spitler et al. |
| 2005/0085818 A1 | 4/2005 | Huebner |
| 2005/0085824 A1 | 4/2005 | Castaneda |
| 2005/0085921 A1 | 4/2005 | Gupta et al. |
| 2005/0113836 A1 | 5/2005 | Lozier et al. |
| 2005/0113892 A1 | 5/2005 | Sproul |
| 2005/0113929 A1 | 5/2005 | Cragg et al. |
| 2005/0119749 A1 | 6/2005 | Lange |
| 2005/0124972 A1 | 6/2005 | Mische et al. |
| 2005/0125066 A1 | 6/2005 | Mcafee |
| 2005/0131407 A1 | 6/2005 | Sicvol et al. |
| 2005/0142163 A1 | 6/2005 | Hunter et al. |
| 2005/0143734 A1 | 6/2005 | Cachia et al. |
| 2005/0154331 A1 | 7/2005 | Christie et al. |
| 2005/0159749 A1 | 7/2005 | Levy et al. |
| 2005/0177172 A1 | 8/2005 | Acker et al. |
| 2005/0182399 A1 | 8/2005 | Levine |
| 2005/0192578 A1 | 9/2005 | Horst |
| 2005/0197537 A1 | 9/2005 | Bonadio et al. |
| 2005/0209557 A1 | 9/2005 | Carroll et al. |
| 2005/0216000 A1 | 9/2005 | Colleran et al. |
| 2005/0216007 A1 | 9/2005 | Woll et al. |
| 2005/0216008 A1 | 9/2005 | Zwirnmann et al. |
| 2005/0228391 A1 | 10/2005 | Levy et al. |
| 2005/0234472 A1 | 10/2005 | Huebner |
| 2005/0240188 A1 | 10/2005 | Chow et al. |
| 2005/0240190 A1 | 10/2005 | Gall et al. |
| 2005/0240193 A1 | 10/2005 | Layne et al. |
| 2005/0245928 A1 | 11/2005 | Colleran et al. |
| 2005/0251142 A1 | 11/2005 | Hoffmann et al. |
| 2005/0261779 A1 | 11/2005 | Meyer |
| 2005/0267483 A1 | 12/2005 | Middleton |
| 2005/0273138 A1 | 12/2005 | To et al. |
| 2005/0277936 A1 | 12/2005 | Siravo et al. |
| 2005/0277978 A1 | 12/2005 | Greenhalgh |
| 2005/0283154 A1 | 12/2005 | Orbay et al. |
| 2005/0283159 A1 | 12/2005 | Amara |
| 2005/0288676 A1 | 12/2005 | Schnieders et al. |
| 2005/0288795 A1 | 12/2005 | Bagga et al. |
| 2006/0002980 A1 | 1/2006 | Ringeisen et al. |
| 2006/0004362 A1 | 1/2006 | Patterson et al. |
| 2006/0004462 A1 | 1/2006 | Gupta |
| 2006/0009771 A1 | 1/2006 | Orbay et al. |
| 2006/0015123 A1 | 1/2006 | Fencl et al. |
| 2006/0036240 A1 | 2/2006 | Colleran et al. |
| 2006/0036244 A1 | 2/2006 | Spitler et al. |
| 2006/0047787 A1 | 3/2006 | Agarwal et al. |
| 2006/0052788 A1 | 3/2006 | Thelen et al. |
| 2006/0058621 A1 | 3/2006 | Wehrli et al. |
| 2006/0058826 A1 | 3/2006 | Evans et al. |
| 2006/0064005 A1 | 3/2006 | Triano et al. |
| 2006/0064106 A1 | 3/2006 | Fernandez |
| 2006/0064164 A1 | 3/2006 | Thelen et al. |
| 2006/0064173 A1 | 3/2006 | Guederian |
| 2006/0069392 A1 | 3/2006 | Renzi Brivio et al. |
| 2006/0079894 A1 | 4/2006 | Colleran et al. |
| 2006/0079905 A1 | 4/2006 | Beyar et al. |
| 2006/0085009 A1 | 4/2006 | Truckai et al. |
| 2006/0089647 A1 | 4/2006 | Culbert et al. |
| 2006/0089648 A1 | 4/2006 | Masini |
| 2006/0100631 A1 | 5/2006 | Sullivan et al. |
| 2006/0100706 A1 | 5/2006 | Shadduck et al. |
| 2006/0106390 A1 | 5/2006 | Jensen et al. |
| 2006/0106394 A1 | 5/2006 | Colleran |
| 2006/0116773 A1 | 6/2006 | Cooney et al. |
| 2006/0122600 A1 | 6/2006 | Cole |

(56) References Cited

U.S. PATENT DOCUMENTS

| | | |
|---|---|---|
| 2006/0122610 A1 | 6/2006 | Culbert et al. |
| 2006/0142760 A1 | 6/2006 | McDonnel |
| 2006/0142858 A1 | 6/2006 | Colleran et al. |
| 2006/0149281 A1 | 7/2006 | Reiley et al. |
| 2006/0149379 A1 | 7/2006 | Kuslich et al. |
| 2006/0155289 A1 | 7/2006 | Windhager et al. |
| 2006/0173454 A1 | 8/2006 | Spitler et al. |
| 2006/0178737 A1 | 8/2006 | Furcht et al. |
| 2006/0184192 A1 | 8/2006 | Markworth et al. |
| 2006/0187748 A1 | 8/2006 | Kozyuk |
| 2006/0189994 A1 | 8/2006 | Wolford et al. |
| 2006/0195103 A1 | 8/2006 | Padget et al. |
| 2006/0200061 A1 | 9/2006 | Warkentine |
| 2006/0200140 A1 | 9/2006 | Lange |
| 2006/0200143 A1 | 9/2006 | Warburton |
| 2006/0217730 A1 | 9/2006 | Termanini |
| 2006/0229602 A1 | 10/2006 | Olsen |
| 2006/0235264 A1 | 10/2006 | Vassallo |
| 2006/0241629 A1 | 10/2006 | Krebs et al. |
| 2006/0241630 A1 | 10/2006 | Brunnett et al. |
| 2006/0241671 A1 | 10/2006 | Greenhalgh |
| 2006/0241776 A1 | 10/2006 | Brown et al. |
| 2006/0247637 A1 | 11/2006 | Colleran et al. |
| 2006/0264944 A1 | 11/2006 | Cole |
| 2006/0264945 A1 | 11/2006 | Edidin et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0271053 A1 | 11/2006 | Schlapfer et al. |
| 2006/0271061 A1 | 11/2006 | Beyar et al. |
| 2006/0271198 A1 | 11/2006 | Mcafee |
| 2006/0276797 A1 | 12/2006 | Botimer |
| 2007/0012491 A1 | 1/2007 | Vasta |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016211 A1 | 1/2007 | Botimer |
| 2007/0016283 A1 | 1/2007 | Greenhalgh et al. |
| 2007/0016300 A1 | 1/2007 | Kuslich |
| 2007/0027230 A1 | 2/2007 | Beyar et al. |
| 2007/0032567 A1 | 2/2007 | Beyar et al. |
| 2007/0043373 A1 | 2/2007 | Sala et al. |
| 2007/0049936 A1 | 3/2007 | Colleran et al. |
| 2007/0055379 A1 | 3/2007 | Stone et al. |
| 2007/0066480 A1 | 3/2007 | Moser et al. |
| 2007/0073342 A1 | 3/2007 | Stone et al. |
| 2007/0100285 A1 | 5/2007 | Griffin et al. |
| 2007/0112427 A1 | 5/2007 | Christy et al. |
| 2007/0118132 A1 | 5/2007 | Culbert et al. |
| 2007/0123876 A1 | 5/2007 | Czartoski et al. |
| 2007/0123877 A1 | 5/2007 | Goldin et al. |
| 2007/0123886 A1 | 5/2007 | Meyer et al. |
| 2007/0123936 A1 | 5/2007 | Goldin et al. |
| 2007/0123995 A1 | 5/2007 | Thelen et al. |
| 2007/0129746 A1 | 6/2007 | Mische |
| 2007/0142919 A1 | 6/2007 | Cooney et al. |
| 2007/0173745 A1 | 7/2007 | Diederich et al. |
| 2007/0173835 A1 | 7/2007 | Medoff et al. |
| 2007/0173838 A1 | 7/2007 | Li |
| 2007/0173839 A1 | 7/2007 | Running et al. |
| 2007/0173939 A1 | 7/2007 | Kim et al. |
| 2007/0179505 A1 | 8/2007 | Culbert |
| 2007/0198043 A1 | 8/2007 | Cox et al. |
| 2007/0213727 A1 | 9/2007 | Bottlang et al. |
| 2007/0219634 A1 | 9/2007 | Greenhalgh et al. |
| 2007/0225568 A1 | 9/2007 | Colleran |
| 2007/0225721 A1 | 9/2007 | Thelen et al. |
| 2007/0225726 A1 | 9/2007 | Dye et al. |
| 2007/0225810 A1 | 9/2007 | Colleran et al. |
| 2007/0233091 A1 | 10/2007 | Naifeh et al. |
| 2007/0233105 A1 | 10/2007 | Nelson et al. |
| 2007/0244485 A1 | 10/2007 | Greenhalgh et al. |
| 2007/0255287 A1 | 11/2007 | Rabiner |
| 2007/0270855 A1 | 11/2007 | Partin et al. |
| 2007/0276392 A1 | 11/2007 | Beyar et al. |
| 2007/0276405 A1 | 11/2007 | Huebner et al. |
| 2007/0282443 A1 | 12/2007 | Globerman et al. |
| 2007/0283849 A1 | 12/2007 | Edidin et al. |
| 2007/0288097 A1 | 12/2007 | Hurowitz |
| 2008/0009868 A1 | 1/2008 | Gotfried et al. |
| 2008/0009874 A1 | 1/2008 | Meridew et al. |
| 2008/0009875 A1 | 1/2008 | Sankaran et al. |
| 2008/0009877 A1 | 1/2008 | Sankaran et al. |
| 2008/0012317 A1 | 1/2008 | Johnson |
| 2008/0015601 A1 | 1/2008 | Castro et al. |
| 2008/0019970 A1 | 1/2008 | Gorman |
| 2008/0021474 A1 | 1/2008 | Bonutti et al. |
| 2008/0039854 A1 | 2/2008 | Rabiner |
| 2008/0041629 A1 | 2/2008 | Aronstam et al. |
| 2008/0053575 A1 | 3/2008 | Cheung et al. |
| 2008/0058804 A1 | 3/2008 | Lechot et al. |
| 2008/0065072 A1 | 3/2008 | Spitler et al. |
| 2008/0065073 A1 | 3/2008 | Perriello et al. |
| 2008/0065074 A1 | 3/2008 | Yeung et al. |
| 2008/0065140 A1 | 3/2008 | Bonutti |
| 2008/0071356 A1 | 3/2008 | Greenhalgh et al. |
| 2008/0077117 A1 | 3/2008 | Miller et al. |
| 2008/0077172 A1* | 3/2008 | Miller ............... A61B 17/3478 606/191 |
| 2008/0077174 A1 | 3/2008 | Mische |
| 2008/0086133 A1 | 4/2008 | Kuslich et al. |
| 2008/0097332 A1 | 4/2008 | Greenhalgh et al. |
| 2008/0103501 A1 | 5/2008 | Ralph et al. |
| 2008/0103519 A1 | 5/2008 | Bonutti |
| 2008/0108996 A1 | 5/2008 | Padget et al. |
| 2008/0114364 A1 | 5/2008 | Goldin et al. |
| 2008/0119886 A1 | 5/2008 | Greenhalgh et al. |
| 2008/0125784 A1 | 5/2008 | Rabiner et al. |
| 2008/0125805 A1 | 5/2008 | Mische |
| 2008/0132896 A1 | 6/2008 | Bowen et al. |
| 2008/0133017 A1 | 6/2008 | Beyar et al. |
| 2008/0140078 A1 | 6/2008 | Nelson et al. |
| 2008/0140130 A1 | 6/2008 | Chan et al. |
| 2008/0149115 A1 | 6/2008 | Hauck et al. |
| 2008/0161805 A1* | 7/2008 | Saravia ............... A61B 17/1725 606/60 |
| 2008/0161825 A1 | 7/2008 | Greenhalgh et al. |
| 2008/0167657 A1 | 7/2008 | Greenhalgh |
| 2008/0177261 A1 | 7/2008 | Mcminn |
| 2008/0183171 A1 | 7/2008 | Elghazaly et al. |
| 2008/0194868 A1 | 8/2008 | Kozyuk |
| 2008/0195104 A1 | 8/2008 | Sidebotham et al. |
| 2008/0195105 A1 | 8/2008 | Sidebotham et al. |
| 2008/0200915 A1 | 8/2008 | Globerman et al. |
| 2008/0200951 A1 | 8/2008 | Mcafee |
| 2008/0208202 A1 | 8/2008 | Williams |
| 2008/0208230 A1 | 8/2008 | Chin et al. |
| 2008/0208261 A1 | 8/2008 | Medoff |
| 2008/0208320 A1 | 8/2008 | Tan-Malecki et al. |
| 2008/0212405 A1 | 9/2008 | Globerman et al. |
| 2008/0228192 A1 | 9/2008 | Beyar et al. |
| 2008/0249436 A1 | 10/2008 | Darr |
| 2008/0255560 A1 | 10/2008 | Myers et al. |
| 2008/0262495 A1 | 10/2008 | Coati et al. |
| 2008/0269742 A1 | 10/2008 | Levy et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0275448 A1 | 11/2008 | Sackett et al. |
| 2008/0275449 A1 | 11/2008 | Sackett et al. |
| 2008/0287950 A1 | 11/2008 | Frigg et al. |
| 2008/0287951 A1 | 11/2008 | Stoneburner et al. |
| 2008/0288003 A1 | 11/2008 | McKinley |
| 2008/0294163 A1 | 11/2008 | Chou et al. |
| 2008/0294166 A1 | 11/2008 | Goldin et al. |
| 2008/0294167 A1 | 11/2008 | Schumacher et al. |
| 2008/0294169 A1 | 11/2008 | Scott et al. |
| 2008/0294205 A1 | 11/2008 | Greenhalgh et al. |
| 2008/0319444 A9 | 12/2008 | Osorio et al. |
| 2009/0005782 A1 | 1/2009 | Chirico et al. |

(56) References Cited

U.S. PATENT DOCUMENTS

| | | |
|---|---|---|
| 2009/0012522 A1 | 1/2009 | Lob |
| 2009/0012564 A1* | 1/2009 | Chirico .............. A61B 17/1671 606/246 |
| 2009/0018542 A1 | 1/2009 | Saravia et al. |
| 2009/0018656 A1 | 1/2009 | Clifford et al. |
| 2009/0018666 A1 | 1/2009 | Grundei et al. |
| 2009/0024204 A1 | 1/2009 | Greenhalgh et al. |
| 2009/0048620 A1 | 2/2009 | Weiss et al. |
| 2009/0048629 A1 | 2/2009 | Rabiner |
| 2009/0048672 A1 | 2/2009 | Essenmacher |
| 2009/0054900 A1 | 2/2009 | Rabiner et al. |
| 2009/0076517 A1 | 3/2009 | Reiley et al. |
| 2009/0088752 A1 | 4/2009 | Metzinger et al. |
| 2009/0104586 A1 | 4/2009 | Cardoso et al. |
| 2009/0112196 A1 | 4/2009 | Rabiner et al. |
| 2009/0112330 A1 | 4/2009 | Grundei |
| 2009/0125028 A1 | 5/2009 | Teisen et al. |
| 2009/0131952 A1 | 5/2009 | Schumacher et al. |
| 2009/0131992 A1 | 5/2009 | Greenhalgh et al. |
| 2009/0138015 A1 | 5/2009 | Conner et al. |
| 2009/0143781 A1 | 6/2009 | Mische |
| 2009/0143827 A1 | 6/2009 | Levy et al. |
| 2009/0149890 A1 | 6/2009 | Martin |
| 2009/0149956 A1 | 6/2009 | Greenhalgh et al. |
| 2009/0157080 A1 | 6/2009 | Warburton |
| 2009/0163918 A1 | 6/2009 | Levy et al. |
| 2009/0177206 A1 | 7/2009 | Lozier et al. |
| 2009/0177239 A1 | 7/2009 | Castro |
| 2009/0216232 A1 | 8/2009 | Buford et al. |
| 2009/0228007 A1 | 9/2009 | Justin et al. |
| 2009/0228008 A1 | 9/2009 | Justin et al. |
| 2009/0275995 A1 | 11/2009 | Truckai et al. |
| 2009/0281628 A1 | 11/2009 | Oglaza |
| 2009/0292323 A1 | 11/2009 | Chirico et al. |
| 2009/0318981 A1 | 12/2009 | Kang |
| 2010/0023010 A1 | 1/2010 | Nelson et al. |
| 2010/0087821 A1 | 4/2010 | Trip et al. |
| 2010/0094292 A1 | 4/2010 | Parrott |
| 2010/0094347 A1 | 4/2010 | Nelson et al. |
| 2010/0100184 A1 | 4/2010 | Krueger et al. |
| 2010/0114181 A1 | 5/2010 | Lob |
| 2010/0131019 A1 | 5/2010 | Lob |
| 2010/0137862 A1 | 6/2010 | Diao et al. |
| 2010/0145397 A1 | 6/2010 | Overes et al. |
| 2010/0161061 A1 | 6/2010 | Hunt |
| 2010/0222884 A1 | 9/2010 | Greenhalgh |
| 2010/0241120 A1 | 9/2010 | Bledsoe et al. |
| 2010/0241123 A1 | 9/2010 | Middleton et al. |
| 2010/0241176 A1 | 9/2010 | Lob |
| 2010/0249785 A1* | 9/2010 | Betts .................. A61B 17/1617 606/79 |
| 2010/0256638 A1 | 10/2010 | Tyber et al. |
| 2010/0286481 A1 | 11/2010 | Sharp et al. |
| 2010/0286692 A1 | 11/2010 | Greenhalgh et al. |
| 2011/0077650 A1 | 3/2011 | Braun et al. |
| 2011/0087227 A1 | 4/2011 | Mazur et al. |
| 2011/0137313 A1 | 6/2011 | Jensen et al. |
| 2011/0144645 A1 | 6/2011 | Saravia et al. |
| 2011/0178520 A1 | 7/2011 | Taylor et al. |
| 2011/0190832 A1* | 8/2011 | Taylor .................. A61B 17/1617 606/86 R |
| 2011/0218585 A1 | 9/2011 | Krinke et al. |
| 2011/0282346 A1 | 11/2011 | Pham et al. |
| 2011/0295255 A1 | 12/2011 | Roberts et al. |
| 2011/0306975 A1 | 12/2011 | Kaikkonen et al. |
| 2011/0307021 A1 | 12/2011 | Anderson et al. |
| 2011/0307072 A1 | 12/2011 | Anderson et al. |
| 2011/0313537 A1 | 12/2011 | Anderson et al. |
| 2012/0029633 A1 | 2/2012 | Anderson et al. |
| 2012/0065638 A1 | 3/2012 | Moore |
| 2012/0152872 A1 | 6/2012 | Didehvar |
| 2012/0179161 A1 | 7/2012 | Rains et al. |
| 2012/0209273 A1 | 8/2012 | Zaretzka et al. |
| 2012/0232533 A1 | 9/2012 | Veldman et al. |
| 2012/0239038 A1 | 9/2012 | Saravia et al. |
| 2012/0253410 A1 | 10/2012 | Taylor et al. |
| 2013/0006245 A1 | 1/2013 | Stoneburner et al. |
| 2013/0012942 A1 | 1/2013 | Nelson et al. |
| 2013/0018376 A1* | 1/2013 | Yoon .................. A61B 17/1617 606/79 |
| 2013/0116693 A1 | 5/2013 | Nelson et al. |
| 2013/0123785 A1 | 5/2013 | Fonte |
| 2013/0165935 A1 | 6/2013 | Griffiths et al. |
| 2013/0204250 A1 | 8/2013 | McDevitt et al. |
| 2013/0231665 A1 | 9/2013 | Saravia et al. |
| 2013/0267953 A1 | 10/2013 | Brenzel et al. |
| 2013/0325007 A1 | 12/2013 | Beyar et al. |
| 2014/0031823 A1 | 1/2014 | Mazur et al. |
| 2014/0058390 A1 | 2/2014 | Taylor et al. |
| 2014/0074093 A9 | 3/2014 | Nelson et al. |
| 2014/0128870 A1 | 5/2014 | Brenzel et al. |
| 2015/0012096 A1 | 1/2015 | Krinke et al. |
| 2015/0141996 A1 | 5/2015 | Taylor et al. |
| 2015/0164514 A1 | 6/2015 | Wlodarski et al. |
| 2015/0320459 A1 | 7/2015 | Bronzel et al. |
| 2016/0066926 A1 | 3/2016 | Taylor et al. |
| 2016/0175012 A1 | 6/2016 | Taylor et al. |

FOREIGN PATENT DOCUMENTS

| | | |
|---|---|---|
| CA | 2609175 A1 | 12/2005 |
| CA | 2608693 A1 | 11/2006 |
| CA | 2537171 C | 8/2007 |
| CA | 2669737 A1 | 5/2008 |
| CA | 2670263 A1 | 5/2008 |
| CA | 2670438 A1 | 5/2008 |
| CA | 2678911 A1 | 9/2008 |
| CA | 2685046 A1 | 11/2008 |
| CA | 2727453 A1 | 12/2009 |
| CA | 2738478 A1 | 4/2010 |
| CN | 2326199 | 6/1999 |
| CN | 1530079 | 9/2004 |
| CN | 1533260 A | 9/2004 |
| CN | 2699849 Y | 5/2005 |
| CN | 1909848 A | 2/2007 |
| CN | 100379388 | 4/2008 |
| CN | 101208053 A | 6/2008 |
| CN | 101404946 | 4/2009 |
| CN | 101636119 A | 1/2010 |
| CN | 101795629 | 8/2010 |
| DE | 923085 | 7/1949 |
| DE | 3146065 A1 | 5/1983 |
| DE | 3234875 A1 | 3/1984 |
| DE | 198800197 U1 | 8/1988 |
| DE | 3922044 A1 | 2/1991 |
| DE | 4217236 | 11/1993 |
| DE | 202006017194 U1 | 2/2007 |
| DE | 102006016213 | 10/2007 |
| EP | 0145166 A2 | 6/1985 |
| EP | 145166 A2 | 6/1985 |
| EP | 145166 A3 | 8/1986 |
| EP | 253526 A1 | 1/1988 |
| EP | 263292 A1 | 4/1988 |
| EP | 275871 A1 | 7/1988 |
| EP | 355035 A2 | 2/1990 |
| EP | 381462 A2 | 8/1990 |
| EP | 396519 A1 | 11/1990 |
| EP | 401650 A1 | 12/1990 |
| EP | 409769 A1 | 1/1991 |
| EP | 420542 A1 | 4/1991 |
| EP | 440371 A1 | 8/1991 |
| EP | 442137 A1 | 8/1991 |
| EP | 475077 A2 | 3/1992 |
| EP | 487669 A1 | 6/1992 |
| EP | 491211 A1 | 6/1992 |
| EP | 508710 A1 | 10/1992 |
| EP | 525352 A1 | 2/1993 |
| EP | 611560 A1 | 8/1994 |
| EP | 745352 A2 | 12/1996 |
| EP | 546162 B1 | 9/1997 |
| EP | 807419 A2 | 11/1997 |
| EP | 819413 A2 | 1/1998 |
| EP | 931513 A2 | 7/1999 |
| EP | 0941037 | 9/1999 |

(56) References Cited

FOREIGN PATENT DOCUMENTS

| | | |
|---|---|---|
| EP | 0941037 B1 | 9/1999 |
| EP | 1099412 A2 | 5/2001 |
| EP | 1132051 A2 | 9/2001 |
| EP | 674495 B1 | 11/2001 |
| EP | 1155661 A1 | 11/2001 |
| EP | 1203569 A1 | 5/2002 |
| EP | 900065 B1 | 6/2002 |
| EP | 1277442 A2 | 1/2003 |
| EP | 1300122 A2 | 4/2003 |
| EP | 1348384 A2 | 10/2003 |
| EP | 1354562 | 10/2003 |
| EP | 1372496 A1 | 1/2004 |
| EP | 1391186 A1 | 2/2004 |
| EP | 1098600 B1 | 3/2004 |
| EP | 1277442 A3 | 3/2004 |
| EP | 1396231 A1 | 3/2004 |
| EP | 1410765 A2 | 4/2004 |
| EP | 1442718 A1 | 8/2004 |
| EP | 1442729 A1 | 8/2004 |
| EP | 1454592 A2 | 9/2004 |
| EP | 1459686 A2 | 9/2004 |
| EP | 1484077 A2 | 12/2004 |
| EP | 1079752 B1 | 1/2005 |
| EP | 1484077 A3 | 1/2005 |
| EP | 1495729 A1 | 1/2005 |
| EP | 15355791 A2 | 1/2005 |
| EP | 1148825 B1 | 3/2005 |
| EP | 1148850 B1 | 4/2005 |
| EP | 1522268 A1 | 4/2005 |
| EP | 1227765 B1 | 5/2005 |
| EP | 1535579 A2 | 6/2005 |
| EP | 1582159 A1 | 10/2005 |
| EP | 1582160 A1 | 10/2005 |
| EP | 1582161 A1 | 10/2005 |
| EP | 1582162 A1 | 10/2005 |
| EP | 1582163 A1 | 10/2005 |
| EP | 1582164 A1 | 10/2005 |
| EP | 1634548 A2 | 3/2006 |
| EP | 1639953 A1 | 3/2006 |
| EP | 1669035 A1 | 6/2006 |
| EP | 1073371 B1 | 8/2006 |
| EP | 1454592 A3 | 8/2006 |
| EP | 1700572 A1 | 9/2006 |
| EP | 1702572 A2 | 9/2006 |
| EP | 1714618 A2 | 10/2006 |
| EP | 787593 A1 | 5/2007 |
| EP | 1808143 A1 | 7/2007 |
| EP | 1815813 A2 | 8/2007 |
| EP | 1820462 A1 | 8/2007 |
| EP | 1011464 B1 | 1/2008 |
| EP | 1905367 A1 | 4/2008 |
| EP | 1905392 A1 | 4/2008 |
| EP | 1915959 A2 | 4/2008 |
| EP | 1920721 A2 | 5/2008 |
| EP | 1923019 A1 | 5/2008 |
| EP | 1277442 B1 | 7/2008 |
| EP | 1972308 A1 | 9/2008 |
| EP | 1987785 A2 | 11/2008 |
| EP | 2014261 A1 | 1/2009 |
| EP | 2025292 A1 | 2/2009 |
| EP | 1459689 B1 | 4/2009 |
| EP | 1484077 B1 | 6/2009 |
| EP | 1073371 B2 | 7/2009 |
| EP | 1459689 B3 | 11/2009 |
| EP | 2770928 A1 | 9/2013 |
| ES | 2251888 | 5/2006 |
| FR | 2653006 A1 | 4/1991 |
| FR | 2686788 | 8/1993 |
| FR | 2781360 | 1/2000 |
| FR | 2861576 | 5/2005 |
| GB | 2173565 A | 10/1986 |
| GB | 2268068 A | 1/1994 |
| GB | 2274993 | 8/1994 |
| JP | 1310664 A | 12/1989 |
| JP | 2000287983 | 10/2000 |
| JP | 2001506524 | 5/2001 |
| JP | 2001509040 | 7/2001 |
| JP | 200481681 | 3/2004 |
| JP | 2007125386 | 5/2007 |
| JP | 2008500140 A | 1/2008 |
| JP | 2008540037 A | 11/2008 |
| JP | 2009160399 | 7/2009 |
| JP | 2010510040 A | 4/2010 |
| JP | 2010510041 A | 4/2010 |
| JP | 2010510042 A | 4/2010 |
| JP | 2010522046 A | 7/2010 |
| JP | 2010524642 A | 7/2010 |
| JP | 2011523889 A | 8/2011 |
| JP | 2012504027 A | 2/2012 |
| JP | 2012518511 | 8/2012 |
| RU | 2004104359 A | 2/2005 |
| WO | WO03068090 A1 | 8/1921 |
| WO | WO8904150 A1 | 8/1989 |
| WO | WO8907056 A1 | 8/1989 |
| WO | WO9003764 A1 | 4/1990 |
| WO | WO9011726 A1 | 10/1990 |
| WO | WO1991002493 A1 | 3/1991 |
| WO | WO9106260 A1 | 5/1991 |
| WO | WO9106265 A1 | 5/1991 |
| WO | WO9111962 A1 | 8/1991 |
| WO | WO1991011962 A1 | 8/1991 |
| WO | WO9119461 A1 | 12/1991 |
| WO | WO9424938 A1 | 11/1994 |
| WO | WO9427507 A1 | 12/1994 |
| WO | WO9428824 A2 | 12/1994 |
| WO | WO9514433 A1 | 6/1995 |
| WO | WO1995014433 A1 | 6/1995 |
| WO | WO9520362 A1 | 8/1995 |
| WO | WO9531159 A1 | 11/1995 |
| WO | WO9602202 A1 | 2/1996 |
| WO | WO9602203 A1 | 2/1996 |
| WO | WO9605783 A1 | 2/1996 |
| WO | WO9606041 A1 | 2/1996 |
| WO | WO9607161 A1 | 3/1996 |
| WO | WO9616607 A1 | 6/1996 |
| WO | WO9617557 A1 | 6/1996 |
| WO | WO9618354 A2 | 6/1996 |
| WO | WO1996018354 A2 | 6/1996 |
| WO | WO9625118 A1 | 8/1996 |
| WO | WO1996018354 A3 | 8/1996 |
| WO | WO9640476 A1 | 12/1996 |
| WO | WO9703611 A1 | 2/1997 |
| WO | WO1997003611 A1 | 2/1997 |
| WO | WO1997018775 A1 | 5/1997 |
| WO | WO9742602 A1 | 11/1997 |
| WO | WO9742912 A1 | 11/1997 |
| WO | WO9747251 A1 | 12/1997 |
| WO | WO9801077 A1 | 1/1998 |
| WO | WO9805261 A2 | 2/1998 |
| WO | WO1998007392 A1 | 2/1998 |
| WO | WO1998019616 A1 | 5/1998 |
| WO | WO9824380 A1 | 6/1998 |
| WO | WO9826725 A1 | 6/1998 |
| WO | WO9838918 A1 | 9/1998 |
| WO | WO9846169 A1 | 10/1998 |
| WO | WO9856301 A1 | 12/1998 |
| WO | WO9922661 A1 | 5/1999 |
| WO | WO9922662 A1 | 5/1999 |
| WO | WO9937219 A1 | 7/1999 |
| WO | WO1999047055 A1 | 9/1999 |
| WO | WO1999051149 A1 | 10/1999 |
| WO | WO1999053843 A1 | 10/1999 |
| WO | WO9955248 A1 | 11/1999 |
| WO | WO9962416 A1 | 12/1999 |
| WO | WO0009024 A1 | 2/2000 |
| WO | WO2000006037 A1 | 2/2000 |
| WO | WO0012036 A1 | 3/2000 |
| WO | WO2000012036 A1 | 3/2000 |
| WO | WO0021455 A1 | 4/2000 |
| WO | WO0025681 A1 | 5/2000 |
| WO | WO0028906 A1 | 5/2000 |
| WO | WO0030551 A1 | 6/2000 |
| WO | WO0030569 A1 | 6/2000 |
| WO | WO0038586 A1 | 7/2000 |

(56) References Cited

FOREIGN PATENT DOCUMENTS

| | | |
|---|---|---|
| WO | WO0042954 A2 | 7/2000 |
| WO | WO0044319 A1 | 8/2000 |
| WO | WO0044321 A2 | 8/2000 |
| WO | WO0044946 A1 | 8/2000 |
| WO | WO0045712 A1 | 8/2000 |
| WO | WO0045714 A1 | 8/2000 |
| WO | WO0045715 A1 | 8/2000 |
| WO | WO0045722 A1 | 8/2000 |
| WO | WO0047119 A1 | 8/2000 |
| WO | WO0048534 A1 | 8/2000 |
| WO | WO0071038 A1 | 11/2000 |
| WO | WO0076414 A1 | 12/2000 |
| WO | WO0108571 A1 | 2/2001 |
| WO | WO0128443 A1 | 4/2001 |
| WO | WO0134045 A1 | 5/2001 |
| WO | WO0149193 A1 | 7/2001 |
| WO | WO0154598 A1 | 8/2001 |
| WO | WO0160268 A1 | 8/2001 |
| WO | WO2001060268 A1 | 8/2001 |
| WO | WO0176493 A1 | 10/2001 |
| WO | WO0176514 A2 | 10/2001 |
| WO | WO0178015 A2 | 10/2001 |
| WO | WO0180751 A1 | 11/2001 |
| WO | WO0185042 A1 | 11/2001 |
| WO | WO0213700 A2 | 2/2002 |
| WO | WO0213716 A1 | 2/2002 |
| WO | WO0217794 A1 | 3/2002 |
| WO | WO0224088 A2 | 3/2002 |
| WO | WO2002017794 A1 | 3/2002 |
| WO | WO0234107 A2 | 5/2002 |
| WO | WO0234148 A2 | 5/2002 |
| WO | WO0237935 A2 | 5/2002 |
| WO | WO0245606 A1 | 6/2002 |
| WO | WO0249517 A1 | 6/2002 |
| WO | WO02058575 A1 | 8/2002 |
| WO | WO2002067824 A2 | 9/2002 |
| WO | WO2002078555 A1 | 10/2002 |
| WO | WO02089683 A1 | 11/2002 |
| WO | WO2002096306 A1 | 12/2002 |
| WO | WO03007830 A1 | 1/2003 |
| WO | WO03013336 A2 | 2/2003 |
| WO | WO2002017794 A8 | 3/2003 |
| WO | WO03030760 A1 | 4/2003 |
| WO | WO2003043488 A2 | 5/2003 |
| WO | WO03047440 A2 | 6/2003 |
| WO | WO2003045257 A2 | 6/2003 |
| WO | WO2002017794 A9 | 9/2003 |
| WO | WO2004008949 A2 | 1/2004 |
| WO | WO0407817 A2 | 3/2004 |
| WO | WO2004021904 | 3/2004 |
| WO | WO2004030549 A1 | 4/2004 |
| WO | WO2004039271 | 5/2004 |
| WO | WO2004064603 A2 | 8/2004 |
| WO | WO2004078220 A2 | 9/2004 |
| WO | WO2004078221 A2 | 9/2004 |
| WO | WO2004086934 A2 | 10/2004 |
| WO | WO2004092431 A1 | 10/2004 |
| WO | WO200409453 A2 | 11/2004 |
| WO | WO2004093633 A2 | 11/2004 |
| WO | WO04103209 A2 | 12/2004 |
| WO | WO04110292 A2 | 12/2004 |
| WO | WO04110300 A2 | 12/2004 |
| WO | WO2004112661 A1 | 12/2004 |
| WO | WO0500159 A2 | 1/2005 |
| WO | WO2005020830 A1 | 3/2005 |
| WO | WO2005020833 A2 | 3/2005 |
| WO | WO2005023085 A2 | 3/2005 |
| WO | WO05032326 A2 | 4/2005 |
| WO | WO05032340 A2 | 4/2005 |
| WO | WO05039651 A2 | 5/2005 |
| WO | WO200504422 A1 | 5/2005 |
| WO | WO2005041799 A1 | 5/2005 |
| WO | WO2005051971 A1 | 6/2005 |
| WO | WO2005055874 A2 | 6/2005 |
| WO | WO2005020833 A3 | 7/2005 |
| WO | WO2005070314 A1 | 8/2005 |
| WO | WO2005092223 A2 | 10/2005 |
| WO | WO2005094693 A1 | 10/2005 |
| WO | WO2005094705 A2 | 10/2005 |
| WO | WO2005094706 A1 | 10/2005 |
| WO | WO2005096975 A2 | 10/2005 |
| WO | WO2005102196 A1 | 11/2005 |
| WO | WO2005107415 A2 | 11/2005 |
| WO | WO2005112804 A1 | 12/2005 |
| WO | WO2005112804 A1 | 12/2005 |
| WO | WO2005122931 A1 | 12/2005 |
| WO | WO2005122932 A2 | 12/2005 |
| WO | WO2005123171 A2 | 12/2005 |
| WO | WO2006011152 A2 | 2/2006 |
| WO | WO2006020530 A2 | 2/2006 |
| WO | WO2005112804 A9 | 3/2006 |
| WO | WO2006023793 A2 | 3/2006 |
| WO | WO2006026323 A2 | 3/2006 |
| WO | WO2006026323 A2 | 3/2006 |
| WO | WO2006026323 A9 | 4/2006 |
| WO | WO2006041460 A1 | 4/2006 |
| WO | WO2006041460 A1 | 4/2006 |
| WO | WO2006042188 A2 | 4/2006 |
| WO | WO2006042189 A2 | 4/2006 |
| WO | WO2006042334 A2 | 4/2006 |
| WO | WO2006034396 A3 | 5/2006 |
| WO | WO2006051547 A2 | 5/2006 |
| WO | WO2006055448 A1 | 5/2006 |
| WO | WO2006063083 A1 | 6/2006 |
| WO | WO2006066228 A2 | 6/2006 |
| WO | WO2006068682 A1 | 6/2006 |
| WO | WO2010065855 A1 | 6/2006 |
| WO | WO2006089929 A1 | 8/2006 |
| WO | WO2006090379 A2 | 8/2006 |
| WO | WO2006034436 A3 | 10/2006 |
| WO | WO2006108067 A2 | 10/2006 |
| WO | WO2006113800 A2 | 10/2006 |
| WO | WO2006116760 A2 | 11/2006 |
| WO | WO2006116761 A2 | 11/2006 |
| WO | WO2006124764 A1 | 11/2006 |
| WO | WO2006124764 A1 | 11/2006 |
| WO | WO2006124937 A2 | 11/2006 |
| WO | WO2006127904 A1 | 11/2006 |
| WO | WO2006127904 A1 | 11/2006 |
| WO | WO200701994 A2 | 1/2007 |
| WO | WO2007002933 A2 | 1/2007 |
| WO | WO2007008177 A1 | 1/2007 |
| WO | WO2007009107 A2 | 1/2007 |
| WO | WO2007009123 A2 | 1/2007 |
| WO | WO2007012046 A2 | 1/2007 |
| WO | WO2007025236 A2 | 3/2007 |
| WO | WO2007040949 A2 | 4/2007 |
| WO | WO2007041665 A2 | 4/2007 |
| WO | WO2006124937 A3 | 5/2007 |
| WO | WO2007053960 A1 | 5/2007 |
| WO | WO2007058943 A2 | 5/2007 |
| WO | WO2007059243 A1 | 5/2007 |
| WO | WO2007059243 A1 | 5/2007 |
| WO | WO2007059246 A1 | 5/2007 |
| WO | WO2007059259 A1 | 5/2007 |
| WO | WO2007059259 A1 | 5/2007 |
| WO | WO2007065137 A2 | 6/2007 |
| WO | WO2007069251 A2 | 6/2007 |
| WO | WO2007073488 A2 | 6/2007 |
| WO | WO2007076308 A2 | 7/2007 |
| WO | WO2007076374 A2 | 7/2007 |
| WO | WO2007076376 A2 | 7/2007 |
| WO | WO2007076377 A2 | 7/2007 |
| WO | WO2007078692 A2 | 7/2007 |
| WO | WO2007079237 A2 | 7/2007 |
| WO | WO2007082151 A2 | 7/2007 |
| WO | WO2007084239 A2 | 7/2007 |
| WO | WO2007092813 A2 | 8/2007 |
| WO | WO2007092813 A2 | 8/2007 |
| WO | WO2007092841 A2 | 8/2007 |
| WO | WO2007092841 A2 | 8/2007 |
| WO | WO2007036815 A2 | 9/2007 |
| WO | WO2007114982 A1 | 10/2007 |
| WO | WO2007115108 A1 | 10/2007 |

(56) References Cited

FOREIGN PATENT DOCUMENTS

| | | |
|---|---|---|
| WO | WO2007117571 A2 | 10/2007 |
| WO | WO2007120539 A2 | 10/2007 |
| WO | WO2007092841 A3 | 11/2007 |
| WO | WO2007124130 A2 | 11/2007 |
| WO | WO2007127255 A2 | 11/2007 |
| WO | WO2007127260 A2 | 11/2007 |
| WO | WO2007131002 A2 | 11/2007 |
| WO | WO2007134134 A2 | 11/2007 |
| WO | WO2007079237 A3 | 12/2007 |
| WO | WO2007145824 A2 | 12/2007 |
| WO | WO2008004229 A2 | 1/2008 |
| WO | WO2008006117 A2 | 1/2008 |
| WO | WO2008016910 A2 | 2/2008 |
| WO | WO2008019397 A2 | 2/2008 |
| WO | WO2008035849 A1 | 3/2008 |
| WO | WO2008037454 A1 | 4/2008 |
| WO | WO2008043254 A1 | 4/2008 |
| WO | WO2008058960 A2 | 5/2008 |
| WO | WO2008059027 A2 | 5/2008 |
| WO | WO2008060277 A2 | 5/2008 |
| WO | WO2008060277 A2 | 5/2008 |
| WO | WO2008063265 A1 | 5/2008 |
| WO | WO2008064346 A2 | 5/2008 |
| WO | WO 2008064347 A2 | 5/2008 |
| WO | WO2008064347 A2 | 5/2008 |
| WO | WO2008064350 A2 | 5/2008 |
| WO | WO2008076330 A1 | 6/2008 |
| WO | WO2008076330 A1 | 6/2008 |
| WO | WO2008076357 A1 | 6/2008 |
| WO | WO2008094407 A1 | 8/2008 |
| WO | WO2007011353 A3 | 9/2008 |
| WO | WO2007092813 A3 | 9/2008 |
| WO | WO2008109566 A1 | 9/2008 |
| WO | WO2008112308 A1 | 9/2008 |
| WO | WO2008116170 A2 | 9/2008 |
| WO | WO2008116175 A2 | 9/2008 |
| WO | WO2008118945 A1 | 10/2008 |
| WO | WO2008121608 A2 | 10/2008 |
| WO | WO2008132728 A1 | 11/2008 |
| WO | WO2008134287 A2 | 11/2008 |
| WO | WO2008134758 A1 | 11/2008 |
| WO | WO2008139456 A2 | 11/2008 |
| WO | WO2008144709 A2 | 11/2008 |
| WO | WO2008144709 A2 | 11/2008 |
| WO | WO2007078692 A3 | 12/2008 |
| WO | WO2008121608 A3 | 1/2009 |
| WO | WO2008134287 A3 | 1/2009 |
| WO | WO2009006622 A2 | 1/2009 |
| WO | WO2009007331 A2 | 1/2009 |
| WO | WO2009009772 A1 | 1/2009 |
| WO | WO2009010412 A1 | 1/2009 |
| WO | WO2009012347 A1 | 1/2009 |
| WO | WO2009026070 A1 | 2/2009 |
| WO | WO2009027325 A1 | 3/2009 |
| WO | WO2009039430 A1 | 3/2009 |
| WO | WO2006026323 A3 | 4/2009 |
| WO | WO2006026397 A3 | 4/2009 |
| WO | WO2009045751 A1 | 4/2009 |
| WO | WO2009059227 A1 | 5/2009 |
| WO | WO2009067568 | 5/2009 |
| WO | WO2009072125 A1 | 6/2009 |
| WO | WO2009076086 A1 | 6/2009 |
| WO | WO2008144709 A3 | 7/2009 |
| WO | WO2009088376 A1 | 7/2009 |
| WO | WO2009094478 A1 | 7/2009 |
| WO | WO2008060277 A3 | 9/2009 |
| WO | WO2008112912 A3 | 9/2009 |
| WO | WO2009132333 A2 | 10/2009 |
| WO | WO2009143374 A2 | 11/2009 |
| WO | WO2009143496 A1 | 11/2009 |
| WO | WO2008112875 A3 | 12/2009 |
| WO | WO2009146457 A1 | 12/2009 |
| WO | WO2009152270 A1 | 12/2009 |
| WO | WO2009152272 A1 | 12/2009 |
| WO | WO2009152273 A1 | 12/2009 |
| WO | WO2009132333 A3 | 1/2010 |
| WO | WO2010/017990 | 2/2010 |
| WO | WO2008139456 A3 | 2/2010 |
| WO | WO2010037038 A2 | 4/2010 |
| WO | WO2010056895 A1 | 5/2010 |
| WO | WO2010062379 A1 | 6/2010 |
| WO | WO2010091242 A1 | 8/2010 |
| WO | WO2010035156 A1 | 11/2010 |
| WO | WO2013063145 A1 | 5/2013 |

OTHER PUBLICATIONS

US 7,201,752, 04/2007, Huebner et al. (withdrawn)
App No. PCT/US 09/30971 International Search Report, dated Mar. 6, 2009.
App No. PCT/US 09/30971 Written Opinion of the International Searching Authority, dated Mar. 6, 2009.
App No. PCT/US2011/21074 International Search Report, dated May 23, 2011.
App No. PCT/US2011/21074 Written Opinion of the International Searching Authority, dated May 23, 2011.
App No. PCT/US2011/021735 International Search Report, dated May 25, 2011.
App No. PCT/US2011/021735 Written Opinion of the International Searching Authority, dated May 25, 2011.
App No. PCT/US2011/027597 International Search Report, dated Jul. 6, 2011.
App No. PCT/US2011/027597 Written Opinion of the International Searching Authority, dated Jul. 6, 2011.
App No. PCT/US2011/027602 International Search Report, dated Jul. 5, 2011.
App No. PCT/US2011/027602 Written Opinion of the International Searching Authority, dated Jul. 5, 2011.
Putnam, Matthew D., et al., "Distal Radial Metaphyseal Forces in an Extrinsic Grip Model: Implications for Post fracture Rehabilitation," American Society for Surgery of the Hand, 25A: 469-475, May 2000.
Higgins, Thomas F., et al., "A Biomechanical Analysis of Fixation of Intra-Articular Distal Radial Fractures with Calcium-Phosphate Bone Cement," The Journal of Bone and Joint Surgery, 84:1579-1586, Needham, Massachusetts, Sep. 2002.
Stoeckel et al., "Self-Expanding Nitinol Stents—Material and Design Considerations," Nitinol Devices & Components, Fremont, California, 2003.
Rozenthal, Tamara D., et al., "Functional Outcome and Complications After Volar Plating for Dorsally Displaced, Unstable Fractures of the Distal Radius," The Journal of Hand Surgery, 31A: 359-365, Mar. 2006.
Keast-Butler, Oliver, et al., "Biology Versus Mechanics in the Treatment of Distal Radial Fractures," The Journal of Orthopedic Trauma, 22: S91-S95, Philadelphia, Pennsylvania, Sep. 2008.
Mudgal, Chaitanya S., et al., "Plate Fixation of Osteoporotic Fractures of the Distal Radius," The Journal of Orthopedic Trauma, 22: S106-S115, 2008, Philadelphia, Pennsylvania, Sep. 2008.
Bogoch, Earl R., et al., "The Osteoporosis Needs of Patients with Wrist Fractures," The Journal of Orthopedic Trauma, vol. 22, No. 8, Supplement, Philadelphia, Pennsylvania, Sep. 2008.
Arora, Rohit, et al., "A Representative Case of Osteoporotic Distal Radius Fracture," The Journal of Orthopedic Trauma, vol. 22, No. 8, Supplement, Philadelphia, Pennsylvania, Sep. 2008.
Firoozabadi, Reza, et al., "Qualitative and Quantitative Assessment of Bone Fragility and Fracture Healing Using Conventional Radiography and Advanced Imaging Technologies—Focus on Wrist Fracture," The Journal of Orthopedic Trauma, vol. 22, No. 8, Supplement, Philadulpllia, Pennsvivania, Sep. 2008.
Goldhan, Jorg, et al., "What Counts: Outcome Assessment After Distal Radius Fractures in Aged Patients," The Journal of Orthopedic Trauma, vol. 22, No. 8, Supplement, Philadelphia, Pennsylvania, Sep. 2008.
Hoang-Kim, Amy, et al, "Wrist Fractures in Osteoporotic Patients," The Journal of Orthopedic Trauma, vol. 22, No. 8, Supplement, Philadelphia, Pennsylvania, Sep. 2008.

(56) References Cited

OTHER PUBLICATIONS

Kettler, Mark, et al., "Do We Need to Include Osteoporosis in Today's Classification of Distal Radius Fractures?" The Journal of Orthopedic Trauma, vol. 22, No. 8, Supplement, Philadelphia, Pennsylvania, Sep. 2008.
Downing, Martin R., et al., "Assessment of Inducible Fracture Micromotion in Distal Radial Fractures Using Radiostereometry," The Journal of Orthopedic Trauma, vol. 22, No. 8, Supplement, Philadelphia, Pennsylvania, Sep. 2008.
Suhm, Norbert, et al., "Injectable Bone Cement Augmentation for the Treatment of Distal Radius Fractures: A Review," The Journal of Orthopedic Trauma, vol. 22, No. 8, Supplement, Philadelphia, Pennsylvania, Sep. 2008.
Van Lenthe, G. Harry, et al., "Quantification of Bone Structural Parameters and Mechanical Competence at the Distal Radius," The Journal of Orthopedic Trauma, vol. 22, No. 8, Supplement, Philadelphia, Pennsylvania, Sep. 2008.
Parkinson, Ian H., et al., "Whole Bone Geometry and Bone Quality in Distal Forearm Fracture," The Journal of Orthopedic Trauma, vol. 22, No. 8, Supplement, Philadelphia, Pennsylvania, Sep. 2008.
"Medtronic—Abdominal Stent Graft System, Instructions for Use," Medtronic, Inc., Minneapolis-Minnesota, 2008.
Jupiter, Jesse B., et al., "Operative Management of Distal Radial Fractures with 2.4-Millimeter Locking Plates. A Multicenter Prospective Case Series," The Journal of Bone and Joint Surgery, 91: 55-65, doi:10.2106-JBJS.G.01498, Needham, Massachusetts, Jan. 1, 2009.
App No. PCT/US2012/028145 International Search Report, dated Sep. 13, 2012.
App No. PCT/US2012/028145 Written Opinion of the International Searching Authority, dated Sep. 13, 2012.
Ilyas, Asif M., "Intramedullary Fixation of Distal Radius Fractures," Elsevier, Inc. on behalf of the American Society for Surgery of the Hand, New York, New York, Feb. 2009.
Figl, Markus, et al., "Volar Fixed-Angle Plate Osteosynthesis of Unstable Distal Radius Fractures: 12 Months Results," Springar, New York, New York, Feb. 19, 2009.
Photograph, OrthopaedicLIST, 2010, Wilmington, North Carolina.
Photograph, OrthopaedicLIST, 2010, Wiimington, North Carolina.
Barnes, C. Lowry, et al., "Advanced Core Decompression System," Wright, 2008, Arlington, Tennessee.
"OptiMesh 1500E—Percutaneous Interbody Fusion Surgical Technique," Spineology Inc., Feb. 2010, Saint Paul, Minnesota.
Corti, G., et al., "Acute Vertebral Body Compression Fracture treated with OptiMesh—Indications, Applications and First Clinical Results," Eurospine, 2005, Uster-Zürich Switzerland.
Advanced Core Decompression System—Surgical Technique, Wright, 2010, Arlington, Tennessee.
Van Kampen et al, "Camparison of a New Intramedullary Scaffold to Volar Plating for Treatment of Distal Radius Fractures," J Orthop Trauma, Tampa, Florida, Nov. 26, 2012.
Pierannunzii, "Endoscopic and Arthroscopic Assistance in Femoral Head Core Decompression," Arthroscopy Techniques, vol. 1, No. 2, pp. e225-e230, Winston-Salem, North Carolina, Dec. 2012.
Strassmair, "Intramedullar osteosynthesis for treatment of distal radius fractures," Orthopadie & Rheuma, Munchen, Germany, 2011.

"Surgical Technique: Advanced Core Decompression System," Wright Medical Technology, Inc., Memphis, Tennessee, Jan. 1, 2014.
"Conventus DRS Implant 2013 Coding and Reimbursement Guide," Conventus Orthopaedics, Inc., Maple Grove, Minnesota, Mar. 18, 2013.
"Conventus DRS—Distal Radius System," Conventus Orthopaedics, Inc., Maple Grove, Minnesota, Feb. 20, 2013.
"Conventus DRS Surgical Technique," Conventus Orthopaedics, Inc., Maple Grove, Minnesota, Aug. 20, 2012.
"Surgical Technique Conventus Distal Radius System," Conventus Orthopaedics, Inc., Maple Grove, Minnesota, Jan. 31, 2013.
"Conventus Distal Radius Reduction Jig," Conventus Orthopaedics, Inc., Maple Grove, Minnesota, Feb. 28, 2012.
"DRS Removal Summary," Conventus Orthopaedics, Inc., Maple Grove, Minnesota, Oct. 2, 2012.
"Biomechanical Testing Summary," Conventus Orthopaedics, Inc., Maple Grove, Minnesota, Oct. 10, 2012.
"Conventus Introduction and Summary," Conventus Orthopaedics, Inc., Maple Grove, Minnesota, Oct. 1, 2012.
"Clinical Investigation Overview," Conventus Orthopaedics, Inc, Maple Grove, Minnesota, Oct. 1. 2012.
"Conventus DRS, Instructions for Use," Conventus Orthopaedics, Inc., Maple Grove, Minnesota, Feb. 18, 2013.
"Conventus DRS, Procedure Instruments Instrument Tray," Conventus Orthopaedics, Inc., Maple Grove, Minnesota, Feb. 18, 2013.
"A New Intramedullary Device for Distal Radius Fracture Fixation Biomechanical Comparison to Volar Plating," Mayo Clinic, Rochester, Minnesota, Nov. 11, 2011.
Strassmair, M. et al., "A Novel Multi-Planar and Less Invasive Approach to Distal Radius Fracture Fixation—Early Clinical Experience," Conventus Orthopaedics, Inc., Maple Grove, Minnesota, 2011.
"Biological Vertebral Augmentation in Thoracic and Lumbal Fractures Using OptiMesh for Spineoplasty—A new minimal invasive procedure," Second International Congress for Biotechnologies for Spinal Surgery—Leipzig, Leipzig, Germany, 2011.
Strassmair et al., "A Novel, Multi-Planar and Less Invasive Approach to Distal Radius Fracture Fixation—A Prospective Case Series," Conventus Orthopaedics, Inc., Maple Grove, Minnesota, Sep. 12, 2014.
International Search Report for International Application No. PCT/US14/69907, dated Jun. 4, 2015.
Written Opinion for International Application No. PCT/US14/69907, dated Jun. 4, 2015.
United States Patent and Trademark Office Action in U.S. Appl. No. 13/009,657, dated Feb. 20, 2014.
European Patent Office Search Report in Application No. 11735124.7, dated Aug. 28, 2015.
European Patent Office Search Report in Application No. 14868843.5, dated Jun. 26, 2017.
State Intellectual Property Office of the People's Republic of China Office Action in Application No. 201480071995.9, dated Aug. 15, 2017.
State Intellectual Property Office of the People's Republic of China Office Action in Application No. 201480071995.9, dated Apr. 2, 2018.

* cited by examiner

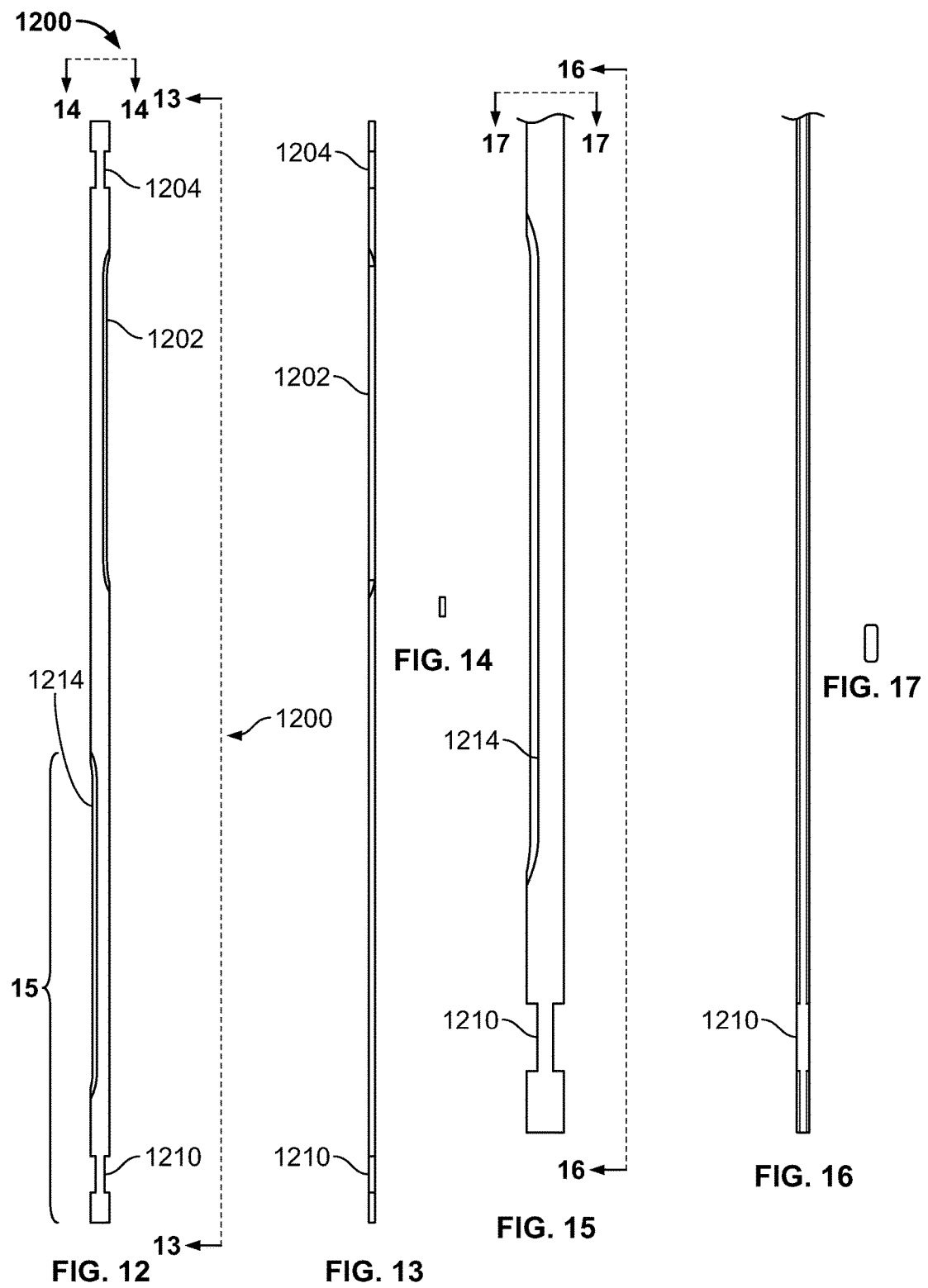

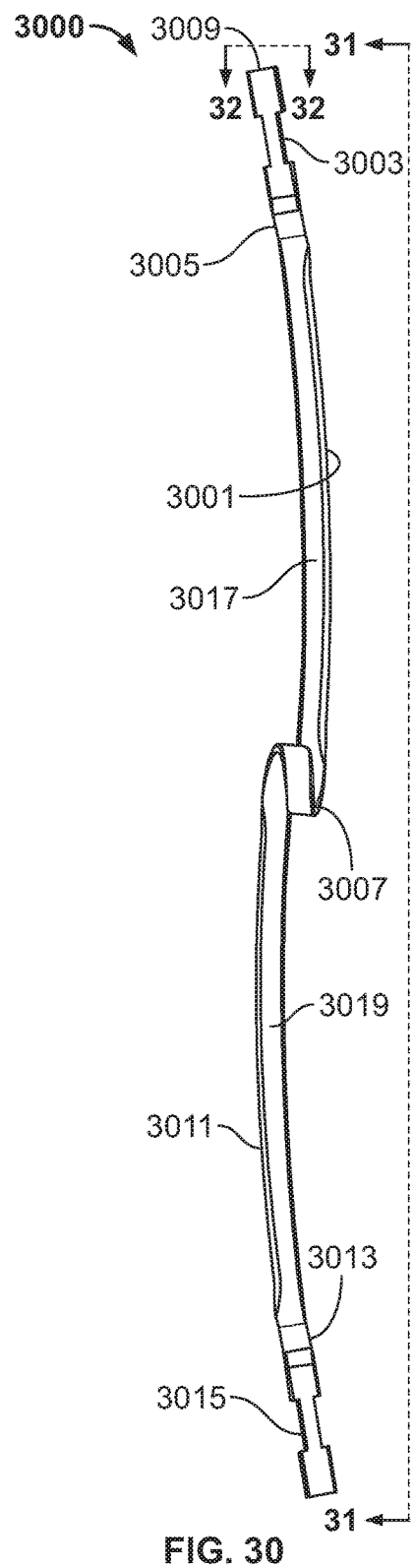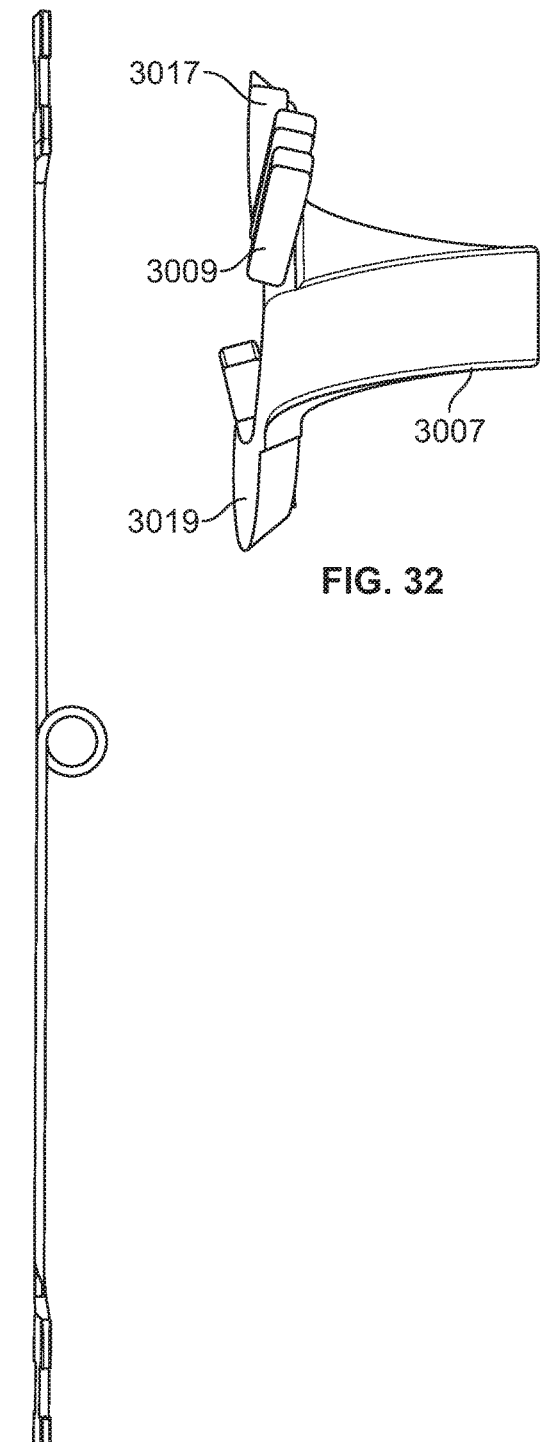
FIG. 30  FIG. 31  FIG. 32

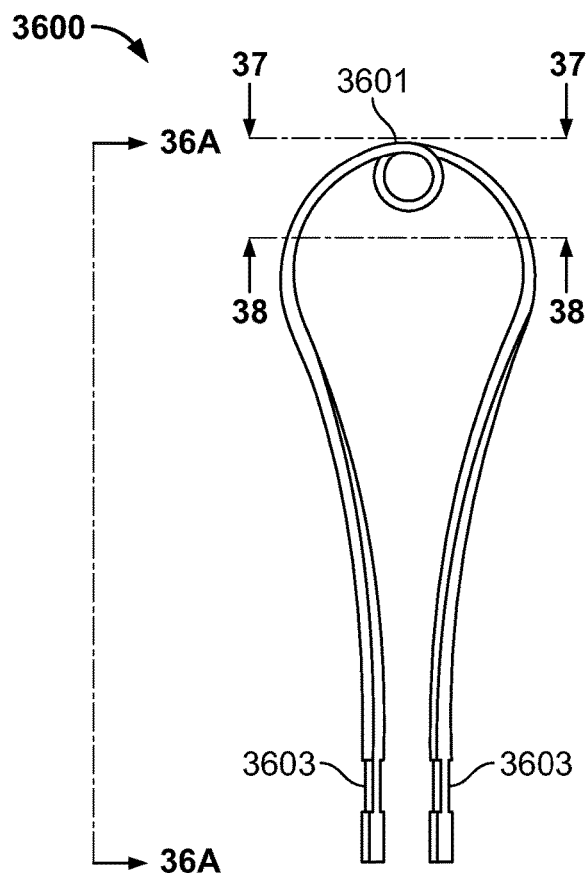
FIG. 36
FIG. 36A
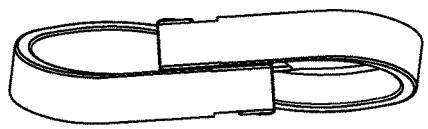
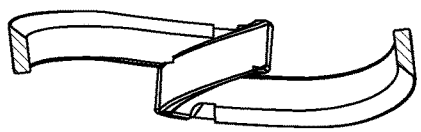
FIG. 37
FIG. 38

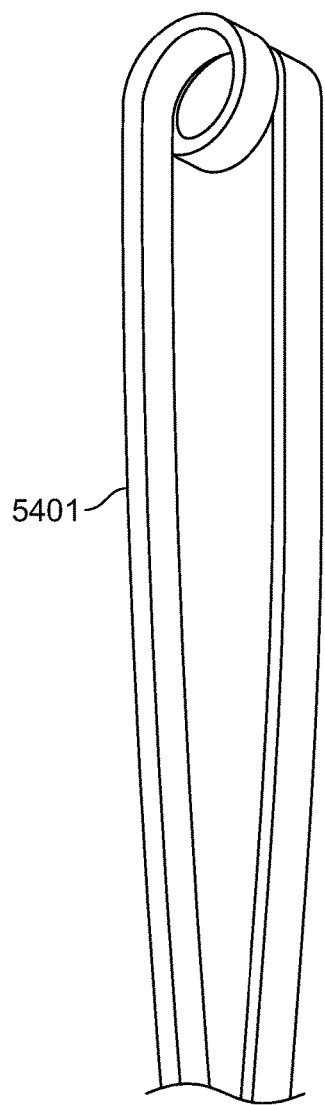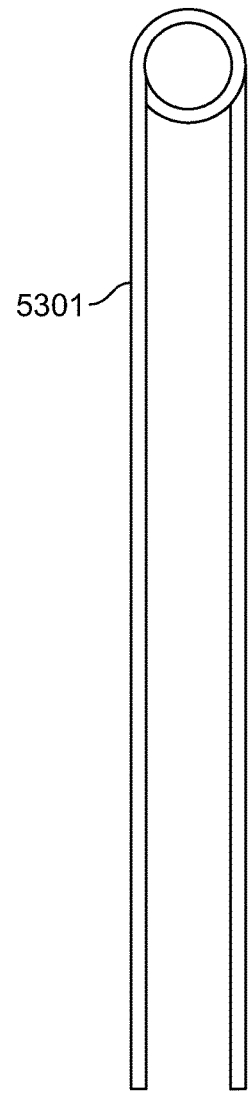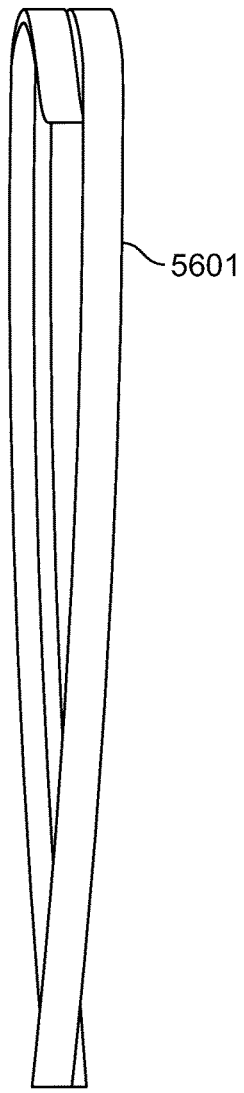
FIG. 57  FIG. 58  FIG. 59
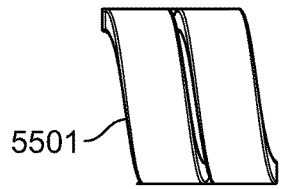
FIG. 60

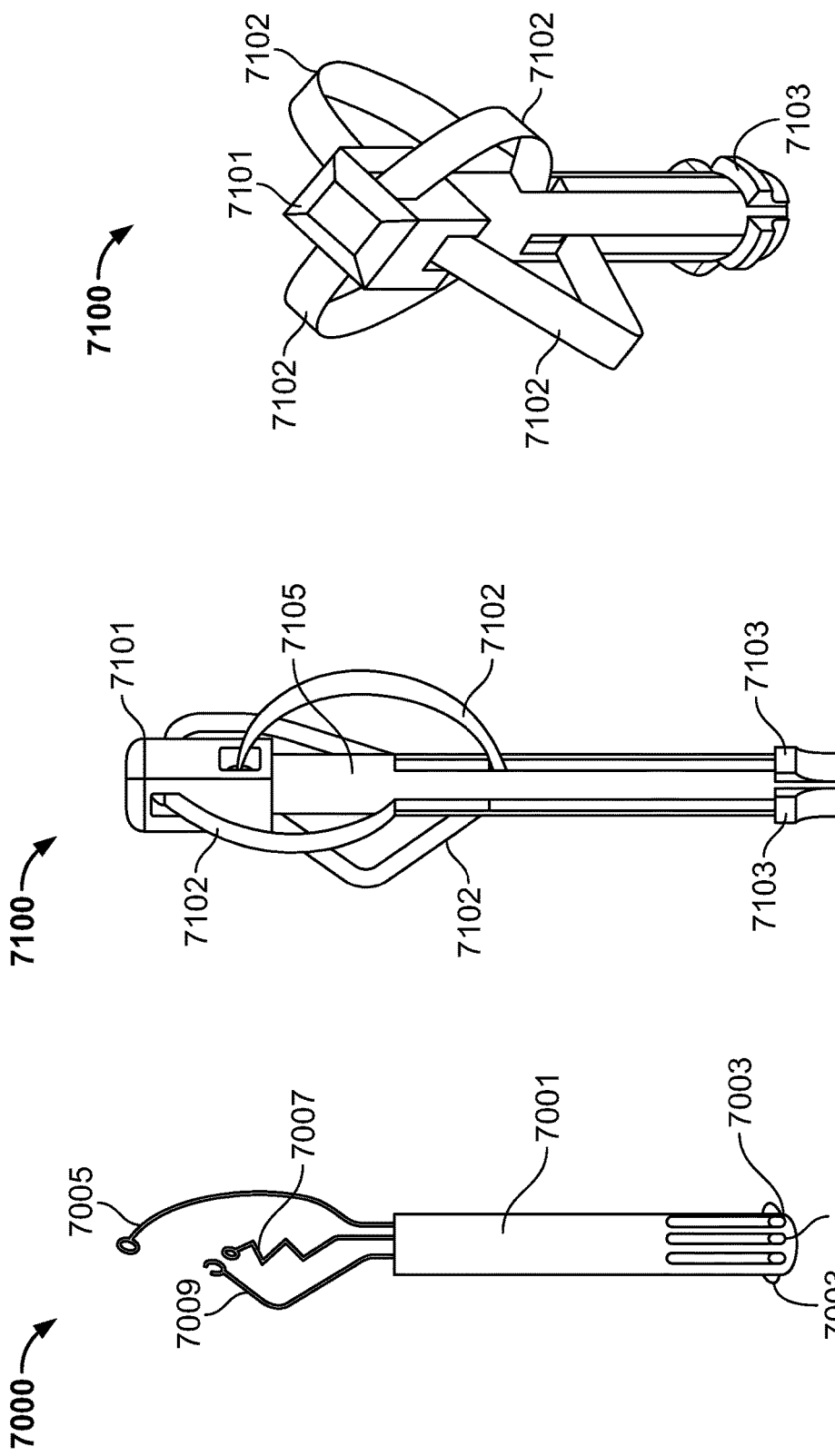

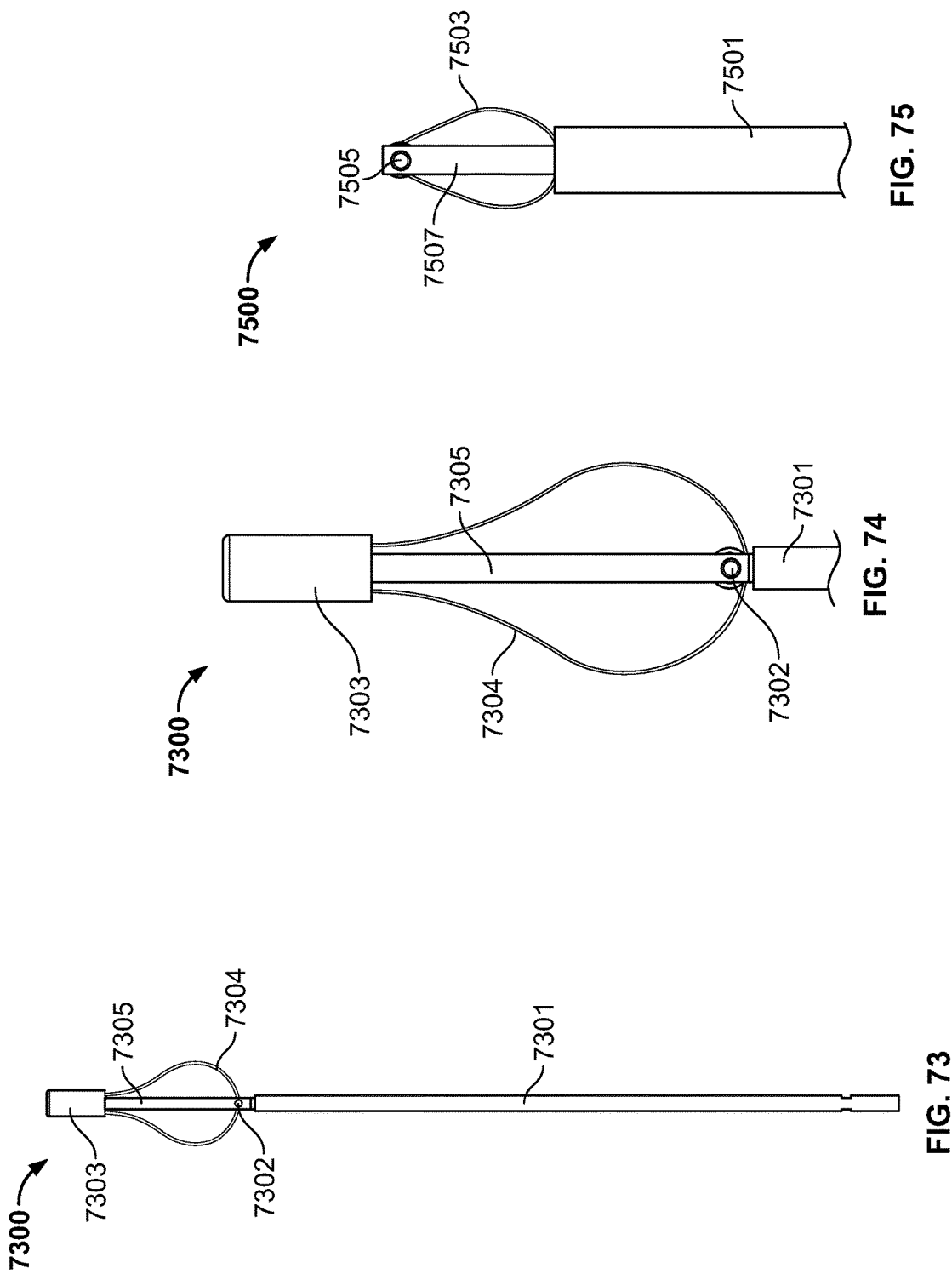

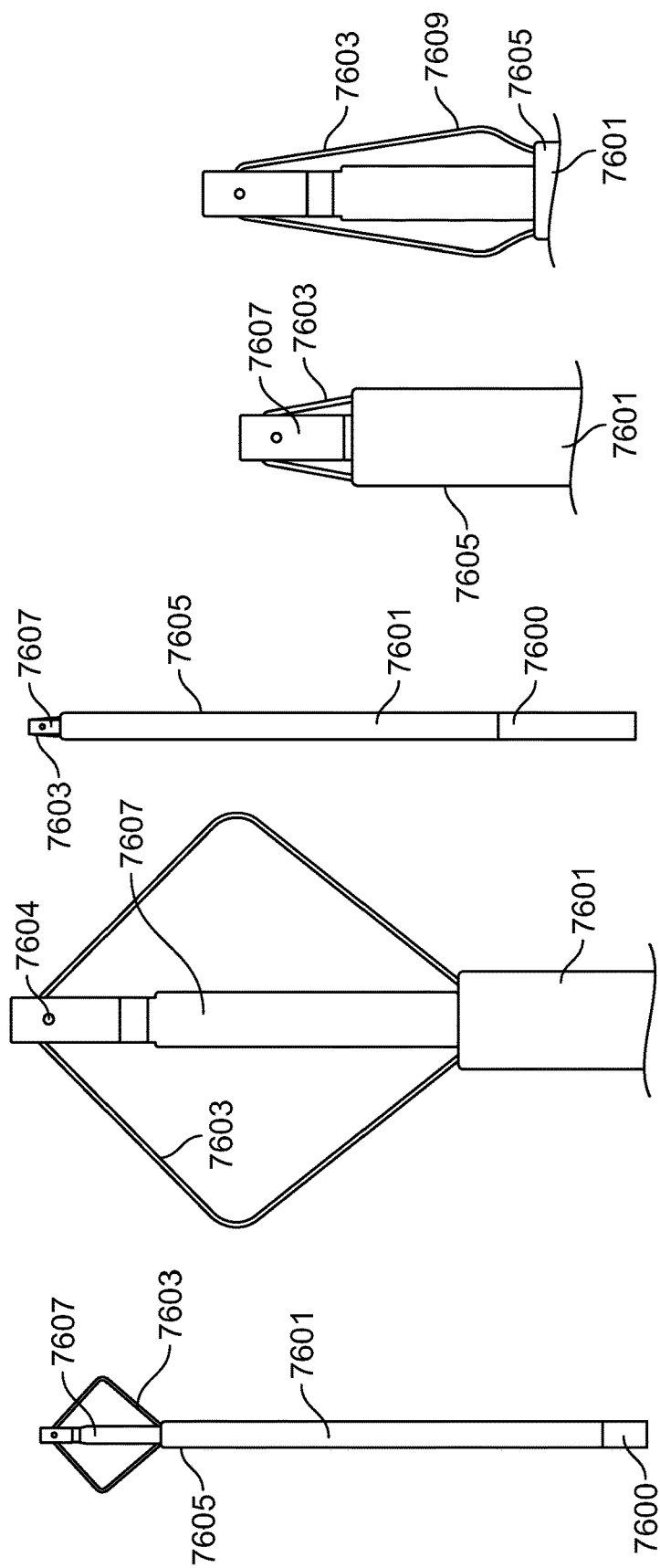

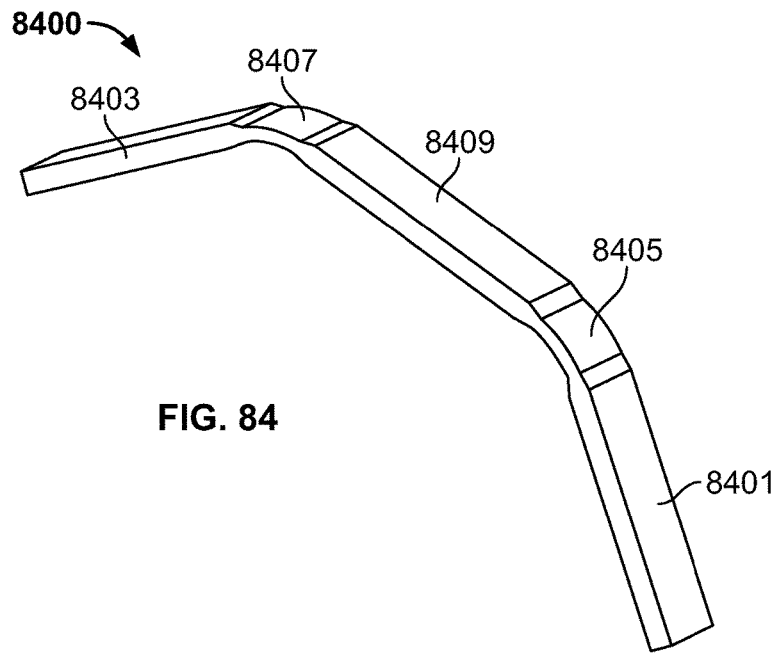
FIG. 84
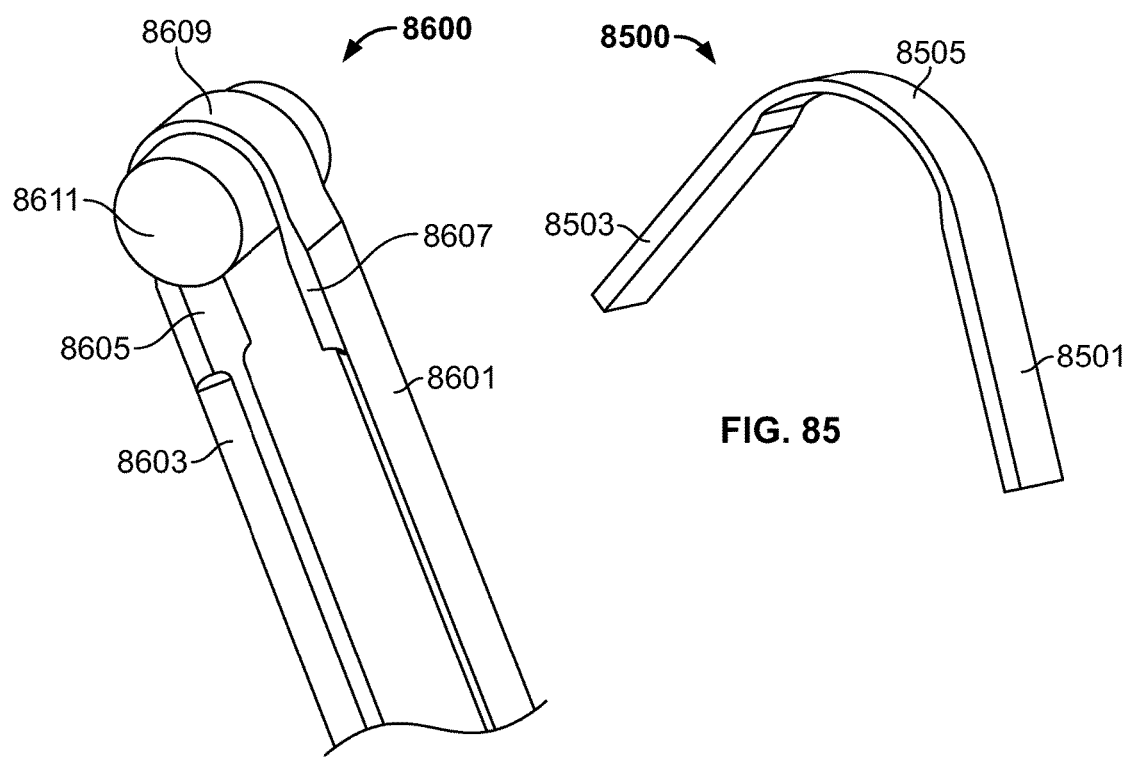
FIG. 86
FIG. 85

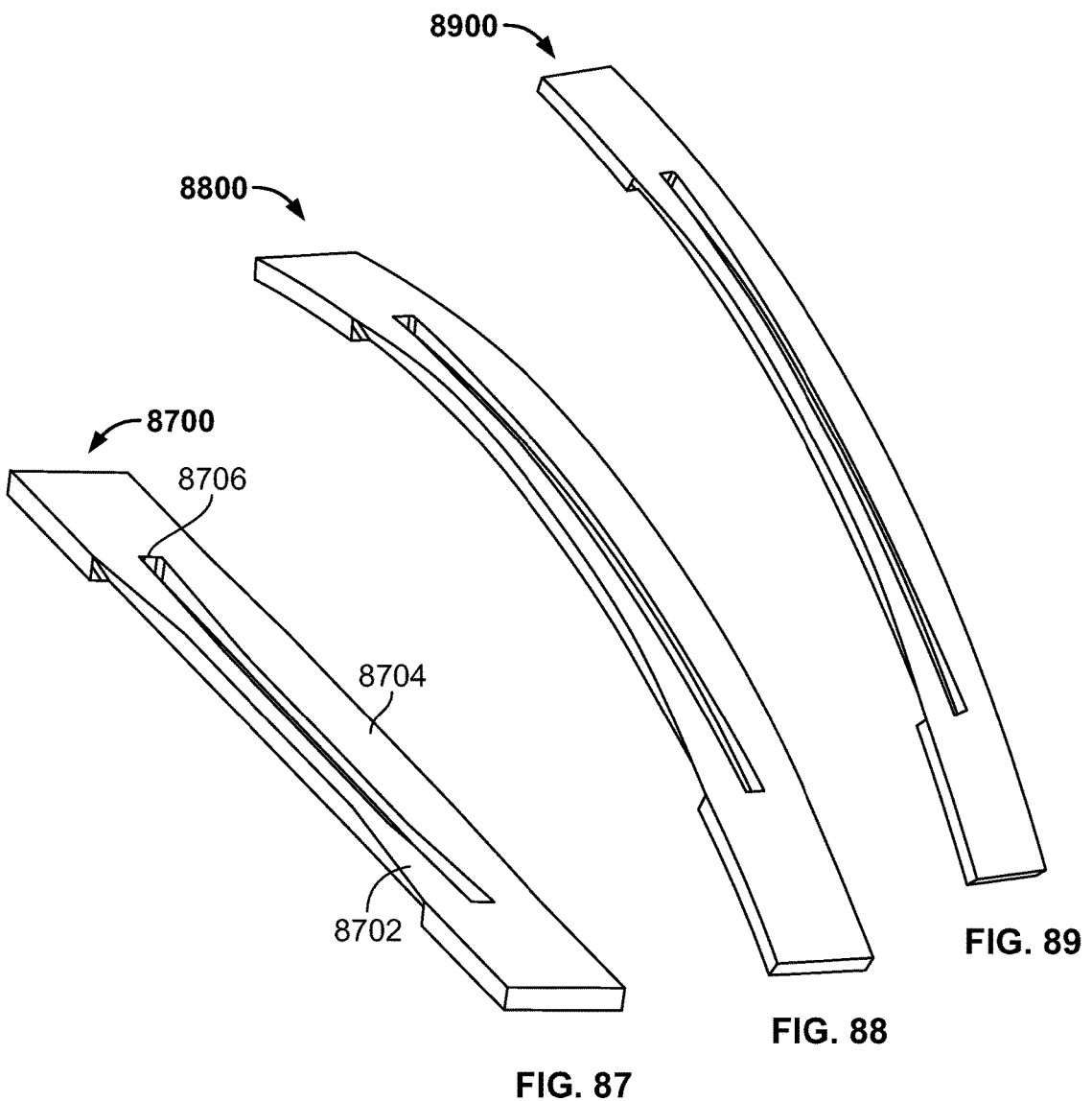

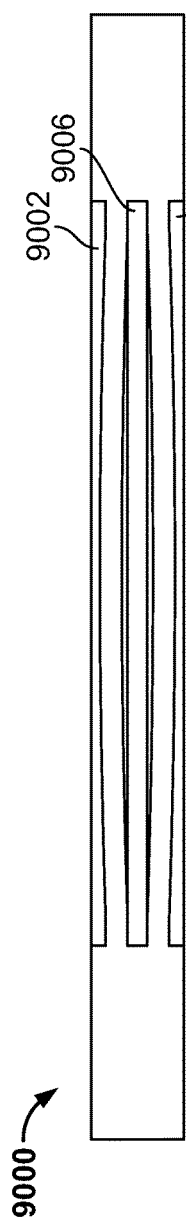
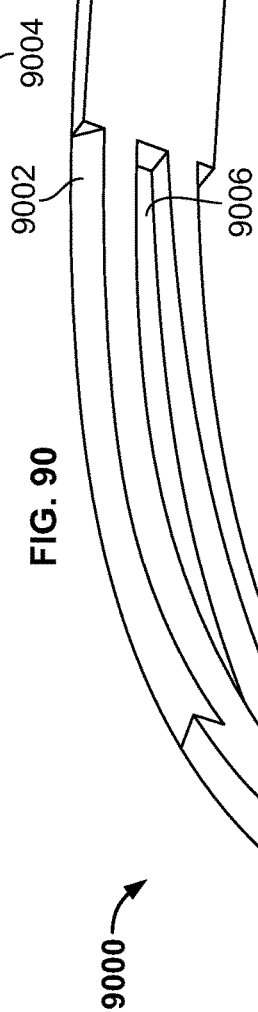
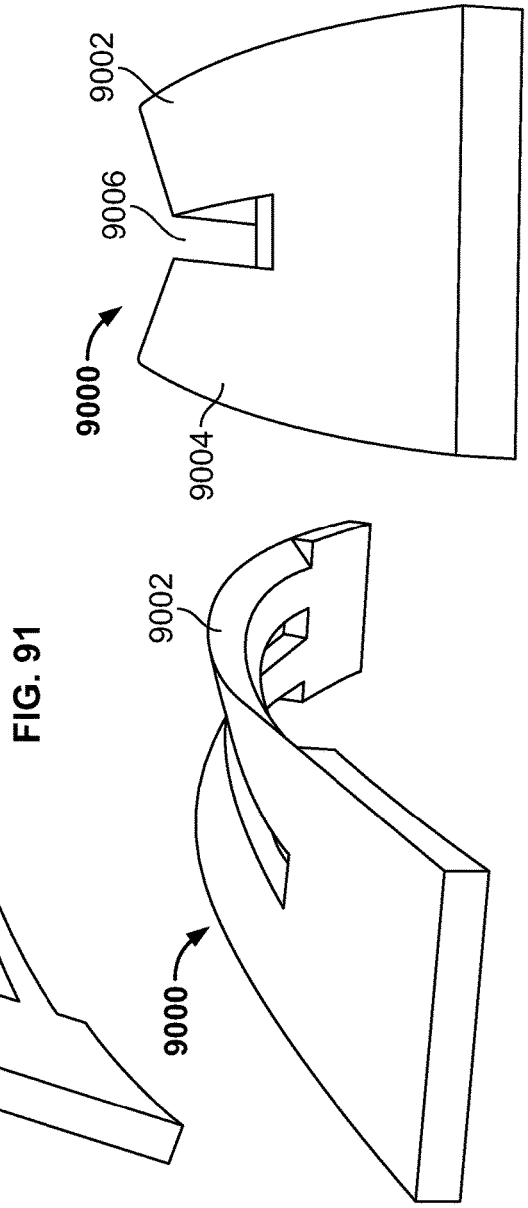
FIG. 90
FIG. 91
FIG. 92
FIG. 93

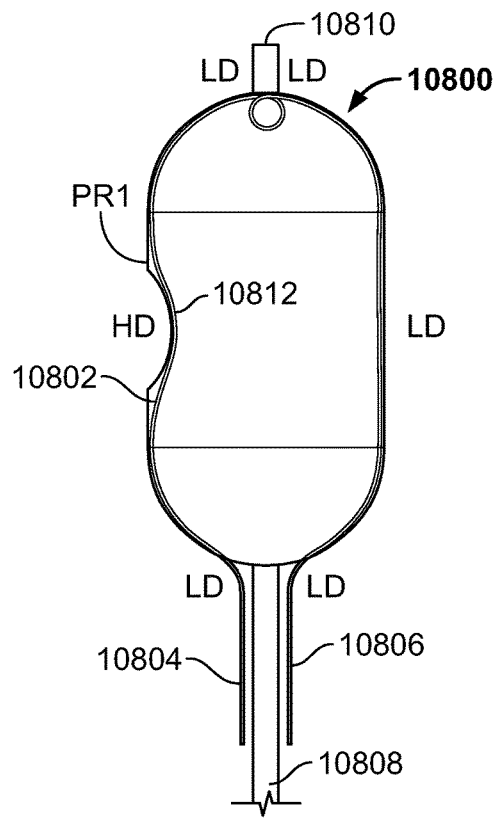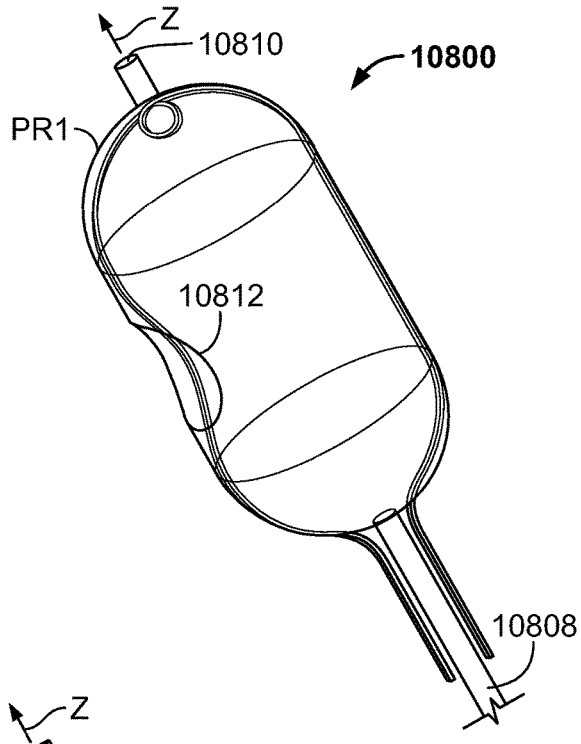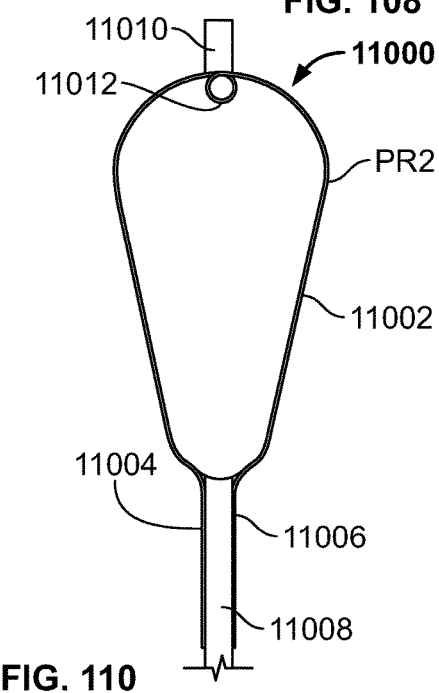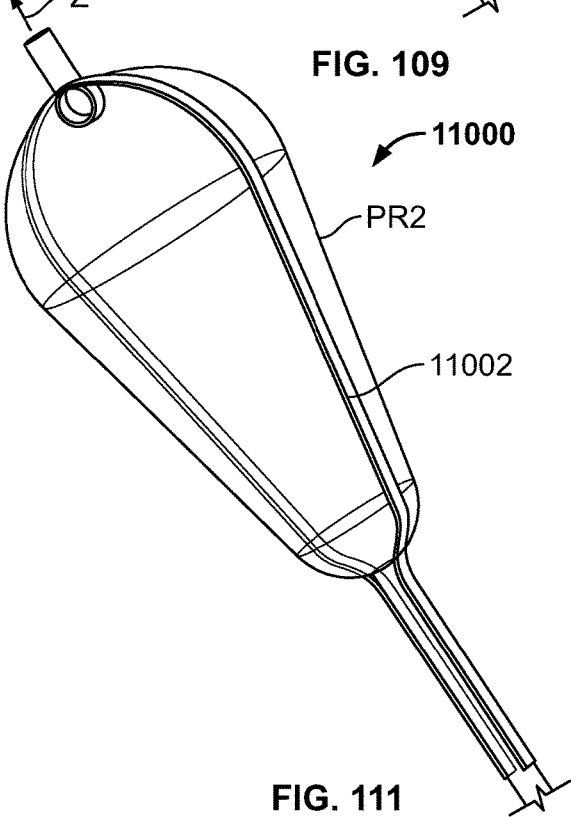
FIG. 108
FIG. 109
FIG. 110
FIG. 111

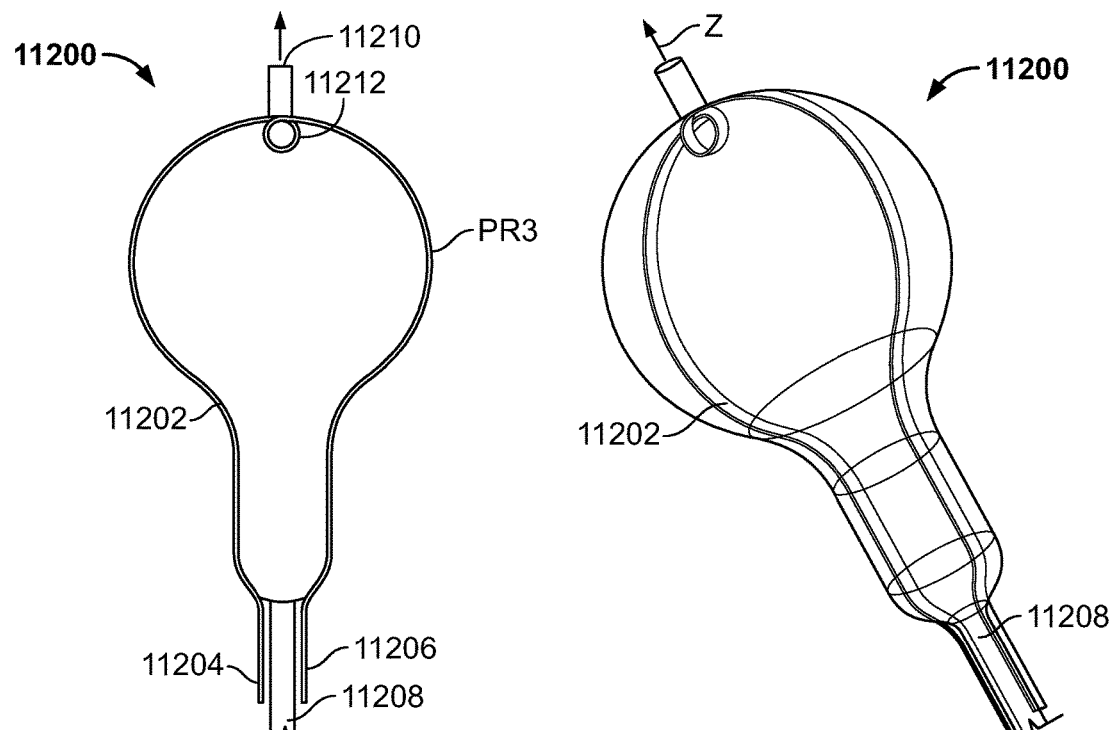
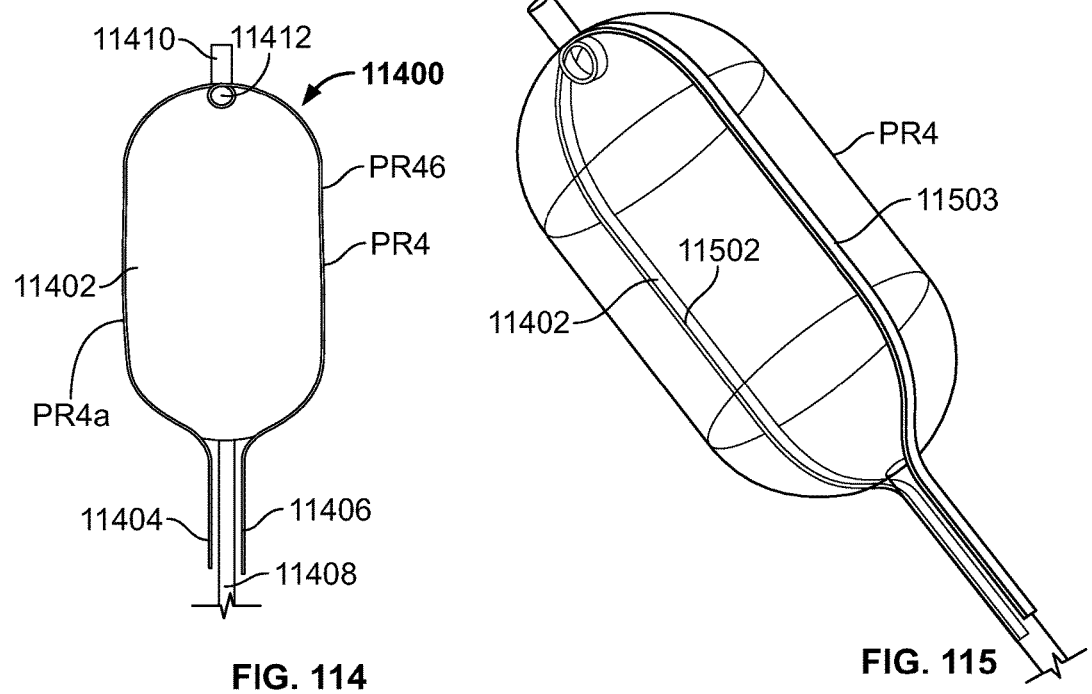
FIG. 112
FIG. 113
FIG. 114
FIG. 115

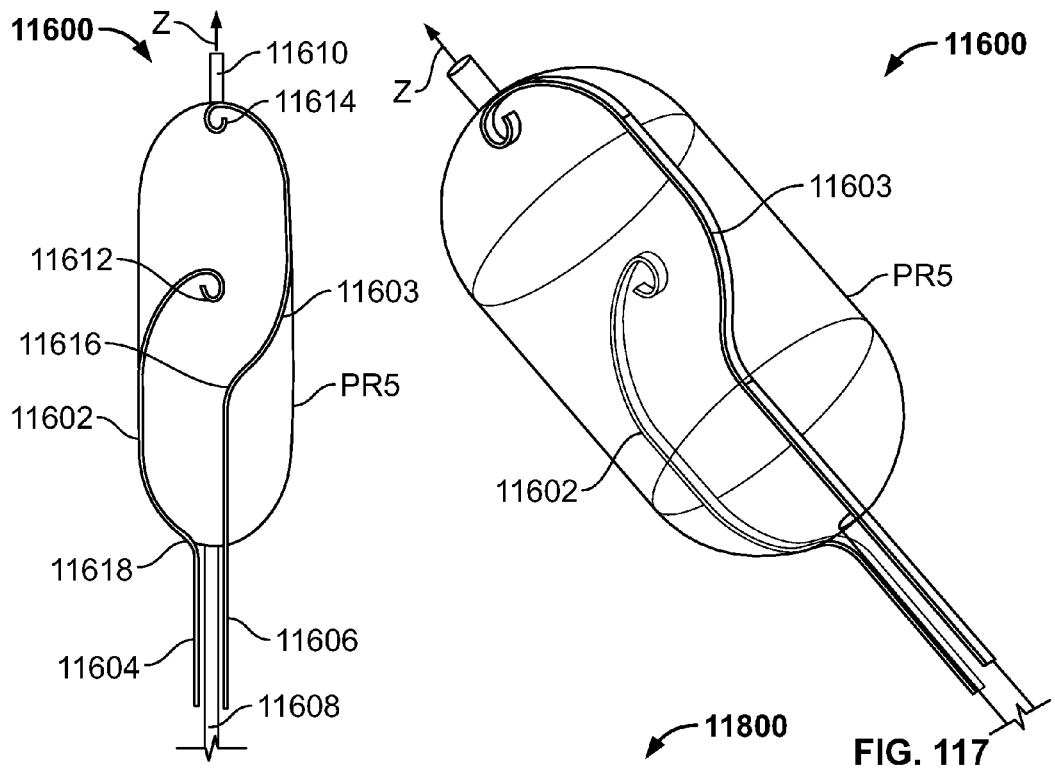
FIG. 116
FIG. 117
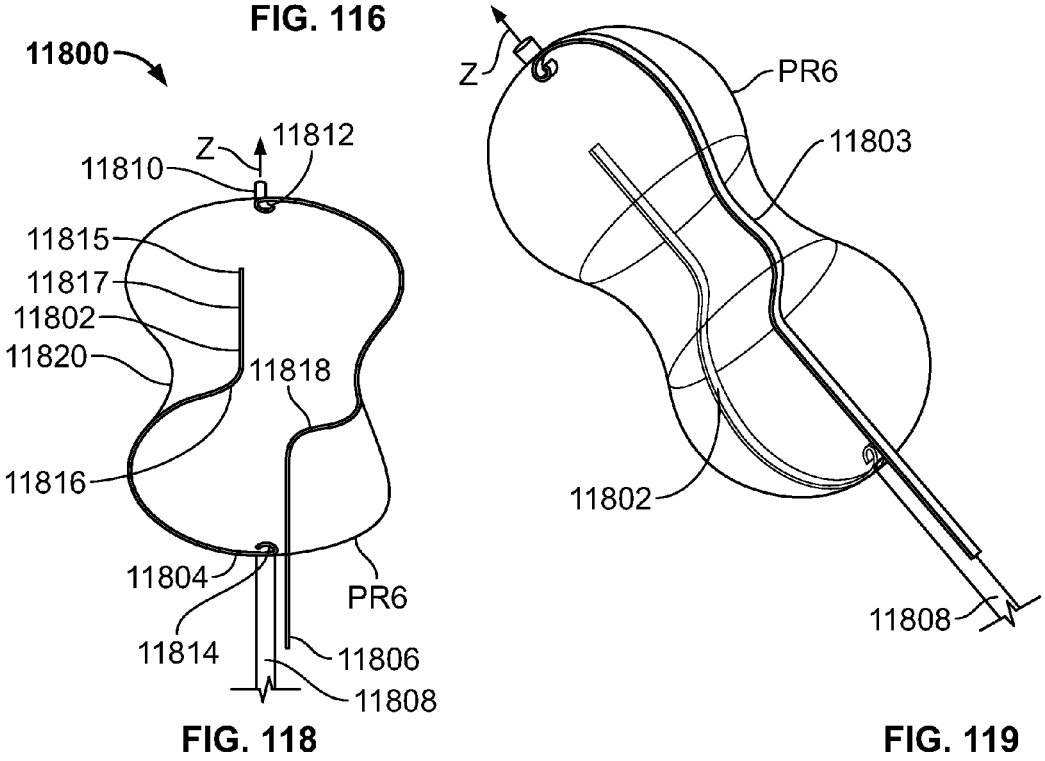
FIG. 118
FIG. 119

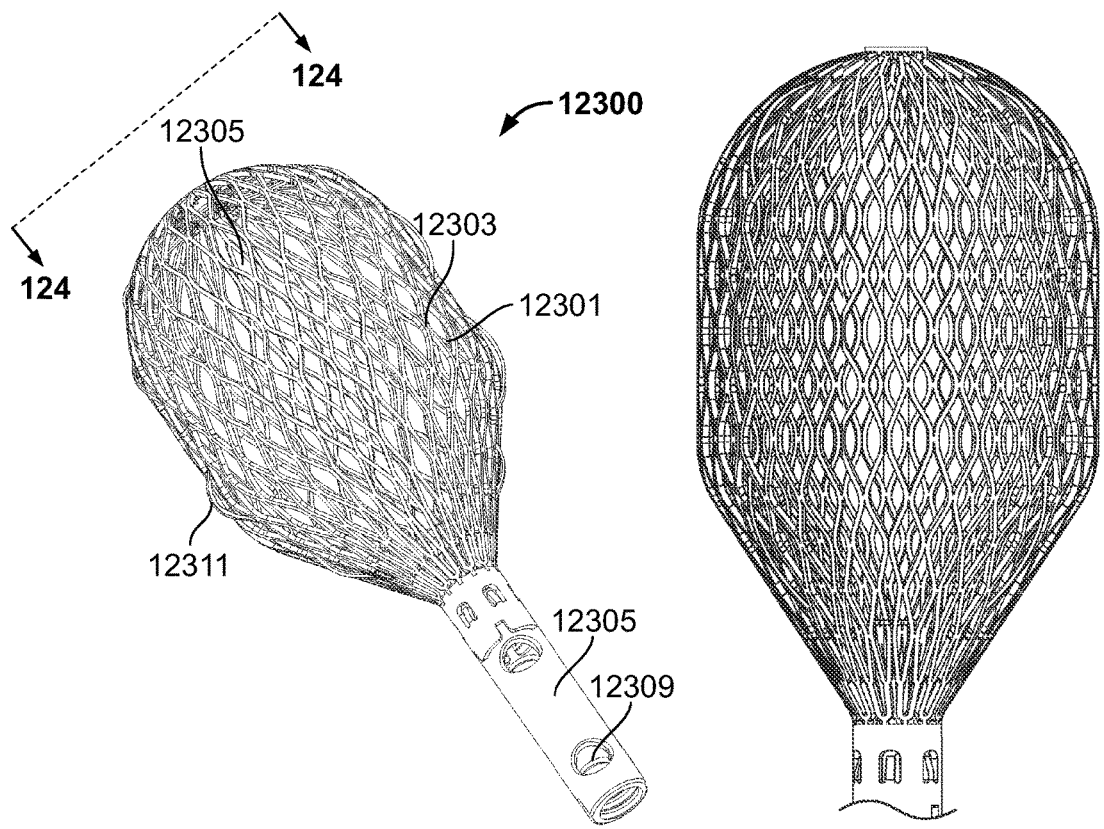
FIG. 123
FIG. 123A
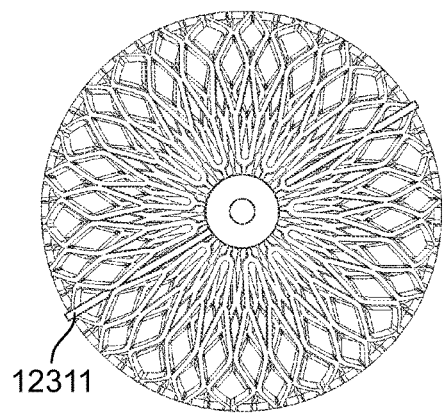
FIG. 123B

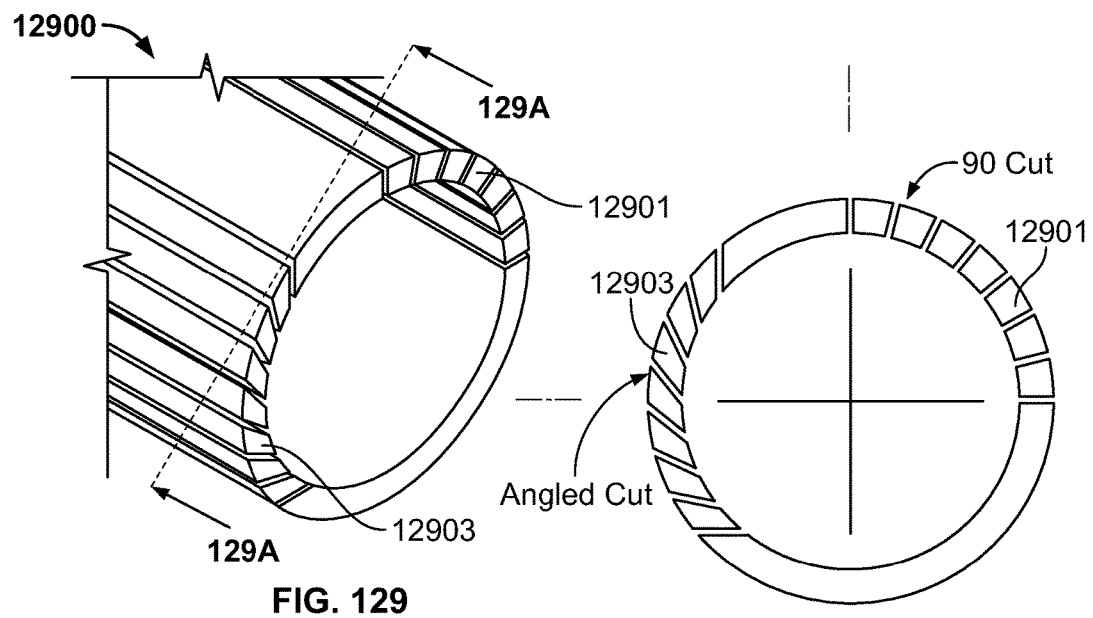
FIG. 129
FIG. 129A
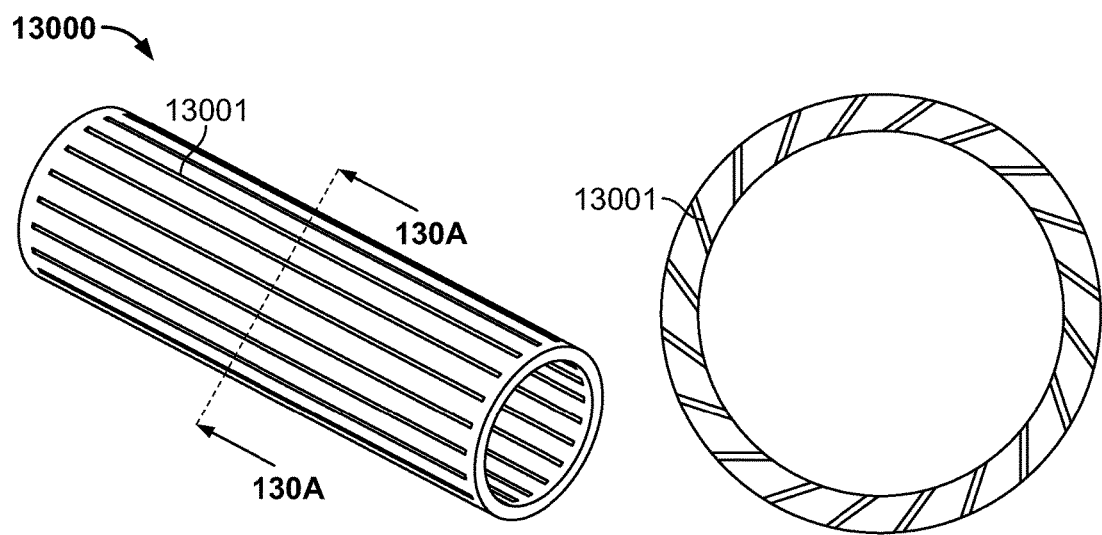
FIG. 130
FIG. 130A

TISSUE DISPLACEMENT TOOLS AND METHODS

CROSS REFERENCE TO RELATED APPLICATIONS

This application is a divisional of U.S. patent application Ser. No. 14/568,301, filed on Dec. 12, 2014, which is a nonprovisional of U.S. Provisional Application Nos. 61/978,239, filed on Apr. 11, 2014, and 61/915,428, filed on Dec. 12, 2013, all of which are hereby incorporated herein by reference in their entireties.

FIELD OF TECHNOLOGY

Aspects of the disclosure relate to providing apparatus and methods for displacing tissue inside bone. In particular, the disclosure relates to apparatus and methods for preparing bone cavities for repairing bone fractures utilizing a device that is inserted into a bone.

BACKGROUND

Bone fracture fixation may involve using a structure to counteract or partially counteract forces on a fractured bone or associated bone fragments. In general, fracture fixation may provide longitudinal (along the long axis of the bone), transverse (across the long axis of the bone), and rotational (about the long axis of the bone) stability. Fracture fixation may also preserve normal biologic and healing function.

Bone fracture fixation often involves addressing loading conditions, fracture patterns, alignment, compression force, and other factors, which may differ for different types of fractures. For example, midshaft fractures may have ample bone material on either side of the fracture in which anchors may be driven. End-bone fractures, especially on the articular surface may have thin cortical bone, soft cancellous bone, and relatively fewer possible anchoring locations. Typical bone fracture fixation approaches may involve one or both of: (1) a device that is within the skin (internal fixation); and (2) a device that extends out of the skin (external fixation).

Internal fixation approaches typically involve one or both of: (a) a plate that is screwed to the outside of the bone; and (b) an implant that is inserted inside the bone.

Plates are often characterized by relatively invasive surgery, support of fractured bone segments from one side outside of bone, and screws that anchor into the plate and the bone.

Implants may include intramedullary rods or screws, such as those used in mid shaft treatments. The typical intramedullary rod or screw is fixed in diameter and is introduced into the medullary canal through an incision. Flexible intramedullary rod-like solutions utilize structures that can be inserted into the medullary cavity through an access site and then be made rigid. The flexible structures may be reinforced with polymers or cements. Multi-segment fractures, of either the midshaft or end-bone, may require alignment and stability in a manner that generates adequate fixation in multiple directions. Implants may be used to treat midshaft fractures and end-bone fractures.

Implant-based therapies may involve removing or displacing bone tissue from the interior of the bone to prepare the interior for the implant. Preparation for the implant may involve providing a space in the bone interior for reception of the implant.

Various tissue densities may be present within a bone. Tissue density may vary within different anatomical locations and from person to person. A bone defect or fracture can further vary tissue density based on a density of tissue surrounding the bone defect or fracture. Manipulating this tissue in a controlled and efficient manner, while imparting minimal energy, is desirable for therapy.

Proper location, size, shape, orientation and proximity to bone fragments and anatomical features, among other factors, may increase the therapeutic effectiveness of the implant.

It would be desirable, therefore,to provide apparatus and methods for preparation of a bone interior.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 12 shows illustrative apparatus in accordance with principles of the invention.

FIG. 13 shows illustrative apparatus in accordance with principles of the invention.

FIG. 14 shows illustrative apparatus in accordance with principles of the invention.

FIG. 15 shows illustrative apparatus in accordance with principles of the invention.

FIG. 16 shows illustrative apparatus in accordance with principles of the invention.

FIG. 17 shows illustrative apparatus in accordance with principles of the invention.

FIG. 30 shows illustrative apparatus in accordance with principles of the invention.

FIG. 31 shows illustrative apparatus in accordance with principles of the invention.

FIG. 32 shows illustrative apparatus in accordance with principles of the invention.

FIG. 36 shows illustrative apparatus in accordance with principles of the invention.

FIG. 36A shows illustrative apparatus in accordance with principles of the invention.

FIG. 37 shows illustrative apparatus in accordance with principles of the invention.

FIG. 38 shows a partial cross-sectional view of FIG. 36 taken along lines 38-38.

FIG. 57 shows illustrative apparatus in accordance with principles of the invention.

FIG. 58 shows illustrative apparatus in accordance with principles of the invention.

FIG. 59 shows illustrative apparatus in accordance with principles of the invention.

FIG. 60 shows illustrative apparatus in accordance with principles of the invention.

FIG. 70 shows illustrative apparatus in accordance with principles of the invention.

FIG. 71 shows illustrative apparatus in accordance with principles of the invention.

FIG. 72 shows illustrative apparatus in accordance with principles of the invention.

FIG. 73 shows illustrative apparatus in accordance with principles of the invention.

FIG. 74 shows illustrative apparatus in accordance with principles of the invention.

FIG. 75 shows illustrative apparatus in accordance with principles of the invention.

FIG. 76 shows illustrative apparatus in accordance with principles of the invention.

FIG. 77 shows illustrative apparatus in accordance with principles of the invention.

FIG. 78 shows illustrative apparatus in accordance with principles of the invention.

FIG. 79 shows illustrative apparatus in accordance with principles of the invention.

FIG. 80 shows illustrative apparatus in accordance with principles of the invention.

FIG. 84 shows illustrative apparatus in accordance with principles of the invention.

FIG. 85 shows illustrative apparatus in accordance with principles of the invention.

FIG. 86 shows illustrative apparatus in accordance with principles of the invention.

FIG. 87 shows illustrative apparatus in accordance with principles of the invention.

FIG. 88 shows illustrative apparatus in accordance with principles of the invention.

FIG. 89 shows illustrative apparatus in accordance with principles of the invention.

FIG. 90 shows illustrative apparatus in accordance with principles of the invention.

FIG. 91 shows illustrative apparatus in accordance with principles of the invention.

FIG. 92 shows illustrative apparatus in accordance with principles of the invention.

FIG. 93 shows illustrative apparatus in accordance with principles of the invention.

FIG. 104 shows illustrative apparatus in accordance with principles of the invention.

FIG. 105 shows illustrative apparatus in accordance with principles of the invention.

FIG. 106 shows illustrative apparatus in accordance with principles of the invention.

FIG. 107 shows illustrative apparatus in accordance with principles of the invention.

FIG. 108 shows illustrative apparatus in accordance with principles of the invention.

FIG. 109 shows illustrative apparatus in accordance with principles of the invention.

FIG. 110 shows illustrative apparatus in accordance with principles of the invention.

FIG. 111 shows illustrative apparatus in accordance with principles of the invention.

FIG. 112 shows illustrative apparatus in accordance with principles of the invention.

FIG. 113 shows illustrative apparatus in accordance with principles of the invention.

FIG. 114 shows illustrative apparatus in accordance with principles of the invention.

FIG. 115 shows illustrative apparatus in accordance with principles of the invention.

FIG. 116 shows illustrative apparatus in accordance with principles of the invention.

FIG. 117 shows illustrative apparatus in accordance with principles of the invention.

FIG. 118 shows illustrative apparatus in accordance with principles of the invention.

FIG. 119 shows illustrative apparatus in accordance with principles of the invention.

Figures 120, 121:
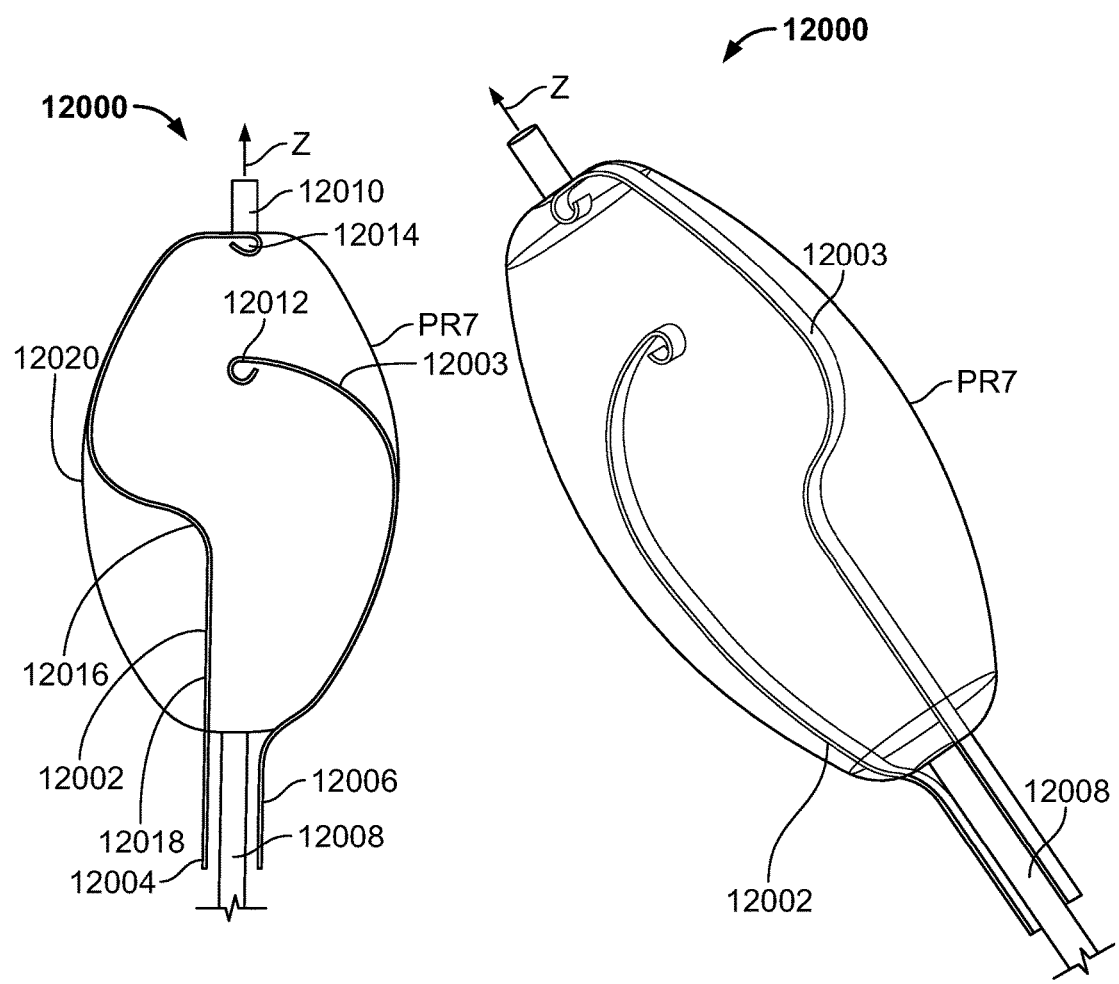

FIG. 120 shows illustrative apparatus in accordance with principles of the invention.

FIG. 121 shows illustrative apparatus in accordance with principles of the invention.

Figures 122, 122A:
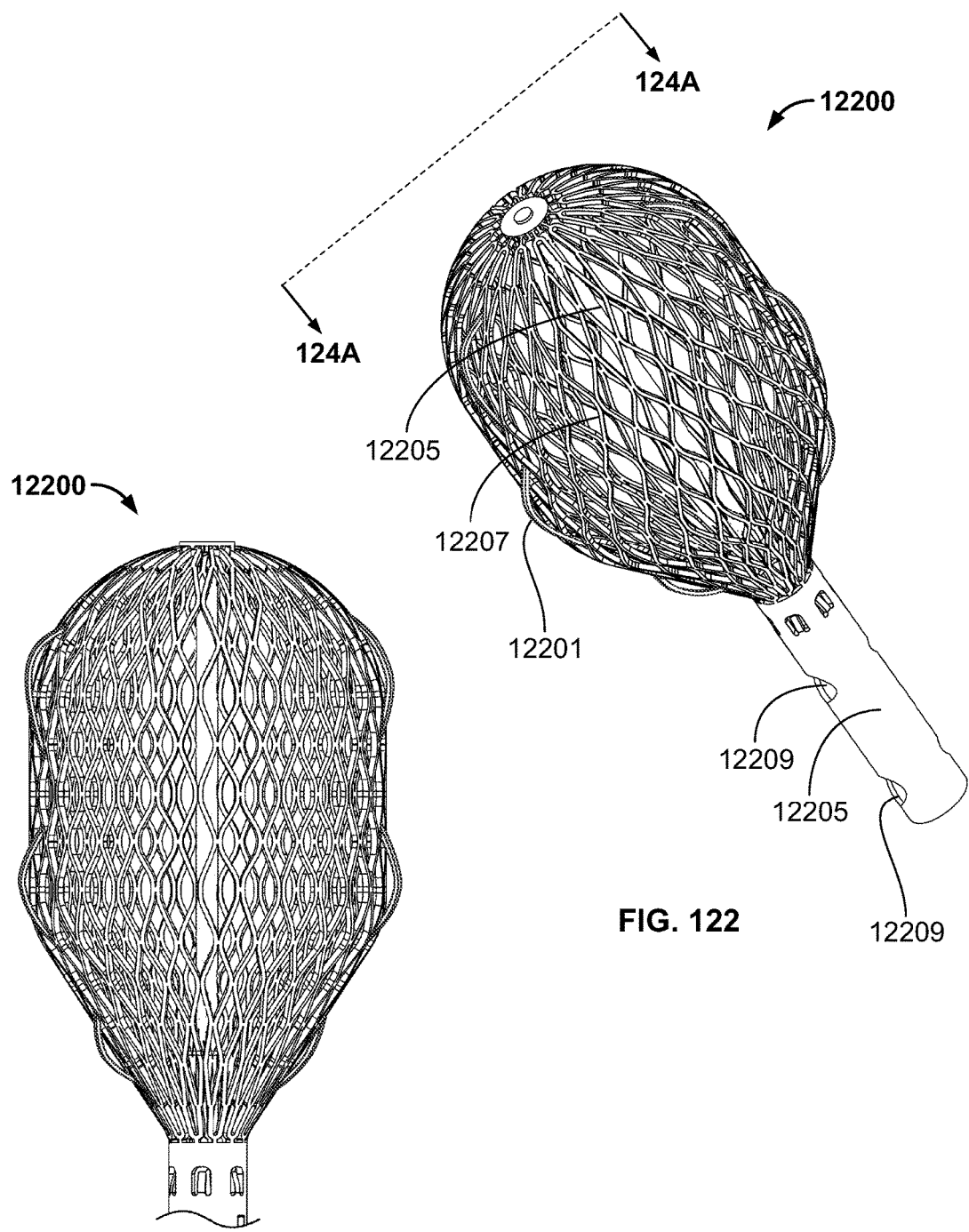

FIG. 122 shows illustrative apparatus in accordance with principles of the invention.

FIG. 122A shows illustrative apparatus in accordance with principles of the invention.

FIG. 123 shows illustrative apparatus in accordance with principles of the invention.

FIG. 123A shows illustrative apparatus in accordance with principles of the invention.

FIG. 123B shows illustrative apparatus in accordance with principles of the invention.

Figure 124:
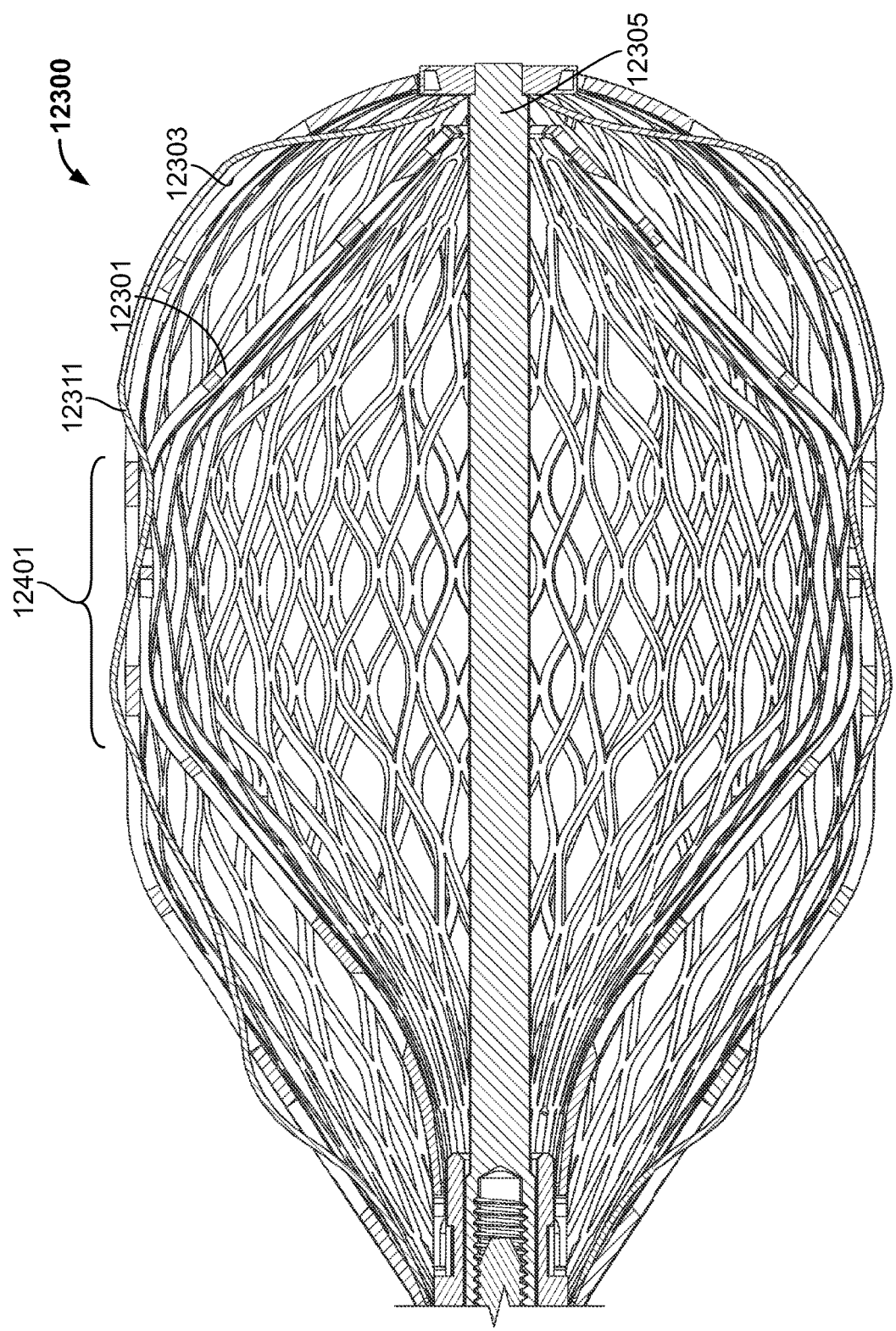

FIG. 124 shows a partial cross-sectional view of FIG. 123 taken along lines 124-124.

Figure 124A:
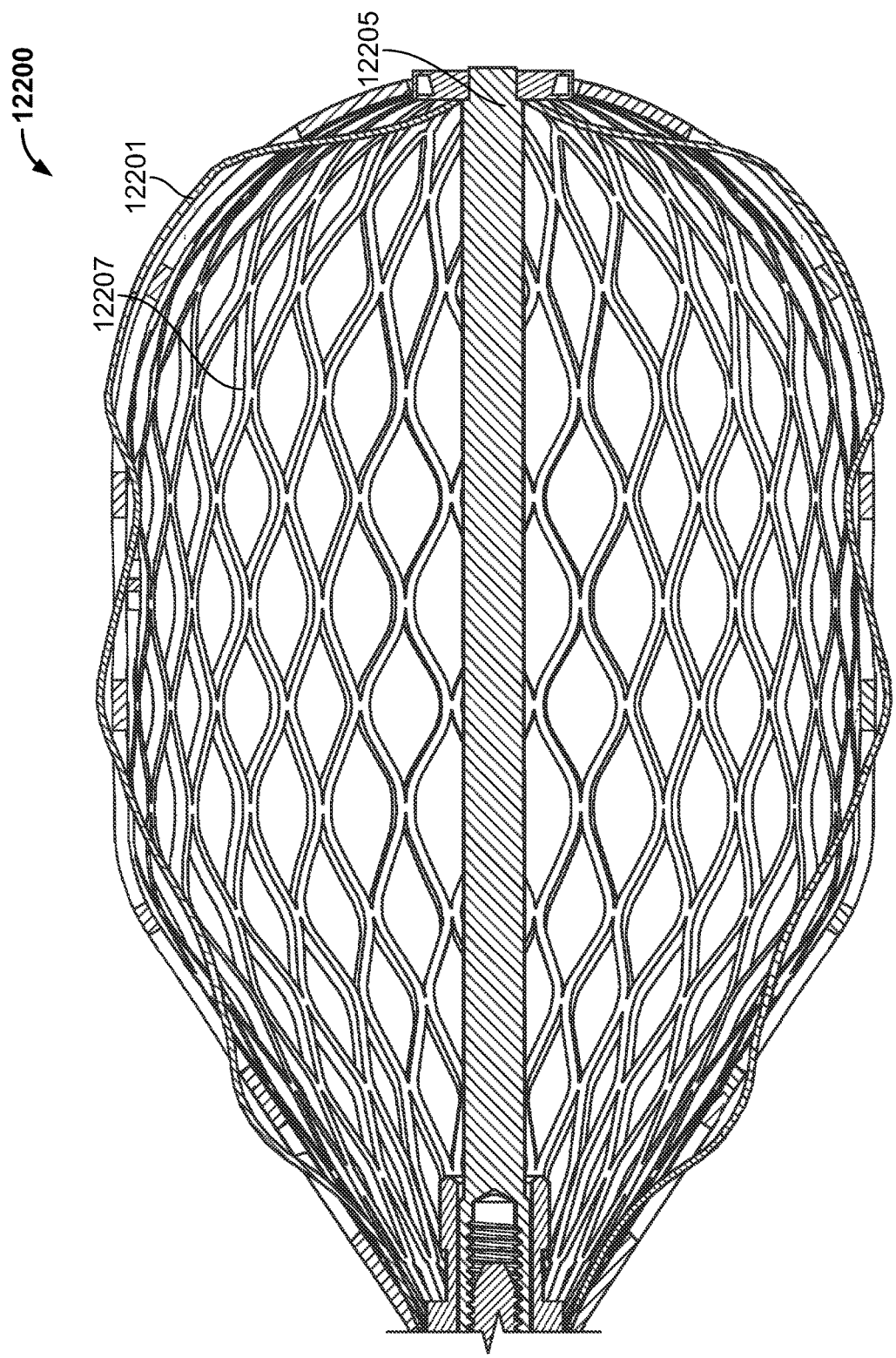

FIG. 124A shows a partial cross-sectional view of FIG. 122 taken along lines 124A-124A.

Figure 125:
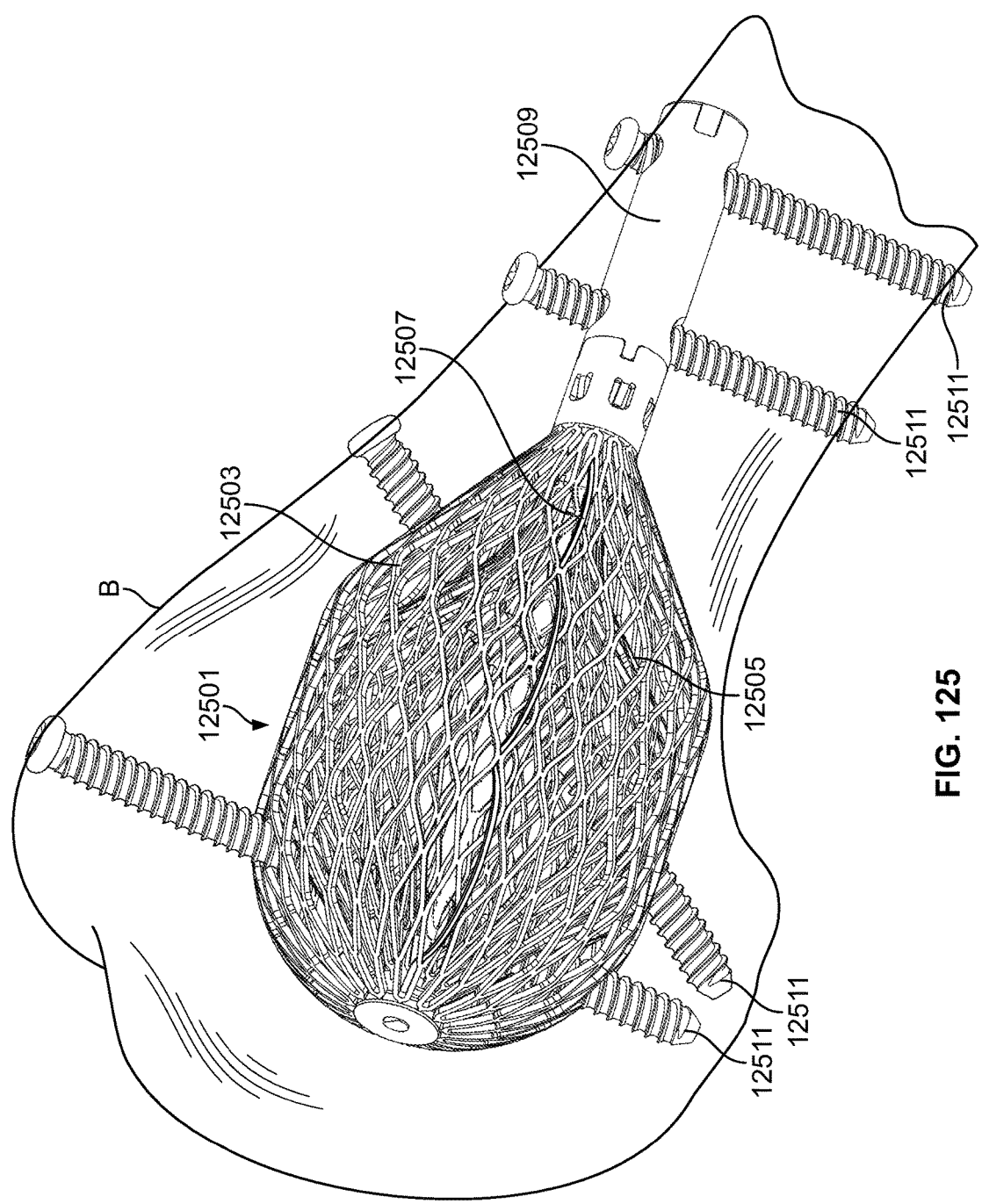

FIG. 125 shows illustrative apparatus in accordance with principles of the invention.

Figure 126:
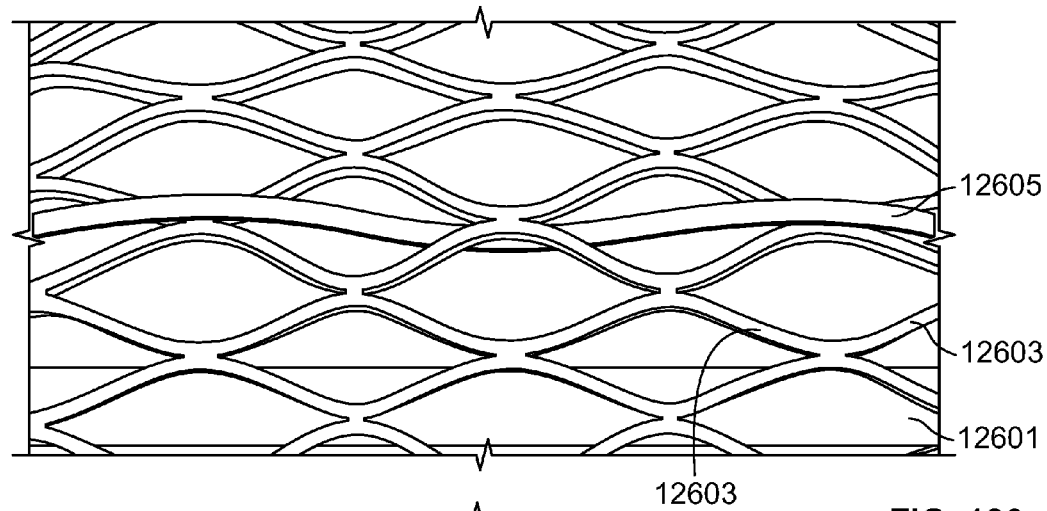

FIG. 126 shows illustrative apparatus in accordance with principles of the invention.

Figure 127:
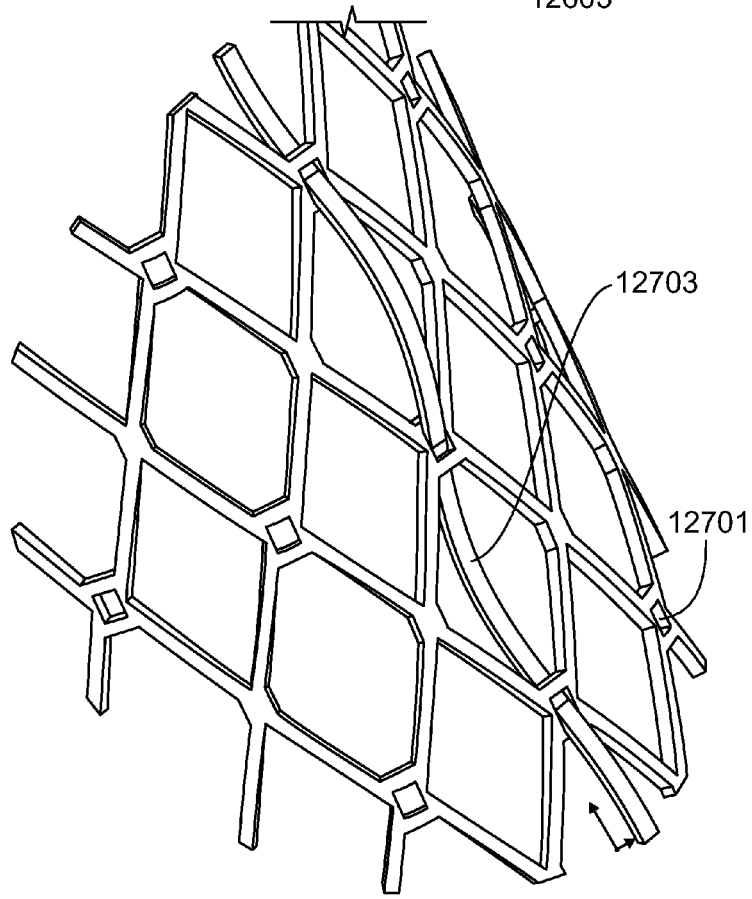

FIG. 127 shows illustrative apparatus in accordance with principles of the invention.

Figure 128:
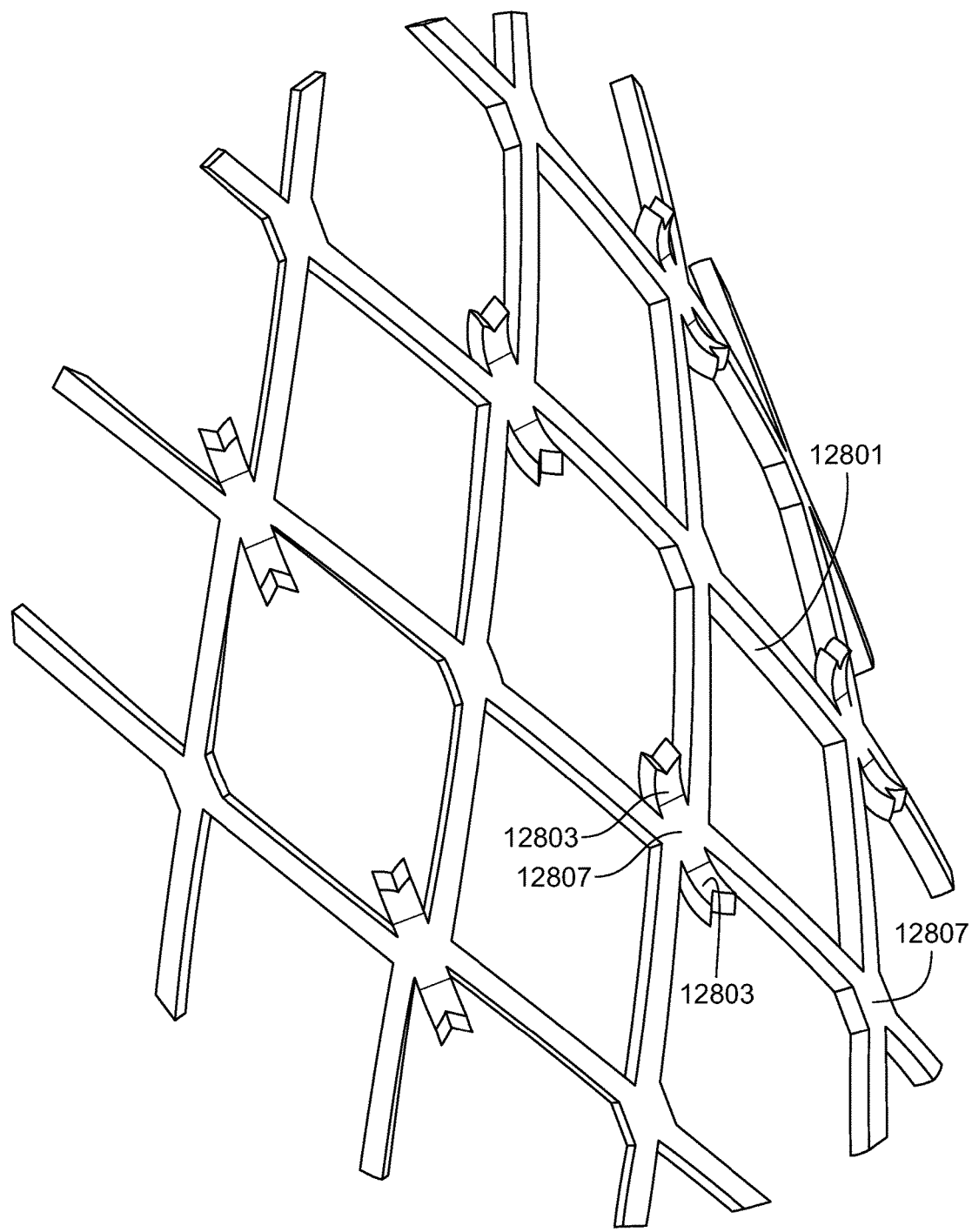

FIG. 128 shows illustrative apparatus in accordance with principles of the invention.

FIG. 129 shows illustrative apparatus in accordance with principles of the invention.

FIG. 129A shows a cross-sectional view of FIG. 129 taken along lines 129A-129A.

FIG. 130 shows illustrative apparatus in accordance with principles of the invention.

FIG. 130A shows a cross-sectional view of FIG. 130 taken along lines 130A-130A.

Figure 131:
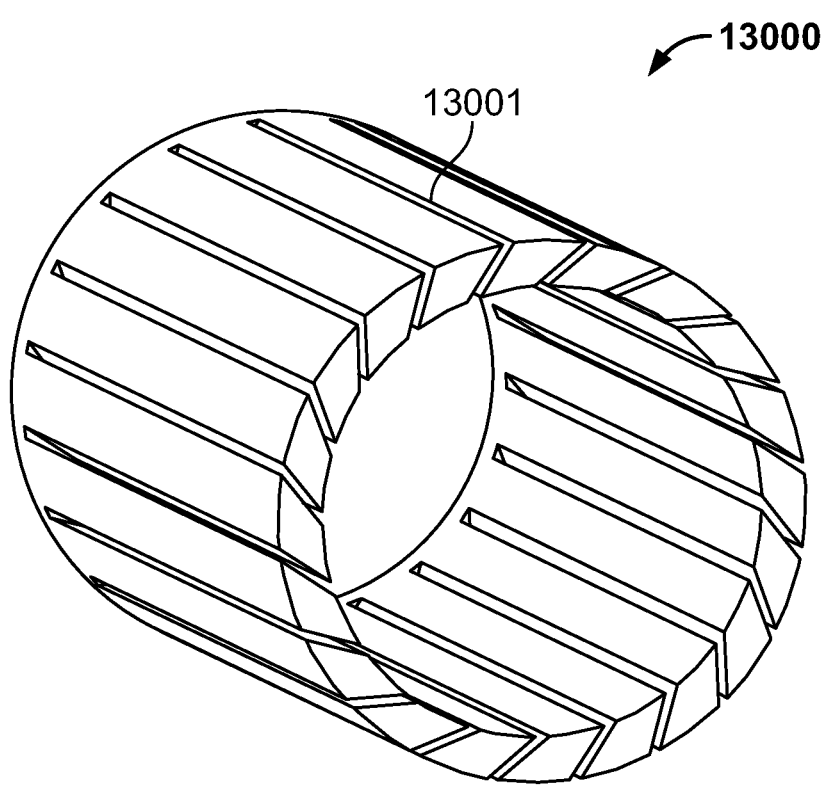

FIG. 131 shows a partial cross-sectional view of FIG. 130 taken along lines 130A-130A.

Figure 132:
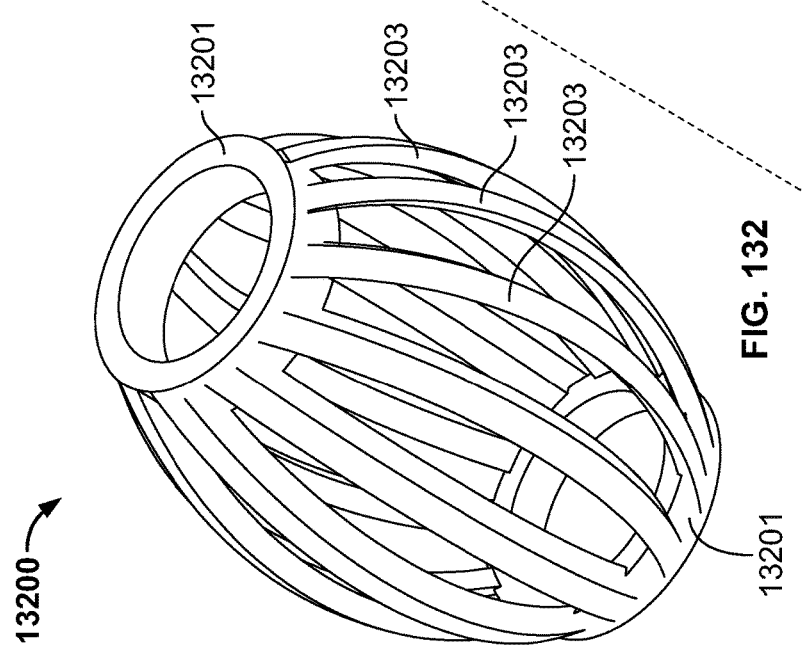

FIG. 132 shows illustrative apparatus in accordance with principles of the invention.

Figure 133:
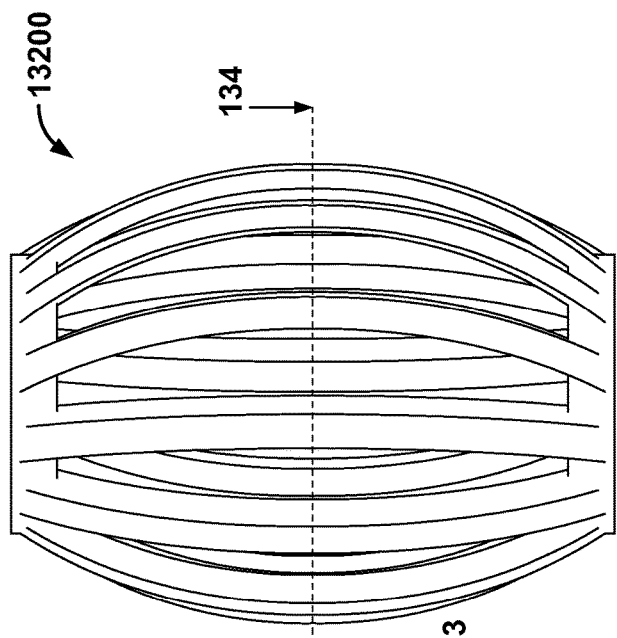

FIG. 133 shows illustrative apparatus in accordance with principles of the invention.

Figure 134:
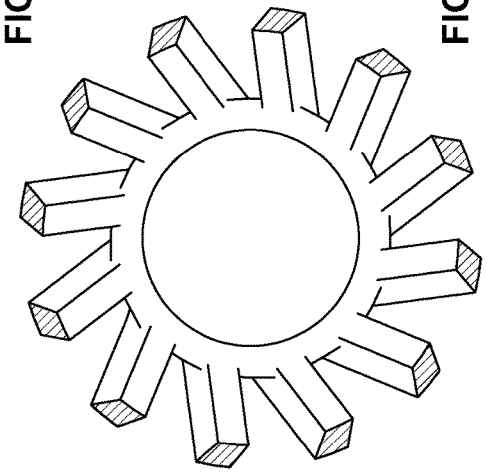

FIG. 134 shows a partial cross-sectional view of FIG. 133 taken along lines 134-134.

Figure 135:
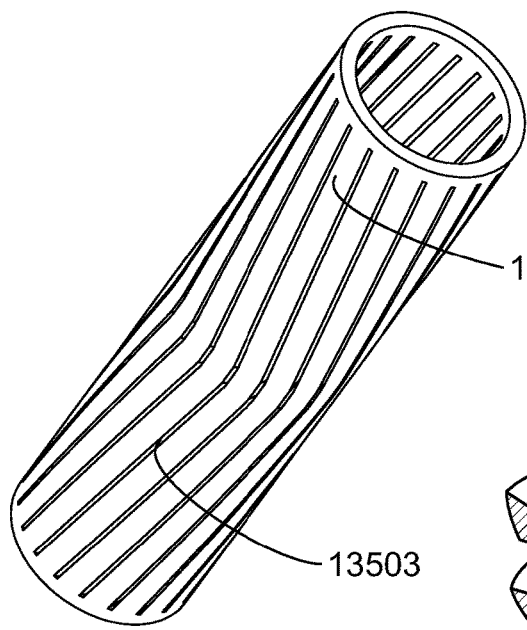

FIG. 135 shows illustrative apparatus in accordance with principles of the invention.

Figure 136:
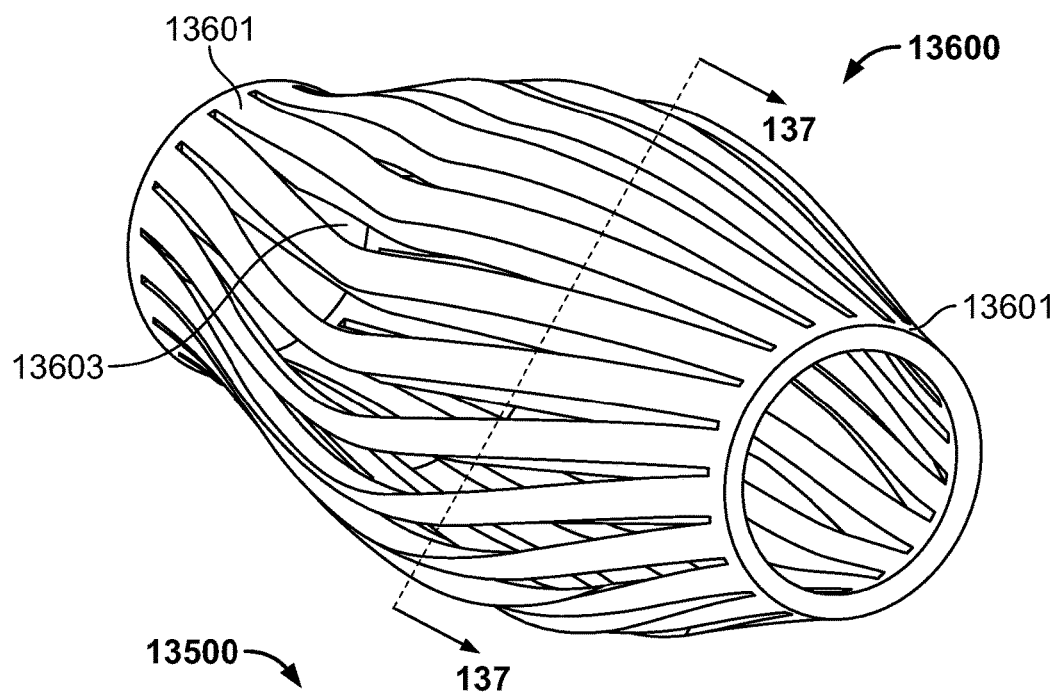

FIG. 136 shows illustrative apparatus in accordance with principles of the invention.

Figure 137:
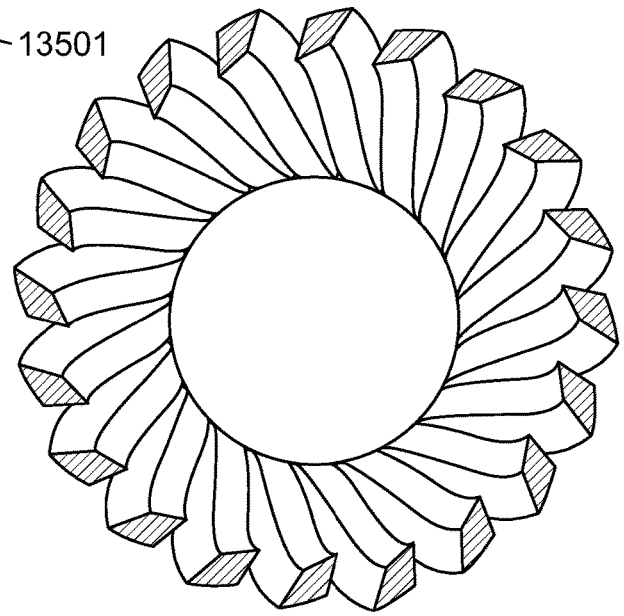

FIG. 137 shows a partial cross-sectional view of FIG. 136 taken along lines 137-137.

Figure 138:
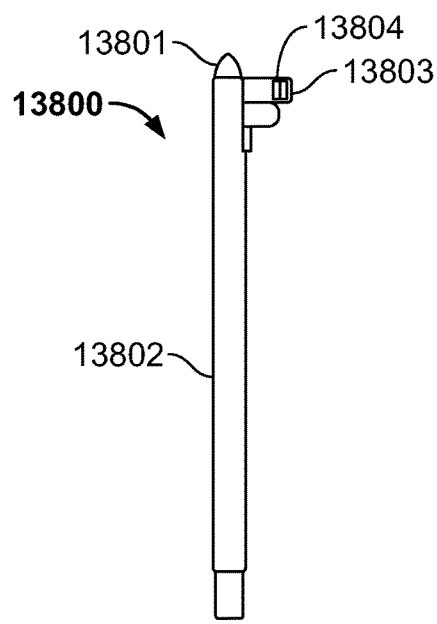

FIG. 138 shows illustrative apparatus in accordance with principles of the invention.

Figure 139:
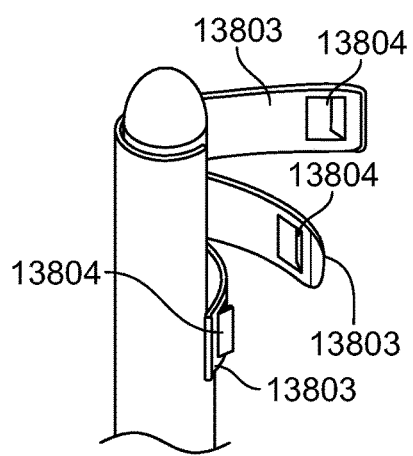

FIG. 139 shows illustrative apparatus in accordance with principles of the invention.

Figure 140:
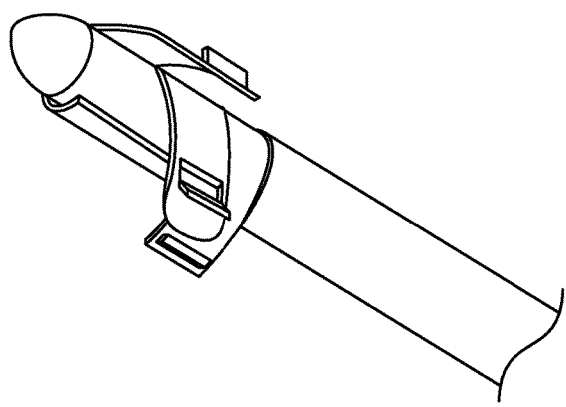

FIG. 140 shows illustrative apparatus in accordance with principles of the invention.

Figure 141:
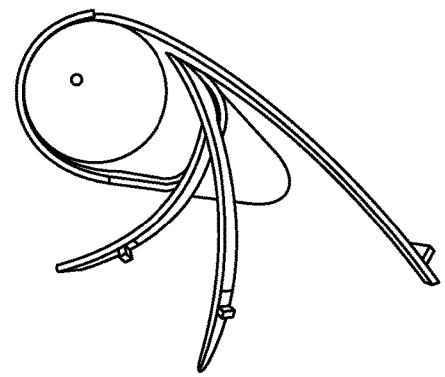

FIG. 141 shows illustrative apparatus in accordance with principles of the invention.

Figure 142:
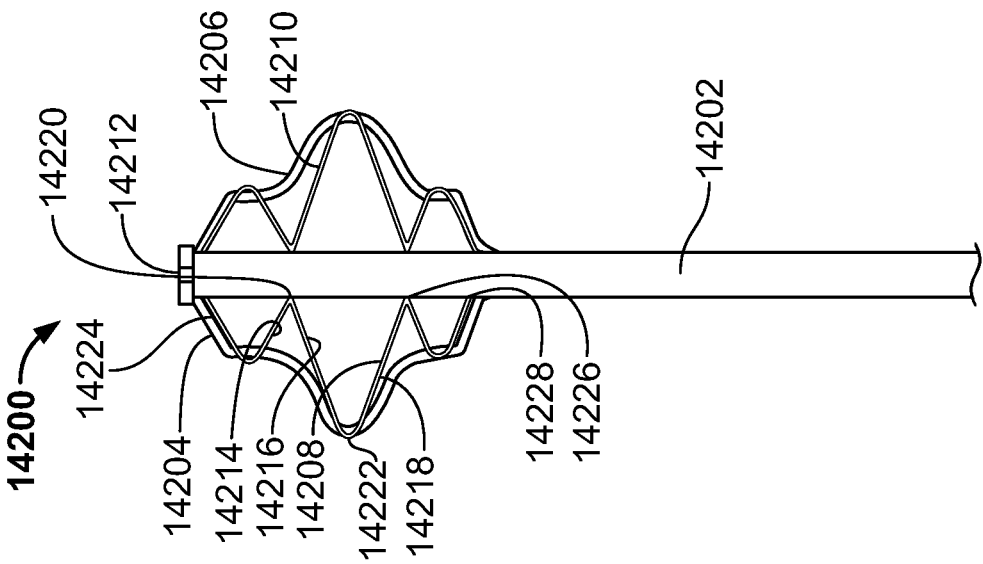

FIG. 142 shows illustrative apparatus in accordance with principles of the invention.

Figure 143:
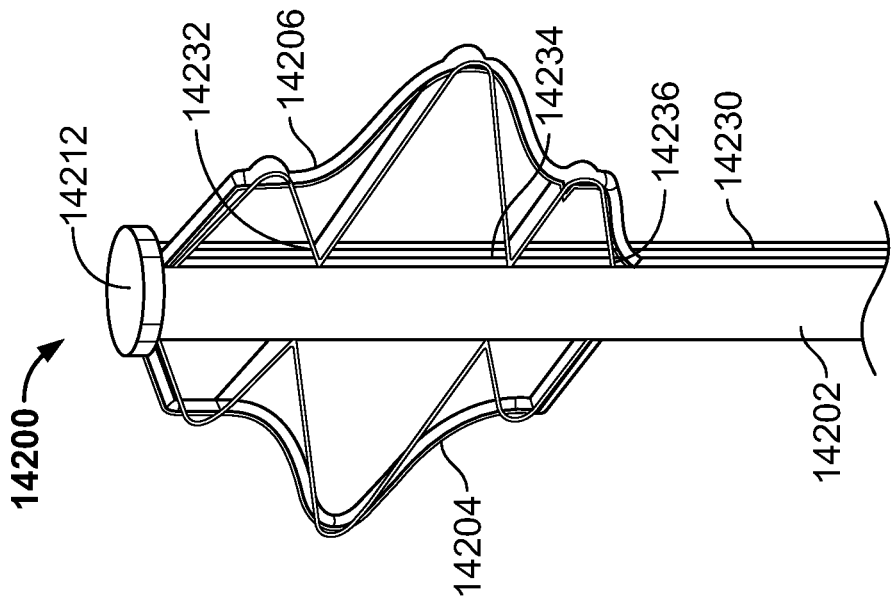

FIG. 143 shows illustrative apparatus in accordance with principles of the invention.

Figure 144:
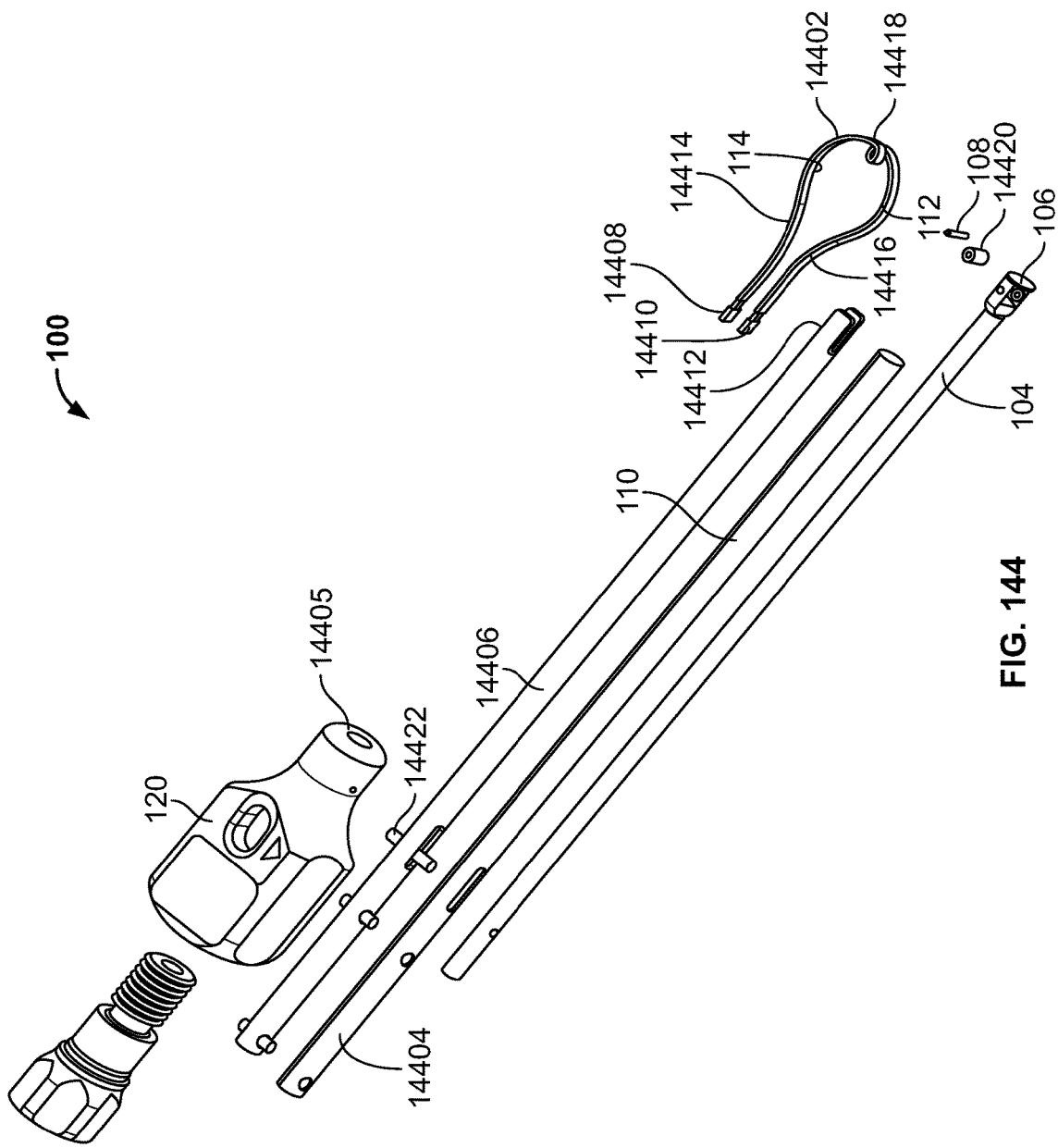

FIG. 144 shows illustrative apparatus in accordance with principles of the invention.

Figure 145:
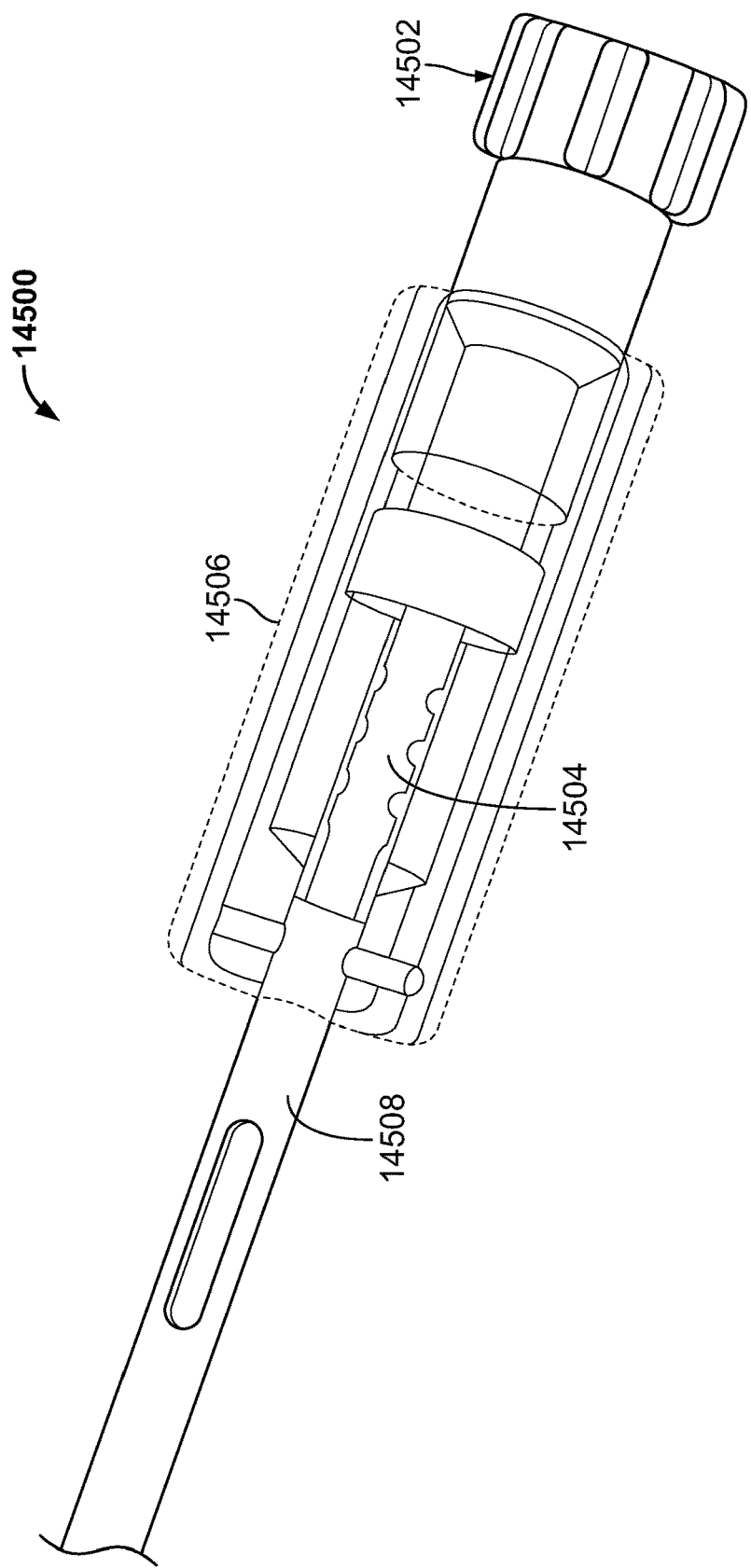

FIG. 145 shows illustrative apparatus in accordance with principles of the invention.

Figure 146:
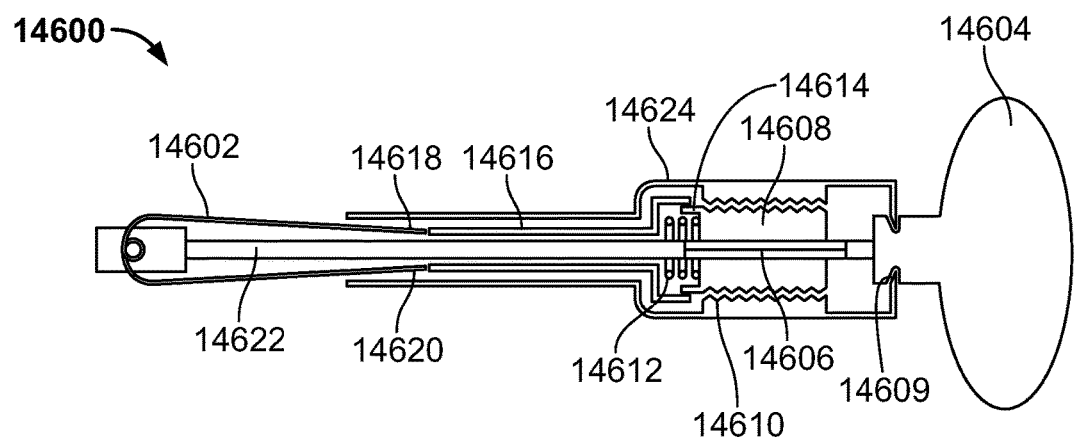

FIG. 146 shows illustrative apparatus in accordance with principles of the invention.

Figure 147:
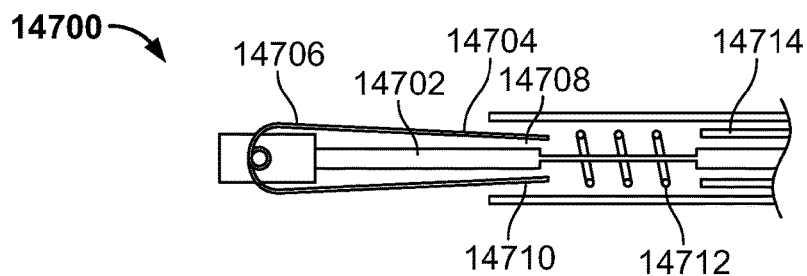

FIG. 147 shows illustrative apparatus in accordance with principles of the invention.

Figure 148A:
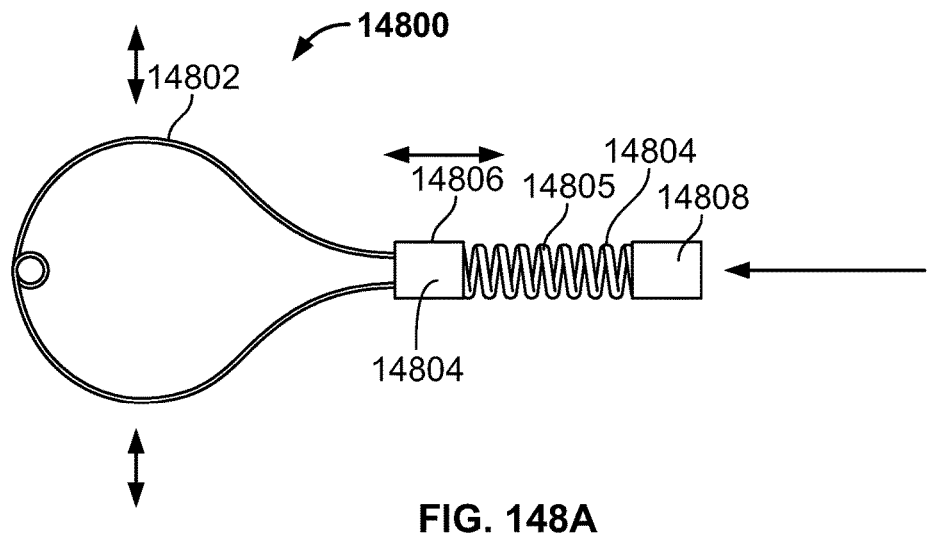

FIG. 148A shows illustrative apparatus in accordance with principles of the invention.

Figure 148B:
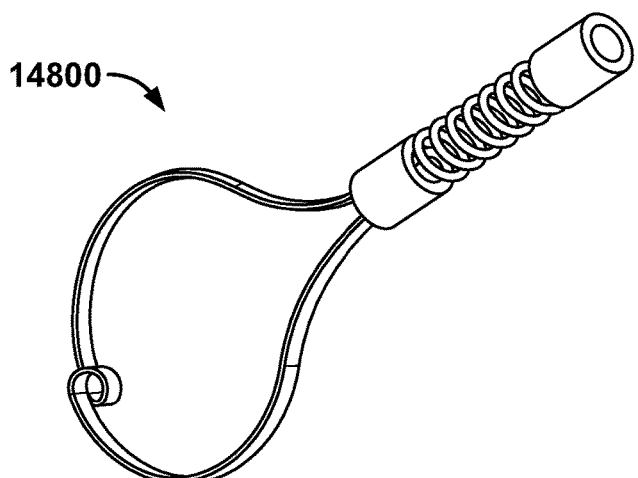

FIG. 148B shows illustrative apparatus in accordance with principles of the invention.

Figure 149:
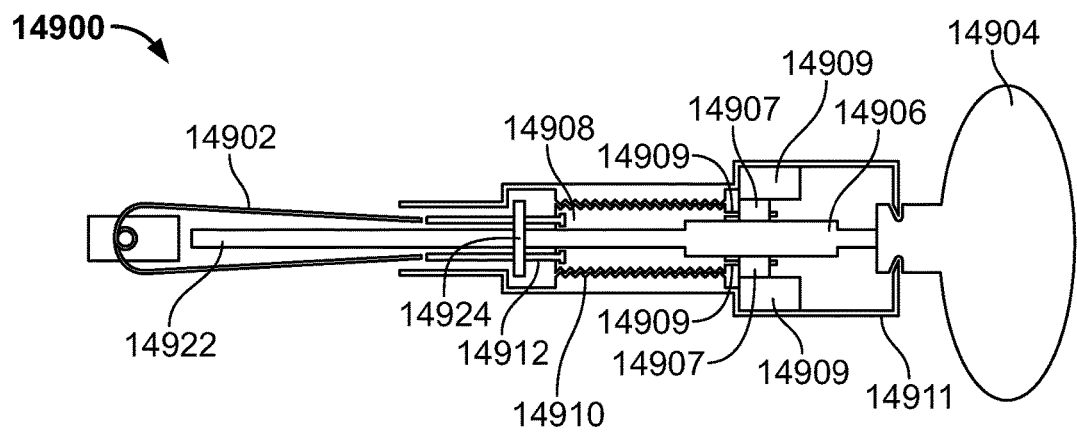

FIG. 149 shows illustrative apparatus in accordance with principles of the invention.

Figure 150:
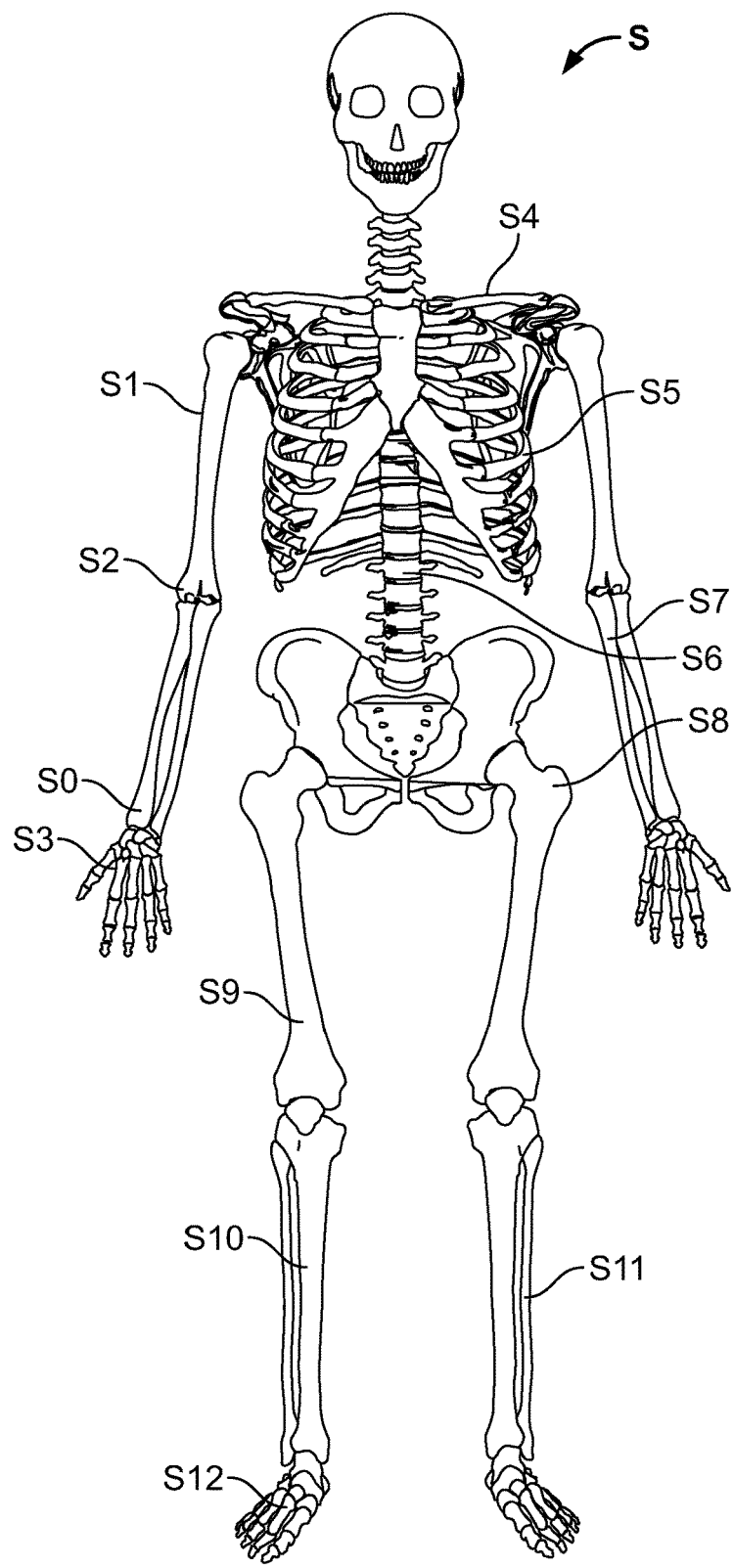

FIG. 150 shows illustrative anatomy in connection with which the invention may be practiced.

Figure 150A:
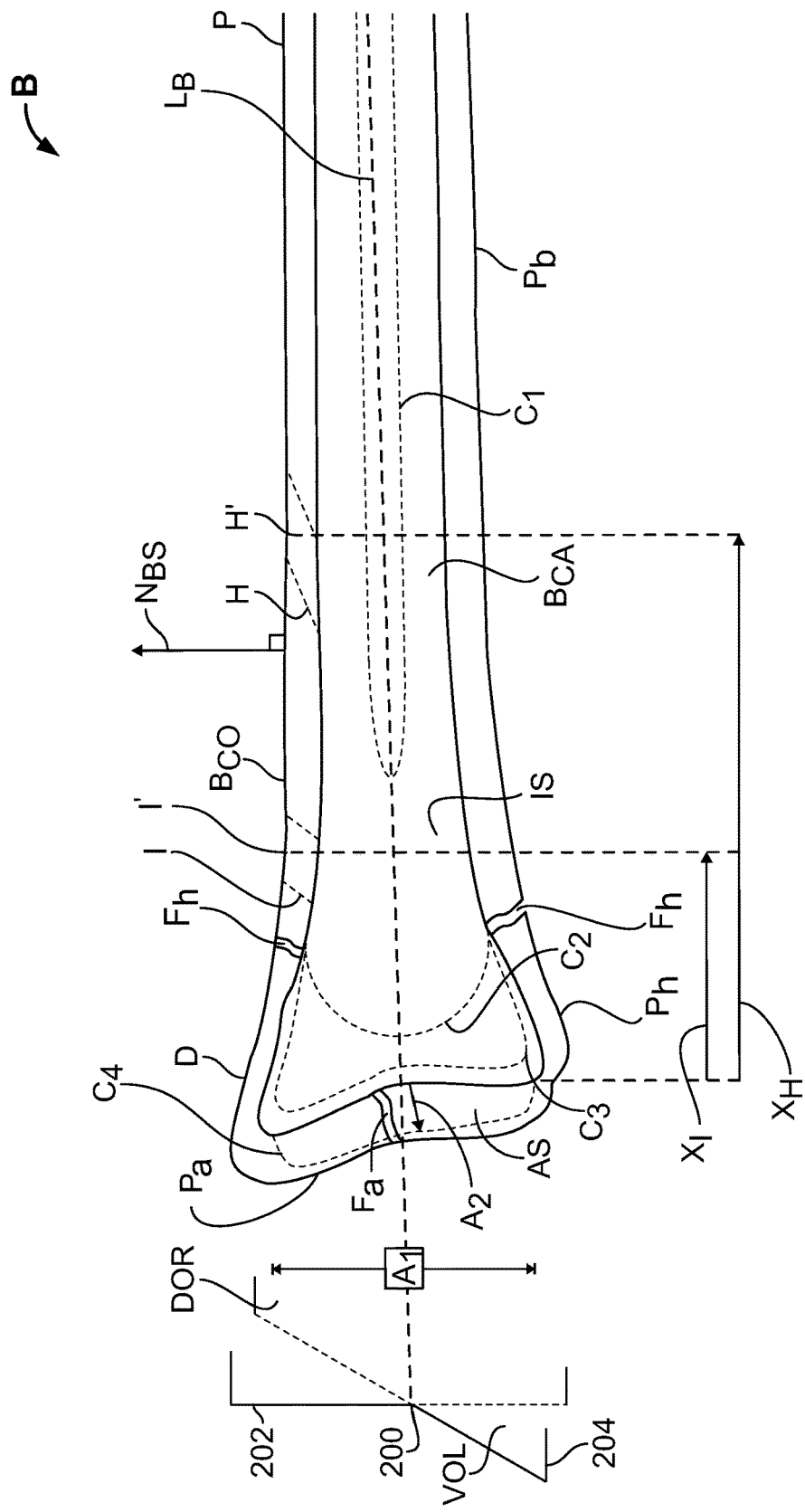

FIG. 150A shows illustrative anatomy in connection with which the invention may be practiced.

Figure 151:
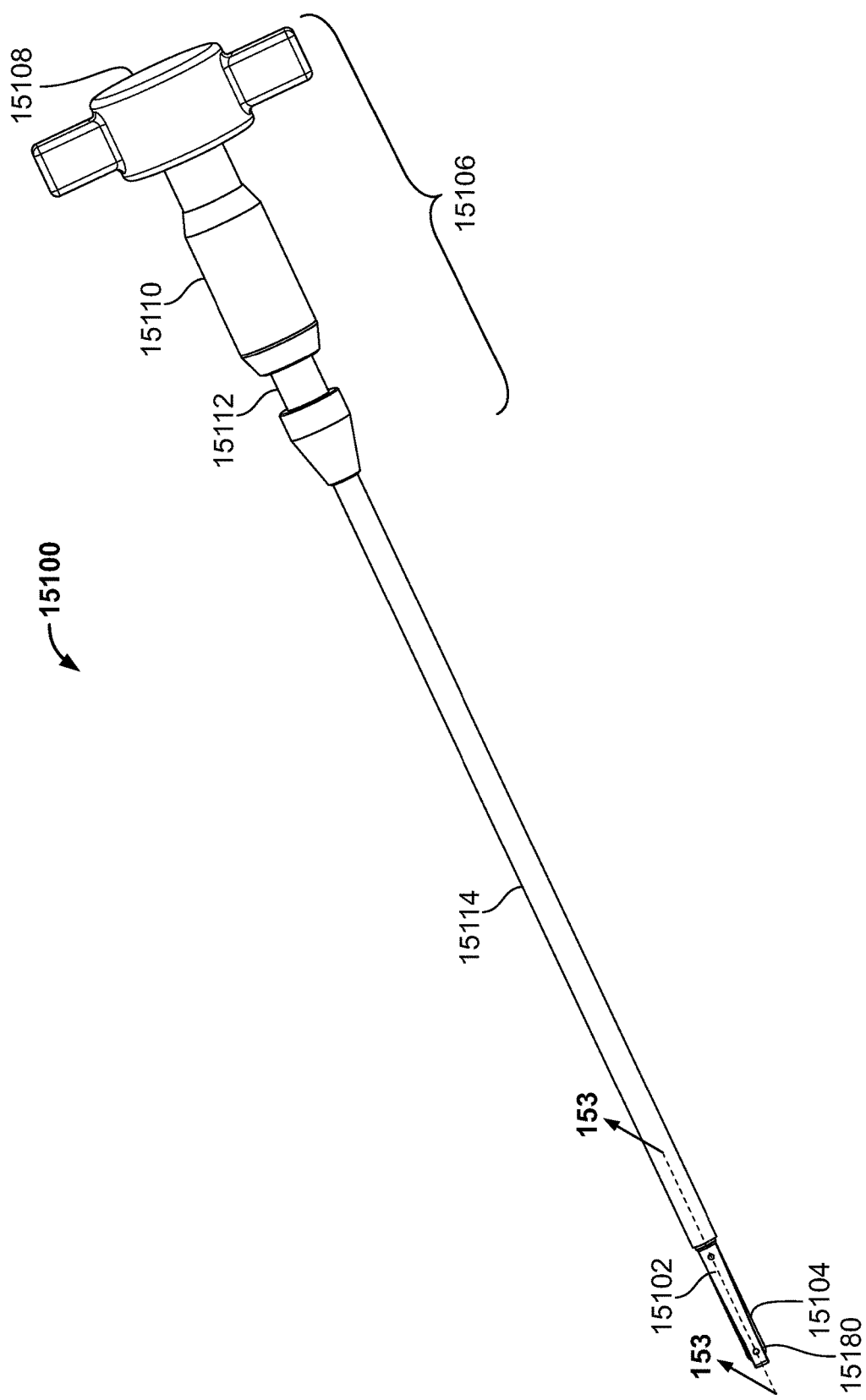

FIG. 151 shows illustrative apparatus in accordance with principles of the invention.

Figure 152:
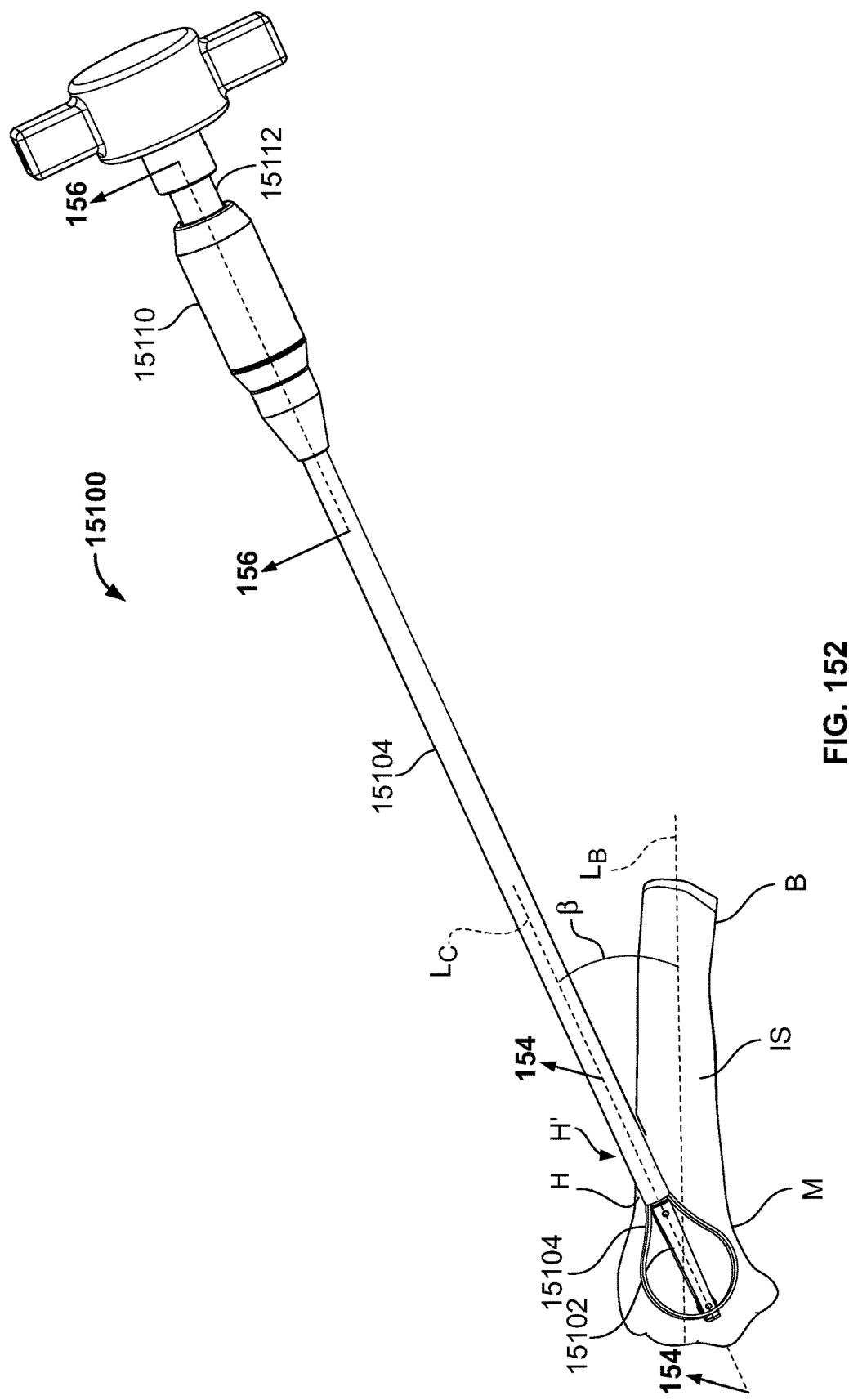

FIG. 152 shows illustrative apparatus in accordance with principles of the invention.

Figure 153:
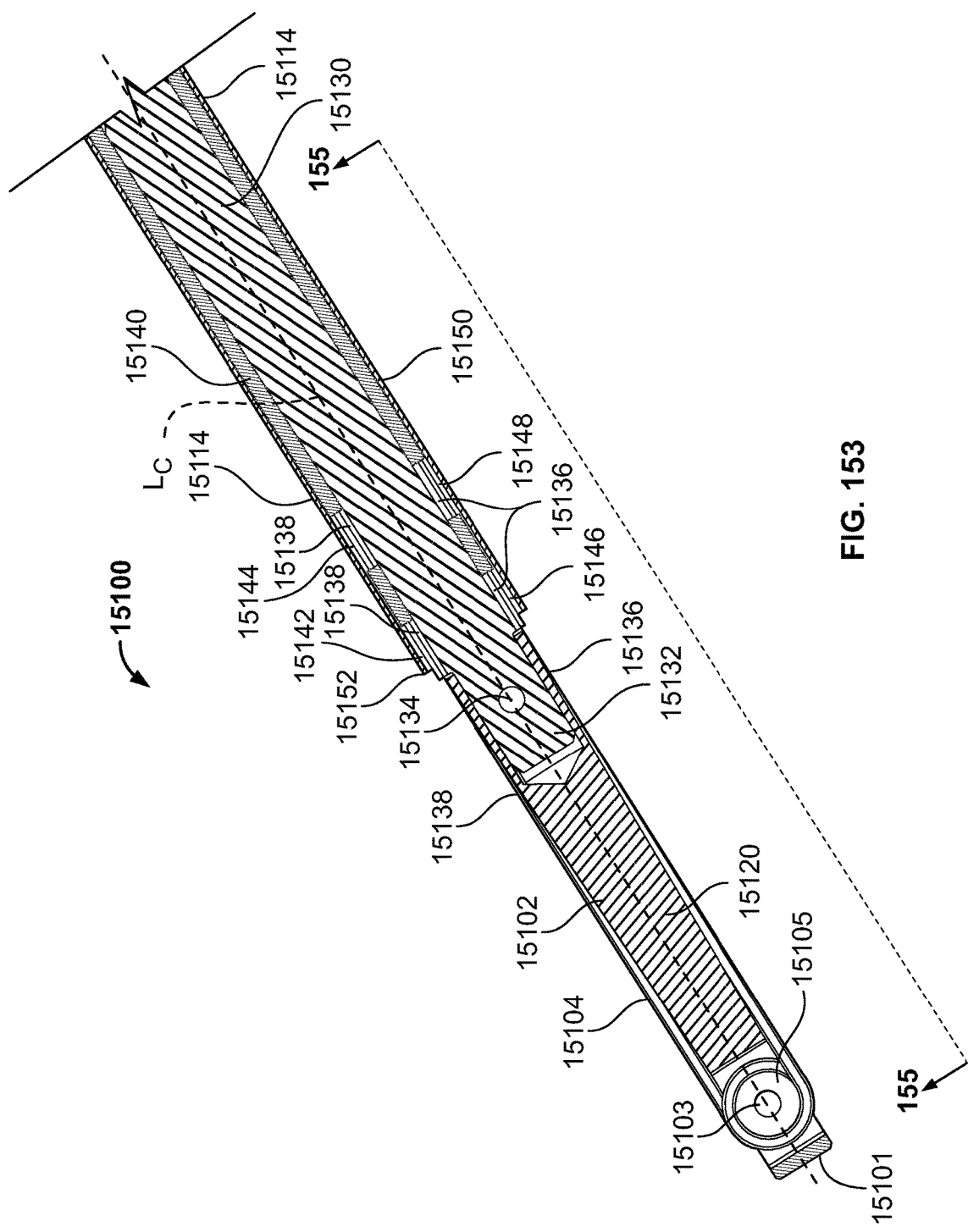

FIG. 153 shows a partial cross-sectional view of FIG. 151 taken along lines 153-153.

Figure 154:
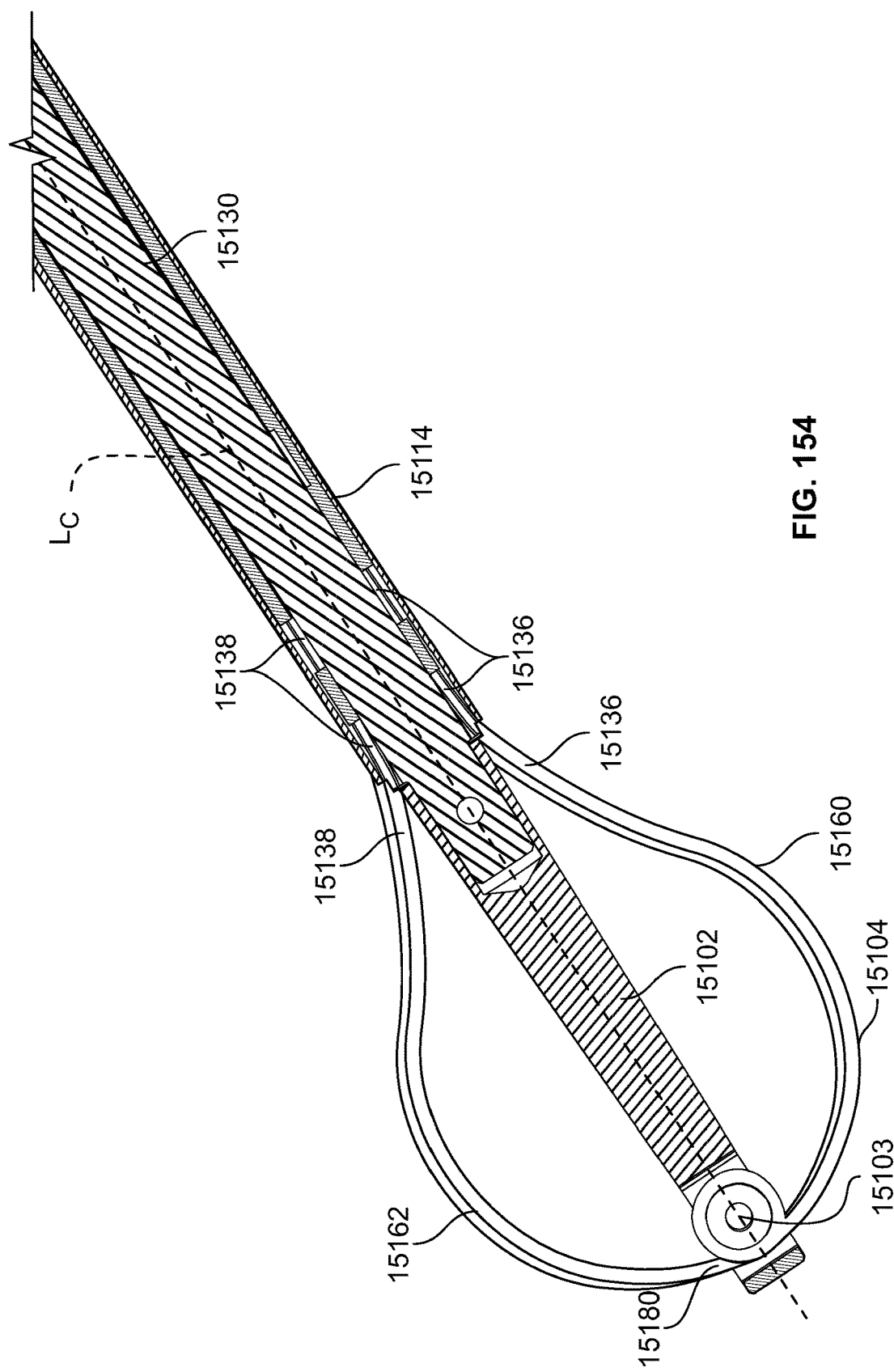

FIG. 154 shows a partial cross-sectional view of FIG. 152 taken along lines 154-154.

Figure 155:
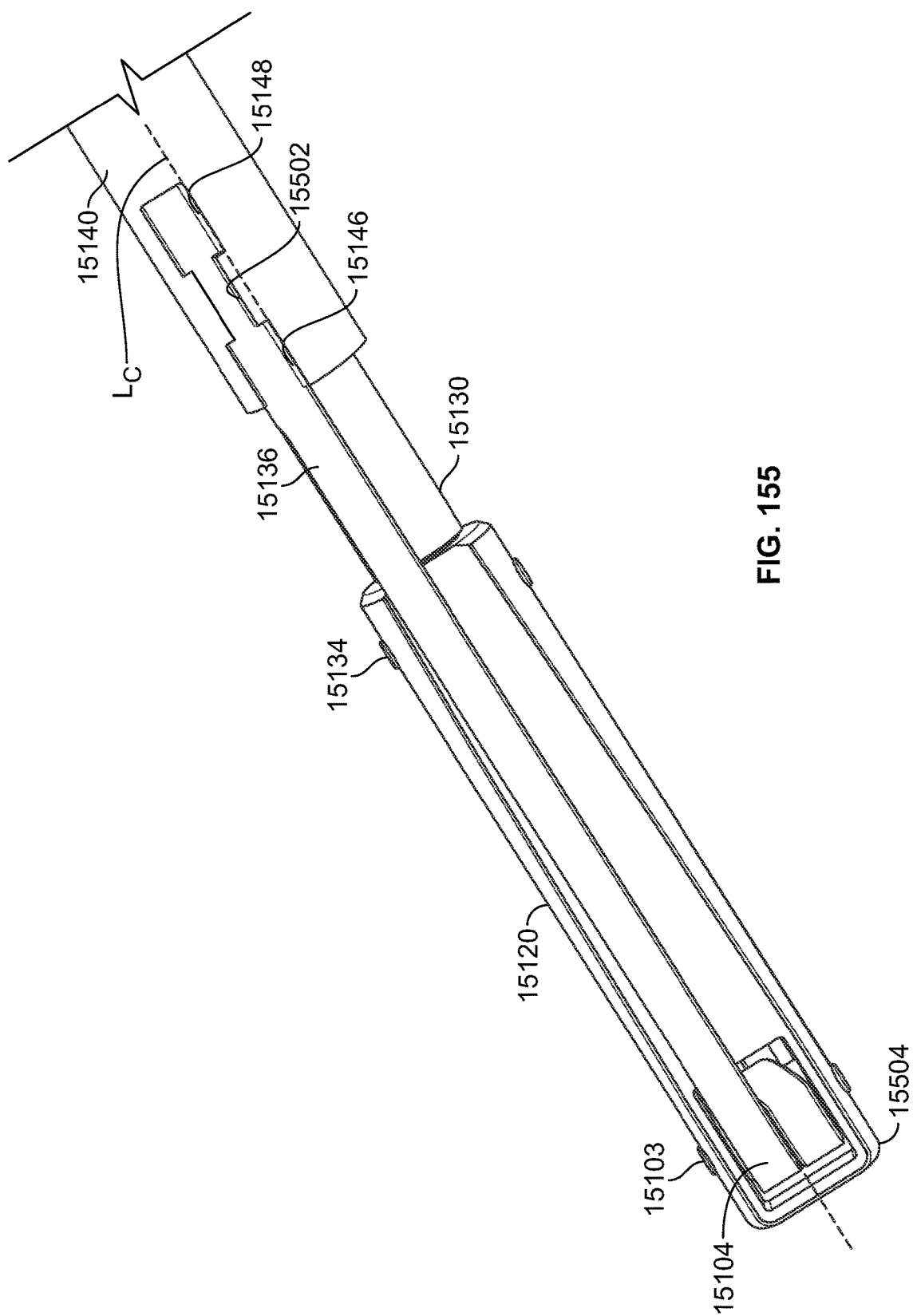

FIG. 155 shows illustrative apparatus in accordance with principles of the invention.

Figure 156:
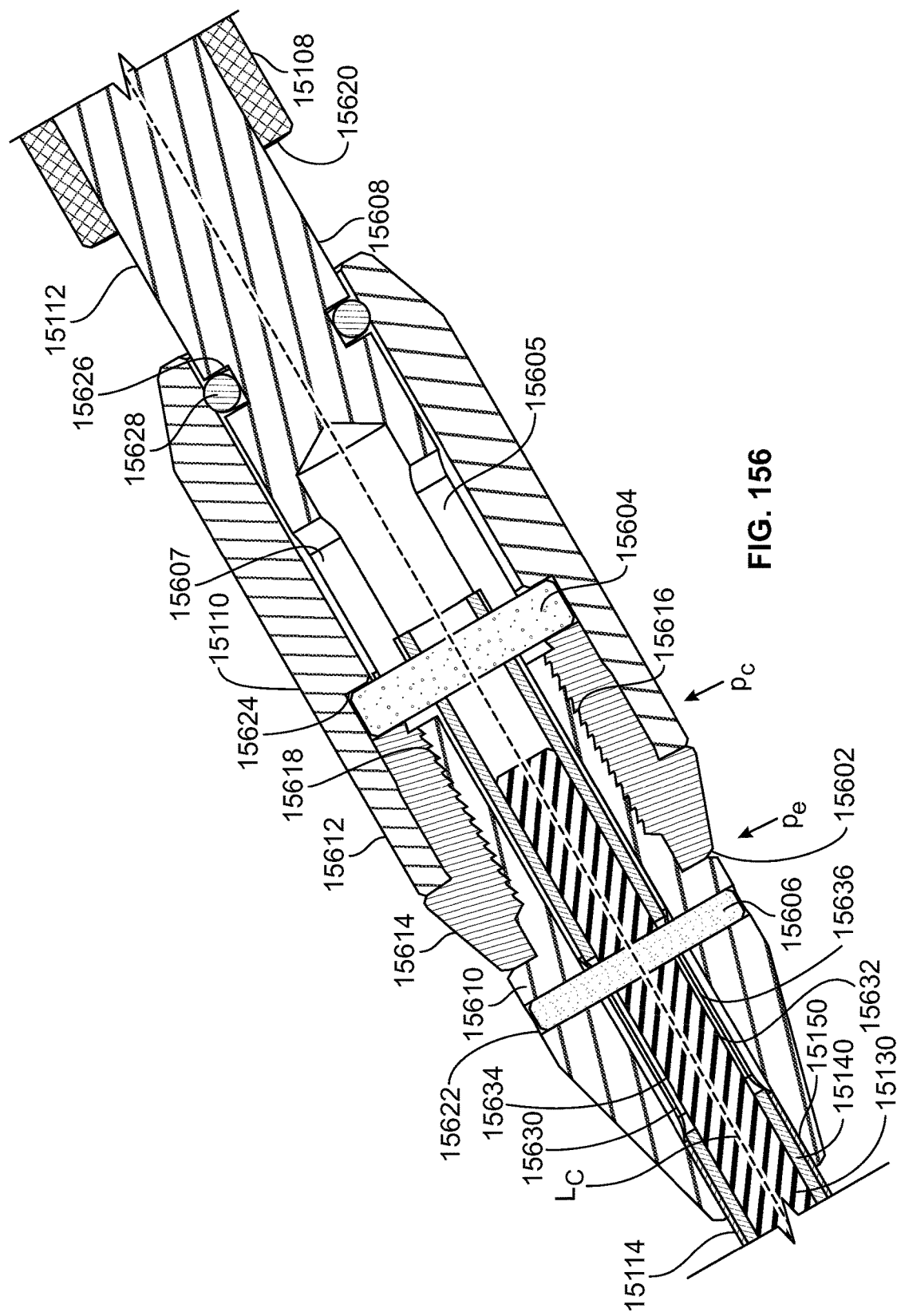

FIG. 156 shows illustrative apparatus in accordance with principles of the invention.

Figure 157:
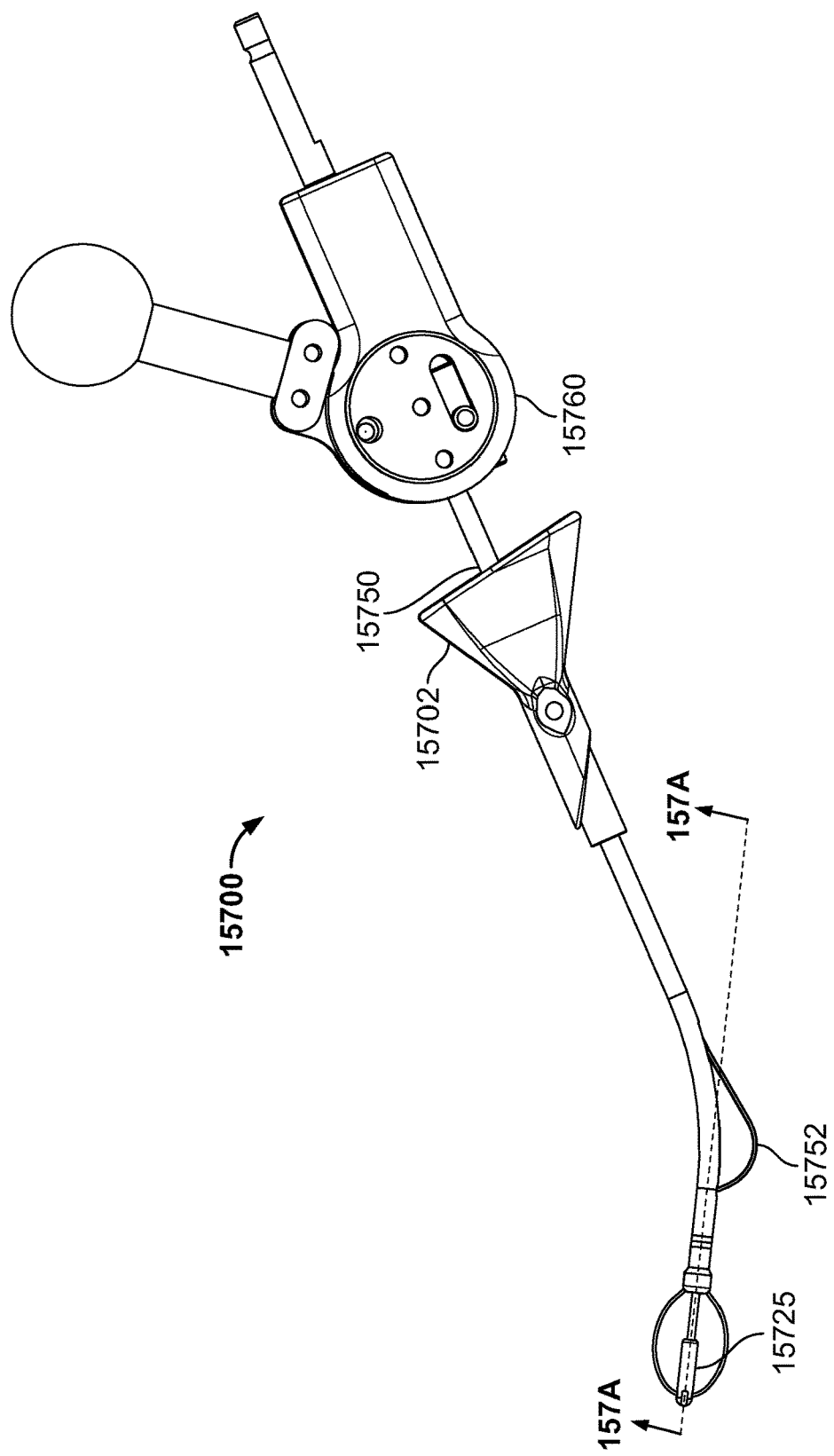

FIG. 157 shows illustrative apparatus in accordance with principles of the invention.

Figure 157A:
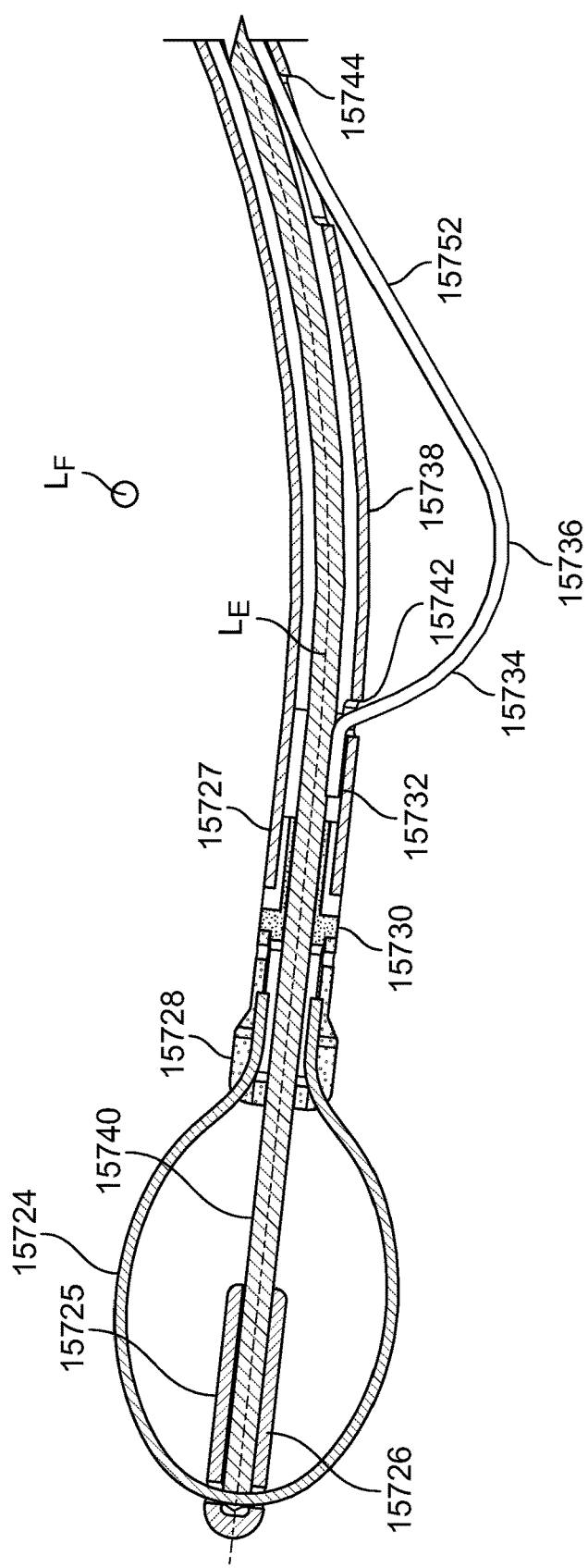

FIG. 157A shows a partial cross-sectional view of FIG. 157 taken along lines 157A-157A.

Figure 158:
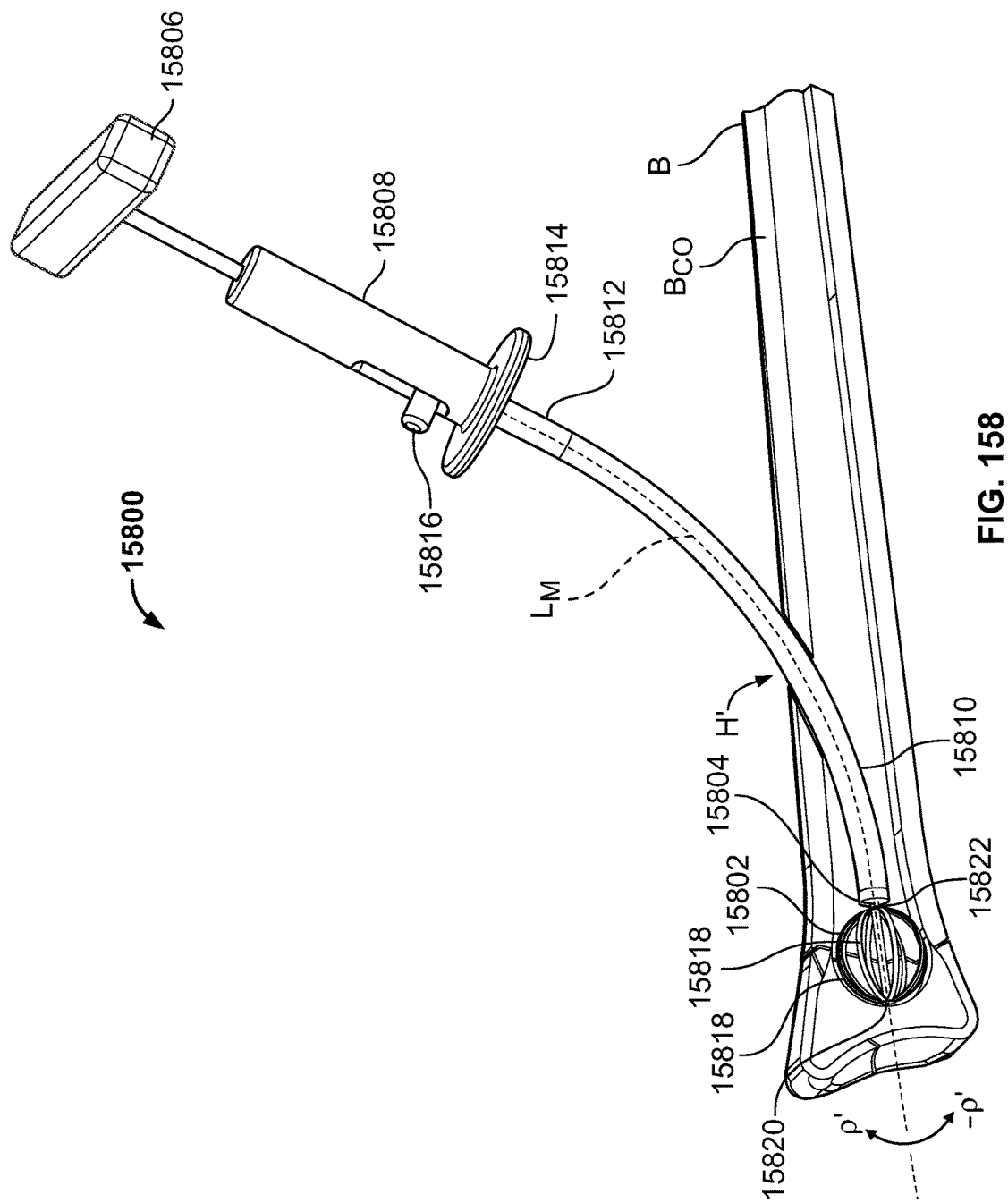

FIG. 158 shows illustrative apparatus in accordance with principles of the invention.

Figure 159:
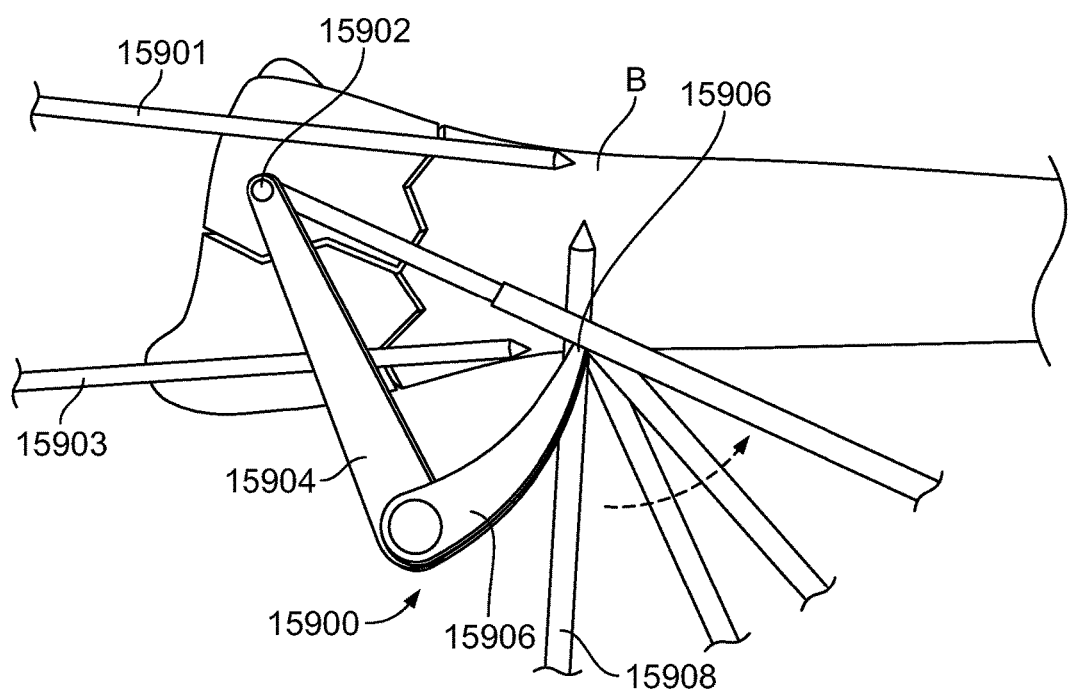

FIG. 159 shows illustrative apparatus in accordance with principles of the invention.

DETAILED DESCRIPTION OF THE INVENTION

Apparatus and methods for preparing the interior of a bone for therapy are provided. The therapy may include therapy for a bone fracture. The apparatus and methods may involve preparing an interior region of the bone for to receive a therapeutic device. The apparatus and methods may include one or more features of devices shown and described in U.S. Patent Application Publication No. 2011/0190832, which is hereby incorporated herein by reference in its entirety.

The therapeutic device may be a prosthetic device. For example, the surgical instrument may include one or more of the features of devices that are shown and described in U.S. Patent Application Publications Nos. 2009/0182336A1 and 2011/0178520, 2011/0218626 and 2011/0218585, which are hereby incorporated herein by reference in their entireties.

Apparatus and methods for broaching an interior region of a bone are provided. The bone may include first bone material. The first bone material may include cancellous bone. The first bone material may include fibrocartilage. The first bone material may include marrow tissue. The first bone material may include fibrocartilage and marrow tissue. The bone may include second bone material. The second bone material may include cortical bone. The second bone material may have a density that is higher than a density of the first bone material.

The apparatus may include a rotator. The apparatus may include a broaching member. The broaching member may be moved in the bone interior to displace, disaggregate, disintegrate, dislocate, excavate, abrade, cut or otherwise broach bone material. The broaching member may be rotated in the bone interior. The rotation may be continuous. The rotation may be pulsed. The rotation may be unidirectional. The rotation may alternate between a first rotational direction and a second rotational direction.

A broaching member may be provided with a twist, a bend or both. A twist or a bend may determine a broaching member's angle relative to the bone tissue. A twist or bend may increase the broaching member's tissue broaching efficiency when the broaching member is in the deployed state. Numerous devices are disclosed for presenting the broaching member to the tissue inside the bone and rotating the broaching member inside the bone.

Apparatus and methods for preparing a bone cavity are provided.

The apparatus may include a tissue cavity preparation tool.

The tool may include an elongated body having a sharp convex edge and in a relaxed state a substantially planar face. The tool may include an elongated rotator. The rotator may define a longitudinal axis. The rotator may be configured to retain a first end of the body and a second end of the body such that the first end is spaced longitudinally apart from the second and the face forms a cone-like surface.

"Cone-like surface" means: evokes a conical surface or part of a conical surface, but the radius of curvature in a plane orthogonal to the conical axis may be nonuniform within the plane and the slope of the radius versus the conical height may be nonuniform along the height.

The tool may include one or more blades, broaching members, tool elements, cages, and torque wrenches.

The elongated body may be a first elongated body. The sharp convex edge may be a first sharp convex edge. The planar face may be a first planar face. The cone-like surface may be a first cone-like surface. The tool may include a second elongated body that has a second sharp convex edge and in a relaxed state a second substantially planar face. The rotator may be configured to retain a first end of the second body and a second end of the second body such that the first end of the second body is spaced longitudinally apart from the second of the second body and the second face forms a second cone-like surface.

The second cone-like surface may be substantially identical to the first cone-like surface. The second cone-like surface may be a cone-like surface that is not identical to the first cone-like surface. The second cone-like surface may correspond to a greater apical angle than does the first cone-like surface. The second cone-like surface may correspond to a greater longitudinal distance from an apical angle than does the first cone-like surface.

The first body may be disposed about 180 around the longitudinal axis from the second body.

The first elongated body may be fixed to the rotator at a distal position and a first intermediate position. The second elongated body may be fixed to the rotator at a second intermediate position and a proximal position. The first and second intermediate positions may be longitudinally between the distal position and the proximal position.

The first elongated body may define a first central axis and have a first length along the first central axis. The second elongated body may define a second central axis and have a second length along the second central axis. The second length may be greater than the first length.

The first elongated body may have a first heat-set shape and the second elongated body may have a second heat-set shape. The second heat-set shape may be different from the first heat-set shape. The second heat-set shape may be substantially similar to the first heat-set shape.

The tool may include a first elongated controller. The first elongated controller may be configured to change a longitudinal distance between the first end of the first elongated body and the second end of the first elongated body. The tool may include a second elongated controller. The second elongated controller may be configured to change a longitudinal distance between the first end of the second elongated body and the second end of the second elongated body. A controller may include a tube, a rod, a strut, a wire or any other suitable elongated structure.

The tool may include a loop from which the first and second elongated bodies extend. The tool may include a coupler. The coupler may couple the loop to the rotator.

The coupler may include a transverse member that is transverse to the longitudinal axis. The transverse member may be supported by the rotator. The transverse member may engage the loop by passing through the loop.

The first elongated body, the second elongated body and the loop may be of monolithic construction. The loop may form a spirally wound spring. The loop may absorb strain from the elongated members when the elongated members are subjected to stress. The stress may be directed radially inward toward the rotator. The stress may be directed circumferentially about the rotator.

The tool may include an outer sleeve. The outer sleeve may be concentric with the rotator. The outer sleeve may be configured to slide axially along the longitudinal axis toward a distal end of the rotator.

The rotator may be flexible. The rotator may be rigid.

The elongated body may define a central axis. The first end may be disposed at an angular displacement, about the central axis, from the edge, when the edge is in a relaxed state. The rotator further may define a radial direction that is orthogonal to the longitudinal direction and is configured to retain the first end in an orientation substantially normal to the radial direction.

The angular displacement may be a first angular displacement. The second end may be disposed at a second angular displacement, about the central axis, from the edge, when the edge is in a relaxed state. The elongated support may be configured to retain the second end in an orientation substantially normal to the radial direction.

The second angular displacement may be about equal in magnitude to the first angular displacement. The second angular displacement may be greater than the first angular displacement. The second angular displacement may be opposite in direction from the first angular displacement. The second angular displacement may be in the same direction as the first angular displacement.

The elongated body may define a central axis that runs through the center of the body. The plane may be a first plane. The second end may define a second plane that is oriented at an angular displacement, about the axial direction, from the first plane.

The broaching member may include a loop. The first end of the first elongated body and a first end of the second elongated body together may form the loop. The fastener may engage the loop.

The loop may have a first width. The first elongated body may have a second width. The second elongated body may have the second width. The second width may be greater than the first width.

The stress may be directed radially inward toward the rotator. The stress may be directed circumferentially about the rotator.

The coupler may include a transverse member that is transverse to the longitudinal axis, is supported by the rotator, and engages the loop by passing through the loop.

The tool may include a first stud oriented transverse to the longitudinal axis and fixed to the support. The tool may include a second stud oriented transverse to the longitudinal axis and fixed to the support offset longitudinally from the first stud. The tool may include a first broaching member. The first broaching member may include a first wrap section that is wrapped about the first stud. The first broaching member may include a first bowed blade extending from the first wrap section and coupled to the support at a first location longitudinally offset from the first stud. The first broaching member may include a second bowed blade extending away from the first wrap section and coupled to the support at a second location. The tool may include a second broaching member. The second broaching member may include a second wrap section that is wrapped about the second stud. The second broaching member may include a third bowed blade extending away from the second wrap section and coupled to the support at a third location longitudinally offset from the second stud. The second broaching member may include a fourth bowed blade extending away from the second wrap section and coupled to the support at a fourth location.

The first location may be substantially opposite the second location. The third location may be substantially opposite the fourth location. The first location may be longitudinally offset along the longitudinal axis from the second location. The third location may be longitudinally offset along the longitudinal axis from the fourth location.

The first bowed blade and the second bowed blade each may have a first heat-set shape. The third bowed blade and the fourth bowed blade each may have a second heat-set shape different from the first heat memory shape.

A first plane may intersect the first location and the second location. A second plane may intersect the third location and the fourth location. The second plane may form an intersection with the first plane within the elongated support.

The planes may intersect at a about ninety degrees. The planes may intersect at an angle that is between about 60 and about 90 degrees. The planes may intersect at an angle that is between about 30 and about 60 degrees. The planes may intersect at an angle that is between about 5 and about 30 degrees.

The support may include an outer tube; a middle tube that is disposed within and is coaxial with the outer tube and includes the first location and the second location; and an inner tube that is disposed within and is coaxial with the middle tube and includes the third location and the fourth location. The outer tube and the middle tube may be coaxial with the inner tube. The middle tube and the inner tube may be configured to be longitudinally displaced along the longitudinal axis.

The methods may include a method of manufacturing a broaching tool. The method may include one or more of selecting a rake angle; selecting a relief angle; providing in a planar blade body a first curved edge and a second curved edge, the first curved edge defining a radius of curvature parallel to the plane of the body, the second curved edge set apart a predetermined distance across a width of the body from the first curved edge; bending the planar body to define a conical axis, a face of the body forming a substantially conical surface that corresponds to the axis, a segment of the second curved edge forming the rake angle and the relief angle; fixing a first end of the body to a support; fixing a second end of the body to a support; and displacing the first end from the second end to draw the body toward the support.

The forming may include configuring the segment to provide the rake angle and the relief angle upon deployment inside tissue.

The body may be included in a broaching head. The configuring may be defined by expansion of the broaching head about the support.

The method may include one or both of forming a loop in the body and supporting the loop at a distal end of the support. The fixing of the first end may include fixing the first end proximal the loop. The fixing of the second end may include fixing the second end proximal the loop.

The method may include twisting the first end about a central axis relative to the segment prior to fixing the first end to the support. The method may include twisting the second end about a central axis relative to the segment prior to fixing the first end to the support.

The tool may include a plurality of broaching members, one or more of the broaching members having a compliance selected such that the one or more broaching members, when applied to a first tissue having a first density, deflect from the first tissue and, when applied to a second tissue having a second density, the second density being lower than the first density, displace the second tissue, the plurality of broaching members being formed from a unitary article. The unitary article may include a monolithic blank. Each of the one or more broaching members may define a cross-section that varies longitudinally. Each of the one or more broaching members may define a rake angle that varies longitudinally.

Each of the one or more broaching members may define a relief angle that varies longitudinally. Each of the one or more broaching members may include a sharpened edge.

Each broaching member may thus define at a point along the broaching member a conical or cone-like profile. The profile may define an apical cone angle. The apical cone angle may vary longitudinally along the broaching member.

The edge may include edge angle. The edge angle may be in one of the following ranges: not less than about 5 degrees and not more than about 70 degrees; not less than about 5 degrees and not more than about 10 degrees; not less than about 10 degrees and not more than about 15 degrees; not less than about 15 degrees and not more than about 20 degrees; not less than about 20 degrees and not more than about 25 degrees; not less than about 25 degrees and not more than about 30 degrees; not less than about 30 degrees and not more than about 35 degrees; not less than about 35 degrees and not more than about 40 degrees; not less than about 40 degrees and not more than about 45 degrees; not less than about 45 degrees and not more than about 50 degrees; not less than about 50 degrees and not more than about 55 degrees; not less than about 55 degrees and not more than about 60 degrees; not less than about 60 degrees and not more than about 65 degrees; and not less than about 65 degrees and not more than about 70 degrees.

The tool may include a support defining a central axis and a distal end; and an end cap coupled to the support at the distal end. Each of the broaching members may include a first end and a second end. The first end may be coupled to the end cap and the second end may be coupled to the support. The second end of the broaching members may be coupled to the support at different positions along the central axis of the support.

The tool may include a first end member at a first end of the body. The first end member may include a face disposed at an angular displacement, about the central axis, from the edge, when the edge is in a relaxed state. The elongated member may define orthogonal longitudinal and radial directions. The support may be configured to retain the first end member of the body spaced longitudinally apart from a second end member, opposite the first end member, of the body to bow the body radially away from the support. The support may be configured to retain the face in an orientation substantially normal to the radial direction.

The face may be a first face. The angular displacement may be a first angular displacement. The second end member may include a second face that is disposed at a second angular displacement, about the central axis, from the edge, when the edge is in a relaxed state; and the elongated support may be configured to retain the second face in an orientation substantially normal to the radial direction.

The second angular displacement may be about equal in magnitude to the first angular displacement. The second angular displacement may be greater than the first angular displacement. The second angular displacement is opposite in direction from the first angular displacement. The second angular displacement may be in the same direction as the first angular displacement. The sharp edge is a sharp convex edge, the body defining a plane that is parallel to a face of the body when the body is in a planar configuration. The support may retain the first end member of the body spaced apart from the second end member the face of the body forms a substantially cone-like configuration.

The second end member may be coupled to a wrap section. The second end member may extend away from the wrap section. The wrap section may include wire that is wrapped about a transverse member coupled to the rotator.

In some embodiments, the wire may include a ribbon. In some embodiments, the wire may have a rectangular transverse cross-section.

The first end of the elongated body may be coupled to the wrap section. The first end of the elongated body may extend away from the wrap section. The second end may be retained by the support.

The wire and the second elongated body may be of monolithic construction.

The first elongated body may have a first length. The second elongated body may have a second length that is different from the first length.

The first elongated body may have a first-heat-set shape. The second elongated body may have a second heat-set-shape that is different from the first heat-set shape.

The support may define a central axis; and the first body may be substantially opposite the second body with respect to the central axis.

The first end member of the first body may be fixed to the rotator at a first position. The second end of the second body may be fixed to the rotator at a second position. The second position may be longitudinally offset along the central axis of the support from the first position.

The tool may include an outer sleeve that is concentric with the support. The outer sleeve may be configured to slide axially along a central axis of the support towards a distal end of the support.

The tool may include a first activation mechanism that is configured to adjust a longitudinal distance along a central axis (defined by the support) between the first end member of the first body and the second end member of the first body. The tool may include a second activation mechanism configured to adjust a longitudinal distance along the central axis between the first end of the second body and the second end of the second body.

The support may be flexible. The support may be rigid.

The wire may have a first width. Each of the first body and the second body may have a second width. The first width may be smaller than the second width.

The apparatus may include a tissue cavity preparation tool. The tool may include an elongated body having a sharp edge and a trailing edge, the body defining a central axis and including one or more of: a first end fixed to a support; a second end fixed to the support; and a bowed portion spanning from the first end to the second end. The body may be rotated about the central axis by an angular displacement that is greater at the bowed portion that at the first end or the second end.

The elongated body may have a sharp edge and a trailing edge, the body defining an axial direction and including: a first end fixed to a support; a second end fixed to the support; and a bowed portion spanning from the first end to the second end; wherein the body is rotated about the axial direction by an angular displacement that is greater at the bowed portion that at the first end or the second end.

The methods may include a method of creating a cavity in bone tissue. The cavity may have a predetermined shape. The method may include: inserting a cavity preparation tool disclosed herein in the tissue; expanding the tool; rotating the tool; contracting the tool; and withdrawing the tool from the tissue.

The rotating may include rotating a blade body segment less than a full revolution about an axis of the tool so that the blade body segment forms a cavity that is not radially symmetrical about the axis; and, at the time of the withdrawing, the cavity is not radially symmetrical about the axis.

The rotating may include one or more of: rotating a first blade body segment about an axis of the tool to form a first cavity portion; rotating a second blade body segment about an axis of the tool to form a second cavity portion; and, the first and second cavity portions being substantially symmetrical about a plane normal to the axis and between the first and second cavity portions.

The apparatus may include an expandable cage for deployment in an intramedullary space. The cage may include an outer mesh. The cage may include an inner mesh. The inner mesh may be disposed inside the outer mesh. The cage may include a support that is coupled to the outer mesh. The support may be coupled to the inner mesh. The cage may include a broaching member. The broaching member may include one or more of the features of the broaching member described above.

Each of the inner mesh and the outer mesh may include a plurality of interconnected cells. The interconnected cells of the inner mesh may be defined by one or more inner mesh segments. The interconnected cells of the outer mesh may be defined by one or more outer mesh segments. The broaching member may extend outward from within the outer mesh through a first cell of the outer mesh. The broaching member may extend inward through a second cell of the outer mesh.

The outer mesh may include an outer mesh proximal end and an outer mesh distal end. The inner mesh may include an inner mesh proximal end and an inner mesh distal end. The support may include a support proximal end and a support distal end. The outer mesh distal end and the inner mesh distal end may be coupled to the support distal end. The inner mesh proximal end and the outer mesh proximal end are coupled to the support proximal end.

A portion of the inner mesh segments may be in direct contact with a portion of the outer mesh segments. The inner mesh may include a longitudinally intermediate region that is between the inner mesh proximal end and the inner mesh distal end. The longitudinally intermediate region may include the inner mesh portion. In regions distal the portion and proximal the portion the inner and outer meshes are not in direct contact with each other.

The inner mesh may be constructed from a first laser-cut tube. The outer mesh may be construed from a second laser-cut tube.

The inner mesh may be self-expanding. The outer mesh may be self-expanding.

The support may be configured to be coupled to a proximal end of a rotator. The rotator may define a longitudinal axis. The rotator may include a first control handle configured to rotate the cage about the longitudinal axis and translate the cage along the longitudinal axis. The rotator may include a second control handle configured to expand the cage about the support. The rotator may include a control handle that is configured to rotate the cage about the longitudinal axis, translate the cage along the longitudinal axis and expand the cage about the support The support may be configured to be decoupled from the rotator.

The support may include at least one hole that configured to receive a fixation device, such as a screw or other suitable anchor, for fixing the cage in the intramedullary space.

The broaching member may include a ribbon. The ribbon may be a wire ribbon. The broaching member may include a wire. The broaching member may include a cutting edge.

The first cell and the second cell may be contiguous with each other. The first cell and the second cell may be cells that are not contiguous with each other.

The methods may include a method for implanting an implant in a bone. The method may include one or more of: drilling a hole in the bone; inserting an expandable cage such as an expandable cage disclosed herein through the hole into an intramedullary space of the bone; expanding the outer mesh and the inner mesh; preparing a cavity in the intramedullary space by rotating the cage in the space; detaching the rotator from the outer mesh and the inner mesh; and removing the rotator from the bone.

The rotating and the expanding may be performed simultaneously.

The apparatus may include an expandable cage for deployment in an intramedullary space. The cage may include an outer mesh. The outer mesh may define an outer mesh surface. The cage may include an inner mesh. The inner mesh may be positioned inside the outer mesh. The cage may include a support. The support may be coupled to the outer mesh and the inner mesh. The support may include a broaching member. The broaching member may be woven through the outer mesh surface.

Each of the inner mesh and the outer mesh may include a plurality of interconnected cells. The interconnected cells of the inner mesh may be defined by one or more inner mesh segments. The interconnected cells of the outer mesh may be defined by one or more outer mesh segments.

The broaching member may extend along a proximal-distal meridian of the cage. The broaching member may extend at an angle that is oblique to a proximal-distal meridian of the cage. The broaching member may include a cutting edge. The broaching member may be connected to the outer mesh by one or more connectors.

Each of the outer mesh interconnected cells may define an opening. The broaching member may be interlaced through the openings.

The outer mesh proximal end may be coupled to a support proximal end. The outer mesh distal end may be coupled to a support distal end. The broaching member may include one or more of: a first end coupled to the support proximal end; a second end coupled to the support distal end; and a span section that includes a cutting edge interlaced through the openings. The broaching member may include one or more of: a first end; a second end; and a span section. The span section may include a cutting edge. The span section may be interlaced through the openings. The span section may distally pass over the support distal end. The first end may be coupled to the support proximal end at a first location. The second end may be coupled to the support proximal end at a second location. The first location may be, relative to the support, diametrically opposite the second location.

The span section may extend along an outer mesh surface along a proximal-distal meridian of the cage. The span section may extend along an outer mesh surface at an angle that is oblique to a proximal-distal meridian of the cage.

The cage may include a second broaching member. The first broaching member may be interlaced through a first opening; and the second broaching member may be interlaced through a second opening.

The cage may include a support proximal end that may be coupled to a proximal end of the outer mesh. The cage may include a support distal end that may be coupled to a distal end of the outer mesh. The first cutting wire may include one or more of: a first proximal end; a first distal end; and a first span section. The first span section may include a cutting edge. The second cutting wire may include: a second proximal end; a second distal end; and a second span section. The second span section may include a cutting edge. The first proximal end and the second proximal end may be coupled to the support proximal end; and the first distal end and the second distal end may be coupled to the support distal end.

The first proximal end may be, relative to the support, diametrically opposite the second proximal end.

Each of the first span section and the second span section may extend at an angle oblique to a proximal-distal meridian of the cage. Each of the first span section and the second span section may extend along a proximal-distal meridian of the cage.

The outer mesh may include two or more nodes. Each node may be defined by an intersection of four of the segments. Each of the nodes may define an opening. The broaching member may be threaded through two or more of the openings.

A proximal end of the broaching member may be coupled to a support proximal end. A distal end of the broaching member may be coupled to a support distal end. A broaching member span section, which may include a cutting edge, may be threaded through two or more openings along a proximal-distal meridian of the cage.

The broaching member span section may include first segments having first thicknesses; and second segments having second thicknesses, the second thicknesses being smaller than the first thicknesses. The second segments may be disposed along the broaching member span section where the span section extends through the openings.

The outer mesh may support a plurality of projections that extend away from the central axis. The projections may be integral with the outer mesh. A projection may be disposed at a node between mesh segments. The projections may be attached to the outer cage at a node between mesh segments. The projections may project radially outward from the cage. The projections may lie in a plane that includes a longitudinal axis of the cage. One or more of the projections may include a cutting edge.

One or more of the outer mesh segments may include one or more cutting edges. One or more of the outer mesh segments may be twisted about a mesh segment central axis to provide each of the cutting edges with a rake angle and a relief angle.

The cage may include one or more of: a central axis member coupled to the mesh distal end; a support coupled to the mesh proximal end; and a broaching member interlaced through the openings.

The apparatus may include an expandable cage for deployment in an intramedullary space. The cage may include one or more of: a mesh having a mesh proximal end and a mesh distal end, the mesh including a plurality of interconnected cells, the interconnected cells being defined by one or more mesh segments; a support coupled to the mesh proximal end and the mesh distal end, the support defining a central axis; and a plurality of projections that extend away from the central axis member, the projections supported by and extending from the mesh.

The apparatus may include an expandable cage for deployment in an intramedullary space. The cage may include one or more of: a mesh having a mesh proximal end and a mesh distal end; a central axis member coupled to the mesh distal end; and a support coupled to the mesh proximal end. The mesh may include a plurality of interconnected cells, the interconnected cells being defined by one or more mesh segments. The mesh segments may include a cutting edge.

The methods may include a method for providing a rake angle and a relief angle in a segment of an intramedullary broach. The method may include one or more of: providing a tube defining a central axis and having a first end and a second end; aligning the central axis orthogonal to, but offset from, a cutting laser beam; and cutting the tube, with the laser beam, in a direction parallel to the central axis.

The method may include one or more of: rotating the tube about the central axis by an angular displacement; and cutting the tube with the laser beam, in the direction, while maintaining the offset.

The method may include recursively repeating the rotating and the cutting until there are substantially evenly spaced cuts along a circumference of the tube. The method may include recursively repeating the rotating and the cutting until there are substantially evenly spaced cuts along substantially all of a circumference of the tube.

The method may include recursively repeating the rotating and the cutting 10 to 15 times. The method may include recursively repeating the rotating and the cutting 15 to 20 times. The method may include recursively repeating the rotating and the cutting more than 20 times.

On an outer surface of the tube, each of the plurality of cuts may span a length of the tube between the first end and the second end. Each of the plurality of cuts may have a cut length that is smaller then the length of the tube.

The method may include sizing the cut to leave an annular rim at the first end. The method may include sizing the cut to leave an annular rim at the second end.

The method may include compressing the tube between the two ends to expand the broach radially relative to the central axis. The broach may be monolithic.

The tube may include a middle. The cutting may be performed from the first end of the tube to the second end of the tube. The cutting may include one or more of: rotating the tube, during the cutting, about the central axis an increasing angular displacement until the cutting reaches the middle of the tube; and, when the cutting reaches the middle of the tube, counter rotating the tube, during the cutting, about the central axis a decreasing angular displacement until the cutting reaches the second end of the tube.

The apparatus may include a cutting tool. The tool may include: a plurality of elongated members, each of the elongated members including: a distal end; a proximal end; and an edge, the edge having a twist along an elongated member central axis forming a rake angle and a relief angle; a distal hub attached to the distal end of each of the elongated members; and a proximal hub attached to the proximal end of each of the elongated members; wherein the elongated members, the distal hub and the proximal hub are formed from process including one or more of: providing a tube defining a central axis and having a proximal end and a distal end; aligning the central axis orthogonal to, but offset from, a cutting laser beam; and cutting the tube, with the laser beam, in a direction parallel to the central axis.

The cutting tool may be self-expanding. The distal hub and the proximal hub may be connected to each other by a cutting tool head. The proximal hub may be coupled to an actuator. When the actuator retracts the cutting tool, the cutting tool may form the shape of a tube. The tube may include longitudinal cuts. The tube may include cuts that are oblique to the longitudinal axis of the tube.

The apparatus may include a cavity preparation tool. The cavity preparation tool may include a central support member. The central support member may define a central axis.

The tool may include a broaching member. The broaching member may be wrapped circumferentially about the central support member. The broaching member may include a base fixed to the central support member. The broaching member may include a free end including a cutting edge. The tool may include a capture sheath coaxial with the central support member. The capture sheath may surround a portion of the broaching member.

The free end may be biased outwardly away from the central support member.

The broaching member may be of monolithic construction with the central support member.

The capture sheath may include a release opening. When the capture sheath is in a first position relative to the central support member, the free end of the broaching member may be constrained by the capture sheath. When the capture sheath is rotated relative to the central support member about the central support member from the first position to a second position, the free end may pass through the release opening and the broaching member may expand away from the central axis.

Rotation of the capture sheath from the second position to the first position may capture the free end of the broaching member in the capture sheath.

The broaching member may include an outer face that faces away from the central support member. The face may include a blade that extends outwardly away from the face from a proximal region on the face to a distal region of the face. The blade may support the cutting edge. The face may include an inner edge that defines an opening in the broaching member. The blade may include a base that runs along the perimeter. The blade may be substantially square-shaped. The blade may be substantially rectangle-shaped. The blade may be a portion of the free end or cut out from the free end and annealed out of plane.

The cutting edge may define a rake angle. The cutting edge may define a relief angle. The cutting edge may define a rake angle and a relief angle.

The broaching member may be a first broaching member. The tool may include a second broaching member. The second broaching member may be wrapped about the central support member. The second broaching member and the first broaching member may be adjacent to each other. The second broaching member and the first broaching member may be positioned apart from each other about 0.5 to about 1 mm, about 1 to about 2 mm, about 2 to about 3 mm, about 3 to about 4 mm, about 4 to about 5 mm or more than 5 mm.

The first broaching member may have a first length along a first broaching member central axis. The second broaching member may have a second length along a second broaching member central axis. The second length may be different from the first length. The second length may be greater than the first length.

The first broaching member may have a first relaxed radius of curvature. The second broaching member may have a second relaxed radius of curvature. The first and second radii may be substantially the same. The second radius may be greater than the first radius.

The apparatus may include a tool for broaching a bone. The tool may include one or more of: a broach head having a proximal end and a distal end; a broaching member looping through the proximal end of the broach head and including a first end and a second end, wherein both the first end and the second end are fixed, at distal end of the broach head, to the distal end of the broach head; and a rotator. The proximal end of the broach head may be coupled to the rotator. A broach head may be a support for a broaching member. A broach head may extend from a rotator to a distal end of a broaching member. The broach head may have a terminal end.

The broaching member may include an elongated body that has a sharp convex edge and in a relaxed state a substantially planar face. The rotator may be elongated. The rotator may define a longitudinal axis. The rotator may be configured to retain a first end of the body and a second end of the body such that the first end is spaced longitudinally apart from the second and the face forms a cone-like surface.

The elongated body may be a first elongated body. The sharp convex edge may be a first sharp convex edge. The planar face may be a first planar face. The cone-like surface may be a first cone-like surface. The broaching member may include a second elongated body having a second sharp convex edge and in a relaxed state a second substantially planar face. The rotator may be configured to retain a first end of the second body and a second end of the second body such that the first end of the second body is spaced longitudinally apart from the second of the second body and the second face forms a second cone-like surface.

The second cone-like surface may be substantially identical to the first cone-like surface. The second cone-like surface may be a cone-like surface that is not identical to the first cone-like surface. The second cone-like surface may correspond to a greater apical angle than does the first cone-like surface. The second cone-like surface may correspond to a greater longitudinal distance from an apical angle than does the first cone-like surface. The first body may be disposed about 180 around the longitudinal axis from the second body.

The first elongated body may be fixed to the rotator at a distal position and a first intermediate position. The second elongated body may be fixed to the rotator at a second intermediate position and a proximal position. The first and second intermediate positions may be disposed longitudinally between the distal position and the proximal position.

The first elongated body may define a first central axis and have a first length along the first central axis. The second elongated body may define a second central axis and have a second length along the second central axis. The second length may be greater than the first length.

The first elongated body may have a first heat-set shape. The second elongated body may have a second heat-set shape. The second shape may be different from the first heat-set shape.

The tool may include a first elongated controller that is configured to change a longitudinal distance between the first end of the first elongated body and the second end of the first elongated body. The tool may include a second elongated controller that is configured to change a longitudinal distance between the first end of the second elongated body and the second end of the second elongated body.

The tool may include a loop, the first and second elongated bodies extending therefrom; and a coupler that couples the loop to the rotator. The coupler may include a transverse member that is transverse to the longitudinal axis, is supported by the rotator, and engages the loop by passing through the loop.

The first elongated body, the second elongated body and the loop may be of monolithic construction. The loop may form a spirally wound spring. The loop may absorbs strain from the elongated members when the elongated members are subjected to stress. The stress may be a stress that is directed radially inward toward the rotator. The stress may be a stress that is directed circumferentially about the rotator.

The apparatus may include a tool for broaching bone. The tool may include an elongated rotator member defining a longitudinal axis. The tool may include a broaching member support. The broaching member support may include a collapsible support. The collapsible support may include: a first hinged span that extends radially away from the rotator as a result of shortening the first hinged span along the longitudinal axis and draws radially toward the rotator as a result of lengthening the first hinged span along the longitudinal axis; and a second hinged span that extends radially away from the rotator as a result of shortening the second hinged span along the longitudinal axis and draws radially toward the rotator as a result of shortening the second hinged span along the longitudinal axis. The tool may include a broaching member that may be suspended between the first and second spans.

The first and second hinged spans may be of a plurality of hinged spans. Each of the spans may extend radially away from the rotator as a result of being shortened along the longitudinal axis and draw radially toward the rotator as a result of being lengthened along the longitudinal axis. Each of the hinged spans may support the broaching member.

Each of the hinged spans may be aligned substantially collinearly with the other of the hinged spans.

Each of the hinged spans may include a distal leg and a proximal leg. Each of the legs may be slidably engaged with the rotator member. Each of the proximal legs may be hingedly fixed to an adjacent one of the distal legs. Each of the hingedly fixed pair of proximal and distal legs may be keyed into a longitudinal keyway on the rotator member.

The tool may include a first slidable fitting that may be fixed to a proximal leg of the first hinged span and a distal leg of the second hinged span. The tool may include a second slidable fitting that may be fixed to a proximal leg of the second hinged span. The first and second slidable fittings may be engaged with the rotator along a proximal-to-distal direction that is parallel to the longitudinal axis.

The elongated rotator member may have a distal end. The broaching member may have a distal end. The broaching member may have a proximal end. The broaching member distal end may be longitudinally fixed at the elongated rotator member distal end to the elongated rotator member distal end. The broaching member proximal end may be slidably engaged with the rotator member.

The broaching member may be fixed to the rotator. The broaching member may be configured to be moved relative to the rotator to displace bone material that is radially away from the rotator.

In some embodiments, the broaching member may be configured to substantially deflect around second bone material.

In some embodiments, the broaching member may be configured to form in the bone a space having a first contour that corresponds to a shape of the broaching member. The broaching member may be configured to form in the bone a space having a second contour that corresponds to anatomy that includes the second bone material. The broaching member may be a first broaching member and the apparatus may include a second broaching member. The second broaching member may be disposed opposite the first broaching member.

In some embodiments, the broaching member may include a cutting edge.

In some embodiments, the broaching member may include a flexible wire segment. The wire segment may include braided wire.

In some embodiments, the apparatus may include a reinforcement that supports the broaching member. The reinforcement may support a cutting edge.

In some embodiments, the broaching member may have a proximal end that is fixed to the rotator and a distal end that is fixed to the rotator.

In some embodiments, the broaching member may have a proximal end that is fixed to the rotator and a distal end that is free.

In some embodiments, the broaching member may include an edge of an open cell in a mesh.

The broaching member may include a segment that has any suitable form. For example, the segment may be straight, circular, rhombic, square, triangular, oval, ellipsoid, spiral, loop-shaped, hoop-shaped, teardrop-shaped, egg-beater-shaped, football-shaped, or any other suitable shape. The segment may be a closed loop. The loop may be asymmetric.

The segment may have one or more of a variety of transverse cross sections, such as square, rectangular, octagonal, contours with sharp edges, stranded cable, or other suitable configurations to facilitate bone displacement.

The segment may have a leading edge. The leading edge may be beveled at a suitable angle, including an angle from about 5° to about 75°. The angle may cause leading edge 2202 to be generally sharp or knife-like.

The segment may be rigid. The segment may be resilient.

The broaching member may have one or more ends that are attached to apparatus such as a drive shaft or a suitable support, such as a hub. The broaching member may have a free end. Broaching members with free distal ends may have any suitable shape at the tine distal ends, such as pointed, forked, rounded, blunt or truncated.

The broaching member may have an end that is attached to apparatus by crimping, welding, set-screw, snap fit or any other suitable fastening. The broaching member may have one or more ends that are of unitary construction with the apparatus.

The broaching member may include a tine. The tine may be resilient or stiff. The tine may have an end that is attached to a drive shaft. The tine may have a free end.

The broaching member may include a blade.

The broaching member may include numerous interconnected cells. The cells may be arranged in a network. The cells may be linked such that when the structure is stressed (e.g., compressed) at a point the stress is distributed to nearby cells. The cells may be constructed from laser-cut tube stock that is expanded into a suitable shape.

The broaching member may be one of a number of broaching members in a broaching head. For example, the broaching head may have one broaching member, 2-6 broaching members, 7-20 broaching members, more than 20 broaching members, 100 broaching members or any suitable number of broaching members.

When a large number (i.e., when the circumferential density of broaching members is relatively high) of broaching members are present during the rotation of a broaching head, a relatively lower torque may be required to drive the broaching head.

Broaching member may rotate in a bone cavity that has an irregular shape, for example, nonround, oblong, or angular. The cavity may be smaller than a diameter of broaching member.

Broaching member may include any suitable structural form such as wire, ribbon, cable, stranded wire, braided wire, braided ribbon, or any other suitable structural form.

Broaching member may include any suitable material, such as polymer, metal, composite, stainless steel, Nitinol (shapeset, superelastic or other Nitinol), other alloy or any other suitable material.

The broaching member may be supported by one or more reinforcements.

The reinforcement may be sized and positioned to support a segment of the broaching member in a desired contour. The reinforcement may provide bone-broaching abrasiveness, momentum or both.

The reinforcement may be a tube.

The reinforcement may be a brace. The brace may be fixed to the broaching member, for example, by crimping, welding or press-fit. The brace may include broaching edges for displacing bone material. The broaching edges may have any suitable form, such as serrated, saw-tooth, knife-edge, rectilinear edge or any other suitable form.

The reinforcement may be formed from polymer, metal, alloy or any other suitable material.

The reinforcement may be formed from a pattern that is cut into a metal tube.

In some embodiments, the apparatus may include a distal hub. The broaching member may have a distal end that is fixed to the distal hub. The distal hub may be configured to move between a first position and a second position. The first and second positions may be located along a longitudinal axis of the rotator.

The distal hub may be constructed of metal, stainless steel, laser-cut tube, polymer, ceramic or any other suitable material.

The distal hub may include flutes. The distal hub may include broaching edges.

The methods may include a method for broaching an interior region of a bone. The interior region may include a bottom surface. The bottom surface may be an surface of a portion of the bone that is opposite an access hole in the bone.

The method may include expanding a bone broaching member in the interior region. The method may include disaggregating relatively low-density material inside the bone using the member. The method may include deflecting the broaching member away from relatively high-density material inside the bone.

In some embodiments, the method may include rotating the bone broaching member using a flexible drive shaft.

In some embodiments, the method may include changing the elevation or direction of the bone broaching member relative to a surface.

In some embodiments, the disaggregating may include cutting the relatively low-density material.

In some embodiments, the disaggregating may include displacing the relatively low-density material.

Apparatus and methods for treating a bone interior are provided.

The apparatus may include a flexible sheath. The flexible sheath may include stress-relief features that allow bending under tension and compression. The stress-relief features may include slots or slot patterns. The stress-relief features may be provided using laser-cutting.

The stress-relief features may include sintered particles. The particles may include metal, polymer, composite or any other suitable material.

The flexible sheath may have a first configuration and a second configuration. The second configuration may have a smaller radius of curvature than the first configuration. The apparatus may include a rotatable shaft. The rotatable shaft may extend through the sheath. The apparatus may include an elongated steering member. The elongated steering member may be configured to deflect the flexible sheath from the first configuration to the second configuration.

In some embodiments, the elongated steering member may be configured to be elastically deformed when the elongated steering member deflects the flexible sheath from the first configuration to the second configuration.

In some embodiments, the elongated steering member may include a first portion. The first portion may translate along a longitudinal direction of the sheath. The elongated steering member may include a second portion. The second portion may be configured to extend radially outward through a passage in the sheath when the elongated steering member deflects the flexible sheath from the first configuration to the second configuration.

In some embodiments, the rotatable shaft may have a distal end and the apparatus may include an expandable head that extends from the distal end. The expandable head may include a compressed configuration for translating within the sheath. The expandable head may include an expanded configuration when the expandable head is deployed outside the sheath.

In some embodiments, the expandable head may be configured to displace cancellous bone and not cortical bone.

Apparatus and methods for preparation of the interior of a bone are provided.

The apparatus may include an elongated member. The elongated member may have a longitudinal axis. The elongated member may be curved about the longitudinal axis. The elongated member may be configured to rotate about the longitudinal axis inside the bone.

In some embodiments, the apparatus may include a circumferential offset. The circumferential offset may be in a circumferential direction about the longitudinal axis. The circumferential offset may be between the second proximal end and the first proximal end. The circumferential offset may be between the second distal end and the first distal end.

In some embodiments, the apparatus may include a support. The support may include a proximal support end. The proximal support end may be fixed to a shaft. The apparatus may include a support segment.

The apparatus may include one or more broaching members. The broaching members may be blades. A first blade may be linked to a second blade by a linkage. The linkage may be configured to be rotated about the longitudinal axis. The linkage maybe configured to be radially displaced from the longitudinal apparatus axis.

In some embodiments, at least one of the first and second blades may be rigid.

In some embodiments, at least one of the first and second blades may include stainless steel.

In some embodiments, at least one of the first and second blades may include Nitinol.

In some embodiments, the linkage may include a pin.

The methods may include a method for preparing the bone interior. The method may include rotating a cutting surface inside a bone about a rotational axis. The method may include moving a control member from a first control position to a second control position.

The cutting surface may be configured to occupy a first radial position that corresponds to the first control position. The cutting surface may be configured to occupy a second radial position that corresponds to the second control position. The cutting surface may be configured to occupy a third radial position that corresponds to an intermediate control position. The intermediate control position may be between the first and second control positions. The third radial position may be at a greater radial distance from the rotational axis than are both the first and second radial positions.

In some embodiments, the first and second radial positions may be at substantially the same distance from the rotational axis.

In some embodiments, when the cutting surface is at one or both of the first and second radial positions, the cutting surface may be disengaged from the bone. When the cutting surface is at the third radial position, the cutting surface may be engaged with the bone.

The methods may include a method for treating a bone. The bone may have a longitudinal bone axis.

The method may include providing a hole in the bone. The hole may be at an angle to the longitudinal bone axis. The hole may provide access to a bone interior region. The method may include advancing a tool through the hole and into the interior region. The method may include displacing cancellous bone using the tool.

In some embodiments, the displacing may include identifying a spatial distribution of low-density matter in the interior region.

The apparatus may include, and the methods may involve, a broaching member. A broaching head may include one or more broaching members. A broaching member may include one or more bodies. A body may be elongated. A body may include one or more blades. The broaching member may include the blade. The blade may run along some or all of the broaching member.

The blade may include a sharp edge. The edge may be convex. The convex edge may define a plane that is parallel to a face of the broaching member when the broaching member is in a planar configuration. The apparatus may include a support member that is configured to retain a first end of the broaching member spaced apart from a second end of the broaching member to conform the face to a conical or pseudo-conical configuration.

A pseudo-conical configuration may include segments that are generally conical, but vary, perhaps continuously, along the axial direction, with respect to the apical cone angle to which they correspond. The apical angle may be the angle between (a) a ray extending from a cone apex and tangent the cone surface; and (b) the longitudinal axis of the cone. (A small apical cone angle may characterize a slowly converging cone. A large apical cone angle may characterize a quickly converging cone.) The support member may define a longitudinal direction. For purposes of illustration, the longitudinal direction may define, relative to the device as configured during operation of the apparatus, a distal direction. The longitudinal direction may define, relative to the device as configured during operation of the apparatus, a proximal direction.

Pseudo-conical configurations may include configurations in which the face defines at a first point a first conical apex angle and at a second point a second conical apex angle. The first and second points may be set apart from each other. The first and second points may be set apart from each other longitudinally. The first and second points may be set apart from each other along a central axis of the face. The conical first and second conical apex angles may be different from each other. Points located between the first and second points may define intervening conical apex angles. The intervening conical apex angles may have magnitudes that vary between the first conical apex angle and the second conical apex angle. The intervening conical apex angles may vary continuously between the first conical apex angle and the second conical apex angle. The first and second conical apex angles may be substantially the same. The intervening conical apex angles may be substantially the same as the first and second conical apex angles.

A first broaching member may be linked to a second broaching member by a joint. A first blade may be linked to a second blade by a joint. A joint may be an articulating joint. A joint may include a pin. The pin may be disposed in a bushing. A joint may include a broaching member wrap about the pin. A joint may include a broaching member wrap about the bushing. The joint may have hinge properties relative to blades or broaching members extending therefrom. The joint may have spring properties relative to blades or broaching members extending therefrom. The joint may be configured to be rotated about the longitudinal axis of the tool. The joint may be configured to be radially displaced from the longitudinal apparatus axis. The joint may be configured to be moved radially away from the longitudinal apparatus axis.

The blade may be one of a plurality of blades. The blade may be supported by a shaft.

The broaching member may define an axial direction. The broaching member may include one or more segments. A segment may include an end of the broaching member. The segment may include a spanning portion of the broaching member. The spanning portion may span between the ends of the broaching member.

The broaching member may include a first end member at a first end of the blade. The first end member may be at an angular displacement, about the axial direction, from the edge, when the edge is in a relaxed state. The relaxed state may be a state of mechanical equilibrium. In the state of mechanical equilibrium, the broaching member may be sufficiently free of stored elastic energy to allow the broaching member to retain its shape and not spontaneously revert to a different shape.

The axial direction may include one or more segments that are non-linear to conform to the broaching member when the broaching member is deformed. The non-linear segment may be curved, helical, angular, tortuous or any other suitable arrangement.

The apparatus may include a support member. The support member may be configured to: retain the first end member of the broaching member spaced along the support member apart from a second end member, opposite the first end member, of the broaching member to bow the broaching member away from the support member; and counter rotate the first end, about the axial direction, by the angular displacement.

The blade may include a trailing edge. The trailing edge may trail behind the sharp edge when the sharp edge is in operation. The broaching member may include a first end that is fixed to the support member. The broaching member may include a second end that is fixed to the support member. The broaching member may include a bowed portion. The bowed portion may span from the first end to the second end. The broaching member may be angularly displaced about the axial direction by an angular displacement that is greater at the bowed portion that at the first end or the second end.

The apparatus may include a first bowed blade that is fixed to the support member at a distal position and at a first intermediate position. The apparatus may include a second bowed blade fixed to the support member at a second intermediate position and at a proximal position. The first and second intermediate positions may be longitudinally between the distal position and the proximal position.

The apparatus and methods may be used to manipulate the tissue.

Apparatus and methods may be used to prepare the interior of a bone for therapy. The therapy may include therapy for a bone fracture. The apparatus may include a broaching member. The broaching member may include the blade. One or more of the broaching members may be used to prepare the region inside the bone for treatment.

A broaching member may be deformable inside the bone. When two or more broaching members are included in a preparation tool, the broaching members may deform away from each other to expand the tool inside the bone.

A broaching member may be flexible such that it broaches tissue having a relatively lower density and it leaves tissue having a relatively higher density substantially intact.

The apparatus may include a first circumferential displacement. The first circumferential displacement may be in a circumferential direction about the longitudinal axis. The circumferential displacement may be between the second proximal end and the first proximal end. The circumferential displacement may be between the second distal end and the first distal end.

The first circumferential displacement may be between a distal segment of the blade and a proximal segment of the blade. The first circumferential displacement may be between a distal segment of the blade and an intermediate segment of the blade. The first circumferential displacement may be between a proximal segment of the blade and an intermediate segment of the blade.

The apparatus may include a second circumferential displacement. The second circumferential displacement may be in a circumferential direction about the axial direction. The second circumferential displacement may be between a first segment of the broaching member and a second segment of the broaching member. For example, a terminal end of a broaching member may be circumferentially displaced relative to the cutting edge of the broaching member.

The second segment may share the longitudinal axis with the first segment. The method may include rotating the substantially second segment about the longitudinal axis.

A first blade may be linked to a second blade by a joint. The joint may be an articulating joint. The joint may include a pin. The joint may include a broaching member wrap about the pin. The joint may include a hinge. The joint may be configured to be rotated about the longitudinal axis. The joint may be along the longitudinal axis. The joint may be eccentric to the longitudinal axis. The joint may be configured to be radially displaced from the longitudinal apparatus axis.

The apparatus may impart force upon the tissue in a rotational manner, an expanding manner, an axial manner or a combination of any or all of these manners. It is to be understood that other embodiments may be utilized and structural, functional and procedural modifications may be made without departing from the scope and spirit of the present invention.

The apparatus may cut the tissue. The apparatus may compact the tissue. The apparatus may displace the tissue. The apparatus may remove the tissue from the bone. The apparatus may do one or more of the foregoing or act in any other suitable way upon the tissue, depending on the desired therapy.

Displacing a broaching member radially outward may be referred to as "activation." Displacing a broaching member radially inward may be referred to as "deactivation." Changing positions of broaching member ends relative to each other may cause activation. Changing positions of broaching member ends relative to each other may cause de-activation. The apparatus may include an activation mechanism. The mechanism may activate an individual broaching member. The activation mechanism may activate a plurality of broaching members. The mechanism may include a linear broaching member actuator. The mechanism may include a rotating broaching member actuator. The rotating broaching member actuator may convert rotation to translation of a broaching member. The mechanism may include one or more of the features. The mechanism may be operated manually. The mechanism may be mechanically assisted. The mechanism may be motorized. The mechanism may be automated. The mechanism may include one or more of the features.

The mechanism may include a spring that assists activation. The mechanism may activate one or more broaching members as the tool is rotated. The mechanism may be robotic. The tool may be robotic.

The tool may be formed based on any suitable design inputs. Table 1 shows illustrative cavity preparation tool design inputs and design output considerations.

TABLE 1

| Illustrative Input | Design Output Considerations |
|---|---|
| Broaching member Material | Superelasticity may tolerate the high strains (above 10%) that may be appropriate in operation and for expansion and collapse. May provide for varied mechanical properties throughout the length of a single broaching member. May provide compliance and resilience to accomplish the desired therapy. |
| Broaching member Shape | |
| Rectangular | Height, width and length may be selected. Different dimensions may provide different resilience in different planes. |
| Broaching member Width (between cutting edge and trailing edge) | Variation of width may yield change in torsional stiffness while the apparatus is being rotated and resistance from tissue may applied to cutting edge. Increasing the width increases the torsional stiffness of the broaching member. The increase in width may increase bending stiffness in the plane orthogonal to the width along the entire length. This may be uniform or varied along the length. This dimension may be controlled to apply a predetermined pressure to the tissue. |
| Broaching member Thickness (dimension parallel to normal vector p) | Variation of thickness may yield a change in bending strength in the radial direction. The change may affect the hoop strength of the blade. This may be uniform or varied along the length. This dimension may be varied to obtain a desired shape. This dimension may be controlled to apply a predetermined pressure to the tissue. |
| Broaching member Length (along central axis S) | Variation of length may yield a change in bending strength in the radial direction. This change may affect the hoop strength of the broaching member. This dimension may be varied to obtain a desired shape. This dimension may be controlled to yield a desired pressure or resistance delivered or imparted onto the tissue. Shorter lengths typically yield high forces and conversely longer lengths that are unsupported typically yield a more compliant broaching member imparting less force on the tissue. |
| Cutting Edge | The broaching member may include a sharpened edge, or other geometry to increase the effectiveness of displacing the tissue in a desired manner. The effect of decreasing the contact surface area increases the overall force and pressure applied to the tissue per unit area. The edge may be straight, jagged, saw type, or any other suitable configuration. |
| Rake and Relief angles | The angle at which the edge engages the tissue may be varied as yield the desired effect upon the tissue. This angle may be constant or varying throughout the expansion of the broaching member; ie. The effectiveness of the cutting tool may be desired to have a constant effectiveness or increasing or decreasing effectiveness throughout the range of expansion of the apparatus. |
| Broaching member Form | |
| Twist or Bend Along Broaching member Central Axis S | The rake and relief angles may be adjusted by bending or twisting the blade along the central axis. This may be used to set the rake and relief angles to achieve the desired tissue engagement along the length of the broaching member and/or throughout the radial expansion of the broaching member. Effective rake and relief angles may depend on tissue type or material, speed of the engagement, and desired outcome. |
| Bending (about axis Lo, e.g.) | Another way to adjust the rake and relief angles along the length or throughout the expansion is to bend the broaching member along the length in the plane of the widest dimension or width. This bend may increase the length of outer edge and shortening the inner edge. This effect then when the blade is bent during radial expansion yields a conical or pseudoconical geometry in which the longer edge is elevated relative to the shorter edge. This bend radius may be constant or variable throughout the length to obtain the desire result, by optimizing the rake and relief angles. |
| Torsion (about axis N) | Torsion may take place as the member engages the tissue and force is applied rotationally or torsionally. The width of the broaching member may be set to have the member bend an optimal amount to yield the desired rake and relief angles. Torsion may be preset into the shape of the broaching member so that the angle is in a desired position regardless of the force being imparted unto it. A combination of preset and operational torsion may be employed. |

TABLE 1-continued

| Illustrative Input | Design Output Considerations |
| --- | --- |
| Bend about axis M, buckling | The radial expansion of the broaching member may be achieved by the bending of the broaching member in this manner. This may be achieved several ways. Different conical/pseudoconical geometries may be formed based on a shape of the member before radial expansion of the broaching member. |
| Operational bend about axis M | The broaching member may be compressed to force a bending or buckling of the member to cause it to expand radially away from the central support member. This action may be controlled by the amount of length that is changed from the constrained ends of the broaching member. The bend may be influenced by the resistant force imparted by the tissue. The length of the blade may be variable in this response. See above. The broaching member may have a preset bent shape. This may affect the shape of the expanded member as well as the amount of length change and force imparted into the member. |
| Hinge | It may be desirable to have a hinge mechanism on one or both of the ends of a broaching member. |
| Strain Relief | The collapsed and expanded configurations of the broaching member may impart strain levels that exceed that of the member itself, therefore it may be desired to have a strain relief mechanism at the captured ends of the broaching members. This strain relief mechanism may include structures such as a coil including the broaching member, a thinned section of the broaching member, a thinned and coiled section of the broaching member. The apparatus may include a separate member that attaches to the blade to yield the desired effect. |
| Take off angle | The broaching member may exit or be attached to the hinge mechanism in a multitude of angles. This variation of angles may impart different amount of forces on the broaching member during collapsed and expanded configurations. This difference may yield different expanded shapes. |
| Spring assist | The hinge mechanism may be constructed in such a way to impart forces upon the broaching member to either collapse or expand the body. |

Cavity preparation may include inserting one or more materials into the cavity. The materials may include one or more of biologics, cement, metal scaffolds, bone graft, antibiotics, medicine and other suitable materials. Cavity preparation may include material removal. The material may include one or more of the aforementioned materials or one or more of a bone graft, a tumor, a cyst, a disk, bone, intramedullary fluid, bone marrow, foreign bodies, cement and other materials.

Apparatus and methods in accordance with the invention will be described in connection with the FIGS. The FIGS. show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods described herein are illustrative. Apparatus and methods of the invention may involve some or all of the features of the illustrative apparatus and/or some or all of the steps of the illustrative methods. The steps of the methods may be performed in an order other than the order shown or described herein. Some embodiments may omit steps shown or described in connection with the illustrative methods. Some embodiments may include steps that are not shown or described in connection with the illustrative methods.

Illustrative embodiments will now be described with reference to the accompanying drawings, which form a part hereof.

The apparatus and methods of the invention will be described in connection with embodiments and features of an illustrative bone repair device and associated hardware and instrumentation. The device and associated hardware and instruments will be described now with reference to the FIGS. It is to be understood that other embodiments may be utilized and structural, functional and procedural modifications may be made without departing from the scope and spirit of the present invention.

Figure 1:
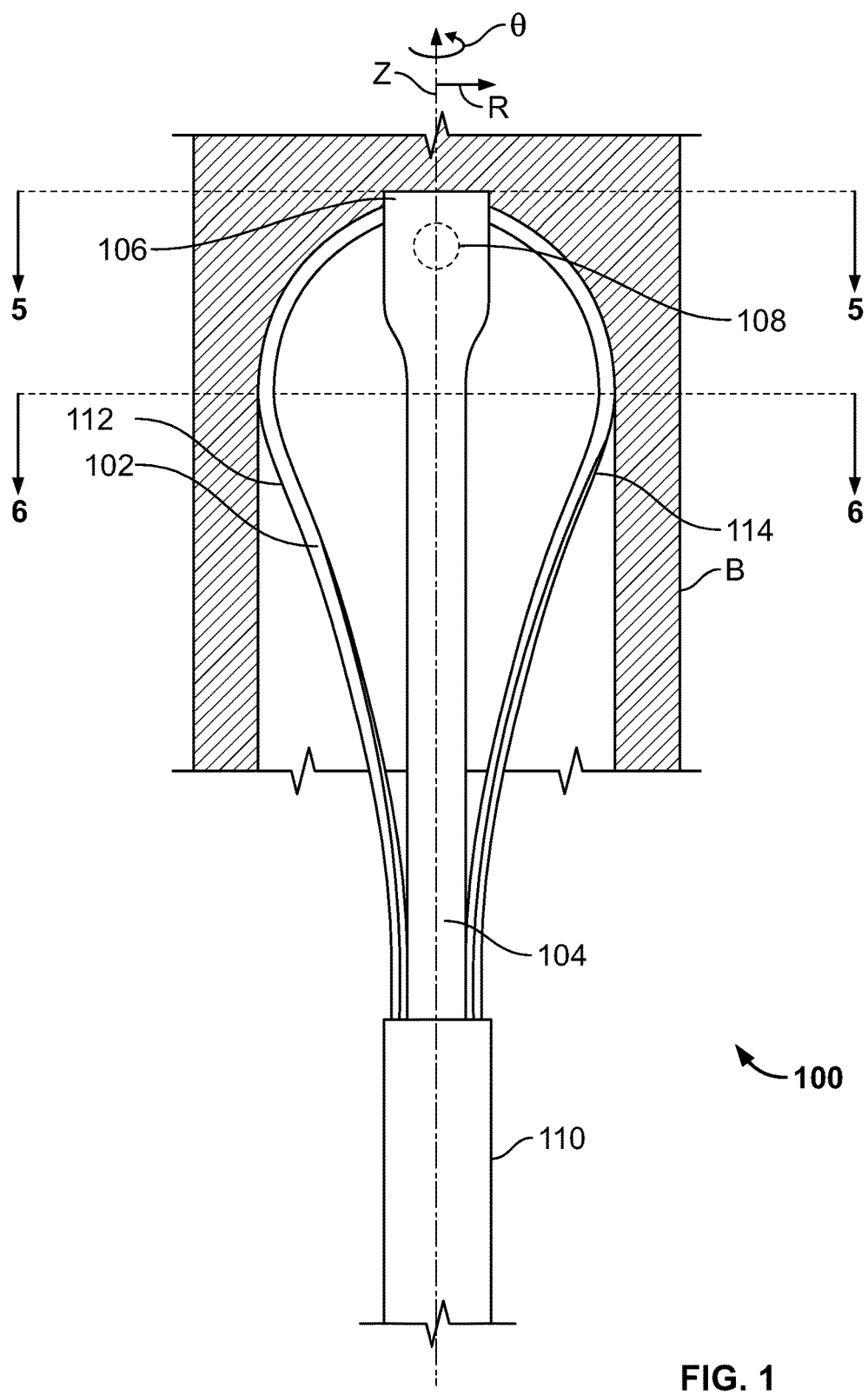
FIG. 1 shows illustrative apparatus in accordance with principles of the invention.

FIG. 1 shows illustrative cavity preparation tool 100 in bone B. Bone B may include cortical tissue. Bone B may include cancellous tissue. Bone B may include fibrocartilage. Bone B may include marrow tissue. Bone B may include fibrocartilage and marrow tissue. Tool 100 may have one or more features in common with broach 15100 (shown in FIG. 151).

Tool 100 may include broaching member 102. Broaching member 102 may include one or more bodies. Broaching member may include one or more loops, loop sections, wraps and/or wrap sections. The bodies may be segments. The bodies may be elongated. The bodies may include a blade. Broaching member may have a heat memory shape.

Tool 100 may include support member 104. The support member may be referred to alternately herein as a broach head. Support member 104 may include a bracket such as bracket 15120 (shown in FIG. 153). Support member 104 may have one or more features in common with a rotator. Support member 104 may support broaching member 102 at distal end 106 of tool 100. Distal end 106 may include joint 108. Support member 104 may support broaching member 102 at a more proximal portion (not shown) of broaching member 102. The more proximal portion of broaching member 102 may be secured inside shaft assembly 110.

Shaft assembly 110 may have one or more features in common with shaft assembly 15114 (shown in FIG. 153). Shaft assembly 110 may be fixed to support member 104. Shaft assembly 110 may be longitudinally fixed to support member 104. Shaft assembly 110 may be radially fixed to support member 104. Shaft assembly 110 may be circumferentially fixed to support member 104. Shaft assembly 110 may be movable longitudinally relative to support member 104. Shaft assembly 110 may be movable rotationally relative to support member 104.

Broaching member 102 may include elongated body 112. Broaching member 102 may include elongated body 114. Bodies 112 and 114 may have one or more features in common. One or both of bodies 112 and 114 may include a cutting edge.

Broaching member 102 may be a unitary body. Broaching member 102 may be a unitary body including bodies 112 and 114. Broaching member 102 may also be a unitary body with a portion of broaching member 102 wrapped around joint 108. Bodies 112 and 114 may be monolithic. Bodies 112 and 114 and a portion of the broaching member wrapped around joint 108 may be monolithic.

Broaching member 102 may be a wire, a ribbon, a wire ribbon, a braided wire, a braided ribbon, or any other suitable body.

Broaching member 102 may have a shape. A shape of broaching member 102 may be heat set into the body base material to provide desired geometries. Heat setting, thickness variation and other geometry control methods may be used in conjunction with each other at a geometry control point in a broaching member. Heat setting, thickness variation and other geometry control methods may be used separately at different geometry control points in a broaching member. Broaching member 102 may be shaped along its length to provide a cavity shape.

Broaching member 102 may include segments that join at joint 108. Joint 108 may include one or more of a pin, a coupling, a weld, an engagement feature or any other suitable joint feature. Bodies 112 and 114 may join at joint 108. Bodies 112 and 114 may join a portion the broaching member wrapped around joint 108 at joint 108.

Body 112 and Body 114 may be individual elements and not part of a body such as broaching member 102. Each of bodies 112 and 114 may be included in a separate body. Each of bodies 114 and 114 may define a broaching member. Bodies 112 and 114 may form one continuous member or body.

Tool 100 may be rotated circumferentially in direction θ about longitudinal axis Z. Axis Z may be analogous to axis $L_C$ (shown in FIG. 154). Tool 100 may include an actuator (not shown) for translating the more proximal portion of broaching member 102 along axis Z, relative to distal end 106 to cause broaching member 102 to expand (translation toward distal end 106) or contract (translation away from distal end 106) in radial direction R or −R, respectively.

Rotation and/or translation of broaching member 102 may form a cavity. The cavity may be symmetric. The cavity may be asymmetric. The cavity created by broaching member 102 may correspond to an implant shape. An exemplary implant may be the double cage shown in FIGS. 122 and 123.

A tool having a broaching member such as broaching member 102 may be rotated at least one full revolution to provide a cavity with cylindrical symmetry. The tool may be rotated less than a full revolution to provide a cavity with a non-cylindrical symmetry. The tool may be rotated in an oscillating manner to provide various cavity shapes.

Broaching member 102 may be supported at a distal hinge. Broaching member 102 may be placed in position and shaped for creating the cavity by a change in length between the hinge and the captured free ends. The free ends may be engaged by an actuator. All or some of broaching member 102 may be constrained for deployment, for example by a sheath, and then released inside the bone.

Figure 1A:
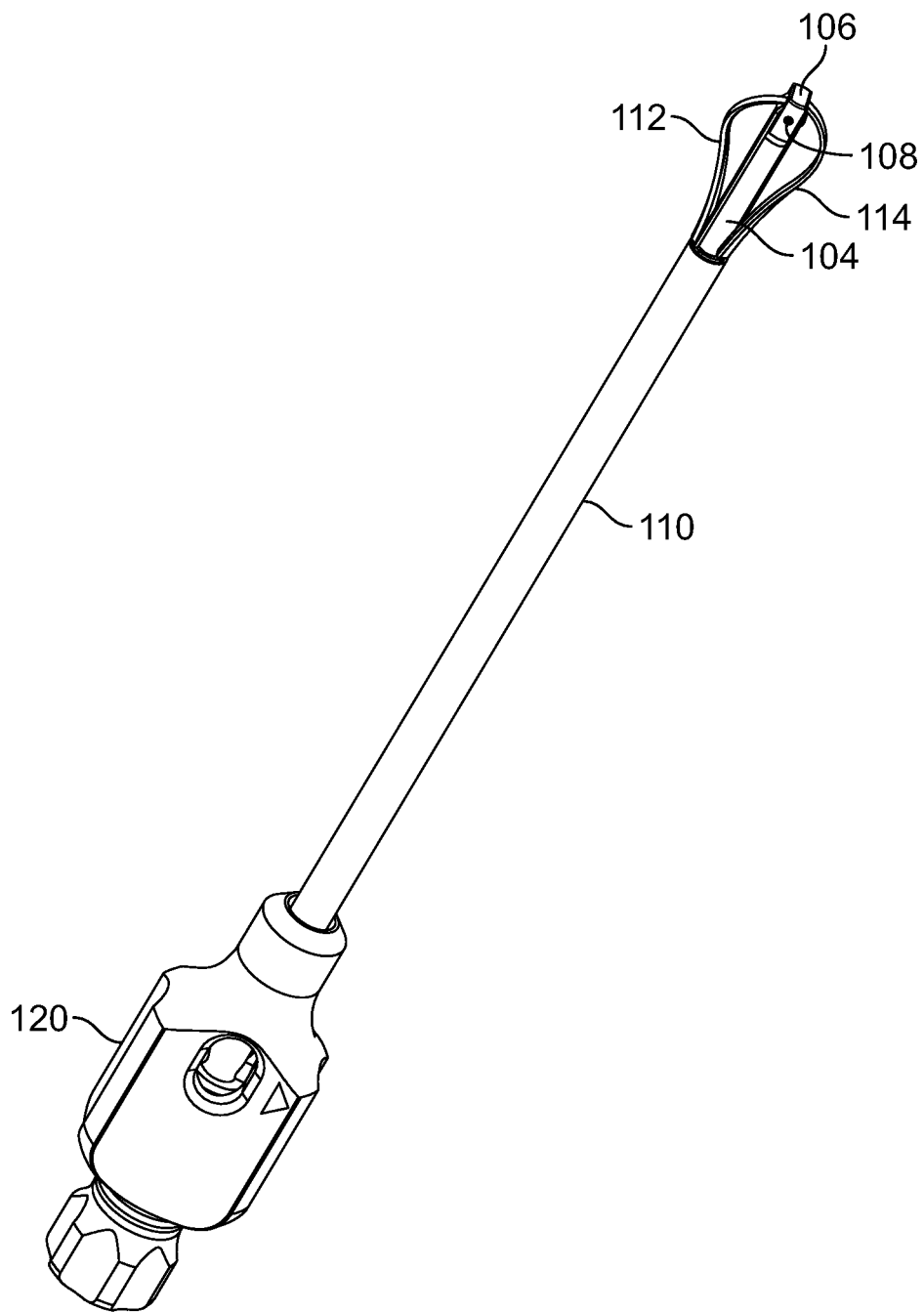
FIG. 1A shows illustrative apparatus in accordance with principles of the invention.

FIG. 1A shows a perspective view of illustrative tool 100 including handle 120. Rotation of a portion of handle 120 may urge shaft assembly 110 longitudinally along axis Z towards, or away from, distal end 106. Longitudinal movement of shaft assembly 110 along axis Z towards distal end 106 may expand broaching member 102. Longitudinal movement of shaft assembly 110 along axis Z away from distal end 106 may contract broaching member 102.

Figure 2:
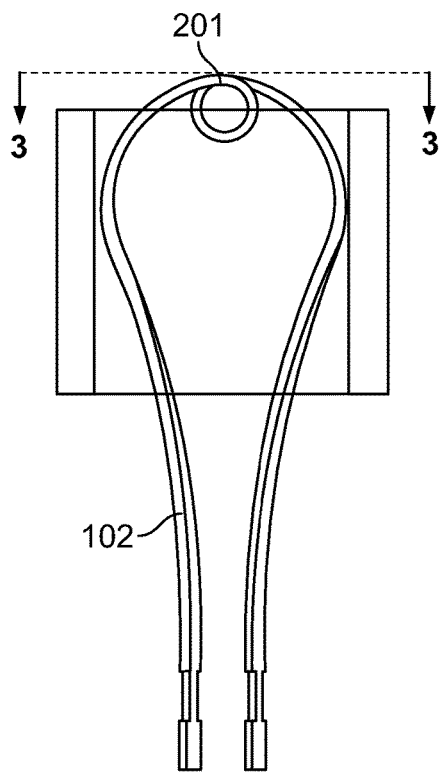
FIG. 2 shows illustrative apparatus in accordance with principles of the invention.

FIG. 2 shows illustrative broaching member 102 without shaft assembly 101 and support member 104. The configuration of broaching member 102 in FIG. 3 may be the substantially same configuration of broaching member 102 in FIG. 1.

FIG. 2 shows illustrative wrap section 201 of broaching member 102. Wrap section 201 includes a portion of broaching member 102 wrapped around joint 108 (not shown)

Figure 3:
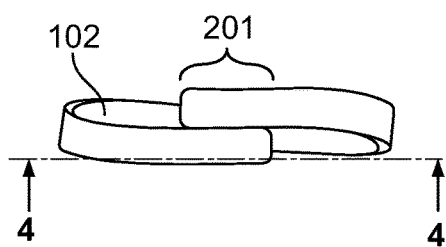
FIG. 3 shows illustrative apparatus in accordance with principles of the invention.

FIG. 3 shows a view of illustrative broaching member 102 and wrap section 201 taken along lines 3-3 (shown in FIG. 2).

Figure 4:
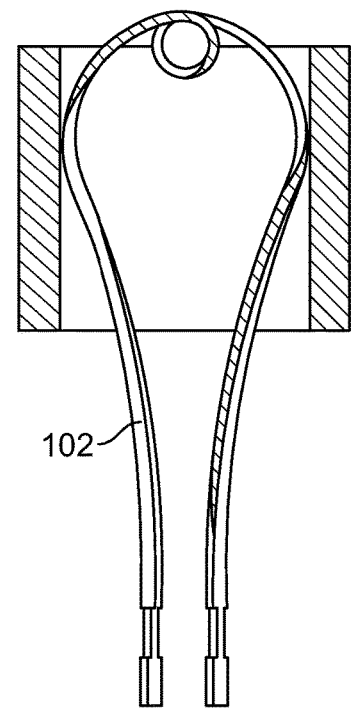
FIG. 4 shows a partial cross-sectional view of FIG. 3 taken along lines 4-4.

FIG. 4 shows a partial cross-sectional view of illustrative broaching member 102 taken along lines 4-4 (shown in FIG. 3).

Figure 5:
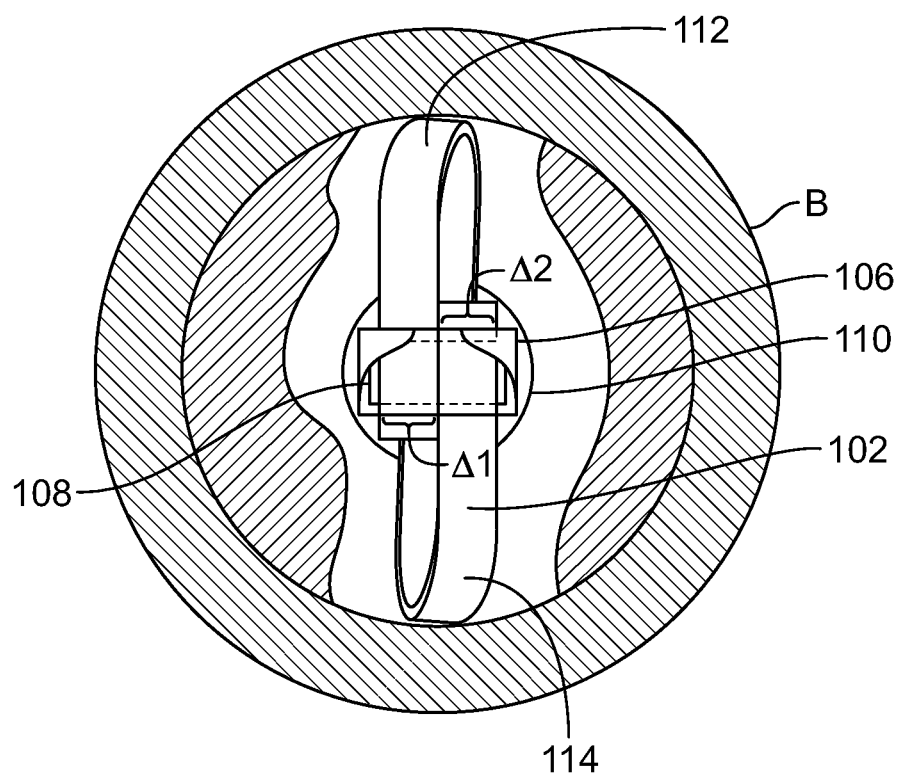
FIG. 5 shows partial cross-sectional view of FIG. 1 taken along lines 5-5.

FIG. 5 shows partial cross-sectional view of illustrative tool 100 taken along lines 5-5 (shown in FIG. 1). A partial cut-away view of distal end 106 shows, in broken line, joint 108, which is illustrated as a pin around which broaching member 116 is wrapped. Bodies 112 and 114 are shown cutting bone B.

Bodies 112 and 114 may wrap around joint 108. The wrapping of bodies 112 and 114 around joint 108 may result in bodies 112 and 114 extending away from joint 108 with an offset from axis Z (as shown in FIG. 1) by offsets $\Delta_1$ and $\Delta_2$ respectively. Appropriate magnitudes of offsets $\Delta_1$ and $\Delta_2$ may be selected. In some embodiments, offsets $\Delta_1$ and $\Delta_2$ may be constrained by the collapsed diameter (overall diameter of tool 100, shown in FIG. 1, in a plane transverse to axis Z when broaching member 102 is collapsed, e.g., for deployment) of the configuration and the desired expanded engagement of broaching member 102 with the tissue. Offsets $\Delta_1$ and $\Delta_2$ may aid in the broaching member's efficiency at displacing tissue.

Figure 5A:
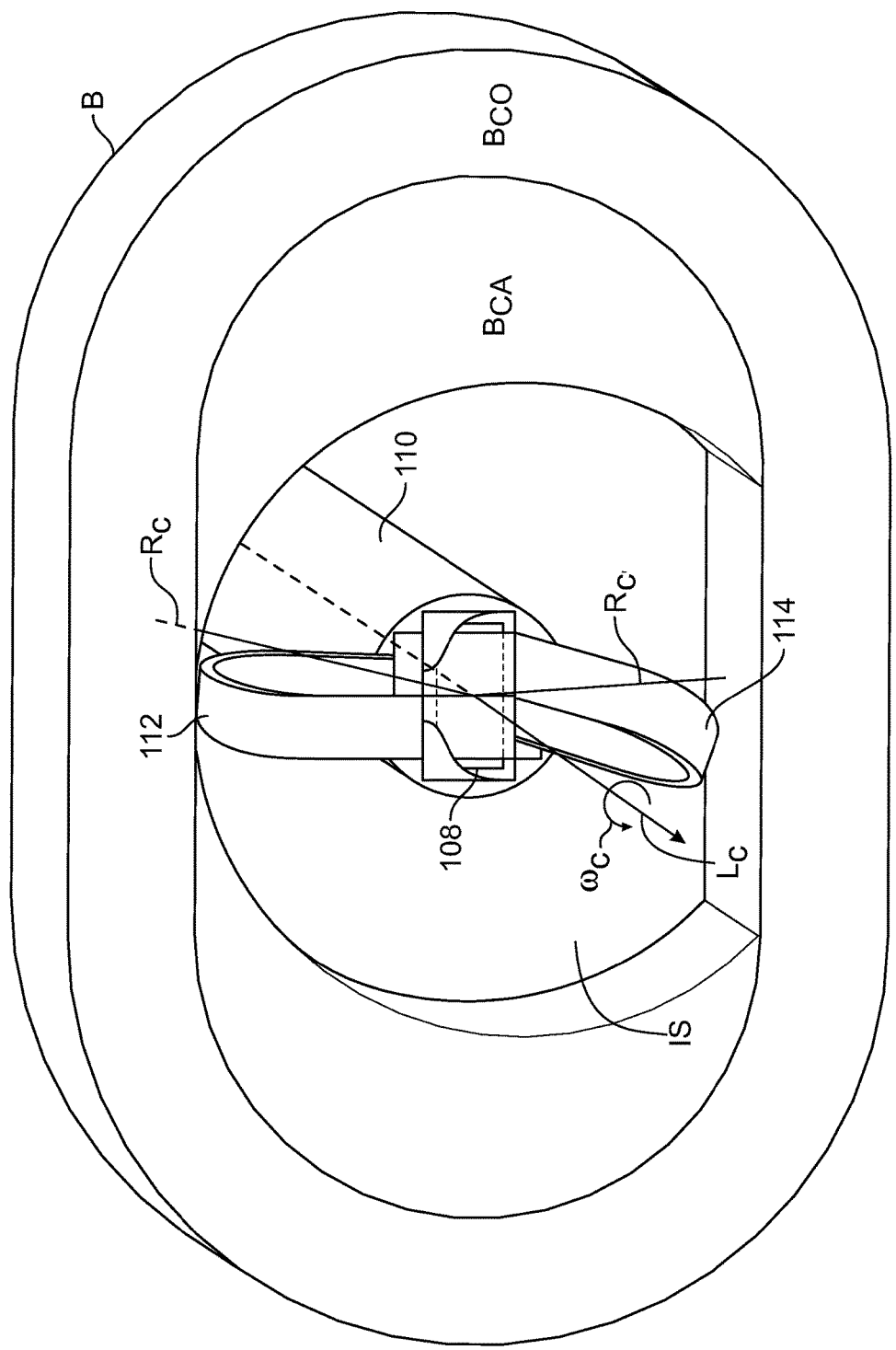
FIG. 5A shows illustrative apparatus in accordance with principles of the invention.

FIG. 5A shows illustrative broaching member 102 in intramedullary space IS of bone B and illustrates how flexible broaching members can broach bone of a relatively lower density and be deflected by bone of a relatively higher density. Bodies 112 and 114 have displaced or removed some of cancellous bone $B_{CA}$ from bone B by rotating in direction $\omega_c$ about axis $L_C$. Bodies 112 and 114 may be sufficiently stiff to remove cancellous bone to radius $R_c$ from axis $L_C$ in the "top" portion of bone B. Because of the placement of axis $L_C$ relative to the bottom portion of bone B, bodies 114 and 112 contact cortical bone $B_{CO}$ at the bottom of bone B. Bodies 112 and 114 may be sufficiently flexible to be deflected by cortical bone $B_{CO}$. Body 114 is shown deflected in direction $-\omega_c$ by bone $B_{CO}$. Bodies 112 and 114 thus remove bone only to radius $R_c'$ in the "bottom" portion of bone B.

The cavity created by tool 100 may thus be bounded in part by cancellous bone $B_{CA}$ and in part by cortical bone $B_{CO}$. The shape of the cavity portion that is bounded by cancellous bone $B_{CA}$ may be governed substantially by the geometry and mechanical properties of broach 100. The shape of the cavity portion that is bounded by cortical bone $B_{CO}$ may be governed substantially by the native anatomy of bone B.

Figure 6:
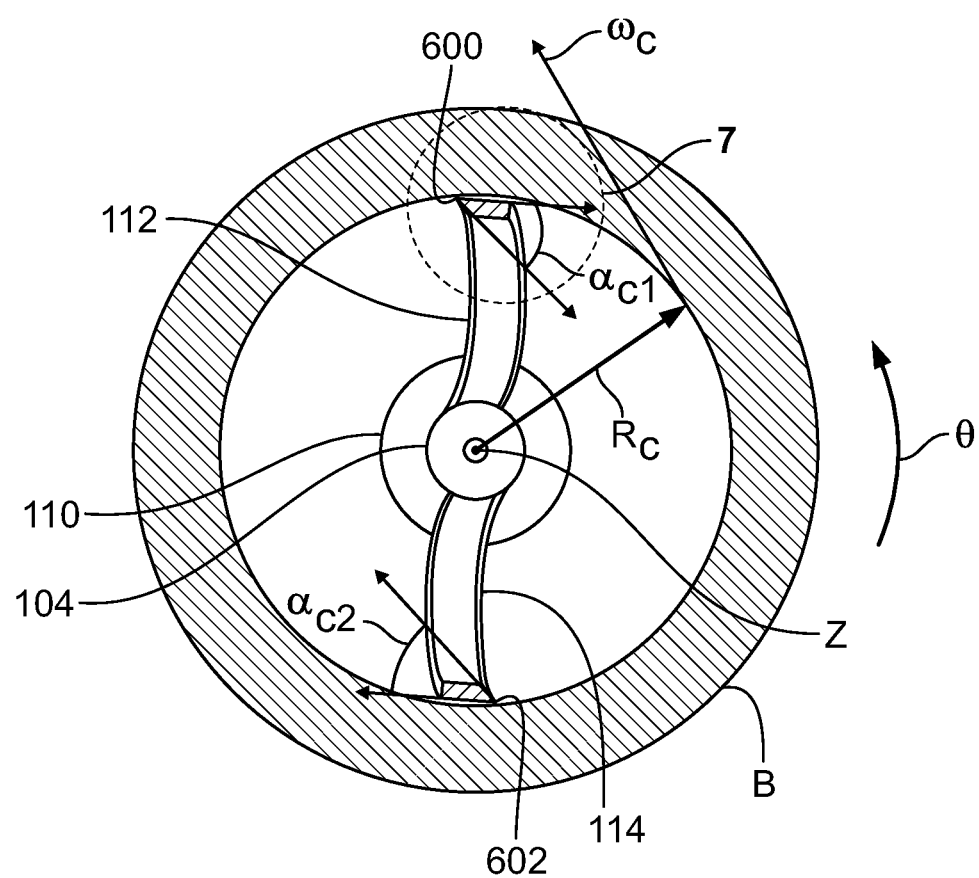
FIG. 6 shows partial cross-sectional view of FIG. 1 taken along lines 6-6.

FIG. 6 shows partial cross-sectional view of illustrative tool 100 taken along lines 6-6 (shown in FIG. 1). Cutting edges 600 and 602 are shown in contact with bone B.

Bodies 112 and 114 may be rotated in direction $\omega_c$ by shaft assembly 110 (shown in FIG. 1). Bodies 112 and 114 may sweep out a space in bone B based on radius $R_c$. Radius $R_c$ may be a maximum radial displacement along radius R (shown in FIG. 1) of bodies 112 and 114 from axis Z.

Cutting edge 600 may be beveled at angle $\alpha_{C1}$. Angle $\alpha_{C1}$ may be any suitable angle, including an angle from about 5° to about 75°. Angle $\alpha_{C1}$ may cause cutting edge 600 to be generally sharp or knife-like. This may aid in the broaching member's ability to remove tissue.

Cutting edge 602 may be beveled at angle $\alpha_{c2}$. Angle $\alpha_{c2}$ may be any suitable angle, including an angle from about 5° to about 75°. Angle $\alpha_{c2}$ may cause leading edge 2204 to be generally sharp or knife-like. This may aid in the broaching member's ability to remove tissue.

As broaching member 102 is rotated clockwise generally about axis Z, leading edges 600 and 602 may generally be the first portion of bodies 112 and 114 to come in contact with tissues such as relatively less dense cancellous bone $B_{CA}$ (shown in FIG. 5A). Bodies 112 and 114 may be configured to be sufficiently flexible such that if either of bodies 112 and 114 contacts relatively more dense materials, such as diaphysis, metaphysis and epiphysis bone, bodies 112 and 114 may deflect generally radially in direction $-\omega_c$ about axis Z and/or in the linear direction towards axis Z at any location along the length of bodies 112 and 114 or any other portion of broaching member 102. Deflection or deformation of bodies 112 and 114 may have the affect of not disturbing the more dense tissues.

Figure 7:
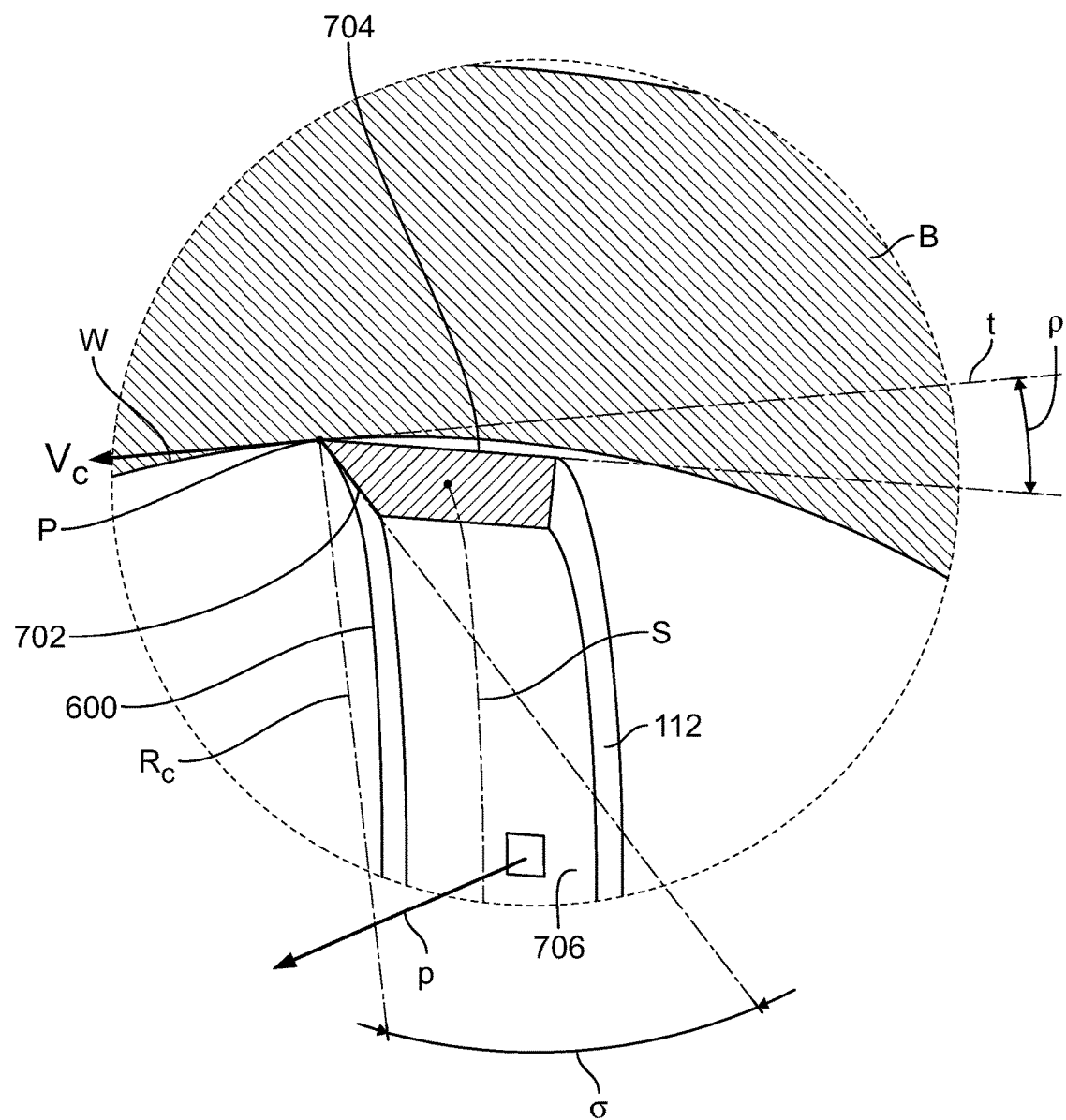
FIG. 7 shows illustrative apparatus in accordance with principles of the invention.

FIG. 7 shows an expanded view of region 7 (shown in FIG. 6) of a portion of illustrative tool 100. Elongated body 112 may include cutting edge 600. Cutting edge 600 may be in contact with bone B at contact point P. Contact point P may be formed at the intersection of rake face 702 and relief face 704. Tangent t is tangent inner surface W of bone B at point P. Relief angle ρ runs between tangent t and relief face 704. Rake angle σ runs between cavity radius $R_c$ (normal to tangent t) and rake face 702.

Body 112 may include face 706. Face 706 may have an aspect that is different at different locations on body 112. Vector p, which is normal to face 706, may have different orientations at the different locations. Central axis S is shown running through the center of body 112 and conforming to curvature of body 112.

Figure 8:
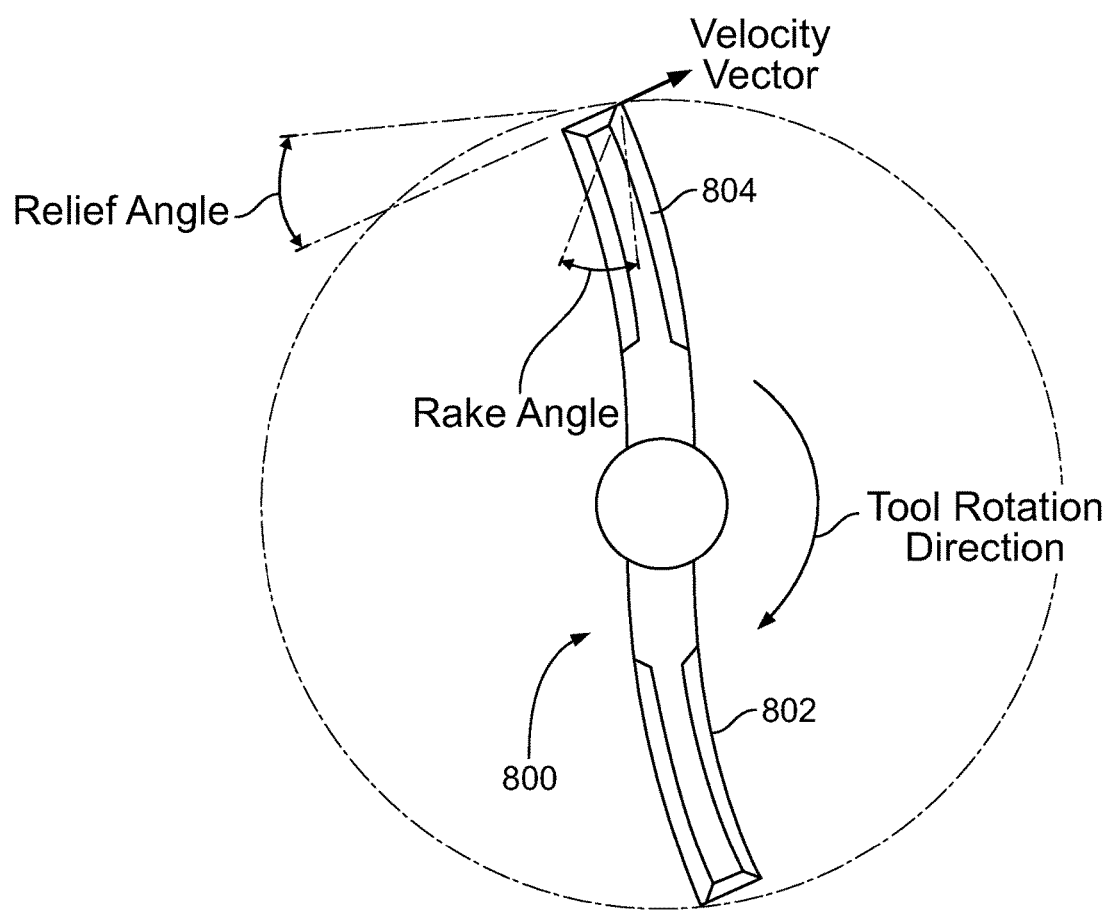
FIG. 8 shows illustrative apparatus in accordance with principles of the invention.

FIG. 8 shows torsional deflection of illustrative member 800. Member 800 includes blades 802 and 804. Each blade may include two cutting edges. One of the cutting edges may be used to cut tissue when the body is rotated in a first direction. The other cutting edge may be used to cute tissue when the body is rotated in a second direction opposite the first direction.

The body may be provided with mechanical compliance characteristics so that as the blades engage with the tissue, body deflects or bends in a circumferential direction. The compliance may be set to deflect when the blades run into tissue of certain densities. The deflection may limit one or more of the load, pressure or energy that is delivered to the tissue. The deflection may act as a shock absorber. The compliance characteristics may allow the blades to selectively remove softer tissue rather than harder tissue. The spring-like deflection may limit or reduce accidental delivery of excessive force.

Thus the radial and circumferential compliance of the broaching member may be set such that the member would deflect around tissue of higher densities. Material of different elastic constants may provide different compliances. Material of different thicknesses in a given direction may provide different compliances. A broaching member may have a radial (R, in FIG. 1) thickness. A broaching member may have a circumferential (θ, in FIG. 1) width. A blade may have a radial (R, in FIG. 1) thickness. A blade may have a circumferential (θ, in FIG. 1) width.

When a broaching member yields to tissue of a certain density, it may provide a non-uniform cavity. When a broaching member yields to tissue of a certain density, but not to tissue of a different density, in the same cavity region, it may provide an asymmetric cavity. The compliance may be selected to discriminate between the two densities.

When a blade yields to tissue of a certain density, it may provide a non-uniform cavity. When a blade yields to tissue of a certain density, but not to tissue of a different density, in the same cavity region, it may provide an asymmetric cavity. The compliance may be selected to discriminate between the two densities.

Figure 9:
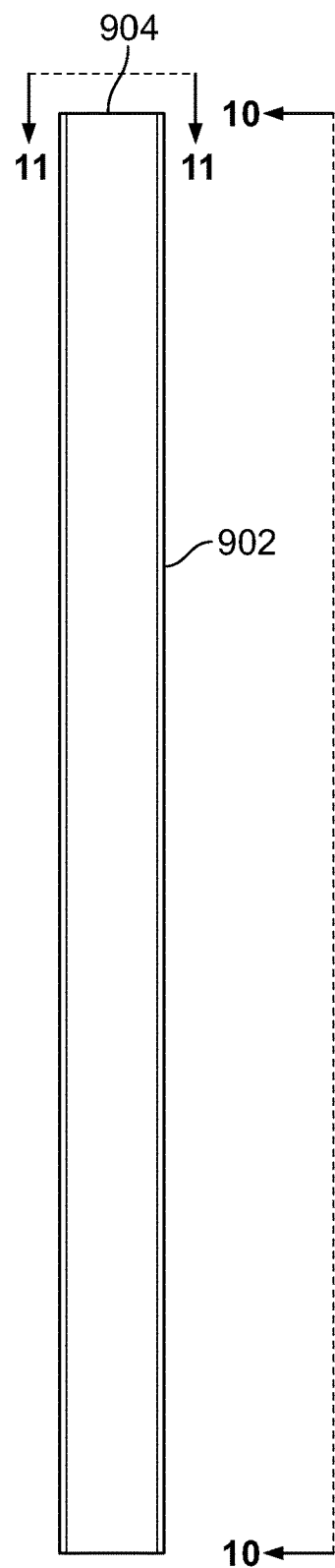
FIG. 9 shows illustrative apparatus in accordance with principles of the invention.

FIG. 9 shows illustrative raw material 902 that may be used to form a broaching member. Raw material 902 may be formed from any suitable material. For example, raw material 902 may include any material that is strong enough to displace the tissue. The material may include one or more of a polymer, a metal, a composite, a stainless steel, a Nitinol (shape set, superelastic or other Nitinol), another alloy or any other suitable material.

Figure 10:
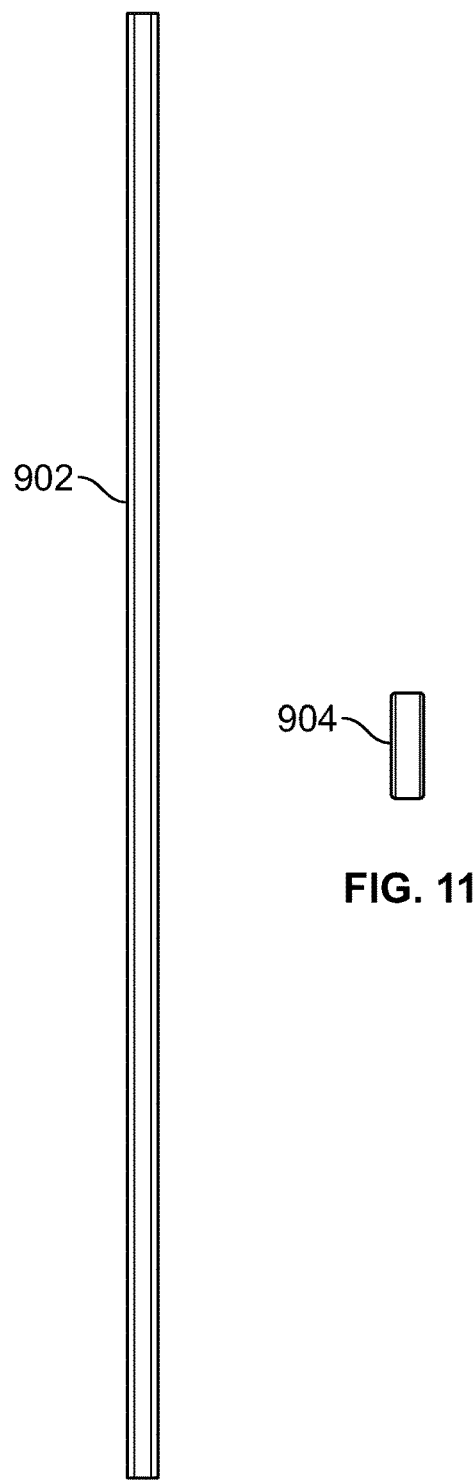
FIG. 10 shows illustrative apparatus in accordance with principles of the invention.

FIG. 10 shows a view of illustrative raw material 902 taken along lines 10-10 (shown in FIG. 9).

Figure 11:
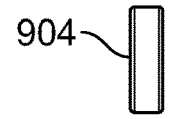
FIG. 11 shows illustrative apparatus in accordance with principles of the invention.

FIG. 11 shows a view of illustrative raw material 902 taken along lines 11-11 (shown in FIG. 9).

FIG. 12 shows illustrative broaching member 1200. Broaching member 1200 may include blade 1202 and blade 1214. Broaching member 1200 may also include retention features 1204 and 1210. Retention features 1204 and 1210 may be fixed to a shaft assembly such as shaft assembly 110 (shown in FIG. 1). Blades 1202 and 1214 may include a cutting edge. The cutting edge may engage tissue in an intramedullary cavity.

Broaching member 1200 may be produced by one or more different processes. Broaching member 1200 may be produced by one or more of EDM, machining, cold-working, hot-working, thermal setting, stamping, shaping, casting, grinding and any other suitable process. The material processes identified in the figure are illustrative.

Broaching member 1200 may be formed from raw material 902 or any other suitable material. Broaching member 1200 may be formed from raw material 902 by electrical discharge machining ("EDM") or any other suitable process known to those skilled in the art.

FIG. 13 shows a view of illustrative broaching member 1200 taken along lines 13-13 (shown in FIG. 12).

FIG. 14 shows a view of illustrative broaching member 1200 taken along lines 14-14 (shown in FIG. 12).

FIG. 15 shows a view of section 15 of illustrative broaching member 1200.

FIG. 16 shows a view of section 15 of illustrative broaching member 1200 taken along lines 16-16 (shown in FIG. 15).

FIG. 17 shows a view of section 15 of illustrative broaching member 1200 taken along lines 17-17 (shown in FIG. 15).

Figure 18:
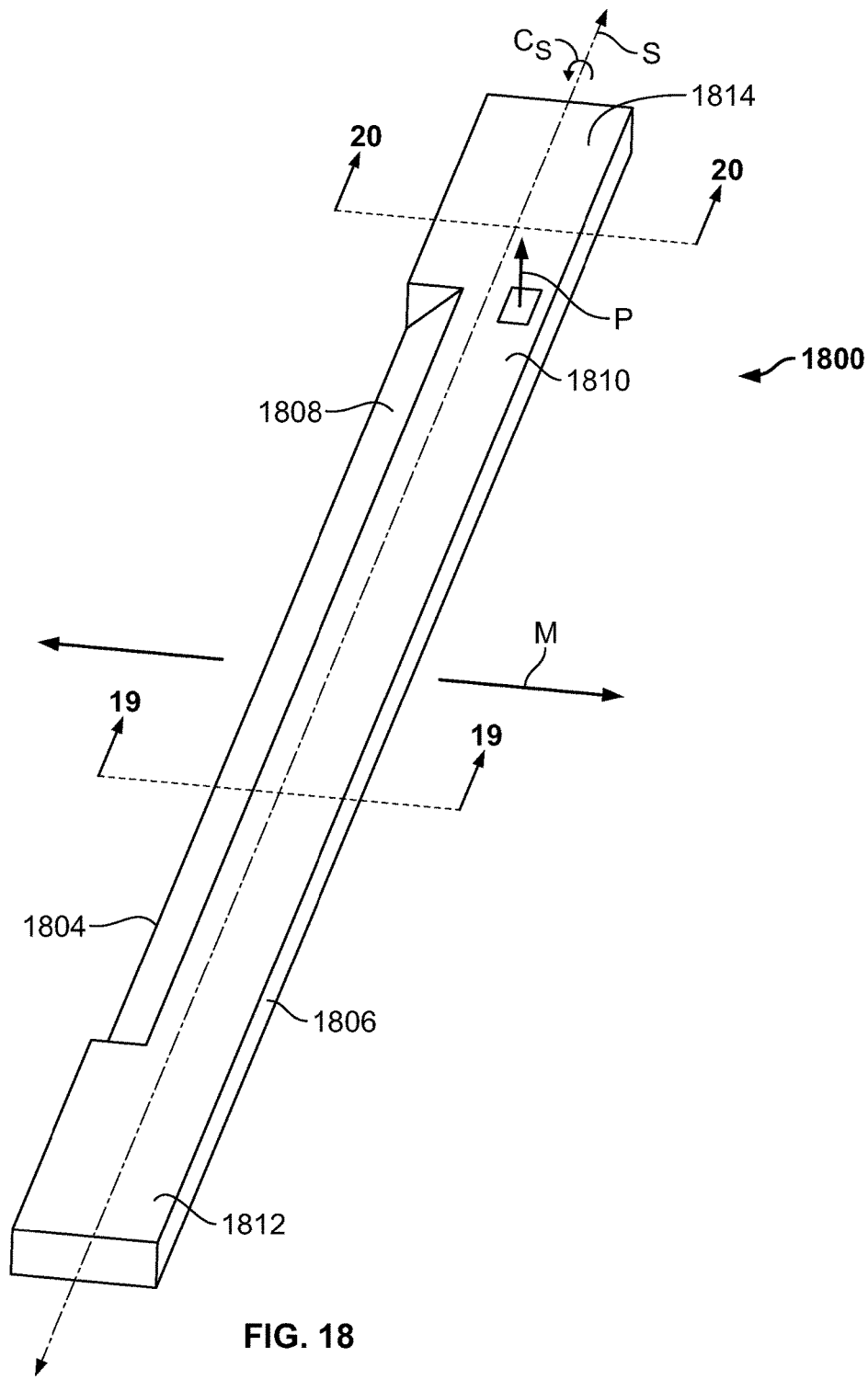
FIG. 18 shows illustrative apparatus in accordance with principles of the invention.

FIG. 18 shows illustrative broaching member 1800. Illustrative broaching member 1800 may be a portion of a broaching member. Illustrative broaching member 1800 may be an elongated body.

Broaching member 1800 may have one or more features in common with broaching member 102 (shown in FIG. 1). Broaching member 1800 may be a portion of broaching member 1200. Broaching member 1800 may be supported by a support such as support member 104 (shown in FIG. 1).

Broaching member 1800 may include cutting edge 1804. Broaching member 1802 may include trailing edge 1806. Cutting edge 1804 may include rake face 1808. Broaching member 1800 is in a planar state. Normal vector p is substantially constant over face 1810.

Axis M is at distance away from (and, as shown, "above") face 1810.

Broaching member 1800 may be deformed about axis M to shape broaching member 1800 for preparing a cavity. Broaching member 1800 may be elastically deformed. Broaching member 1800 may be plastically deformed. Broaching member 1800 may be deformed and thermally set. Broaching member 1800 may be cast to be curved about axis M. Broaching member 1800 may be machined to be curved about axis M. Broaching member 1800 may be deformed about axis M during deployment in bone B.

Broaching member 1800 may include first end 1812. Broaching member 1800 may include second end 1814. Bodies 112 and 114 (shown in FIG. 1) may each have features in common with broaching member 1800.

Body 112 may have a first end such as 1812. Body 114 may have a first end such as 1812. The first ends may be captured within shaft assembly 110.

Body 112 may have a second end such as 1814. Body 114 may have a second end such as 1814. The second ends may be captured at tool distal end 106 (shown in FIG. 1).

The second ends may be joined together at tool distal end 106. The second ends may be of a unitary piece with each other. The unitary piece may be captured at joint 108 (shown in FIG. 1). Joint 108 may be a hinge. Joint 108 may be a pin. When joint 108 is a pin, the unitary piece may be wrapped about the pin. The pin may provide torsional (about the pin) strain relief for the broaching member. A different securement device, such as a clamp, a crimp, a brace, a weld or other such securement device, may be a device that does not provide such relief.

The first ends may be proximal ends. The first ends may be distal ends.

Figure 19:
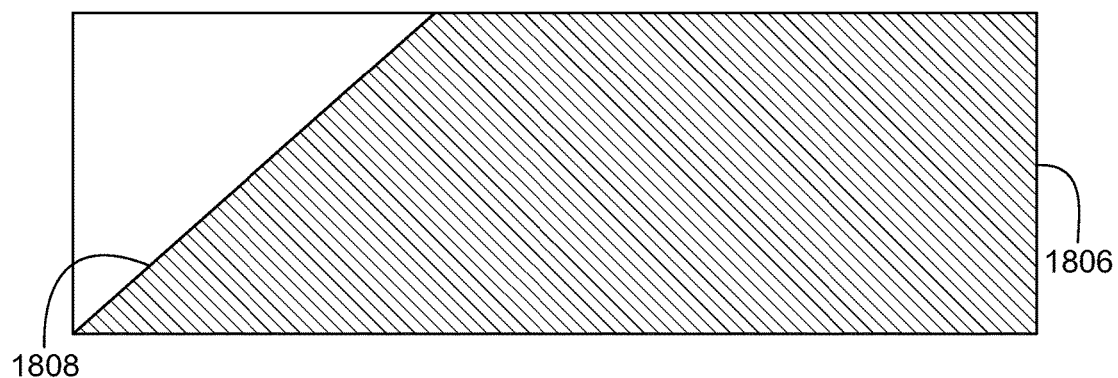
FIG. 19 shows a cross-sectional view of FIG. 18 taken along lines 19-19.

FIG. 19 shows a cross-section showing a view taken along lines 19-19 (shown in FIG. 18).

Figure 20:
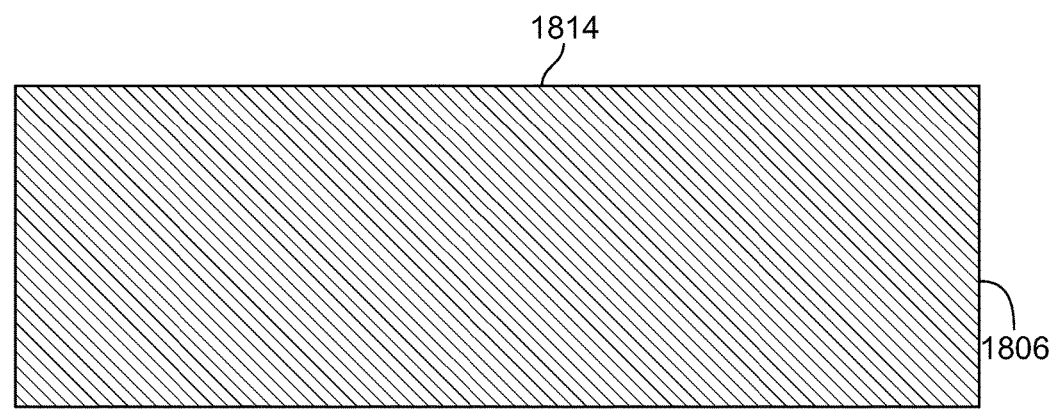
FIG. 20 shows a cross-sectional view of FIG. 19 taken along lines 20-20.

FIG. 20 shows a cross-section showing a view taken along lines 20-20 (shown in FIG. 18).

Figure 21:
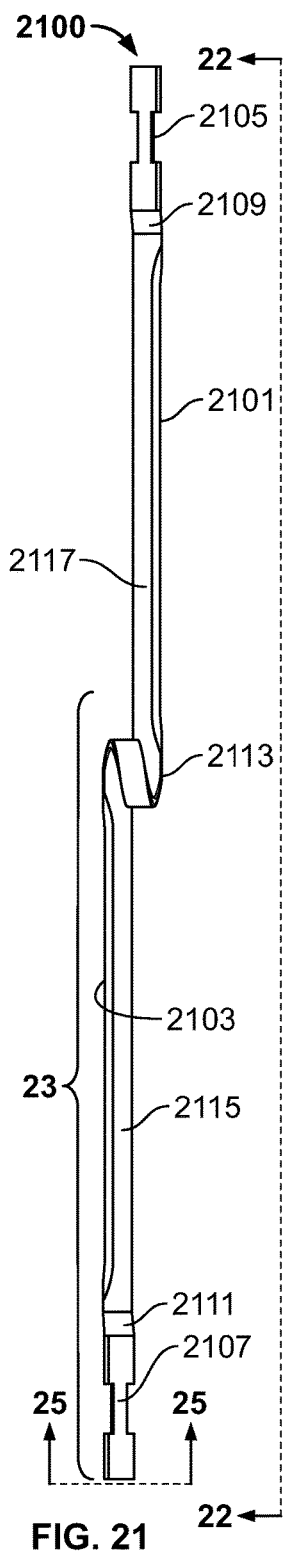
FIG. 21 shows illustrative apparatus in accordance with principles of the invention.

FIG. 21 shows illustrative broaching member 2100. Broaching member 2100 may include cutting edge 2101 and cutting edge 2103. Broaching member 2100 may include loop 2113. Broaching member may include retention feature 2105 and retention feature 2107.

Broaching member 2100 may include twist 2109 and twist 2111. Twist 2109 may represent a portion of broaching member 2100 that has been axially displaced from a central axis of elongated body 2117 including cutting edge 2101. Twist 2111 may represent a portion of broaching member 2100 that has been axially displaced from a central axis of elongated body 2115 including cutting edge 2103.

Body 2117 may define a central axis. Twist 2109 may position retention feature 2105 at an angular displacement along the central axis relative to body 2117.

Body 2115 may define a central axis. Twist 2111 may position retention feature 2107 at an angular displacement along the central axis relative to body 2115.

Figure 22:
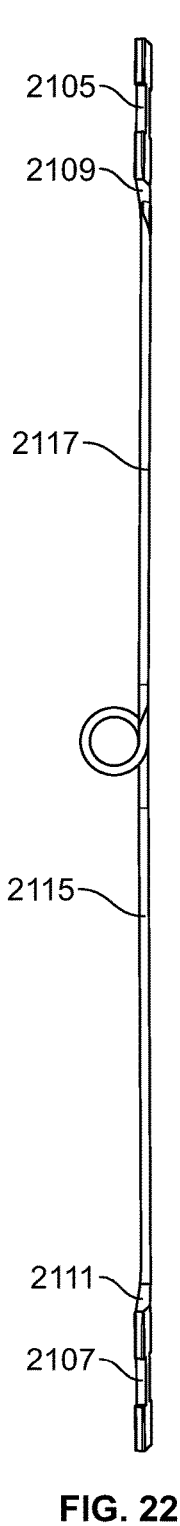
FIG. 22 shows illustrative apparatus in accordance with principles of the invention.

FIG. 22 shows a view of illustrative broaching member 2100 taken along lines 22-22 (shown in FIG. 21). The view in FIG. 22 shows retention features 2107 and 2105 positioned at an angular displacement in relation to a central axis of each of bodies 2115 and 2117.

Figure 23:
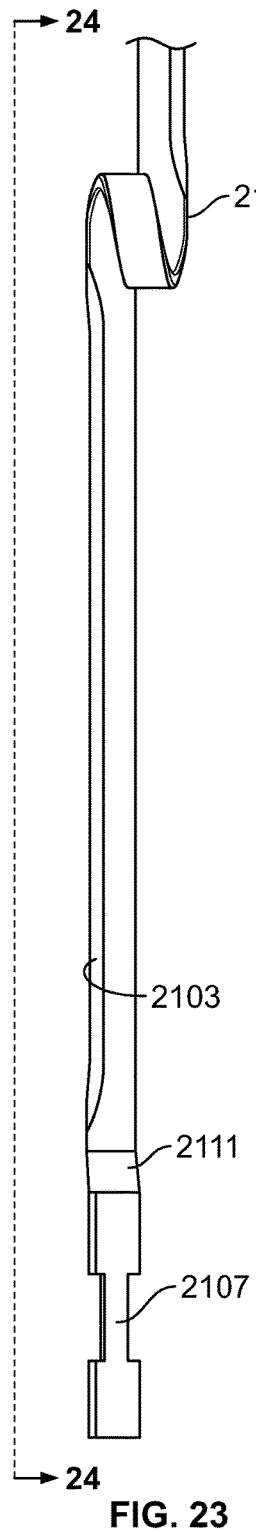
FIG. 23 shows illustrative apparatus in accordance with principles of the invention.

FIG. 23 shows section 23 of illustrative broaching member 2100 (shown in FIG. 21).

Figure 24:
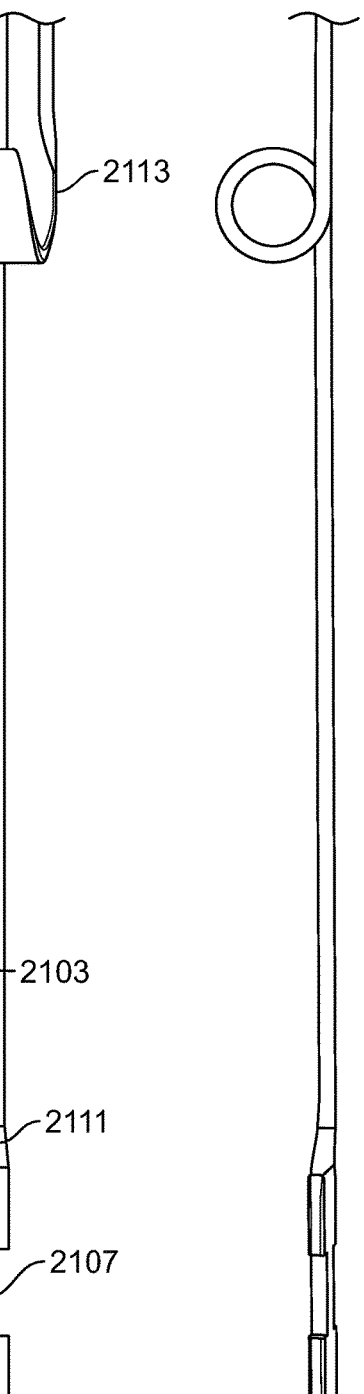
FIG. 24 shows illustrative apparatus in accordance with principles of the invention.

FIG. 24 shows a view of section 23 of illustrative broaching member 2100 (shown in FIG. 23).

Figure 25:
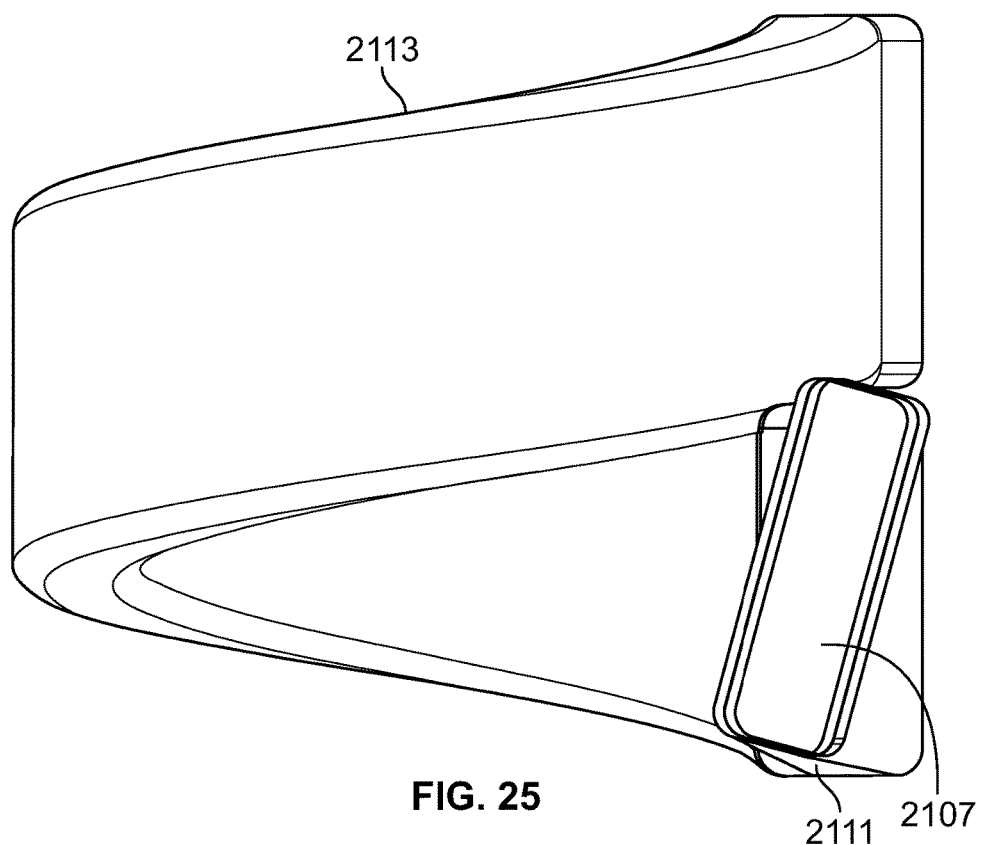
FIG. 25 shows illustrative apparatus in accordance with principles of the invention.

FIG. 25 shows loop 2113 of illustrative broaching member 2100 (shown in FIG. 21). FIG. 25 also shows twist 2111. Twist 2111 is opposite loop 2113 and is twisted relative to the intervening blade 2103.

The amount of twist in twist 2111 may affect an engagement angle of a cutting edge of blade 2103 with tissue. The twist may be axial in nature and may vary from 0-90 degrees. Twists may be discrete in the broaching member. Twists may be continuous or distributed along a broaching member. A twist may function as an engagement feature, for example, to engage a support. A twist may provide strain relief, for example, to "wind" or "unwind" in response to tension or compression along a blade or body. A twist may provide an attachment location, for example, the twist may be secured to the support by a pin. The twist may alter the rake and relief angle of the cutting edge relative to a bone.

Figure 26:
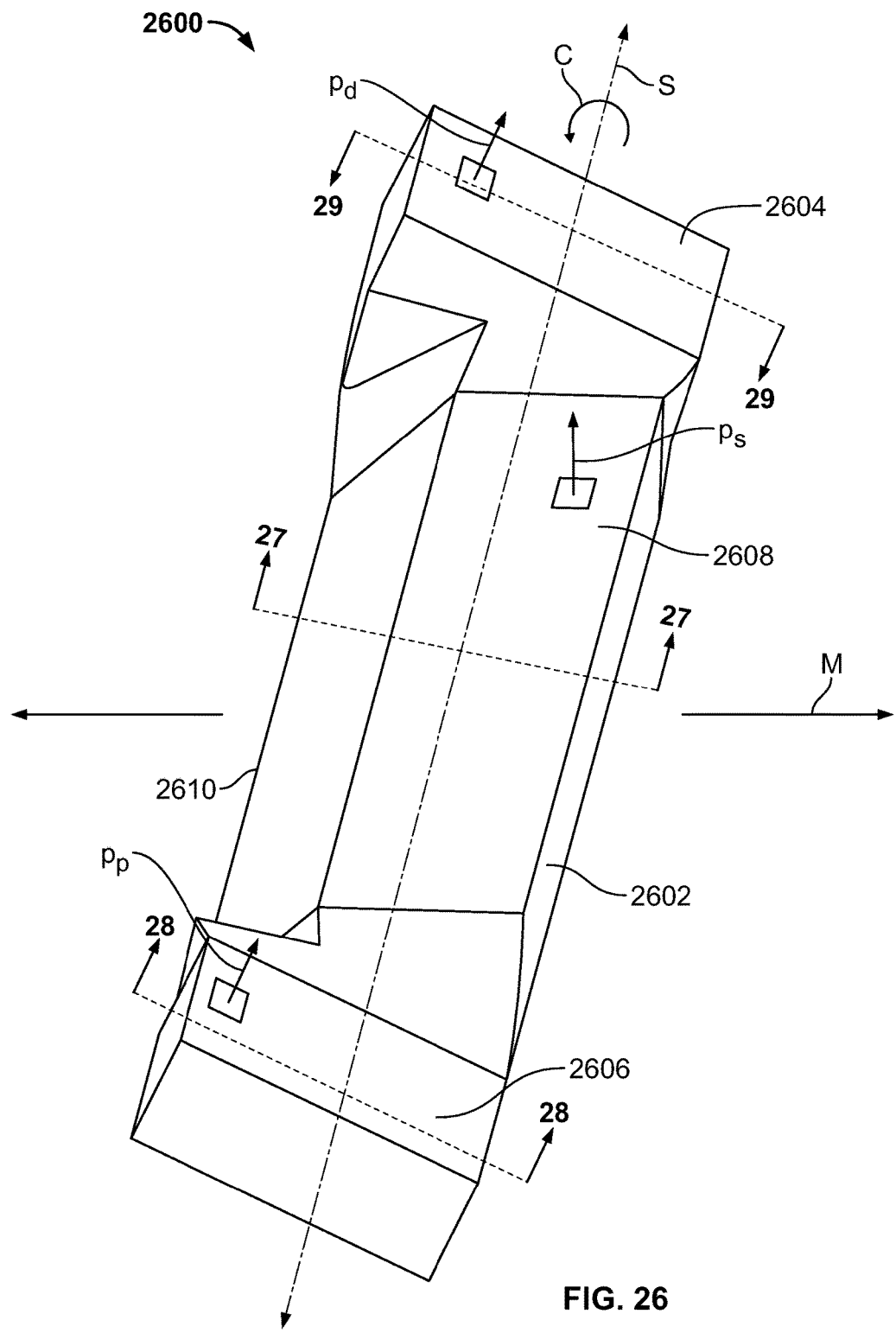
FIG. 26 shows illustrative apparatus in accordance with principles of the invention.

FIG. 26 shows illustrative broaching member 2600. Illustrative broaching member 2600 may have one or more features in common with broaching member 102 (shown in FIG. 1), broaching member 1800 (shown in FIG. 18) and bodies 2115 and 2117. Broaching member 2600 may be a portion or section of a broaching member. Broaching member 2600 may be an elongated body.

Broaching member 2600 may include distal segment 2604. Normal vector $p_d$ may indicate the orientation of distal segment 2604. Broaching member 2600 may include proximal segment 2606. Normal vector $p_p$ may indicate the orientation of proximal segment 2606. Broaching member 2600 may include span segment 2608. Normal vector $p_s$ may indicate the orientation of span segment 2608. Span segment 2608 may span from distal segment 2604 to proximal segment 2606. Broaching member 2600 may include trailing edge 2602.

Broaching member 2600 may be supported by a support such as support member 104 (shown in FIG. 1). Broaching member 2600 may be deformed about axis M to shape broaching member 2600 for preparing the cavity.

Distal segment 2604 and proximal segment 2606 may be secured to the support. Distal segment 2604 and proximal segment 2606 may be secured to the support in any suitable manner. Distal segment 2604 and proximal segment 2606 may be secured to the support such that normal vectors $p_d$ and $p_p$ are oriented in the same direction as each other. Distal segment 2604 and proximal segment 2606 may be secured to the support such that normal vectors $p_d$ and $p_p$ are oriented in opposite directions from each other. Distal segment 2604 and proximal segment 2606 may be secured to the support such that normal vectors $p_d$ and $p_p$ are oriented oblique to each other. Distal segment 2604 and proximal segment 2606 may be secured to the support such that normal vectors $p_d$ and $p_p$ are oriented normal to each other. Distal segment 2604 and proximal segment 2606 may be secured to the support such that normal vectors $p_d$ and $p_p$ are oriented at any suitable angle to each other.

Distal segment 2604 and proximal segment 2606 may be secured to the support such that one or both of normal vectors $p_d$ and $p_p$ are oriented in the same direction as radial direction R (shown in FIG. 1). Distal segment 2604 and proximal segment 2606 may be secured to the support such that one or both of normal vectors $p_d$ and $p_p$ are oriented opposite radial direction R (shown in FIG. 1). Distal segment 2604 and proximal segment 2606 may be secured to the support such that one or both of normal vectors $p_d$ and $p_p$ are oblique to radial direction R. Distal segment 2604 and proximal segment 2606 may be secured to the support such that one or both of normal vectors $p_d$ and $p_p$ are normal to radial direction R. Distal segment 2604 and proximal segment 2606 may be secured to the support such that one or both of normal vectors $p_d$ and $p_p$ are oriented in any suitable fashion relative to radial direction R (shown in FIG. 1).

Distal segment 2604 may be secured to the support by being monolithic with a broaching member wrap section. Distal segment 2606 may be secured to the support by being monolithic with a broaching member wrap section. A broaching member wrap section may include a looped section of a broaching member.

Because distal segment 2604 and distal segment 2606 are, in a relaxed state, counter rotated, in the –C direction, about central axis S, the securement of vectors $p_d$ and $p_p$ antiparallel to radius R causes a rotation of normal vector $p_s$ in direction C. This may increase the relief angle of cutting edge 2610. This may decrease the rake angle of cutting edge 2610.

Figure 27:
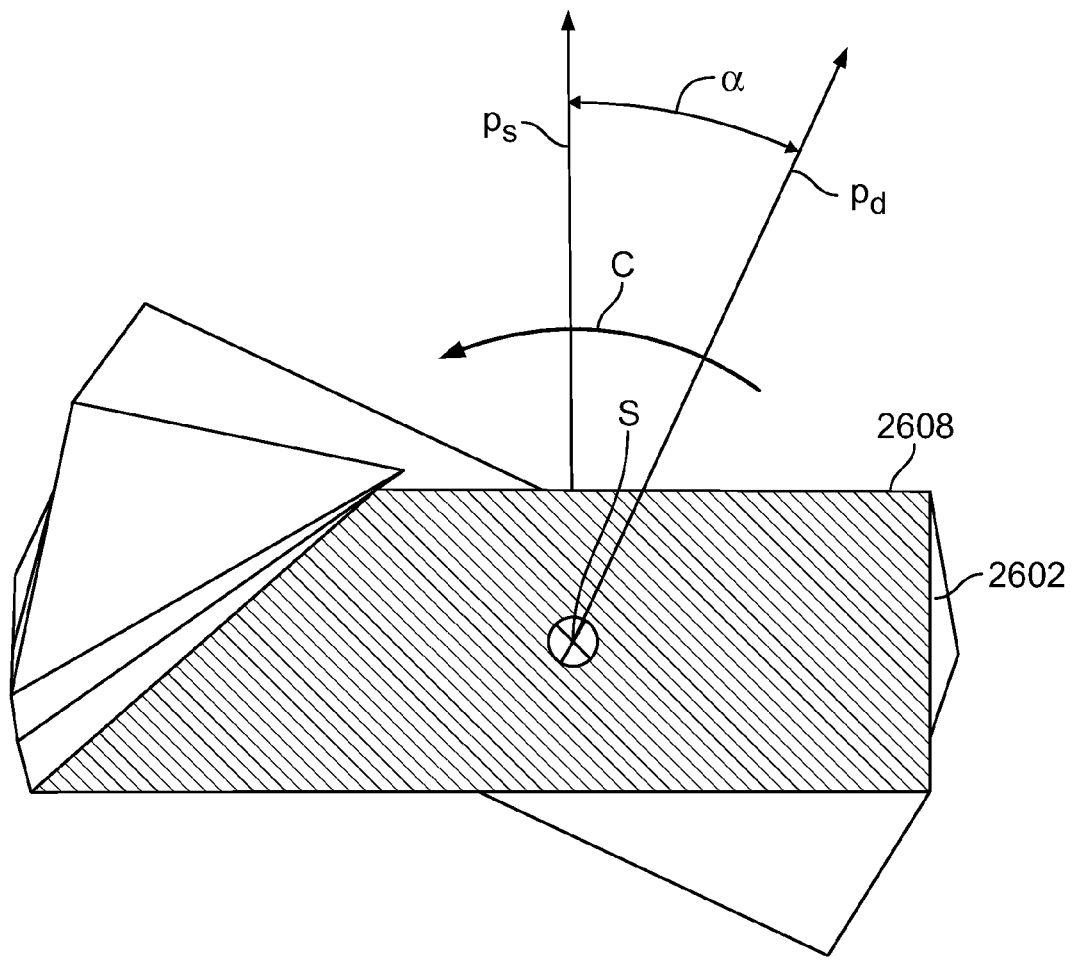
FIG. 27 shows a partial cross-sectional view of FIG. 26 taken along lines 27-27.

FIG. 27 shows a partial cross-section showing a view taken along lines 27-27 (shown in FIG. 26). Normal vector $p_d$ is shown counter-rotated, relative to normal vector $p_s$, in direction –C, by angular displacement α.

Figure 28:
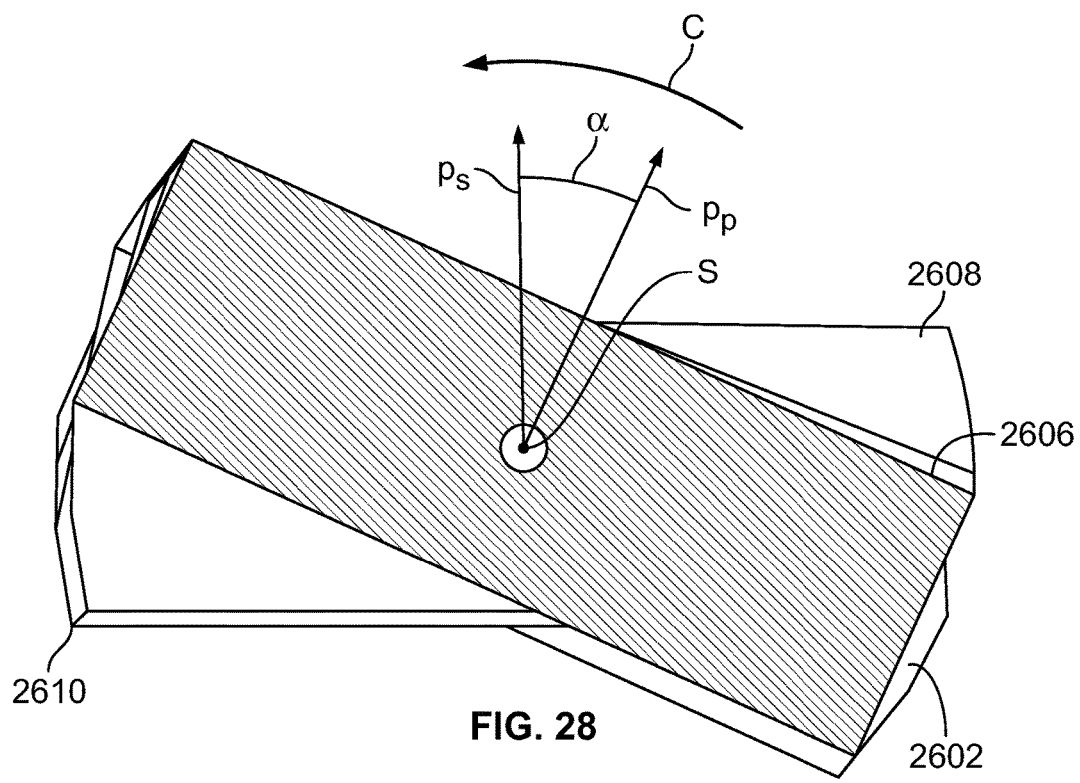
FIG. 28 shows a partial cross-sectional view of FIG. 26 taken along lines 28-28.

FIG. 28 shows a partial cross-section showing a view taken along lines 28-28 (shown in FIG. 26). Normal vector $p_p$ is shown counter-rotated, relative to normal vector $p_s$, in direction –C, by angular displacement α.

Figure 29:
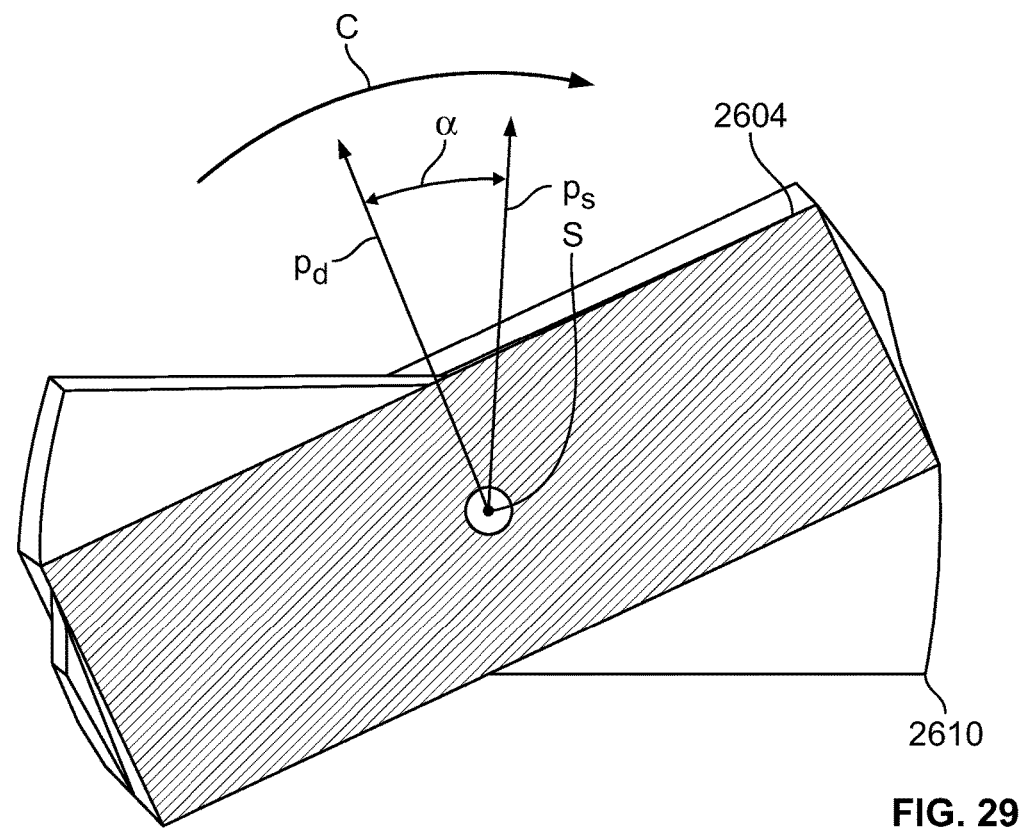
FIG. 29 shows a partial cross-sectional view of FIG. 26 taken along lines 29-29.

FIG. 29 shows a partial cross-section showing a view taken along lines 29-29 (shown in FIG. 26). Normal vector $p_d$ is shown counter-rotated, relative to normal vector $p_s$, in direction –C, by angular displacement α.

FIG. 30 shows illustrative broaching member 3000. Broaching member 3000 may include loop 3007, cutting edge 3001, cutting edge 3011, twist 3005, twist 3013, retention feature 3009 and retention feature 3015. Loop 3007 may function as a hinge when wrapped around a transverse member. Loop 3007 may relieve strain in broaching member 3000 when wrapped around a transverse member. Loop 3007 may function as a control point.

Broaching member may also include elongated body 3017 and elongated body 3019. Elongated bodies 3017 and 3019 may be curved. The shaping may involve a bend that is in a plane parallel to the widest aspect of bodies 3017 and 3019 and around an axis that is perpendicular to the edge of the bodies that contains cutting edges 3001 and 3011. The bend may lengthen the cutting edges 3001 and 3011 relative to the opposite (trailing) edges. The length difference then may effect, when bodies 3017 and 3019 undergo a second shaping around an axis perpendicular to the length of broaching member 3000, a radial difference between the cutting edges and the trailing edges.

FIG. 31 shows a view of illustrative broaching member 3000 taken along lines 31-31 (shown in FIG. 30). The view in FIG. 31 shows retention features 3003 and 3015 positioned at an angular displacement in relation to a central axis of each of bodies 3017 and 3019.

FIG. 32 shows a view of illustrative broaching member 3000 taken along lines 32-32 (shown in FIG. 30). The view in FIG. 32 shows loop 3007 and bodies 3017 and 3019 curving away from loop 3007.

Figure 33:
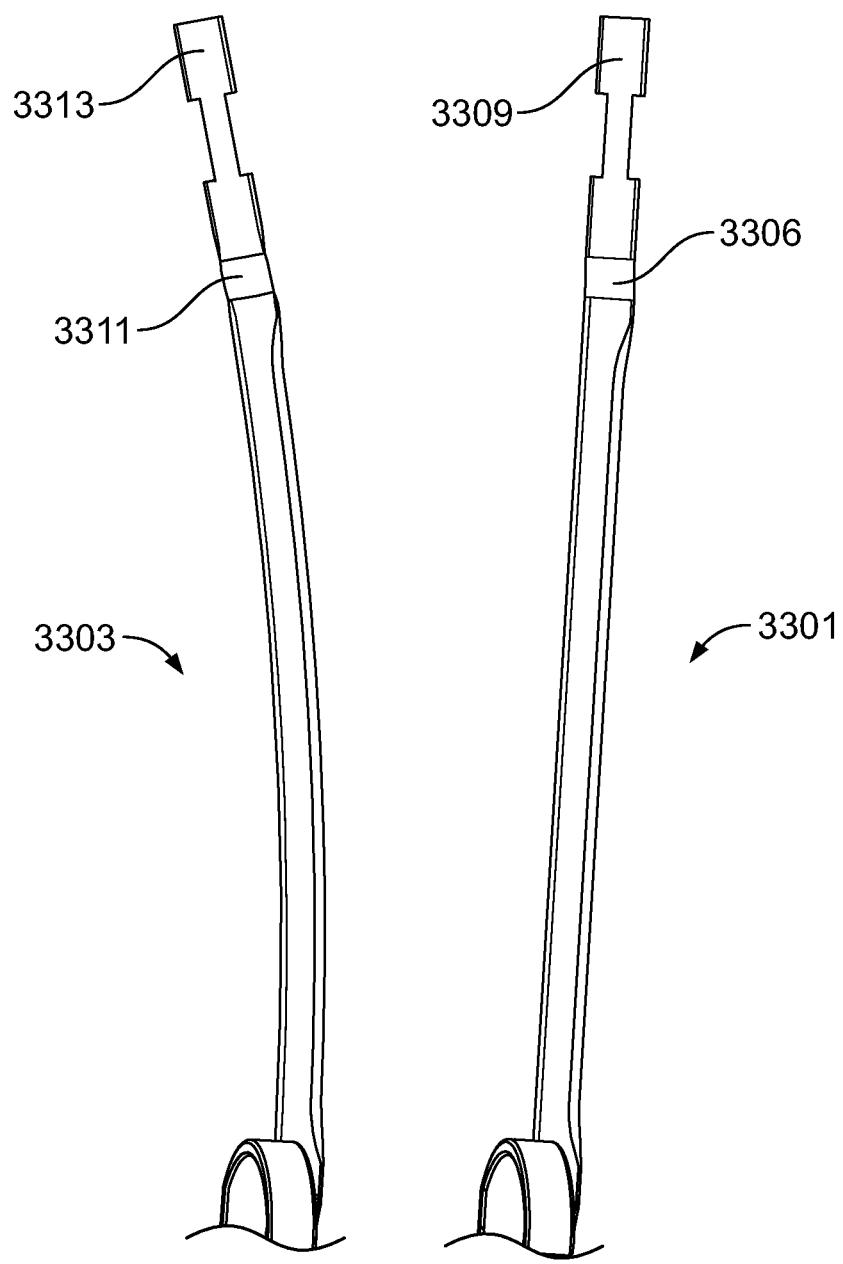
FIG. 33 shows illustrative apparatus in accordance with principles of the invention.

FIG. 33 shows a portion of illustrative bladed bodies 3301 and 3303 produced by one or more different processes. Body 3301 may include twist 3306. Twist 3306 may angularly displace retention feature 3309 about a central axis of body 3301. Body 3303 may be curved. Body 3303 may include twist 3311. Twist 3311 may angularly displace retention feature 3313 about a central axis of body 3303.

A broaching member may be produced by one or more of EDM, machining, cold-working, hot-working, thermal setting, stamping, shaping, casting and any other suitable process. An elongated body may be produced by one or more of EDM, machining, cold-working, hot-working, thermal setting, stamping, shaping, casting and any other suitable process.

A broaching member may have bends and/or twists to facilitate the shape and tissue engagement of the tool. An elongated body may have bends and/or twists to facilitate the shape and tissue engagement of the tool. Twists may be chosen to provide a desired expanded shape. Twists may be chosen to provide a desired distribution of rake angle along the blade. Twists may be chosen to provide a desired distribution of relief angle along the blade. Twists may be chosen to provide a desired distribution of rake and relief angle along the blade.

A broaching member may include engagement features at the ends to facilitate the engagement of the broaching member with other assembly features. An elongated body may include engagement features at the ends to facilitate the engagement of the elongated body with other assembly features. The loop or hinge feature may provide one or more of strain relief, attachment points, shape control points, tool-engagement and other suitable features. Control points may include locations, for example on a support, where one or more bodies may be manipulated through application of forces applied by a user (e.g., through an actuator) to achieve a desired effect. A control point may constrain one or more of displacement or orientation of a body portion such that a user may apply a force to the body, the control point may provide a reactive force, and the body may deform as result in whole or in part of the displacement or orientation constraint at the control point.

Figure 34:
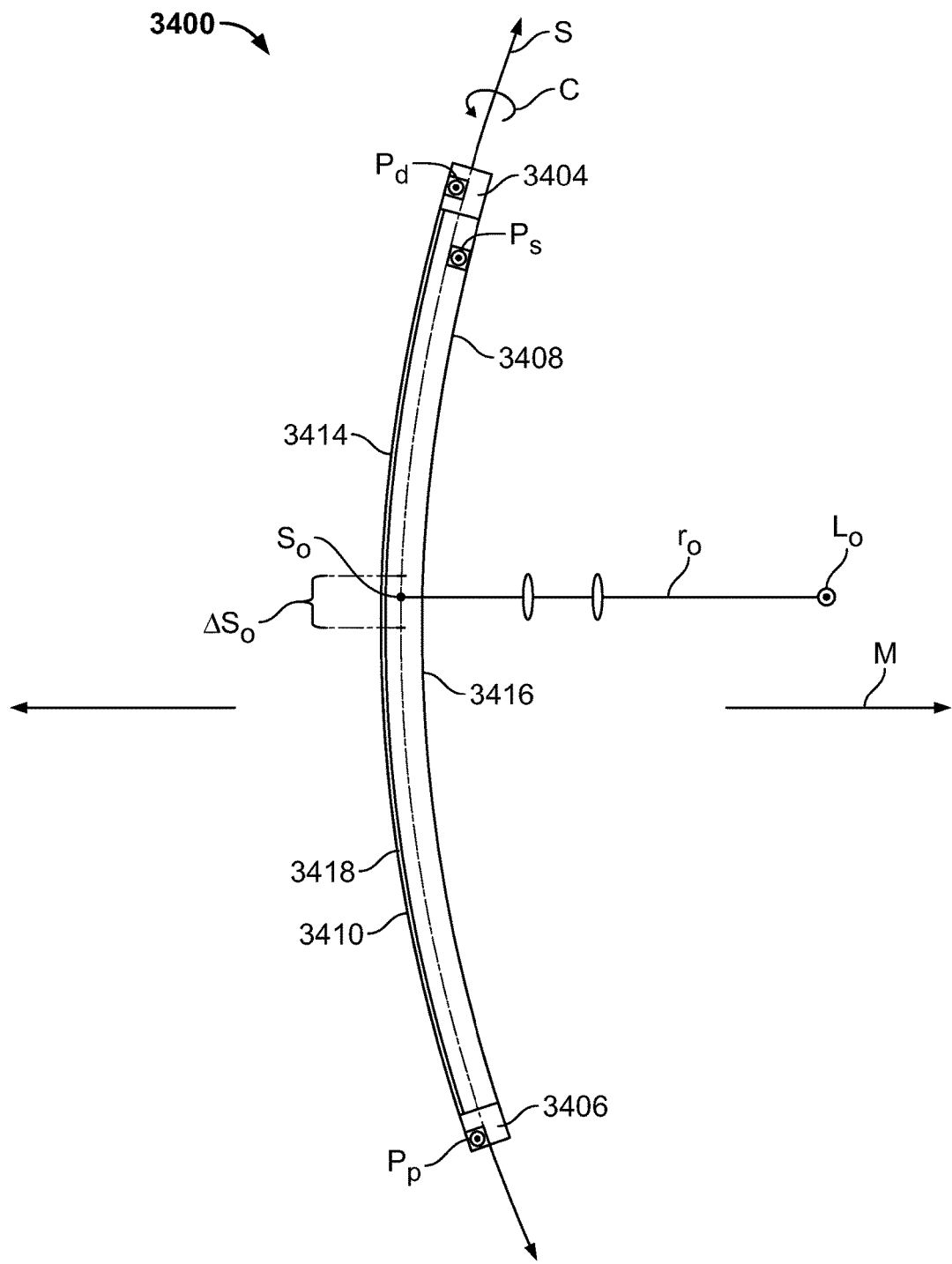
FIG. 34 shows illustrative apparatus in accordance with principles of the invention.

FIG. 34 shows illustrative broaching member 3400. Illustrative broaching member 3400 may have one or more features in common with one or more of broaching members 102 (shown in FIG. 1), 1800 (shown in FIG. 18), 2600 (shown in FIG. 26) and 3000 (shown in FIG. 30). Broaching member 3400 may be an elongated body.

Broaching member 3400 may include distal segment 3404. Normal vector $p_d$ may indicate the orientation of distal segment 3404. Broaching member 3400 may include proximal segment 3406. Normal vector $p_p$ may indicate the orientation of proximal segment 3406. Broaching member 3400 may include span segment 3408. Normal vector $p_s$ may indicate the orientation of span segment 3408. Span segment 3408 may span from distal segment 3404 to proximal segment 3406.

Normal vectors $p_d$, $p_s$ and $p_d$ are parallel to each other and to axis Lo. Normal vector $p_s$ may be perpendicular to span segment 3408.

Broaching member 3400 may be supported by a support such as support member 104 (shown in FIG. 1). Broaching member 3400 may be deformed about axis M to shape broaching member 3400 for preparing the cavity.

Distal segment 3404 and proximal segment 3406 may be secured to the support such that normal vectors $p_d$ and $p_p$ are antiparallel to radius R (shown in FIG. 1). When distal segment 3404 and distal segment 3406 are, in a relaxed state, counter rotated, in the –C direction, about central axis S, the securement of vectors $p_d$ and $p_p$ antiparallel to radius R causes a rotation of normal vector $p_s$ in direction C. This may increase the relief angle of cutting edge 3410. This may decrease the rake angle of cutting edge 3410. Cutting edge 3410 may run along rake face 3418.

Distal segment 3404 may be secured to the support by being monolithic with a broaching member wrap section. Distal segment 3404 may be secured to the support by being attached to a broaching member wrap section. Distal segment 3406 may be secured to the support by being monolithic with a broaching member wrap section. Distal segment 3406 may be secured to the support by being attached to a broaching member wrap section. A broaching member wrap section may include a looped section of a broaching member.

Cutting edge 3410 may run along some or all of leading edge 3414. Broaching member 3400 may include an outer surface (not shown) that may be spaced apart, as along direction R (shown in FIG. 1), from span segment 3408. Span segment 3408 may be parallel to the outer surface. Trailing edge 3416 may be spaced apart, as along direction −θ (shown in FIG. 1), from leading edge 3414.

Broaching member 3400 may include segment $\Delta s_o$ at point $S_o$ along central axis S. Segment $\Delta s_o$ may be curved about axis Lo and have radius of curvature $r_o$. Point S may be representative of one or more points along central axis S.

Because of shaping about axis $L_O$, such as radius of curvature $r_0$, for a segment $\Delta s_O$, leading edge 3414 may have an arclength that is greater than the corresponding arclength of trailing edge 3416. Leading edge 3414 may have an overall shaped length that is greater than that of trailing edge 3416.

Radius of curvature $r_o$ may be obtained by one or more of stamping, cutting, machining, any other suitable manufacturing process, deformation, such as bending, thermal shape setting or any other suitable process. Deformation about axis M may be performed after setting of radius of curvature $r_o$. Deformation about axis M may be performed before setting of radius of curvature $r_o$.

Figure 35:
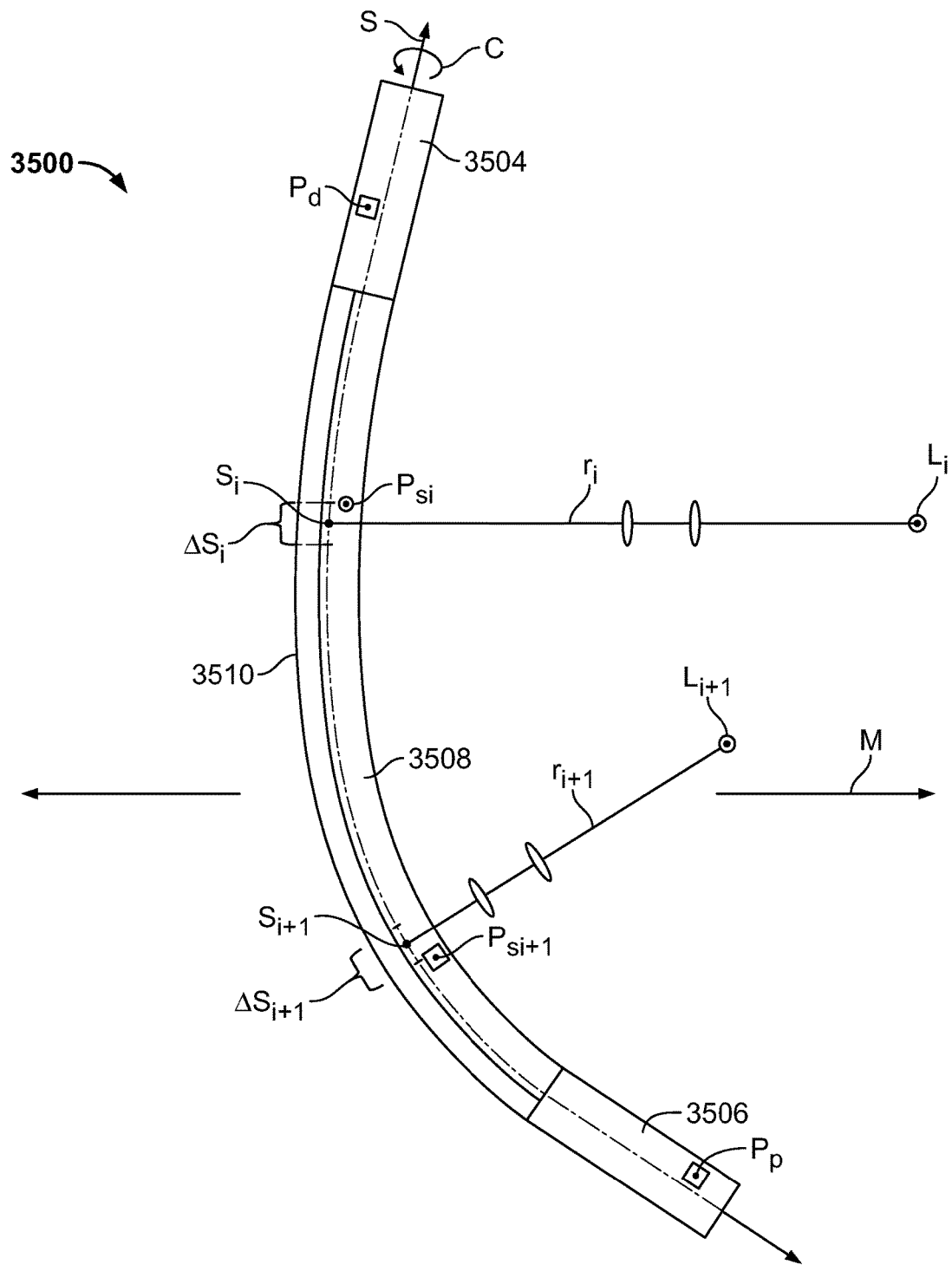
FIG. 35 shows illustrative apparatus in accordance with principles of the invention.

FIG. 35 shows illustrative broaching member 3500. Illustrative broaching member 3500 may have one or more features in common with one or more of broaching members 102 (shown in FIG. 1), 1800 (shown in FIG. 18), 2600 (shown in FIG. 26) and 3400 (shown in FIG. 34). Broaching member 3500 may include an elongated body.

Broaching member 3500 may include distal segment 3504. Normal vector $p_d$ may indicate the orientation of distal segment 3504. Broaching member 3500 may include proximal segment 3506. Normal vector $p_p$ may indicate the orientation of proximal segment 3506. Broaching member 3500 may include span segment 3508. Normal vectors $p_s$ such as normal vectors psi and psi+1 may indicate orientation of corresponding different span segments Δs, such as Δsi and Δsi+1, i=1 . . . I−1, located at points S, such as Si and Si+1 along central axis S.

Span segment 3508 may span from distal segment 3504 to proximal segment 3506.

Normal vectors $P_d$, $P_{Si}$, $P_{Si+1}$ and $P_p$ are parallel to each other. Normal vectors $P_d$, $P_{Si}$, $P_{Si+1}$ and $P_p$ may be parallel to one or more of axes Li, Li+1, . . . .

Broaching member 3500 may be supported by a support such as support member 104 (shown in FIG. 1). Broaching member 3500 may be deformed about axis M to shape blade 3500 for preparing the cavity.

Figure 43:
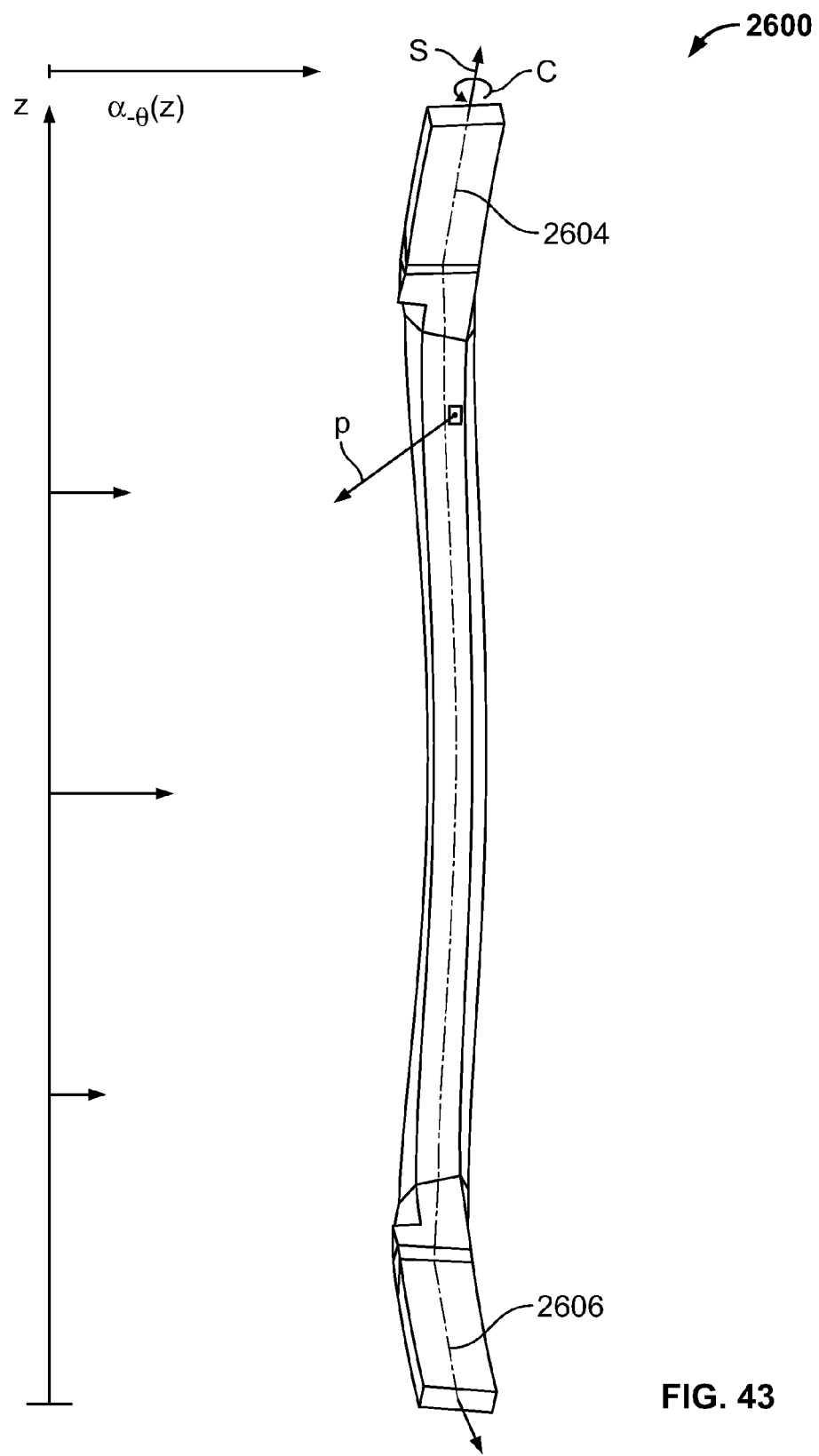
FIG. 43 shows illustrative apparatus in accordance with principles of the invention.

Distal segment 3504 and proximal segment 3506 may be secured to the support such that normal vectors $p_d$ and $p_p$ are antiparallel to radius R (shown in FIG. 43). When distal segment 3504 and distal segment 3506 are, in a relaxed state, counter rotated, in the −C direction, about central axis S, the securement of vectors $p_d$ and $p_p$ antiparallel to radius R causes a rotation of normal vector $p_s$ in direction C. This may increase the relief angle of cutting edge 3510. This may decrease the rake angle of cutting edge 3510.

Distal segment 3504 may be secured to the support by being monolithic with a broaching member wrap section. Distal segment 3504 may be secured to the support by being attached to a broaching member wrap section. Distal segment 3506 may be secured to the support by being monolithic with a broaching member wrap section. Distal segment 3506 may be secured to the support by being attached to a broaching member wrap section. A broaching member wrap section may include a looped section of a broaching member.

Segments Δsi may be curved about corresponding axes Li and may have corresponding radii of curvature ri. The radii of curvature ri may be different from each other. For example, ri is shown as being greater than ri+1.

Radii of curvature ri may be obtained by stamping, cutting, machining, any other suitable manufacturing process, deformation, such as bending, thermal shape setting or any other suitable process. Deformation about axis M may be performed after setting of radius of curvature $r_o$. Deformation about axis M may be performed before setting of radius of curvature $r_o$.

FIG. 36 shows an illustrative broaching member. The broaching member may be formed from a unitary body. The unitary body may have one or more features in common with broaching member 102 (shown in FIG. 1). The unitary body may include a loop, a turn-around, a wrap section, or a hinge point as shown at 3601. The loop, turn-around, wrap section or hinge point may be supported by a support. The support may be a pin, a transverse member, a cylindrical form, a bushing, or any other support known to those skilled in the art.

The loop may include one or more of a wrap, a half-wrap, two wraps and any suitable combination of wraps and half-wraps to yield the desired final shape. The portion of the broaching member coming into the loop and the portion of the broaching member coming out of the loop may be as shown. The two portions may form any suitable angle from 0 to 180° to facilitate the desired expanded shape. The broaching member may have a preset shape that the body assumes upon expansion inside the bone.

One of ordinary skill in the art would understand how to support, deploy and operate the broaching member.

Ends 3603 may be supported by a support such as shaft assembly 110 (shown in FIG. 1).

The distance between the loop and the ends may be changed to change the shape of the body. For example, the body may have a preset curved shape. The distance may then be lengthened (by moving the ends away from the loop) to reduce the diameter for insertion into the bone. The distance may then be shortened to expand the body back to the preset shape. The same or a different length setting may be used to deliver the desired therapy.

FIG. 36A shows a view of illustrative broaching member 3600 taken along lines 36A-36A (shown in FIG. 36).

FIG. 37 shows a view of illustrative broaching member 3600 taken along lines 37-37 (shown in FIG. 36).

FIG. 38 shows a partial cross sectional view of illustrative broaching member 3600 taken along lines 38-38 (shown in FIG. 36).

Figure 39:
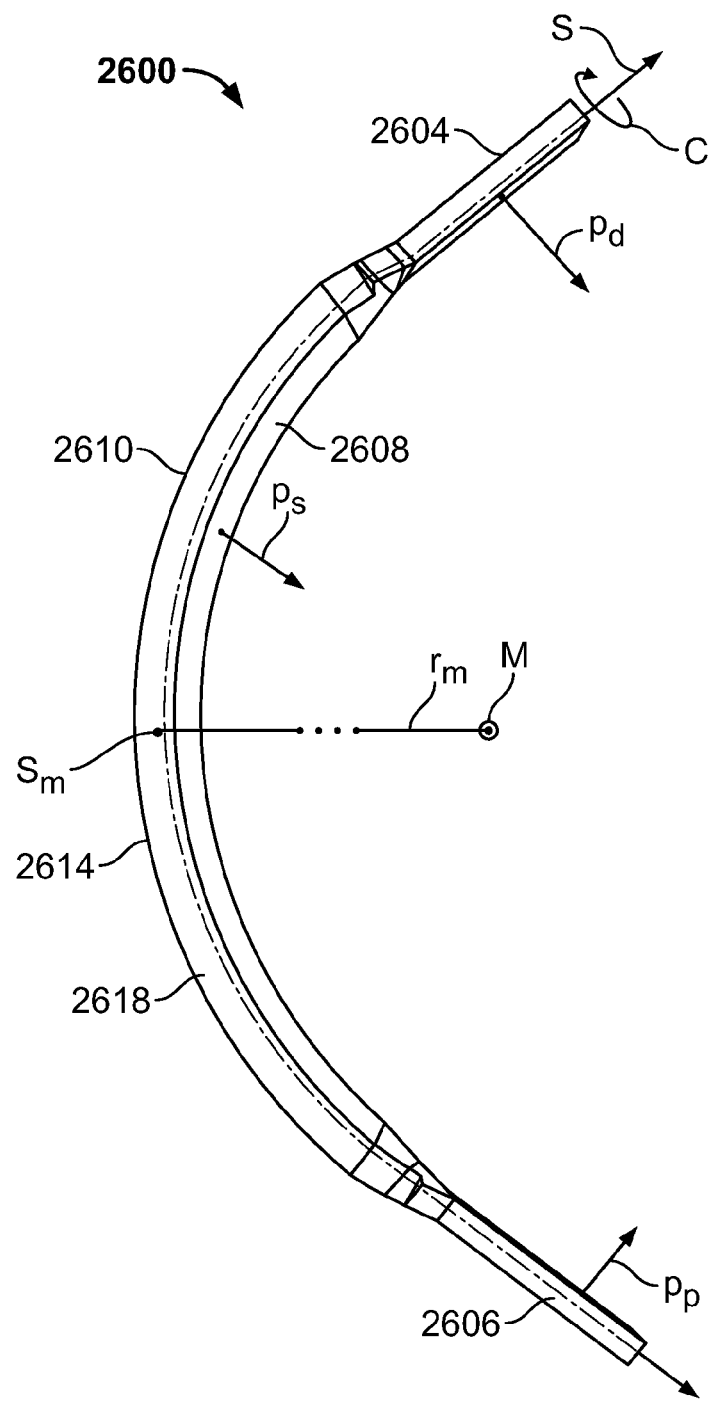
FIG. 39 shows illustrative apparatus in accordance with principles of the invention.

FIG. 39 shows illustrative broaching member 2600 (shown in FIG. 26) shaped about axis M. Central axis S may be shaped in any suitable shape about axis M. Central axis S is illustrated as circumscribing a circle about, and perpendicular to, axis M. The circle may have radius $r_M$. Because leading edge 2614 is greater than the trailing edge (not visible), leading edge 2614 may lie at a radius from axis M that is greater than the radius from axis M at which lies the trailing edge. Span segment 2608 and the opposite outer surface would thus be conical or pseudoconical surfaces with axis M running along a conical or pseudoconical axis. In this configuration, rake face 2618 may have a rake angle that is lesser than the rake angle that rake face 2618 would have if one or both of ends 2604 and 2606 were not counterrotated in direction −C prior to securement of ends 2604 and 2606 to a support. Counterroation of one of the ends may decrease the rake angle. Counterrotation of both ends may further decrease the rake angle. Counterroation of one of the ends may increase the relief angle. Counterrotation of both ends may further increase the relief angle.

Figure 40:
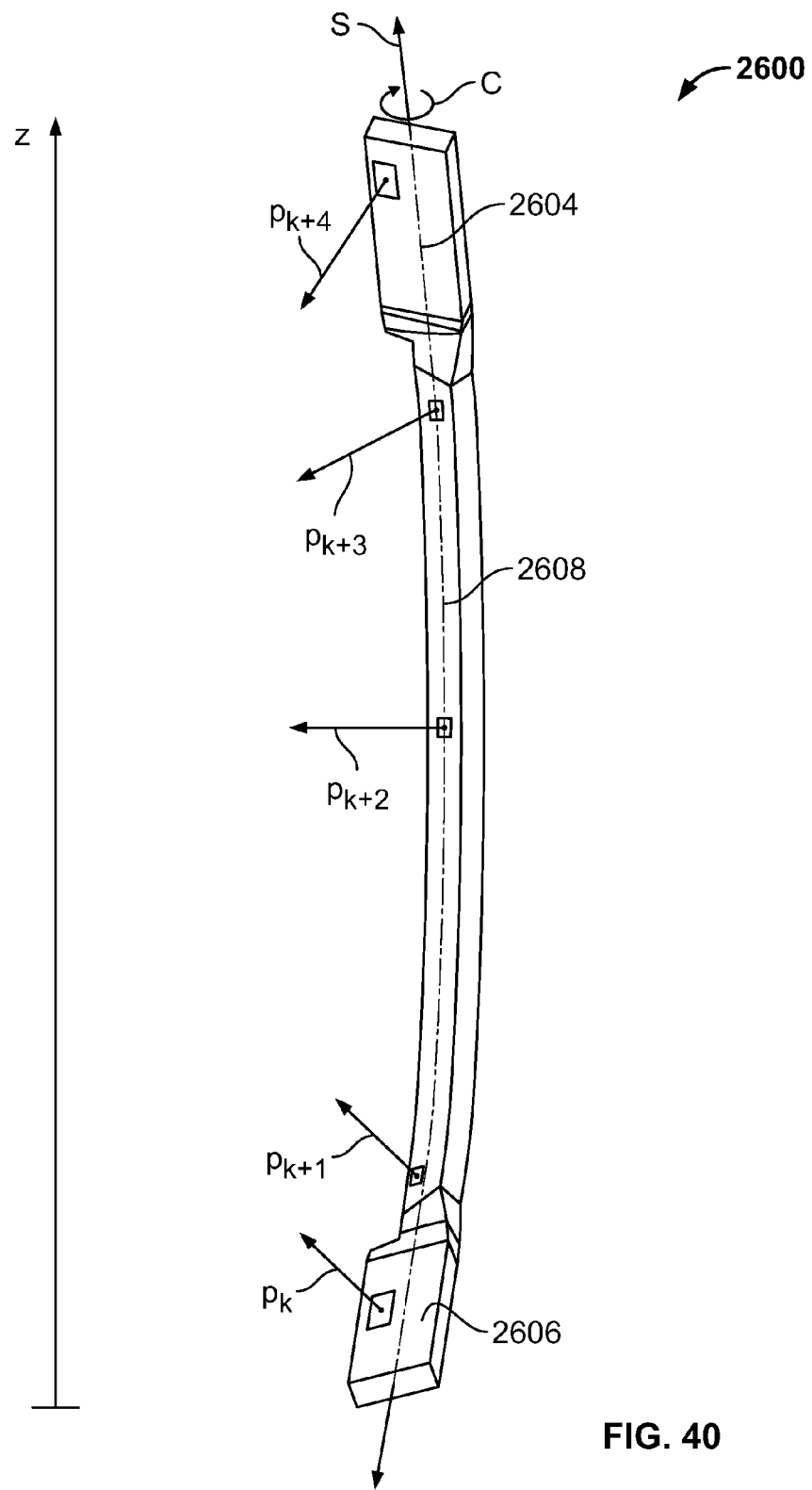
FIG. 40 shows illustrative apparatus in accordance with principles of the invention.

FIG. 40 shows illustrative broaching member 2600, after shaping about axis M, from a perspective that is different from that shown in FIG. 39. Surface normal vectors $p_k$, $p_{k+1}$, $p_{k+2}$, $p_{k+3}$ and $p_{k+4}$ are shown at different positions along the Z axis (shown also in FIG. 1). The orientations of the surface normal vectors are dependent in part on the counter-rotations of ends 2604 and 2606 prior to securement to the support.

Figure 41:
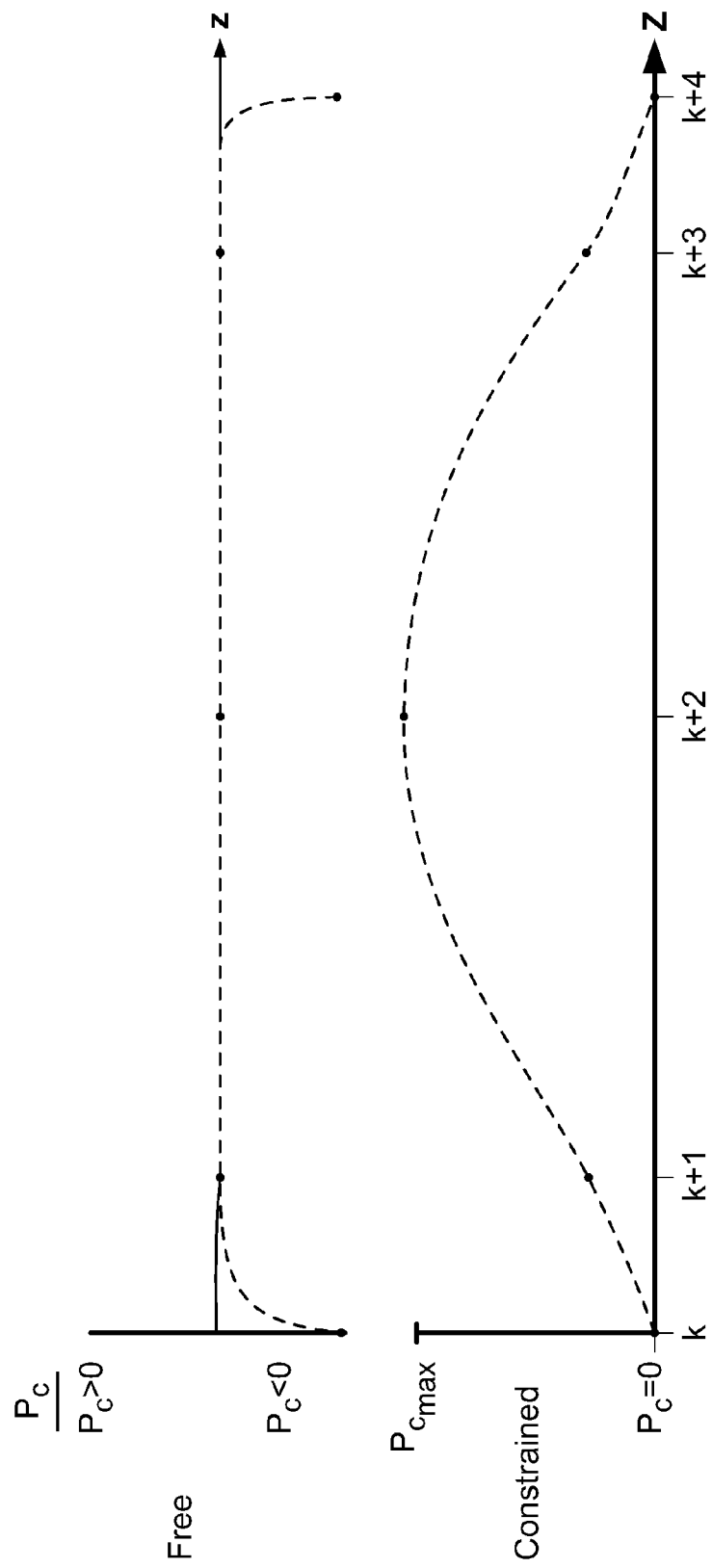
FIG. 41 shows illustrative apparatus in accordance with principles of the invention.

FIG. 41 shows hypothetical distribution Pc of surface normal rotation in direction C for different positions (k, k+1, k+2, k+3, k+4, shown in FIG. 40) along axis Z for a first condition (top graph) in which ends 2604 and 2606 are counter-rotated but free and a second condition (bottom graph) in which ends 2604 and 2606 are both secured to a support. If one of ends 2604 or 2606 were monolithic with a broaching member wrap section the hypothetical distribution Pc of surface normal rotation would be different from what is shown in FIG. 41.

Counter-rotation is shown at k and k+4, where Pc is negative. Central span 2608, corresponding to k+1, k+2 and k+3 may be at mechanical equilibrium with no surface normal rotation in the C direction.

When broaching member 2600 is secured to the support, surface normals $p_k$ and $p_{k+4}$ of ends 2604 and 2606 may be constrained to be directly radially inward (direction −R). The surfaces may be substantially flush against the support. The constraint may transmit stress from the counter-rotation into span segment 2608. The stress may cause rotation of span segment 2608 in the C direction. A maximum rotation may occur at k+2.

Figure 42:
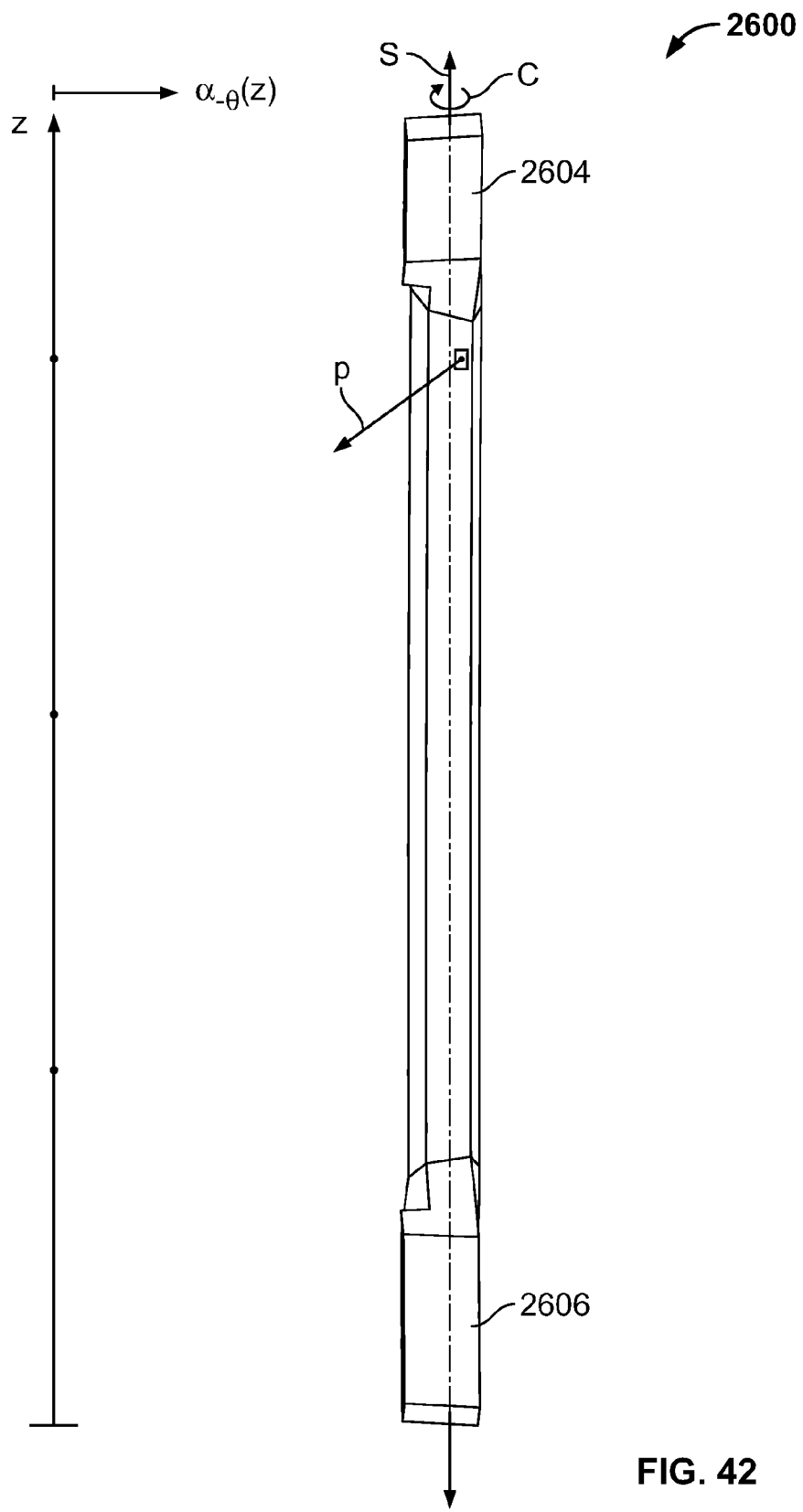
FIG. 42 shows illustrative apparatus in accordance with principles of the invention.

FIG. 42 shows illustrative broaching member 2600 shaped about axis M with ends 2604 and 2606 unconstrained. Hypothetical sweep angle $\alpha_{-\theta}$ may occur in broaching member 2600 at different locations on axis Z. (In this figure, broaching member 2600 is shown in a state where the sweep angle is zero representative locations, as indicated by the dots at $\alpha_{-\theta}=0$ along the Z axis.)

Sweep angle $\alpha_{-\theta}$ corresponds to arclength in direction −θ that broaching member 2600 may be displaced. The displacement may be relative to ends 2604 and 2606, which in operation would be constrained to the support and defined to have $\alpha_{-\theta}=0$, but are shown unconstrained for simplicity. The displacement may be a dynamic displacement caused by resistive forces from tissue with which the broaching member is engaged. The displacement may be a static displacement that is preset in the broaching member. The displacement may vary as a function of Z along central axis S. The displacement may cause a decrease in rake angle along S. The displacement may cause an increase in relief angle along S. The changes in rake and relief angles may increase with increasing displacement.

FIG. 43 shows illustrative broaching member 2600 in a condition in which $\alpha_{-\theta}$ varies along Z. $\alpha_{-\theta}$ is highest near the middle.

Figure 44:
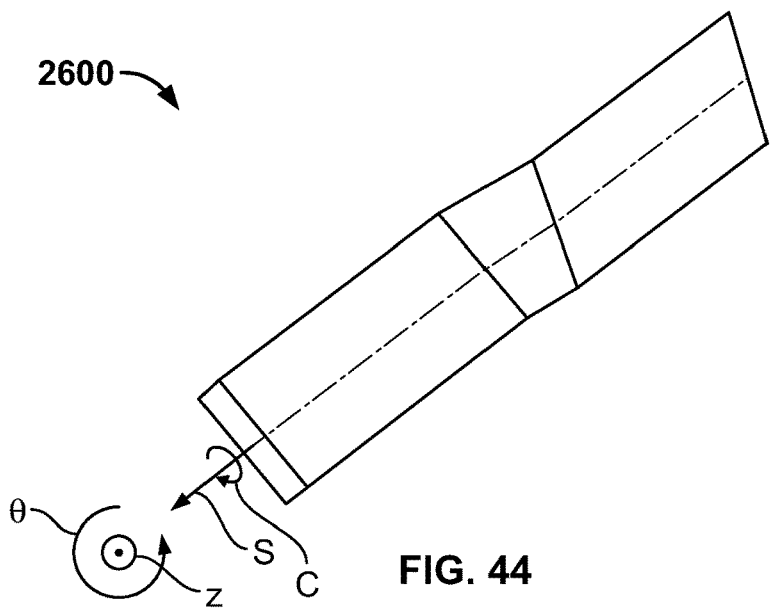
FIG. 44 shows illustrative apparatus in accordance with principles of the invention.

FIG. 44 shows a view (looking down axis Z) of illustrative broaching member 2600 in the condition shown in FIG. 42.

Figure 45:
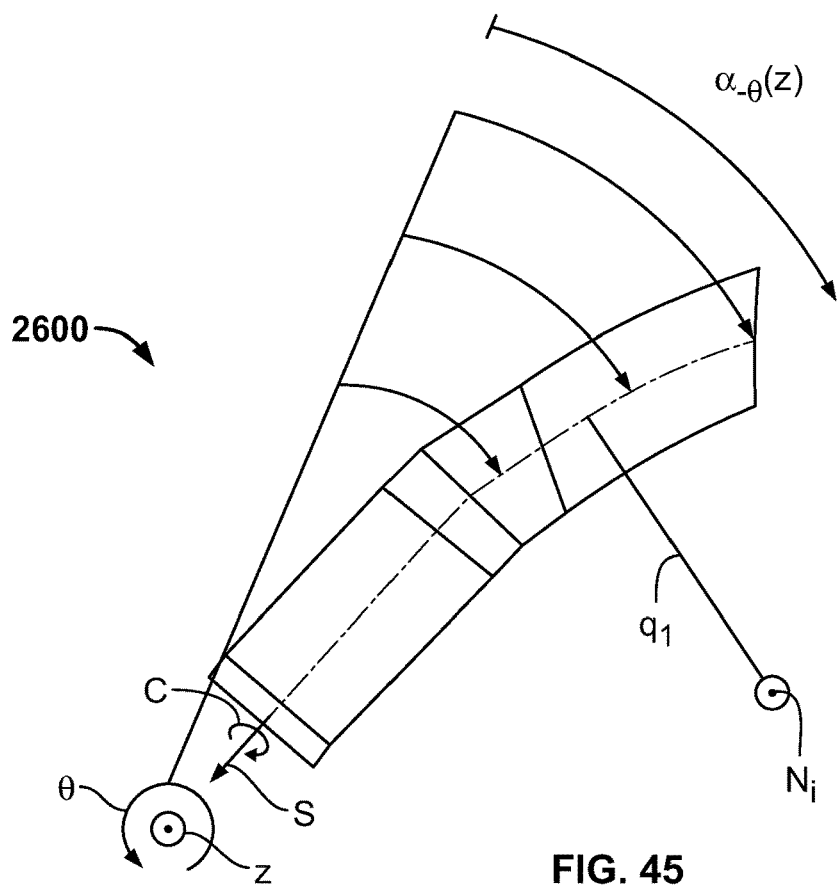
FIG. 45 shows illustrative apparatus in accordance with principles of the invention.

FIG. 45 shows a view (looking down axis Z) of illustrative broaching member 2600 in the condition shown in FIG. 43. The top portion of broaching member 2600 may be increasingly displaced in direction −θ with distance from axis Z and with decreasing elevation along axis Z. The bottom portion of broaching member 2600 (not shown) may be increasingly displaced in direction −θ with distance from axis Z and with increasing elevation along axis Z. Broaching member 2600 may be shaped about one or more bending axes, such as Ni, which corresponds to radius of curvature $q_i$.

Figure 46:
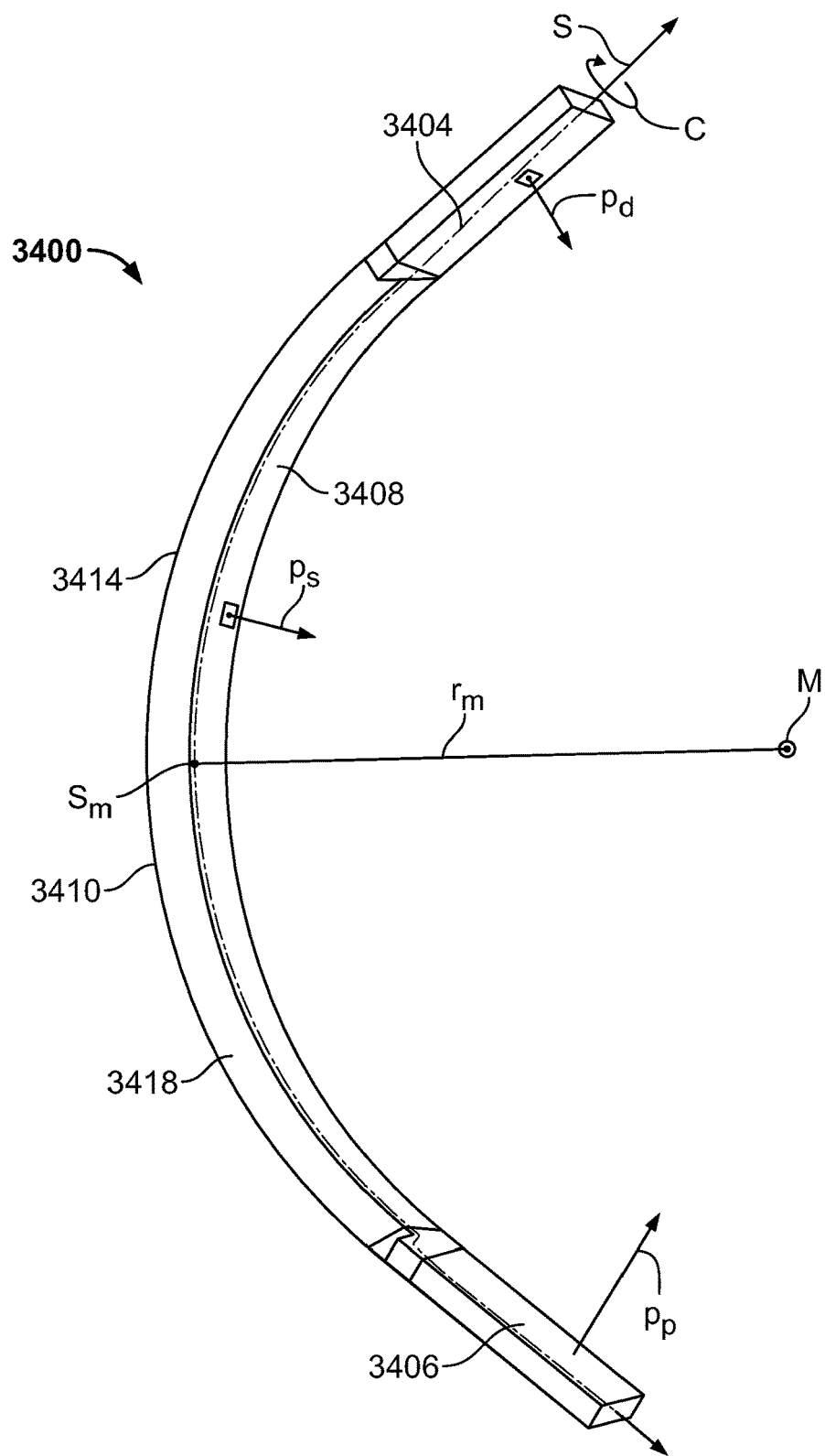
FIG. 46 shows illustrative apparatus in accordance with principles of the invention.

FIG. 46 shows illustrative broaching member 3400 (shown in FIG. 34) shaped about axis M. Central axis S may be shaped in any suitable shape about axis M. Central axis S is illustrated as circumscribing a circle about, and perpendicular to, axis M. The circle may have radius $r_M$. Because leading edge 3414 is greater than trailing edge 3416 (not shown), leading edge 3414 may lie at a radius from axis M that is greater than the radius from axis M at which lies trailing edge 3416. Span segment 3408 would thus be a pseudo-conical surface with axis M running along a conical axis. In this configuration, rake face 3418 may have a rake angle that is lesser than the rake angle that rake face 3418 would have if broaching member 3400 were not shaped about axis Lo prior to shaping about axis M. In this configuration, broaching member 3400 may have a relief angle that is greater than the relief angle that broaching member 3400 would have if broaching member 3400 were not shaped about axis Lo prior to shaping about axis M.

Angular displacement in direction C or −C of normal vector $p_d$ relative normal vector $p_s$ may be caused on the shaping of broaching member 3400 about axis M. Angular displacement in direction C or −C of normal vector $p_d$ relative normal vector $p_s$ may be caused only by the shaping of broaching member 3400 about axis M. Angular displacement in direction C or −C of normal vector $p_d$ relative normal vector $p_s$ may be caused only by the shaping of broaching member 3400 about axis M and securement of distal segment 3404 to the support. The securement may constrain normal vector $p_d$ to have a vector component in outward radial direction R or inward radial direction −R. The securement may allow normal vector $p_d$ to have a vector component in longitudinal directions Z or −Z.

Angular displacement in direction C or −C of normal vector $p_p$ relative normal vector $p_s$ may be caused on the shaping of broaching member 3400 about axis M. Angular displacement in direction C or −C of normal vector $p_p$ relative normal vector $p_s$ may be caused only by the shaping of broaching member 3400 about axis M. Angular displacement in direction C or −C of normal vector $p_p$ relative normal vector $p_s$ may be caused by the shaping of broaching member 3400 about axis M and securement of proximal segment 3406 to the support. The securement may constrain normal vector $p_p$ to have a vector component in outward radial direction R or inward radial direction −R. The securement may allow normal vector $p_p$ to have a vector component in longitudinal directions Z or −Z.

Figure 47:
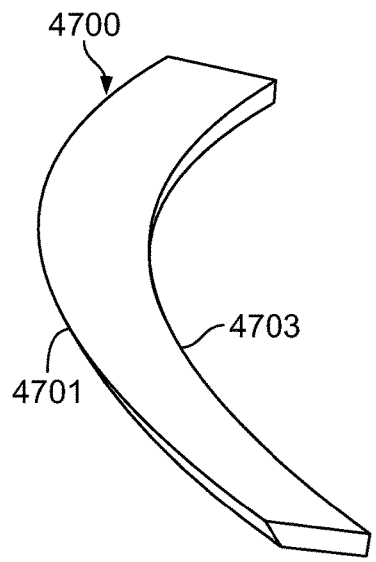
FIG. 47 shows illustrative apparatus in accordance with principles of the invention.

FIG. 47 shows illustrative curved body 4700 in a planar configuration.

Figure 47A:
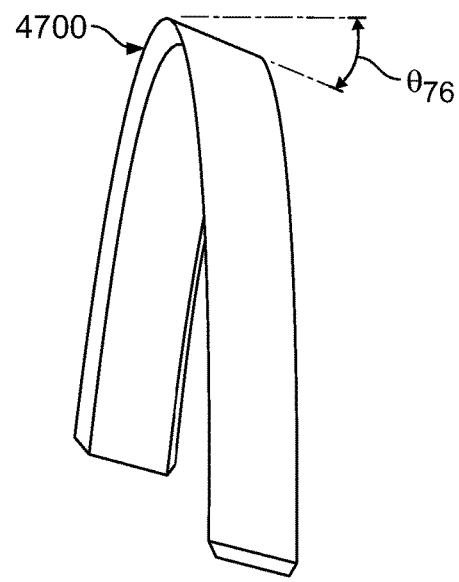
FIG. 47A shows illustrative apparatus in accordance with principles of the invention.
Figure 47B:
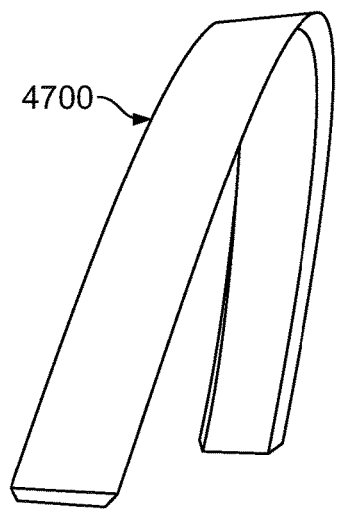
FIG. 47B shows illustrative apparatus in accordance with principles of the invention.

FIGS. 47A and 47B show two different perspective views of a shaping of illustrative curved body 4700. The shaping may involve a bend that is in a plane parallel to the widest aspect of curved body 4700 and around an axis that is perpendicular to the edge that contains the cutting edge. The bend may lengthen edge 4701 relative to the opposite (trailing) edge 4703. The length difference then may effect, when the broaching member undergoes a second shaping around the axis (such axis M, shown in FIG. 34) perpendicular to the length of the broaching member, a radial (direction R in FIG. 1) difference between edge 4701 and the trailing edge 4703.

The radial difference may create a conical or pseudo-conical shape. The radial difference may create a cone-like surface.

The radial difference may create a shape in which edge 4701 occupies a radially outward position than does the trailing edge 4703. The shaping may thus be selected to obtain desired relief and rake angles of edge 4701. The desired relief and rake angles may be targeted for delivery of effective therapy.

Figure 48:
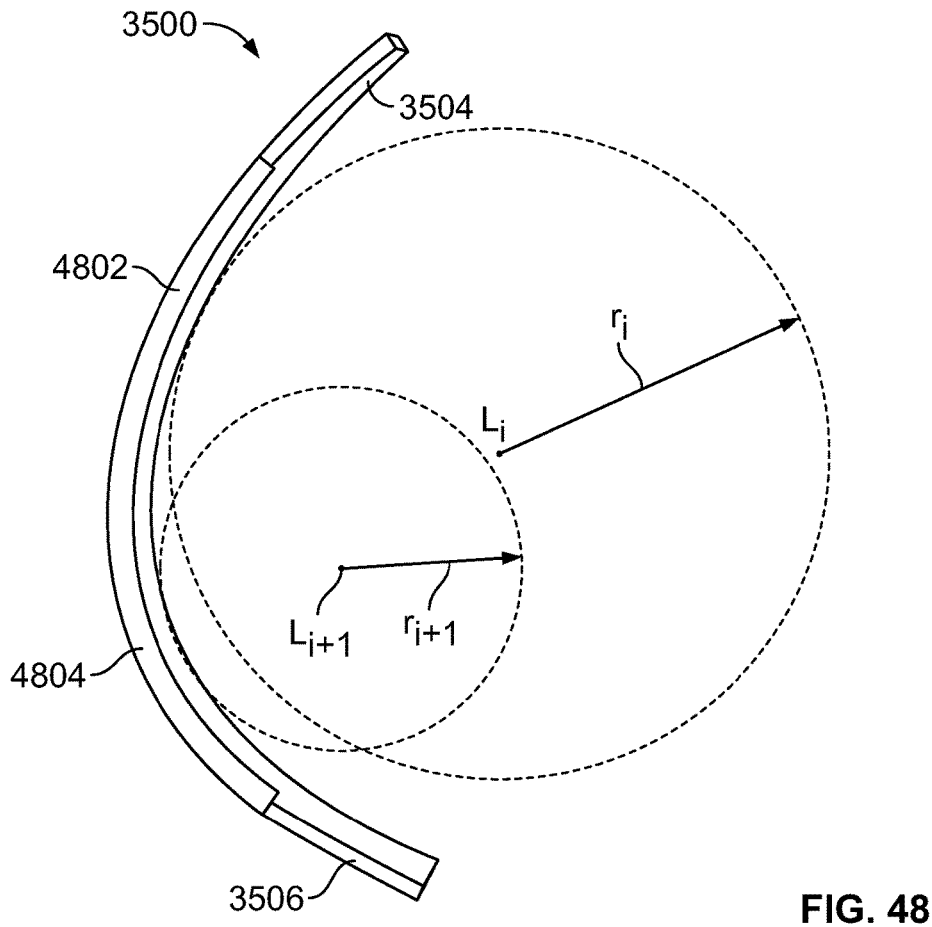
FIG. 48 shows illustrative apparatus in accordance with principles of the invention.

FIG. 48 shows illustrative broaching member 3500 (shown in FIG. 35) shaped about axis M with ends 3504 and 3506 unconstrained by the support. Segment 4802 has a rake angle corresponding to radius $r_i$. Segment 4804 has a rake angle corresponding to radius $r_{i+1}$. Because radius $r_{i+1}$ is smaller than radius $r_i$, the segment 4804 rake angle is decreased more than that of segment 4802.

Figure 48A:
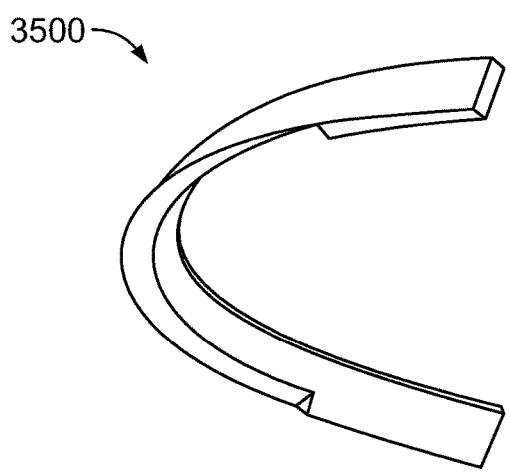
FIG. 48A shows illustrative apparatus in accordance with principles of the invention.

FIG. 48A shows a different view of illustrative broaching member 3500 shaped about axis M as shown in FIG. 48.

Figure 49:
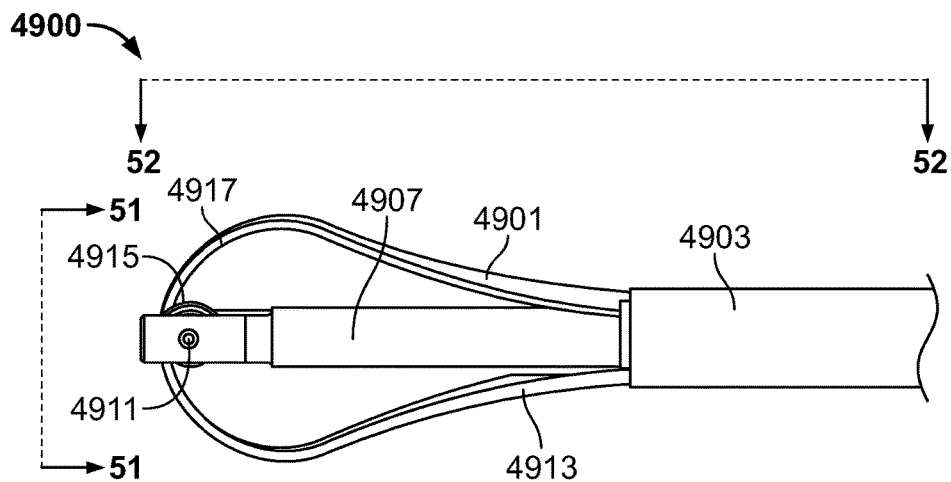
FIG. 49 shows illustrative apparatus in accordance with principles of the invention.

FIG. 49 shows illustrative tool 4900. Tool 4900 may include broaching member 4917. Broaching member 4917 may be in an expanded state.

Broaching member 4917 may include elongated body 4901 and elongated body 4913. Broaching member 4917 may also include broaching member wrap section 4915. Broaching member wrap section 4915 may include a portion of broaching member 4917 looped around pin 4911. A coaxial member (not shown) may surround pin 4911.

Pin may be supported by central support member 4907. Central support member 4907 may be coupled to rotator 4903.

The body may include a metal that behaves like a spring, such as super elastic Nitinol. The tool may be operated for therapy by rotating the tool about its longitudinal axis.

Rotation of the tool may actuate radial expansion of the body and blades thereon. The expansion may be indexed to the rotation. For example, a predetermined amount of expansion may be linked to a predetermined number of turns of the body.

Expansion of the body and blades thereon may be actuated independently from the rotation. This may facilitate control of the amount of force imparted to the tissue. For a given angular velocity, the more expanded the body, the more force is applied to the tissue. Therefore, the independent control of expansion may limit the amount of energy imparted into the tissue. Complete expansion of the body may be performed before rotation of the tool. However, the amount of energy delivered to the tissue would be different from that obtained by slow or step-wise expansions.

Figure 50:
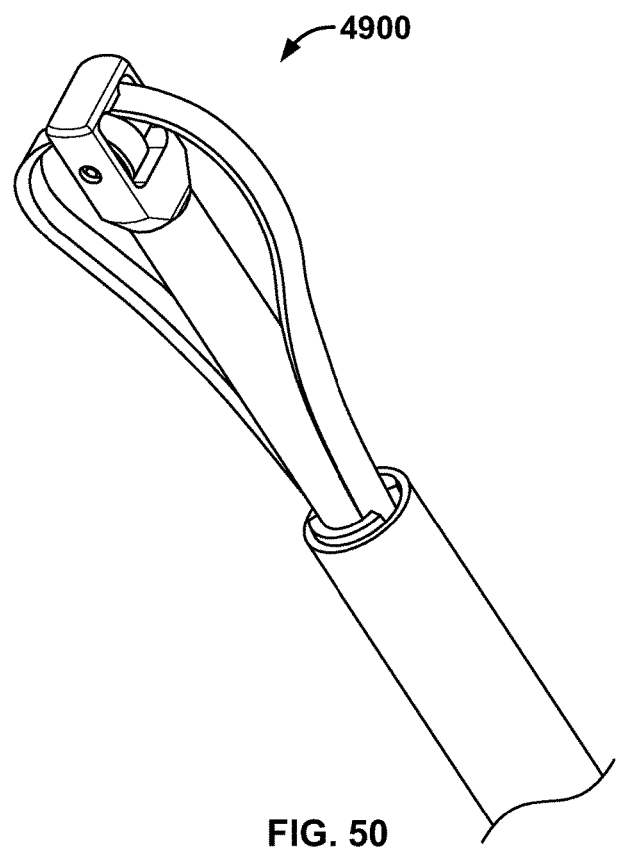
FIG. 50 shows illustrative apparatus in accordance with principles of the invention.

FIG. 50 shows a perspective view of illustrative tool 4900 (shown in FIG. 49).

Figure 51:
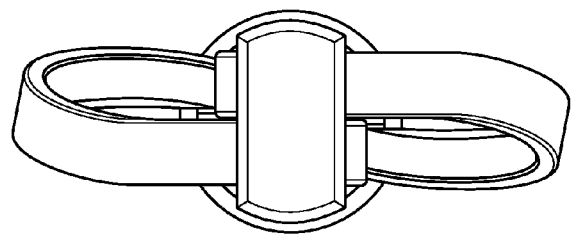
FIG. 51 shows illustrative apparatus in accordance with principles of the invention.

FIG. 51 shows a view of illustrative tool 4900 taken along lines 51-51 (shown in FIG. 49).

Figure 52:
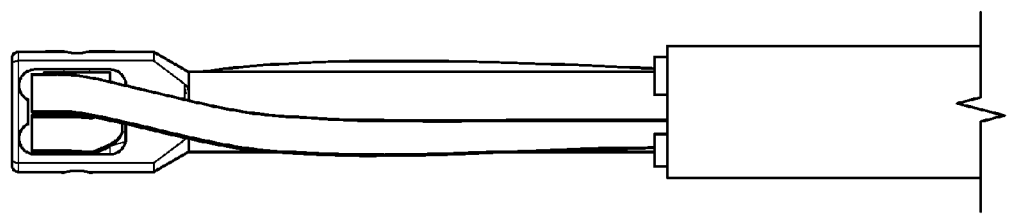
FIG. 52 shows illustrative apparatus in accordance with principles of the invention.

FIG. 52 shows a view of illustrative tool 4900 taken along lines 52-52 (shown in FIG. 49).

Figures 53, 54:
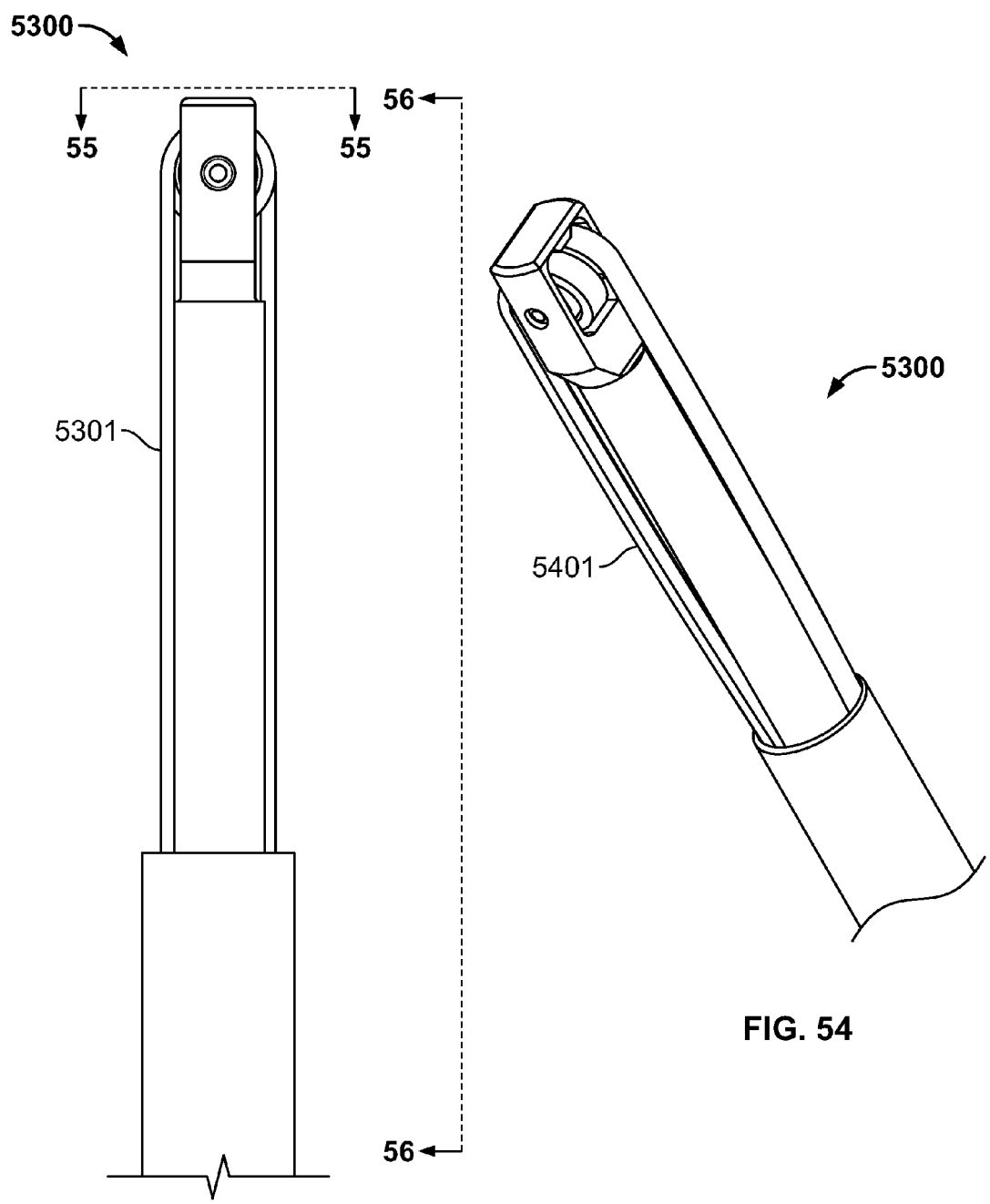
FIG. 53 shows illustrative apparatus in accordance with principles of the invention.
FIG. 54 shows illustrative apparatus in accordance with principles of the invention.

FIG. 53 shows a view of illustrative tool 5300. Tool 5300 may include broaching member 5301. Broaching member 5301 may be a retracted state.

FIG. 54 shows a perspective view of illustrative tool 5300 (shown in FIG. 53).

Figure 55:
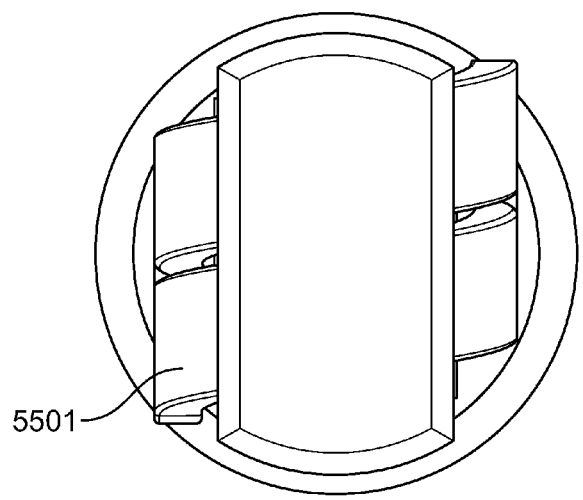
FIG. 55 shows illustrative apparatus in accordance with principles of the invention.

FIG. 55 shows a view of illustrative tool 5300 taken along lines 55-55 (shown in FIG. 53).

Figure 56:
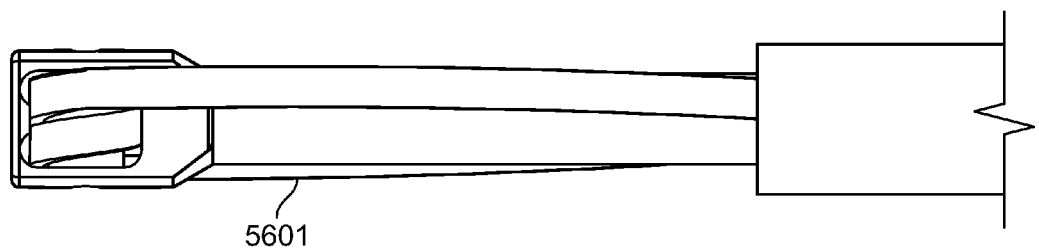
FIG. 56 shows illustrative apparatus in accordance with principles of the invention.

FIG. 56 shows a view of illustrative tool 5300 taken along lines 56-56 (shown in FIG. 53).

FIG. 57 shows illustrative broaching member 5301 (shown in FIG. 53) in a retracted state without illustrating a support member.

FIGS. 58, 59 and 60 show different perspective views of illustrative broaching member 5301 (shown in FIG. 53).

Figure 61:
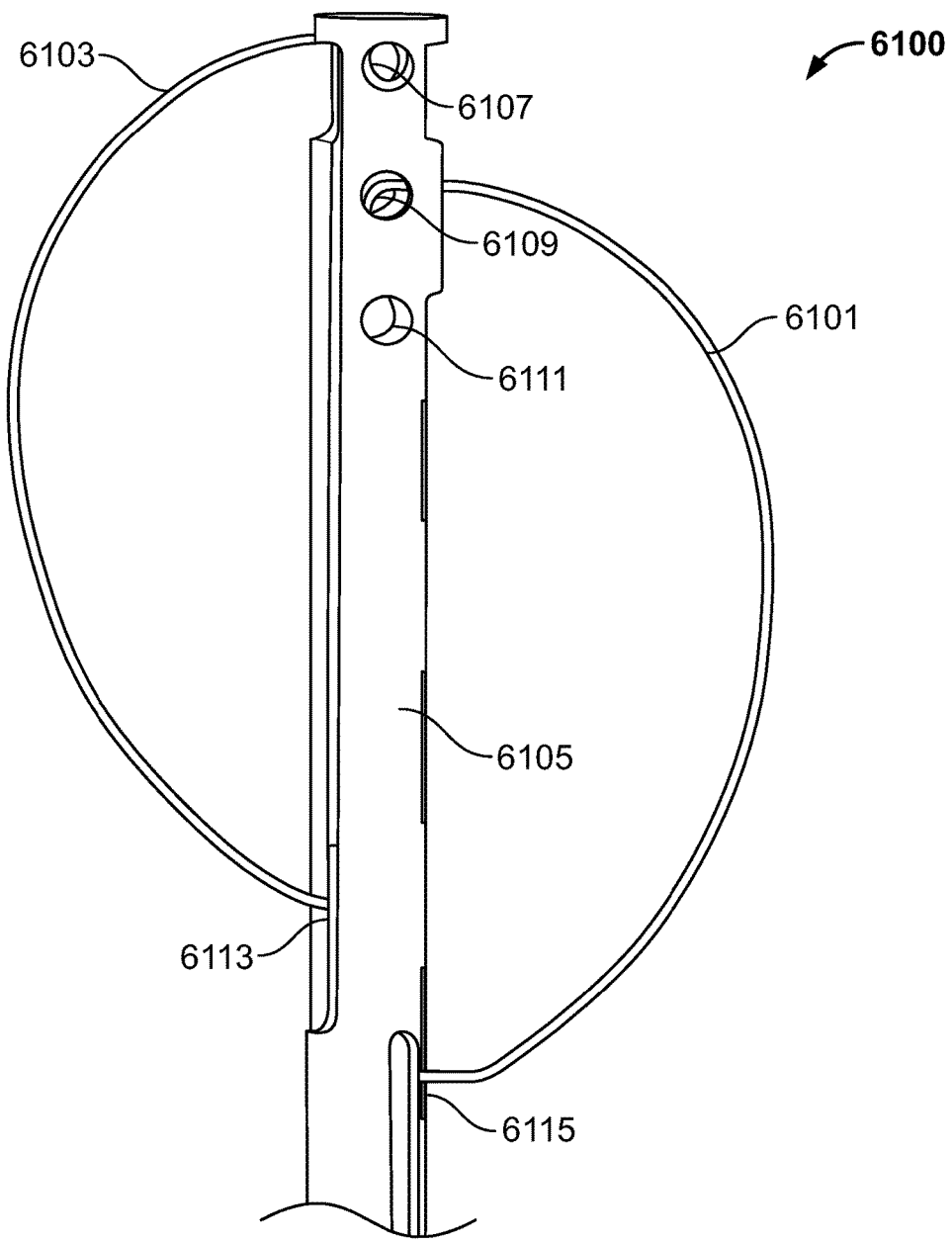
FIG. 61 shows illustrative apparatus in accordance with principles of the invention.

FIG. 61 shows illustrative tool 6100. Tool 6100 may include a support and an actuator for a 4-hinge broaching member with non-symmetrical segments.

Tool 6100 may include broaching member 6103 and broaching member 6101. Broaching members 6103 and 6101 may each be monolithic. Broaching members 6103 and 6101 may each be formed from one or more segments. Broaching members 6103 and 6101 may be jointed within support member 6105. Broaching members 6103 and 6101 may together form a monolithic structure. Broaching members 6103 and 6101 may together be formed from one or more segments. Broaching members 6103 and 6101 may each be elongated bodies.

Each of broaching members 6101 and 6103 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching members 6101 and 6103 may be coupled to support member 6105. Support member 6105 may include holes 6107, 6109 and 6111. A transverse member, or a pin (not shown) may be supported by one or more of holes 6107, 6109 and 6111.

A first section of broaching member 6101 may enter support 6105 through hole 6109 and wrap around at least a portion of a transverse member disposed in hole 6109. A second section of broaching member 6101 may also enter support 6105 through opening 6115.

A first section of broaching member 6103 may enter support 6105 through hole 6107 and wrap around a transverse member disposed in hole 6107. A second section of broaching member 6103 may also enter support 6105 through opening 6113.

Support 6105 may include one or more inner cylindrical tubes. Support 6105 may be coaxial with the inner cylindrical tubes. A first inner cylindrical tube may be coupled to the second section of broaching member 6101. A second inner cylindrical tube may be coupled to the second section of 6103. Each of the first and second inner cylindrical tubes may be moved independently.

Support 6105 may define a central axis. Movement of the first inner cylindrical tube along the central axis and towards a distal end of support 6105 may expand broaching member 6101. Movement of the first inner cylindrical tube along the central axis and away from the distal end of support 6105 may retract broaching member 6101.

Movement of the second inner cylindrical tube along the central axis and towards the distal end of support 6105 may expand broaching member 6103. Movement of the second inner cylindrical tube along the central axis and away from the distal end of support 6105 may retract broaching member 6103.

Broaching members 6101 and 6103 may be independently moved to create cavity shapes in an intramedullary cavity or any other suitable cavity. One or both of broaching members 6101 and 6103 may be at expanded during the rotation or translation of support 6105. One or both of broaching members 6101 and 6103 may be retracted during the rotation or translation of support 6105. Expanding or retracting one or both of broaching members 6101 and 6103 during cavity creation may allow a practitioner to create an asymmetric cavity within the intramedullary space.

Figure 62:
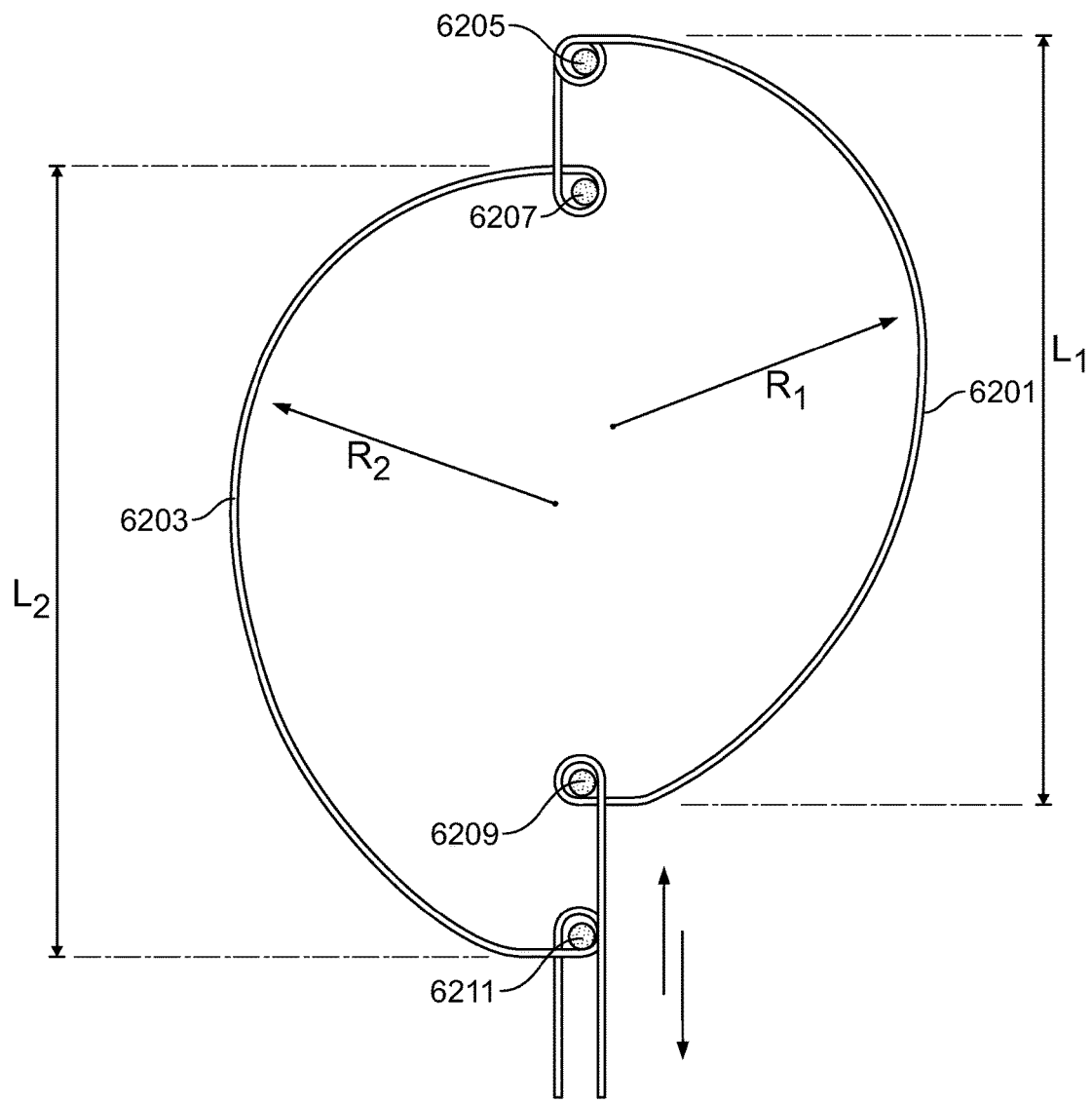
FIG. 62 shows illustrative apparatus in accordance with principles of the invention.

FIG. 62 shows an illustrative broaching member that includes a broaching member wrapped about four hinge points. The broaching member may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

A support (not shown) such as support 6105 (shown in FIG. 61) may surround at least a portion of the broaching member. One or more of the hinge points may be displaced relative to the support independently of each other. Two or more of the hinge points may be displaced relative to the support in coordination with each other. Two or more of the hinge points may be fixed in a support such as support 6105 (shown in FIG. 61) or in any other support known to those skilled in the art.

The broaching member may include a blade. The broaching member may include a cutting edge.

The broaching member may include a first segment 6203 and a second segment 6201. Segments 6201 and 6203 may lie in or near a plane parallel to the page. The plane may include longitudinal axis Z of a tool that includes the broaching member. (Orientations of Z axis, radius R and circumferential direction θ are shown in FIG. 1.) Segment 6201 may be offset from segment 6203 in a direction perpendicular to the plane to account for broaching member width between adjacent hinges.

The four hinge points may include hinge 6213, hinge 6215, hinge 6217 and hinge 6219. The broaching member may be wrapped around hinges 6213, 6215, 6217 and 6219.

The tool may include a support such as support 6105 (shown in FIG. 61) that supports hinges 6205 and 6207 at fixed distal positions along Z. The tool may include one or more control elements that are displaceable along Z relative to the support. Hinges 6209 and 6211 may be fixed to one of the control elements. Hinge 6209 may be fixed to a first control element. Hinge 6211 may be fixed to a second control element. The first segment may be activated by distal displacement, by the first control element, of hinge 6209. The second segment may be activated by distal displacement, by the appropriate control element, of hinge 6211.

The first and second segments are shown in an activated state. In the activated state, segment 6201 may have, as shown, length $L_1$, which is an illustrative displacement along Z between hinge 6205 and 6209. In the activated state, segment 6203 may have, as shown, length $L_2$, which is an illustrative displacement along Z between 6207 and 6211. $L_1$ and $L_2$ may be equal or substantially equal. $L_1$ may be greater than $L_2$. $L_1$ may be lesser than $L_2$.

The first segment is shown as having radius $R_1$. The second segment is shown as having radius $R_2$. Each of the first and second segments may have one or more radii of curvature that define the contours of the segments in the planes shown.

The first segment contour may be described as $r_1(Z)$. $r_1$ is the radial distance (along radius R) from the segment to longitudinal axis Z at a point along the Z axis. The second segment contour may be described as $r_2(Z)$. $r_2$ is the radial distance (along radius R) from the segment to longitudinal axis Z at a point along the Z axis. For a given value of Z, a cavity diameter may be governed by the larger of $r_1$ and $r_2$. $r_1$ and $r_2$ may be selected to match at a Z-value such as $Z_{match}$. This may provide a continuous or near-continuous transition in the Z direction between cavity diameter above $Z_{match}$ and cavity diameter below $Z_{match}$. If both above and below $Z_{match}$ at least one of $r_1$ and $r_2$ is greater than $r_1(Z_{match})$ ($=r_2(Z_{match})$), the cavity may have a waist at $Z_{match}$. If both above and below $Z_{match}$ both $r_1$ and $r_2$ are lesser than $r_1(Z_{match})$ ($=r_2(Z_{match})$), the cavity may have a bulge, a maximum diameter or a local maximum diameter at $Z_{match}$. If the greater of $r_1$ and $r_2$ is similar to $r_1(Z_{match})$ in a region that extends longitudinally away from $Z_{match}$, an extended cylindrical cavity region may be formed.

The use of multiple offset segments, such as segment 6201 and segment 6203, to form such shapes may provide radial strength that may not be present in a smaller number of, or single, segments that span longitudinally a distance greater than the longitudinal span of one of the segments. This may occur because the greater longitudinal span may compromise radial strength.

The use of multiple offset segments in this manner may provide broach heads that have longitudinally distributed radial strength that may be used to provide longitudinally extending cavities. The multiple segments may include 2, 3, 4, 5, 6-10, 11-20, 20-50, 51-100 or more than 100 segments.

Figure 63:
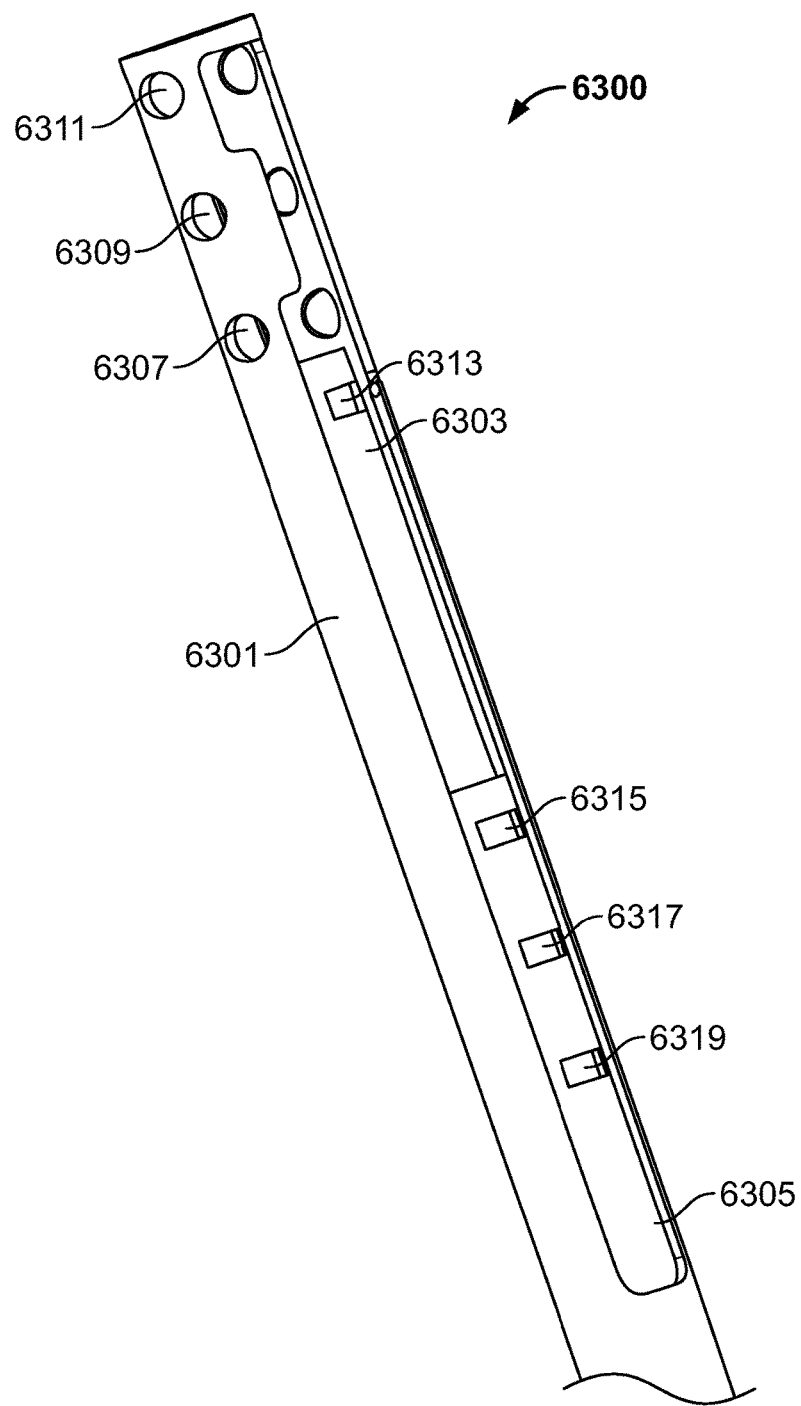
FIG. 63 shows illustrative apparatus in accordance with principles of the invention.

FIG. 63 shows features of illustrative support 6300. Support 6300 may support one or more broaching members. The support may include laser-machined tubes. The tubes may include outer tube 6301, middle tube 6303 and inner tube 6305. The tubes may be arranged concentrically.

Outer tube 6301 may include holes 6307, 6309 and 6311. Each of holes 6307, 6309 and 6311 may support a transverse member. Each of holes 6307, 6309 and 6311 may support a broaching member wrapped around the transverse member.

Middle tube 6303 may include hole 6313. Hole 6313 may be configured to receive one end of a broaching member. The other end of the broaching member may be coupled to outer tube 6301 or inner tube 6306. Hole 6313, and an additional hole on middle tube 6303 (not shown) may be configured to receive both ends of a broaching member. A section of the broaching member may be looped through a transverse member supported by one of holes 6311, 6309 and 6309. Hole 6313 may be configured to receive one or both ends of two or more broaching members. An end of a broaching member received by hole 6313 may be crimped to a portion of middle tube 6303, inserted into a receiver, or otherwise fixed, removably or permanently, to hole 6313.

Inner tube 6305 may include holes 6315, 6317 and 6319. Each of holes 6315, 6317 and 6319 may be configured to receive one end of a broaching member. The other end of the broaching member may be coupled to outer tube 6301 or middle tube 6303. Each of holes 6315, 6317 and 6319, or additional holes on inner tube (not shown) may be configured to receive both ends of a broaching member. A section of the broaching member may be looped through a transverse member supported by one of holes 6311, 6309 and 6309. Each of holes 6315, 6317 and 6319 may be configured to receive one or both ends of two or more broaching members. An end of a broaching member received by one of holes 6315, 6317 and 6319 may be crimped to a portion of the hole, inserted into a receiver, or otherwise fixed, removably or permanently, to the hole.

One end (e.g., distal), or both ends, of each of one or more broaching members, or elongated bodies, may be secured to one of the tubes. A different end (e.g., proximal) of each of the one or more broaching members in the broach head may be secured to a different tube or to a different support. For example, when the middle tube is moved away from the outer tube along a tube central axis, broaching members secured onto both the middle tube and the outer tube may be contracted radially inwardly toward the center of the tool. This may be referred to as blade "de-activation." This may be referred to as broaching member "de-activation." When the middle tube is moved towards the outer tube along a tube central axis, broaching members secured onto the middle tube may be expanded radially outwardly away from the center of the tool. This may be referred to as blade "activation." This may be referred to as broaching member "activation."

Any suitable number of tubes may be present in support 6300. For example, support 6300 may include 1-10, 11-20, 21-30, 31-40, 41-50, 51-60, 61-70, 71-80, 81-90, 91-100, or more than 100 tubes. Any suitable number of holes may be present in a broaching member support. For example, a broaching member support may include 1-10, 11-20, 21-30, 31-40, 41-50, 51-60, 61-70, 71-80, 81-90, 91-100, or more than 100 holes.

The tubes may be operable in a manner in which they are dependent upon each other. The tubes may be operable independently from each other.

Some tubes may be configured to move axially relative to each other. Some tubes may be configured to move rotationally relative to each other. Some tubes may be configured to be axially fixed to each other. Some tubes may be configured to be rotationally fixed to each other. Tubes may be configured to form any suitable geometric shapes.

Outer tube 6301 may be fixed relative to middle tube 6303 and inner tube 6305. Middle tube 6303 may slide relative to outer tube 6301. Middle tube 6303 may slide relative to outer tube 6301 and inner tube 6303. Inner tube 6305 may slide relative to outer tube 6301. Inner tube 6305 may slide relative to outer tube 6301 and middle tube 6303. The tubes may slide along a longitudinal axis towards and away from a distal end of outer tube 6301.

Although illustrated as tubes, the tubes may be solid rods. The tubes may be parallel to each other. The tubes may have not parallel segments to provide suitable control of a broaching member end.

Figure 64:
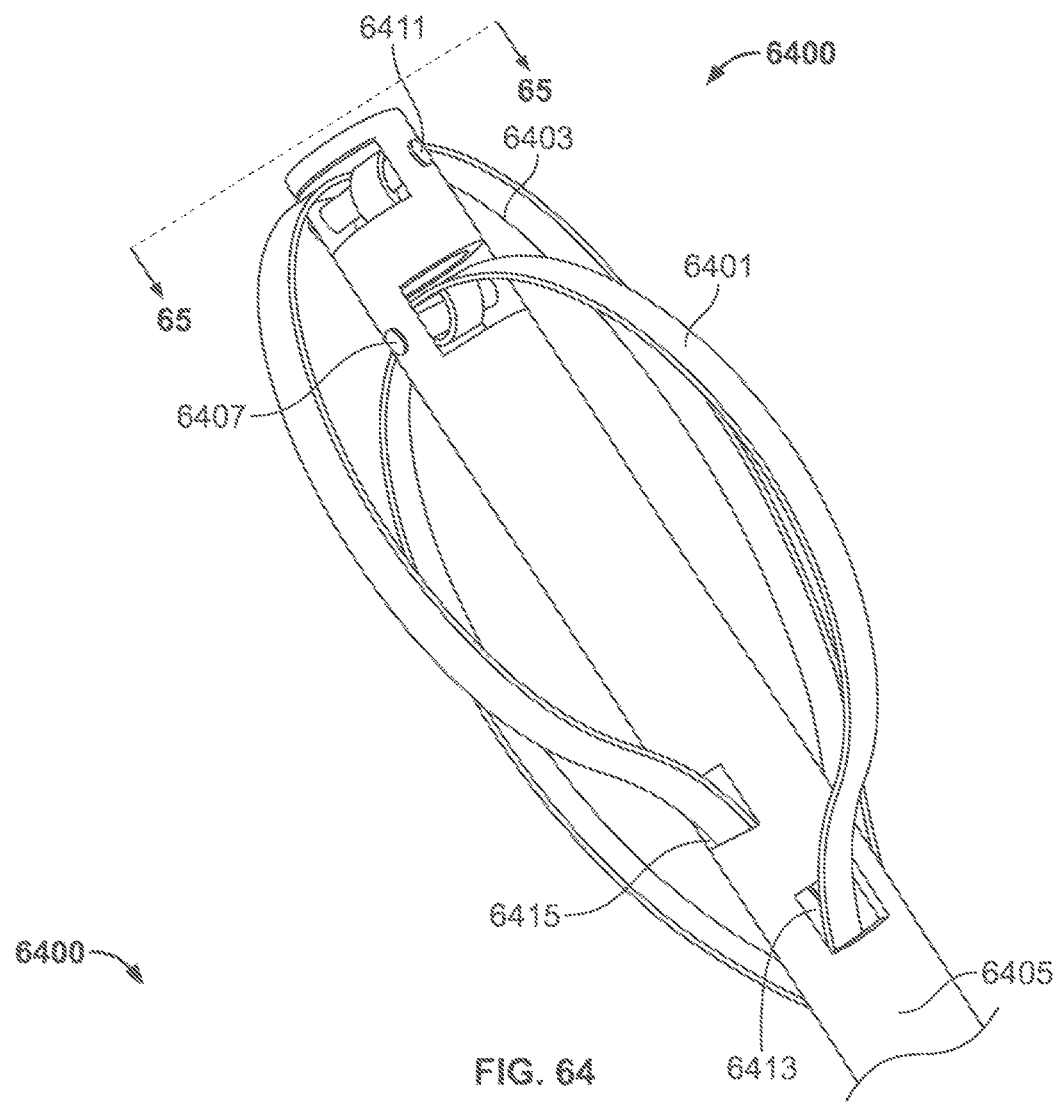
FIG. 64 shows illustrative apparatus in accordance with principles of the invention.

FIG. 64 shows illustrative tool 6400. Tool 6400 includes a pair of non-symmetrical broaching members 6401 and 6403. Each of broaching members 6401 and 6403 may define a different plane. Each of broaching members 6401 and 6403 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Tool 6400 may include support 6405. Support 6405 may include transverse members 6407 and 6411. Broaching member 6401 may wrap around transverse member 6407. Broaching member 6403 may wrap around transverse member 6411. Both ends of each of broaching members 6401 and 6403 may enter support 6401 through a window. One end of broaching member 6401 is shown entering support 6405 through window 6413. One end of broaching member 6403 is shown entering support 6405 through window 6415.

Both ends of broaching member 6401 may be coupled to a tube supported inside support 6405. Movement of the tube towards a distal end of support 6405 may expand broaching member 6401. Movement of the tube away from the distal end of support 6406 may retract broaching member 6401.

A first end of broaching member 6401 may be coupled to a first tube supported inside support 6405. A second end of broaching member 6401 may be coupled to a second tube supported inside support 6405. Movement of the first tube towards the distal end of support 6405 may expand a first section of broaching member 6401, the first section including the first end. Movement of the second tube towards the distal end of support 6406 may expand a second section of broaching member 6401, the second section including the second end.

Both ends of broaching member 6403 may be coupled to a tube supported inside support 6405. Movement of the tube towards a distal end of support 6405 may expand broaching member 6403. Movement of the tube away from the distal end of support 6406 may retract broaching member 6403.

A first end of broaching member 6403 may be coupled to a first tube supported inside support 6405. A second end of broaching member 6403 may be coupled to a second tube supported inside support 6405. Movement of the first tube towards the distal end of support 6405 may expand a first section of broaching member 6403, the first section including the first end. Movement of the second tube towards the distal end of support 6406 may expand a second section of broaching member 6403, the second section including the second end.

Tool 6400 may provide a non-symmetrical cavity. Tool 6400 with broaching members in different orientations may be self-centering in a cavity due to the reaction force of the tissue on each of the broaching members.

Broaching members 6401 and 6403 may have the same orientations. Broaching members 6401 and 6403 may define the same plane.

Figure 65:
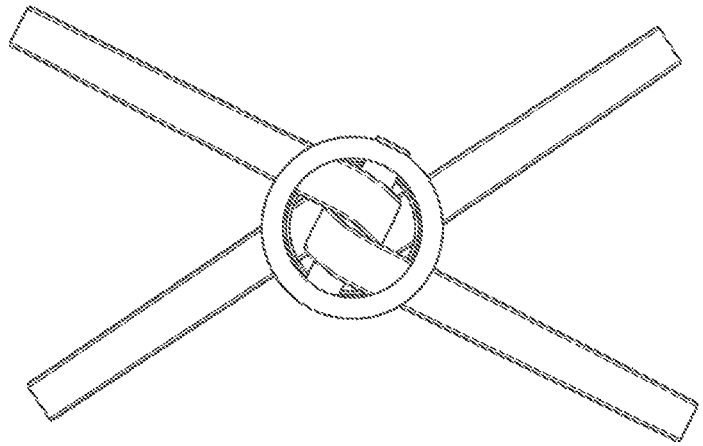
FIG. 65 shows illustrative apparatus in accordance with principles of the invention.

FIG. 65 shows a view of illustrative tool 6400 (shown in FIG. 64). A distal end of support 6405 (shown in FIG. 65) is shown to be open. A distal end of support 6405 may include an end cap.

Figures 66, 67:
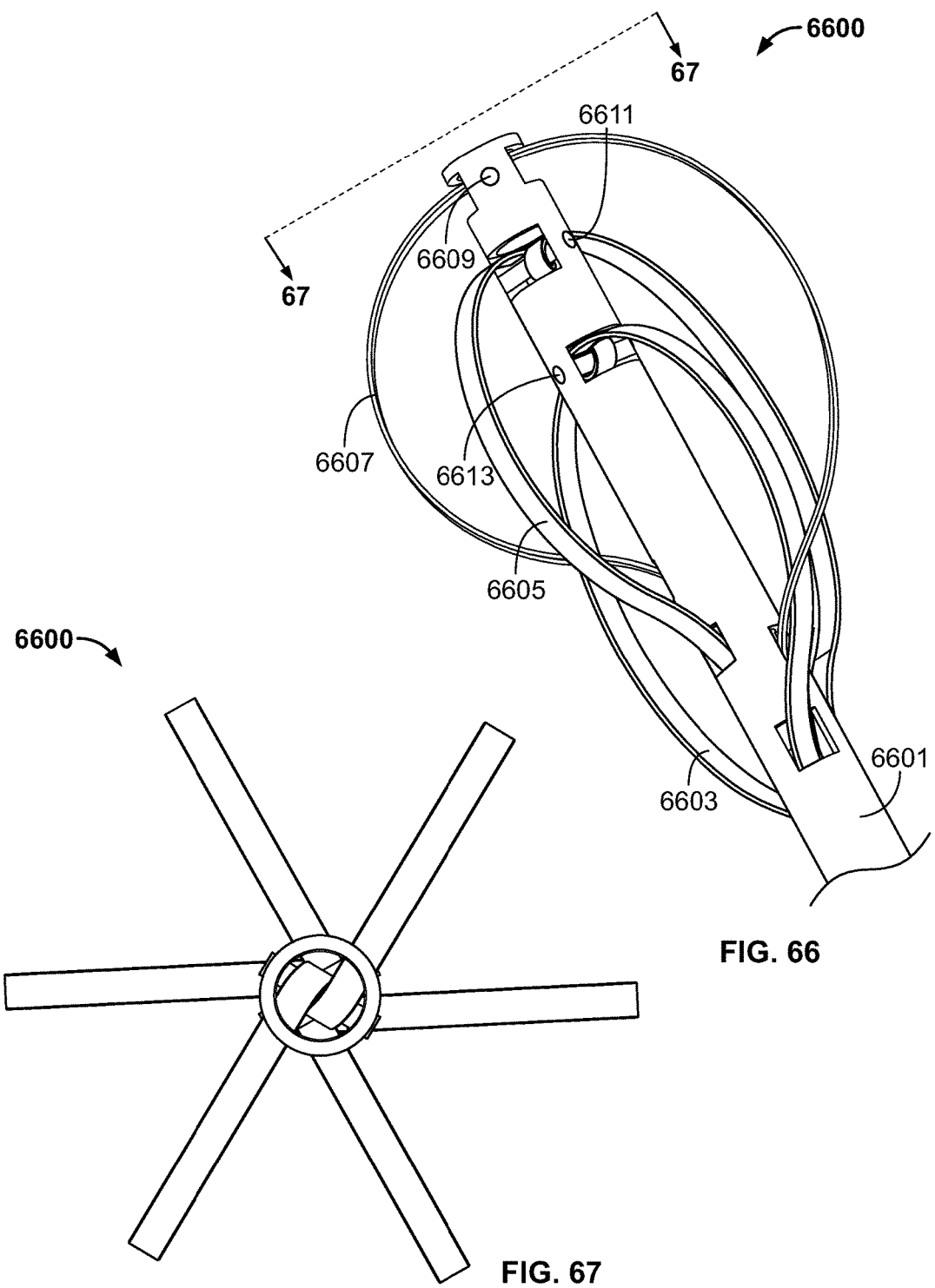
FIG. 66 shows illustrative apparatus in accordance with principles of the invention.
FIG. 67 shows illustrative apparatus in accordance with principles of the invention.

FIG. 66 shows illustrative tool 6600 that includes broaching members 6603, 6605 and 6607. Each of broaching members 6603, 6605 and 6607 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Each of broaching members 6603, 6605 and 6607 may include a pair of blades. The pair of blades may be disposed on opposite sides of broaching members 6603, 6605 and 6607. Each of broaching members 6603, 6605 and 6607 may include a blade.

Broaching member 6603 may wrap around transverse member 6613. Broaching member 6605 may wrap around transverse member 6611. Broaching member 6607 may wrap around transverse member 6609. Transverse members 6609, 6611 and 6613 may be supported by support member 6601.

Broaching members 6603, 6605 and 6607 may be mounted on support member 6601 in multiple planes. Broaching members 6603, 6605 and 6607 may be activated together. Both ends of each of broaching member 6603, 6605 and 6607 may be coupled to a single activation mechanism such as a tube, cylinder, or any activation mechanism known to those skilled in the art. Broaching members 6603, 6605 and 6607 may be activated independently. Independent activation of broaching members 6603, 6605 and 6607 may have one or more features in common with the independent activation of broaching member 6401 (shown in FIG. 64). Two of broaching members 6603, 6604 and 6607 may be activated together, by their respective ends being attached to the same activation mechanism, and the remaining broaching member may be activated separately.

Tool 6600 may be multi-planar. Tool 6600 may provide a non-symmetrical cavity. Tool 6600 may be self-centering in a cavity due to distribution of tissue reaction forces on the blades. Tool 6600 may include multiple broaching members. Tool 6600 may include multiple blades. Tool 6600 may include 1, 2, 5, 10, 20, 50, 100 or more blades. The blades may be present on broaching members that may be of unitary construction with each other. For example, the broaching members may be derived from a single tube. Multiple tubes, each having one or more broaching members extending therefrom, may be nested together. Multiple blades may extend from each tube. The multiple blades may include one or more pairs of blades present on opposite sides of a broaching member. The multiple blades may include individual blades that are not paired with a corresponding blade on the same broaching member.

FIG. 67 shows a view of illustrative tool 6600 (shown in FIG. 66). A distal end of support 6601 (shown in FIG. 66) is shown to be open. A distal end of support 6601 may include an end cap.

Figure 68:
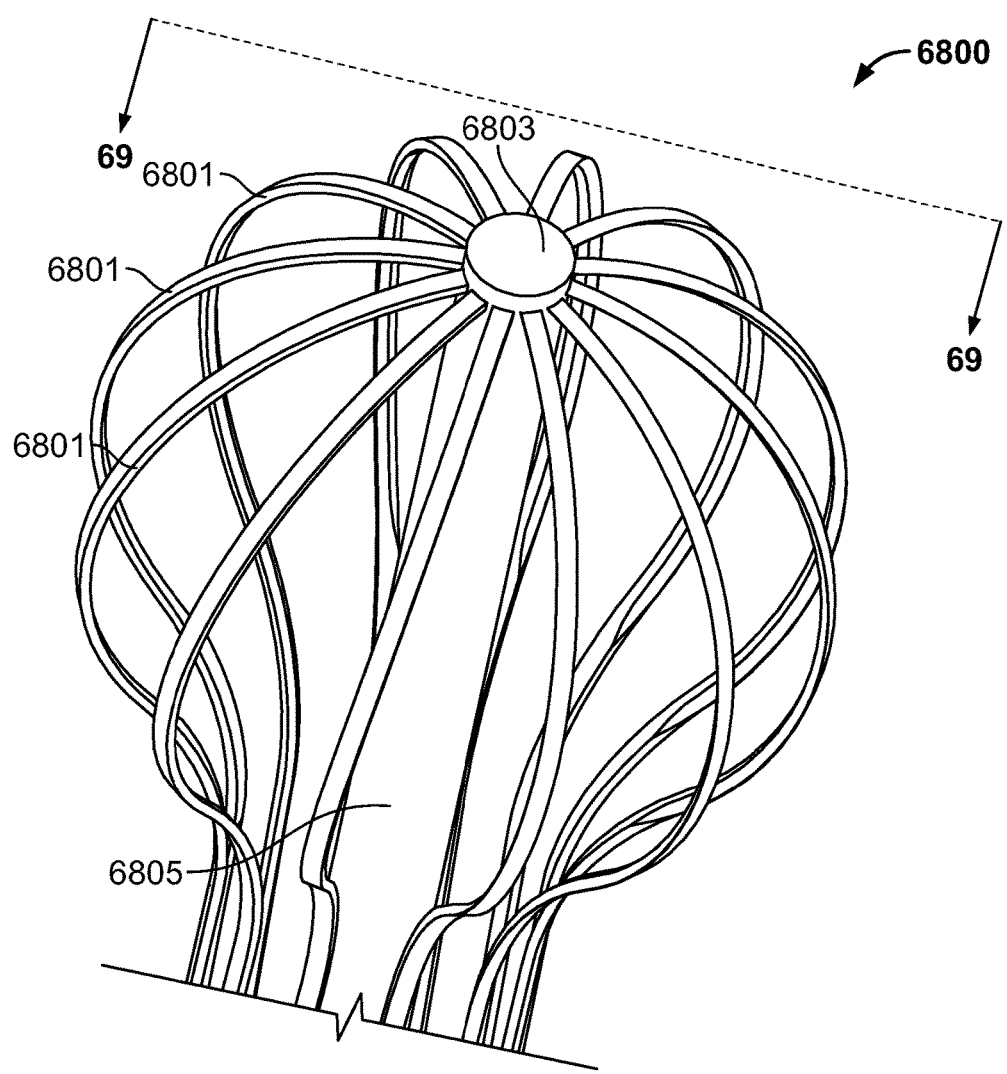
FIG. 68 shows illustrative apparatus in accordance with principles of the invention.

FIG. 68 shows illustrative tool 6800 that may include multiple broaching members 6801 in different orientations. The orientations may correspond to different planes. Broaching members 6801 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching members 6801 may extend continuously through distal hub 6803. Distal hub 6803 may be located at a distal end of support 6805. Broaching members 6801 may radiate away from distal hub 6803.

Broaching members may span from distal hub 6803 to a proximal engagement member (not shown). Broaching members 6801 may have two segments that span from distal hub 6803 to a proximal engagement member. The proximal engagement member may be any engagement member known to those skilled in the art.

When the distal hub includes a distal engagement member that is configured to engage a broaching member end, the broaching members may extend only from the proximal engagement member to the distal hub. The distal hub may include a slotted ring for accepting a terminal t-connector on the end of a broaching member, for example.

The broach head may include as many broaching members, and as many blades, as may geometrically fit.

Tool 6800 may provide a symmetrical cavity. Tool 6600 may include multiple broaching members. Tool 6600 may include multiple blades. Tool 6600 may include 1, 2, 5, 10, 20, 50, 100 or more blades. The blades may be present on broaching members that may be of unitary construction with each other.

The broaching members may be derived from a single tube. Multiple tubes, each having one or more broaching members extending therefrom, may be nested together. Multiple blades may extend from each tube. The multiple blades may include one or more pairs of blades present on opposite sides of a broaching member. The multiple blades may include individual blades that are not paired with a corresponding blade on the same broaching member.

Figure 69:
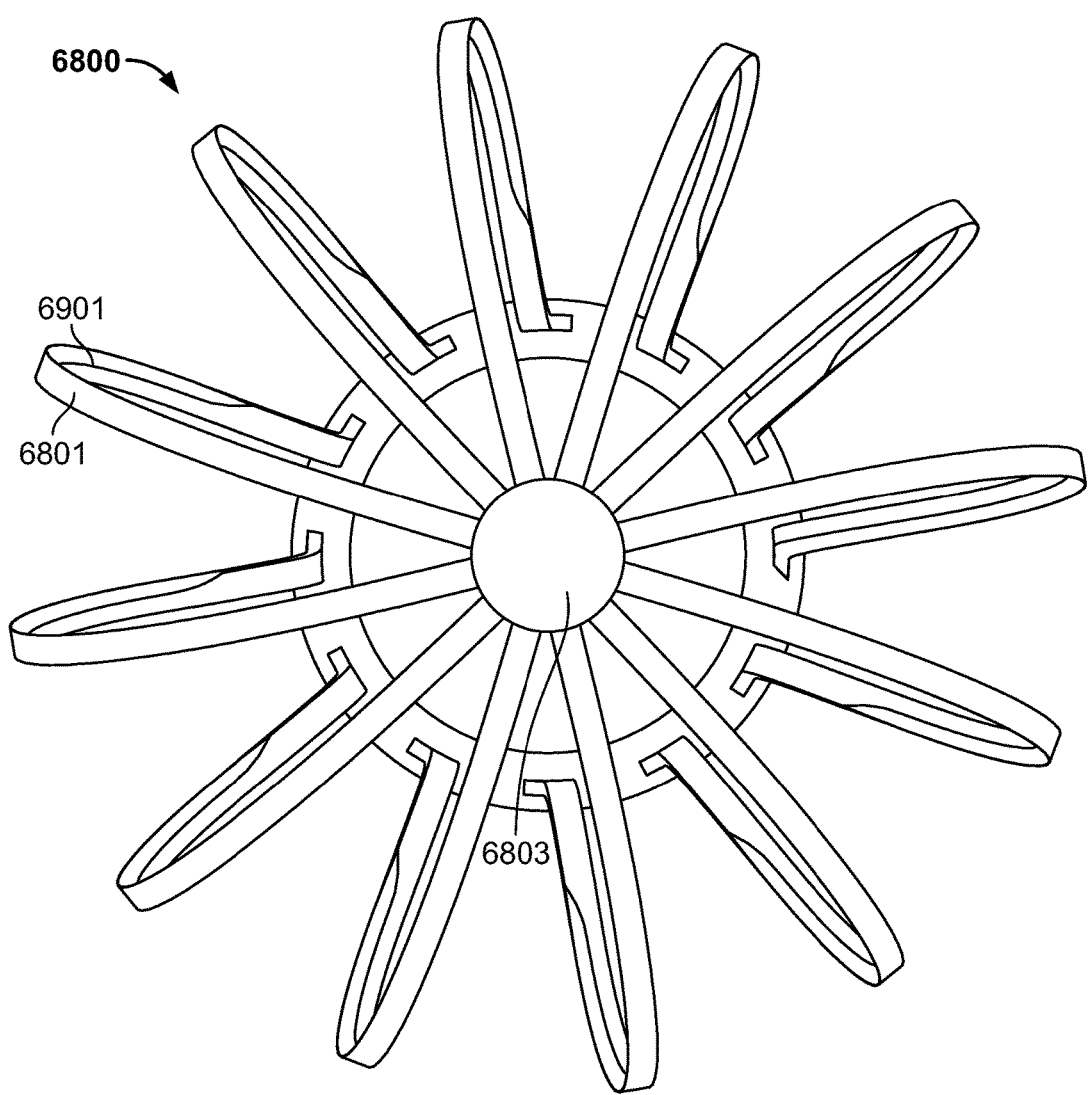
FIG. 69 shows illustrative apparatus in accordance with principles of the invention.

FIG. 69 shows a view of illustrative tool 6800 (shown in FIG. 68). The view shown in FIG. 69 shows cutting edge 6901 on broaching member 6801 radiating from end cap 6803.

FIG. 70 shows illustrative activation tool 7000. Activation tool 7000 includes activation mechanisms 7003. Activation tool includes support 7001. Activation tool includes wires 7005, 7007 and 7009. Each of wires 7005, 7007 and 7009 may be coupled to one of activation mechanisms 7003. Movement of activation mechanism 7003 upwards may move a wire attached to activation mechanism 7003 in an upwards direction. Movement of activation mechanism 7003 downwards may move a wire attached to activation mechanism 7003 in a downwards direction.

FIG. 71 shows illustrative tool 7100. Tool 7100 may include support 7105. Support 7105 may have a length considerably longer than the length shown in FIG. 71. Support 7105 may include end cap 7101.

Support 7105 may support broaching members 7102. Broaching members 7102 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Each of broaching members 7102 may be independently activated. Each of broaching members 7102 may be coupled to one of activation mechanisms 7103. Movement of an activation mechanism 7103 upwards may move the broaching member 7102 coupled to the activation mechanism 7103 in an upwards direction. Movement of an activation mechanism 7103 downwards may move a broaching member coupled to the mechanism 7103 in a downwards direction. A broaching member 6102 may be coupled to one of activation mechanisms 7103 directly, or through one or more members, by any mechanism known to those skilled in the art.

A first end of a broaching member 7102 may be coupled to an activation mechanism 7103. A second end of the broaching member 7102 may be coupled to support 7105. A first and a second end of a broaching member 7102 may each be coupled to a different activation mechanism 7103. The first and second end of the broaching member 7102 may be independently activated by the two activation mechanisms 7103. A portion of the broaching member 7102 may loop around a transverse member supported in support 7105.

FIG. 72 shows a perspective view of illustrative tool 7100 (shown in FIG. 71).

FIG. 73 shows illustrative tool 7300. Tool 7300 may include broach head 7305. Terminal end 7303 may be coupled to a distal end of broach head 7305. Tool 7300 may include broaching member 7304. A first end and a second end of broaching member 7304 may be fixed at the distal end of broach head 7305.

Broaching member 7304 may loop through a proximal end of broach head 7305. Broaching member 7304 may loop around pin 7303 disposed in broach head 7305.

Broach head 7305 may be coupled to rotator 7301. Rotator 7001 may have an inner member (not shown) that is located within rotator 7301 and is attached to terminal end 7303. Movement, by the inner member, of terminal end 7303 towards rotator 7301 may expand broaching member 7304. Movement, by the inner member, of terminal end 7303 away from rotator 7301 may contract broaching member 7304.

Terminal end 7303 may be monolithic with broach head 7305. Terminal end 7303 may be joined to broach head 7305.

The shape of broaching member 7304 is partially or wholly inverted relative to the support in comparison with tools having a distal hinge point. An access hole into the bone may therefore be drilled at an opposite or near-opposite position from the access hole required for the tool having a distal hinge point.

Broaching members 7304 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

FIG. 74 shows a view of illustrative tool 7300 (shown in FIG. 73).

FIG. 75 shows illustrative tool 7500. Illustrative tool 7500 may include support 7501. Support 7501 may support broach head 7507. Pin 7505 may be disposed in broach head 7507. Broaching member 7503 may be looped around pin 7505. Both ends of broaching member 7503 may be fastened to support 7501.

Broaching member 7501 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35), such as the heat memory shape of broaching member 102.

FIG. 76 shows illustrative tool 7600. Tool 7600 may include assembly 7601 for activating broaching member 7603. Element 7601 may include outer sheath 7605. Outer sheath 7605 may slide longitudinally relative to broaching head 7607 to constrain broaching member 7603 and cause broaching member 7603 to collapse against broaching head 7607.

FIG. 77 shows the distal end of illustrative tool 7600. Broaching member 7603 may be engaged with broaching head 7607 by transverse member 7604.

FIG. 78 shows illustrative tool 7600 in a configuration in which broaching head 7607 and broaching member 7603 are withdrawn into sheath 7605.

FIG. 79 shows illustrative broaching head 7607 almost completely withdrawn inside sheath 7605.

FIG. 80 shows illustrative broaching head 7607 extending from sheath 7605 to expose curve 7607 in broaching member 7603.

Figure 81:
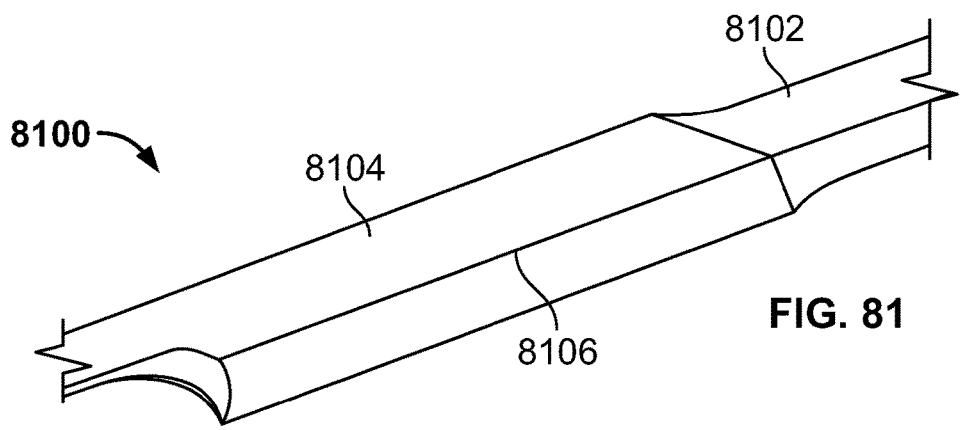
FIG. 81 shows illustrative apparatus in accordance with principles of the invention.

FIG. 81 shows illustrative elongated body portion 8300. Portion 8300 illustrates that a broaching member may include segments such as segment 8302, which is relatively thinner (in width, depth, both perpendicular to length, or both) than segment 8104. The narrower segments may provide one or more of strain relief, attachment, a control point, and engagement. The narrower segments may facilitate formation of relatively smaller-radius bends, for example, about a transverse member or in a loop. The narrower segments may facilitate positioning of bending along a broaching member. An attachment member, such as a transverse member, that is fixed to the tool may engage a narrow section. The engagement of the narrow segment may limit the magnitude of displacement of the narrow segment relative to the tool. For example, when a broaching member is wrapped about a transverse member, a narrower segment in the wrap will occupy less transverse space along the transverse member than will a relatively thicker segment. The engagement of the narrow section may limit the direction of displacement of the narrow segment relative to the tool.

A blade may have an edge in any desired angle extending the length or partial length of the body. The edge may be provided on any side of the body to facilitate tissue engagement. The body may have many sides. For example, the body may have, in cross-section, 3, 4, 5, 6, 7, 8 or more sides. The body may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Figure 82:
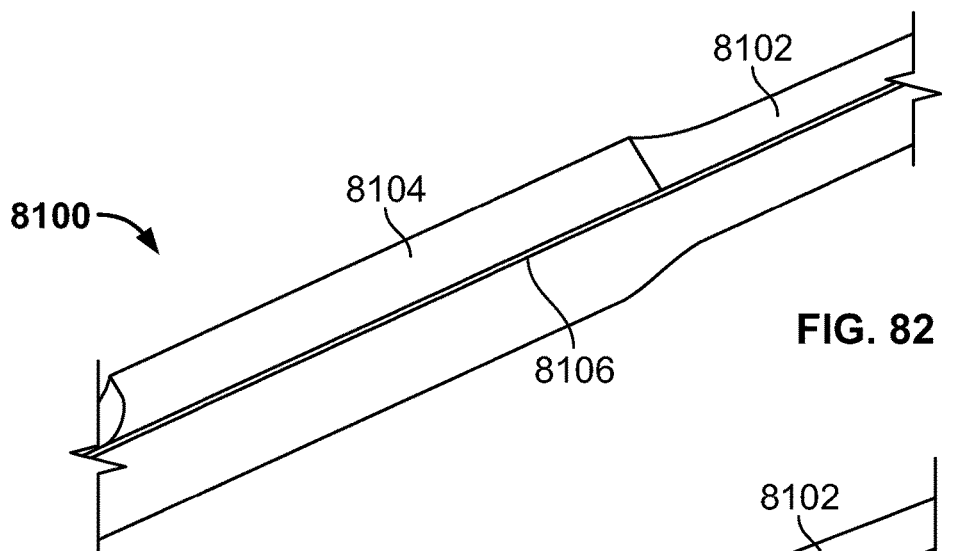
FIG. 82 shows illustrative apparatus in accordance with principles of the invention.

FIG. 82 shows portion 8100 rotated so that edge 8106 is forward.

Figure 83:
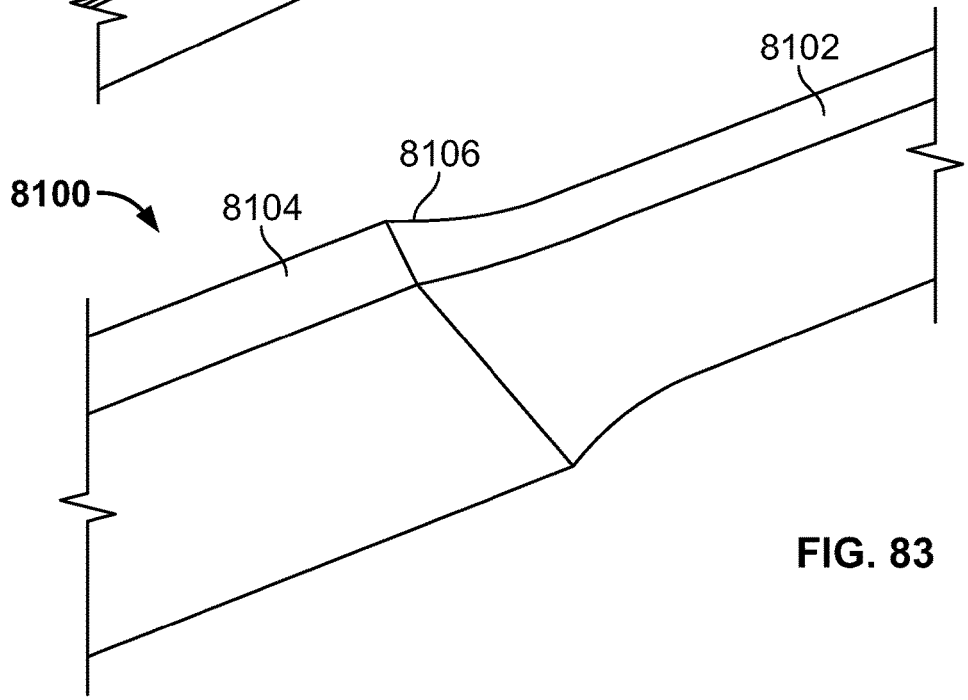
FIG. 83 shows illustrative apparatus in accordance with principles of the invention.
Figure 94A:
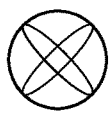
FIG. 94A shows a schematically anatomical cavity that may be obtained using apparatus in accordance with principles of the invention.
Figure 94B:
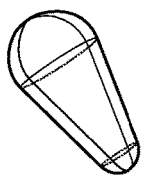
FIG. 94B shows a schematically anatomical cavity that may be obtained using apparatus in accordance with principles of the invention.
Figure 94C:
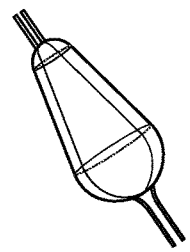
FIG. 94C shows a schematically anatomical cavity that may be obtained using apparatus in accordance with principles of the invention.
Figure 94D:
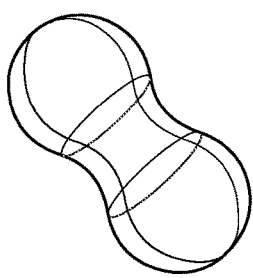
FIG. 94D shows a schematically anatomical cavity that may be obtained using apparatus in accordance with principles of the invention.
Figure 94E:
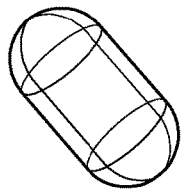
FIG. 94E shows a schematically anatomical cavity that may be obtained using apparatus in accordance with principles of the invention.
Figure 94F:
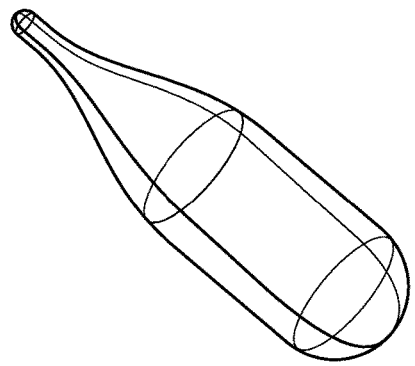
FIG. 94F shows a schematically anatomical cavity that may be obtained using apparatus in accordance with principles of the invention.
Figure 94G:
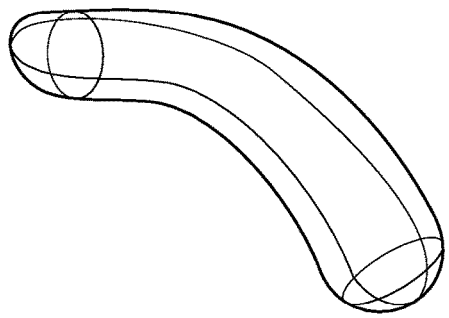
FIG. 94G shows a schematically anatomical cavity that may be obtained using apparatus in accordance with principles of the invention.
Figure 94H:
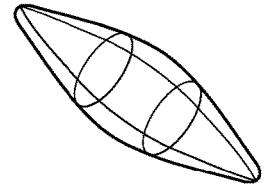
FIG. 94H shows a schematically anatomical cavity that may be obtained using apparatus in accordance with principles of the invention.
Figure 94I:
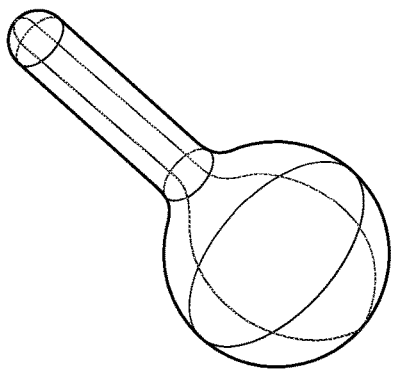
FIG. 94I shows a schematically anatomical cavity that may be obtained using apparatus in accordance with principles of the invention.
Figure 94J:
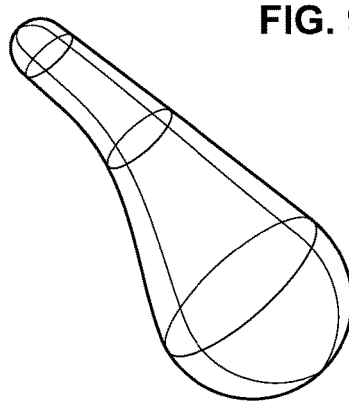
FIG. 94J shows a schematically anatomical cavity that may be obtained using apparatus in accordance with principles of the invention.

FIG. 83 shows portion 8100 rotated so that edge 8106 is at top rear.

FIG. 84 shows illustrative elongated body portion 8400. Narrow segments 8405 and 8407 intervene between thick segments 8401 and 8409 and thick segments 8409 and 8403, respectively. Narrow segments 8405 and 8407 facilitate bending and are shown as the loci of bending in portion 8400. Different cross-sectional shapes that may be used to control bending. When a broaching member is subjected to stress, a thinned section of the broaching member may bend before a non-thinned section of the broaching member bends.

FIG. 85 shows illustrative elongated body portion 8500. Narrow segment 8505 intervenes between thick portions 8501 and 8503. Bending in portion 8500 is concentrated in narrow segment 8505. Thicker portions 8501 and 8503 may be unbent.

FIG. 86 shows illustrative elongated body portion 8600. Body portion 8600 includes elongated body hinge 8609. The body portion 8600 is locally thinned in hinge 8609 to accommodate a bending radius around transverse member 8611 without over-straining body portion 8600. This may allow for a reduced bend radius and therefore a smaller insertion, or collapsed, size of the distal end of the tool. Body portion 8600 includes thicker segments 8605 and 8607 in which bladed segments 8603 and 8601 are provided.

FIG. 87 shows illustrative elongated body 8700. Body 8700 may include one or more blades. For example, body 8700 may include blade 8702. Body 8700 may include blade 8704. Blades 8702 and 8704 may be separated by gap 8706. Body 87 may include multiple blades. Each of the blades may have one or more cutting edges. A broaching member may have several cutting edges.

FIG. 88 shows illustrative elongated body 8800. Illustrative elongated body 8800 may have one or more features in common with illustrative elongated body 870 (shown in FIG. 87).

FIG. 89 shows illustrative elongated body 8900. Illustrative elongated body 8900 may have one or more features in common with illustrative elongated body 870 (shown in FIG. 87).

FIG. 90 shows illustrative elongated body 9000. Body 9000 includes blades 9002 and 9004 separated by gap 9006. An elongated body may include 1, 2, 3, 4, 5, 6 or more blades. One or more of the blades may be configured to cut in a first direction. One or more of the blades may configured to cut in a second direction that is opposite the first direction.

Multiple blades, blades with multiple cutting edges, or both may provide relatively more tissue engagement per unit of operational driving energy. Multiple blades, blades with multiple cutting edges, or both may facilitate operation of the tool in different directions.

FIG. 91 shows a bend in illustrative body 9000.

FIG. 92 shows mirror symmetry in rake and relief angles between illustrative blades 902 and 9004.

FIG. 93 shows gap 9006 between illustrative blades 9002 and 9004.

FIG. 94 shows illustrative profiles a-j of three-dimensional shapes to which the cavity may conform. The profiles may represent end-on views. The profiles may represent side views. The cavity may conform to any suitable shape, whether symmetrical or nonsymmetrical. Symmetrical shapes may have radial symmetry about an axis of rotation of the tool. Symmetrical shapes may have mirror symmetry across a plane that includes the axis of rotation. Symmetrical shapes may have mirror symmetry across a plane that is normal to the axis of rotation.

The apparatus may be delivered to a region inside the bone through an access hole. The region may be where the cavity is to be created. The access hole may be located at an access point. The access point may be at any suitable location on the perimeter of the bone. The access point may be at any suitable location on the surface of the bone. The access hole may have a diameter that is smaller than the diameter of the cavity. The apparatus may be delivered inside the bone through the access hole and then expanded to a state having a diameter greater than the access hole diameter to create the cavity.

Figure 95:
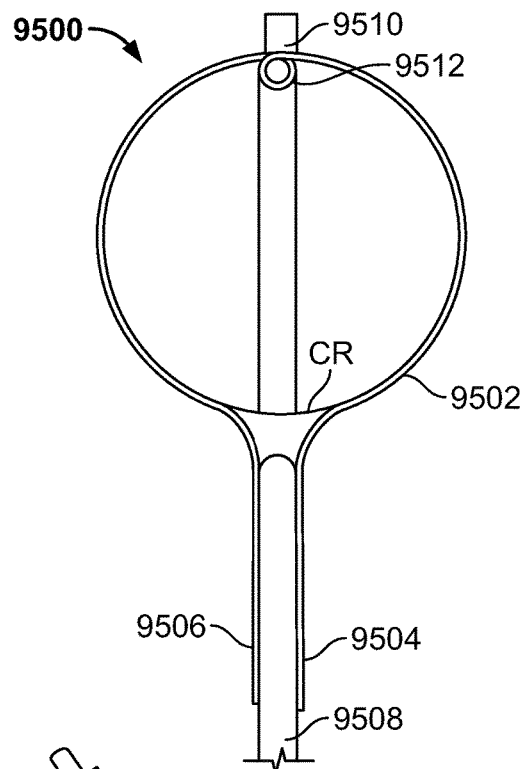
FIG. 95 shows illustrative apparatus in accordance with principles of the invention.

FIG. 95 shows illustrative tool 9500. Illustrative tool 9500 may have one or more features in common with tool 100 (shown in FIG. 1). Illustrative tool 9500 may include broaching member 9502. Broaching member 9502 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching member 9502 may include proximal ends 9504 and 9506. Rotator 9508 may support ends 9504 and 9506. Distal support 9510 may support loop 9512. Broaching member 9502 is shown conforming to reference circle CR. Based on reference circle CR, broaching member 9502 may form a cavity having a spherical or near-spherical surface. A practitioner may translate tool 9500 longitudinally while rotating rotator 9508 about its longitudinal axis. The practitioner may rotate tool 9500 about a transverse axis. The practitioner may rotate tool 9500 about any suitable axis. The practitioner may translate tool 9500 along any suitable axis. The practitioner may combine one or more of the rotations with one or more of the translations to form any suitable cavity surface. The practitioner may combine any suitable broaching member shape or shapes with one or more of the translations and rotations.

Figure 96:
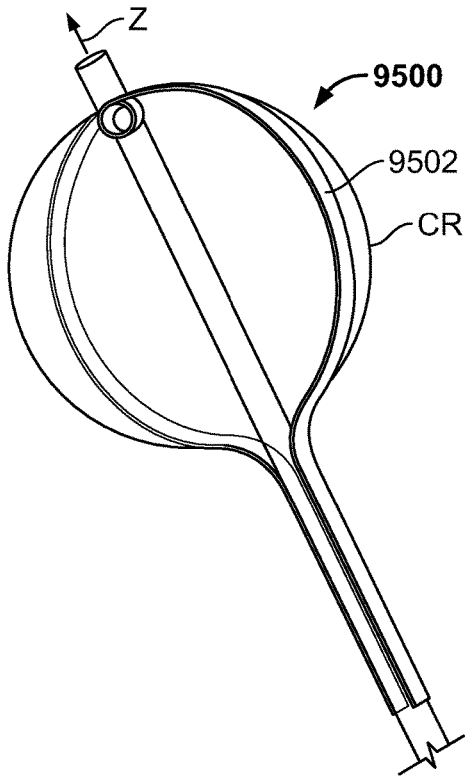
FIG. 96 shows illustrative apparatus in accordance with principles of the invention.

FIG. 96 shows illustrative tool 9500 rotated about longitudinal axis Z relative to reference circle CR.

Figure 97:
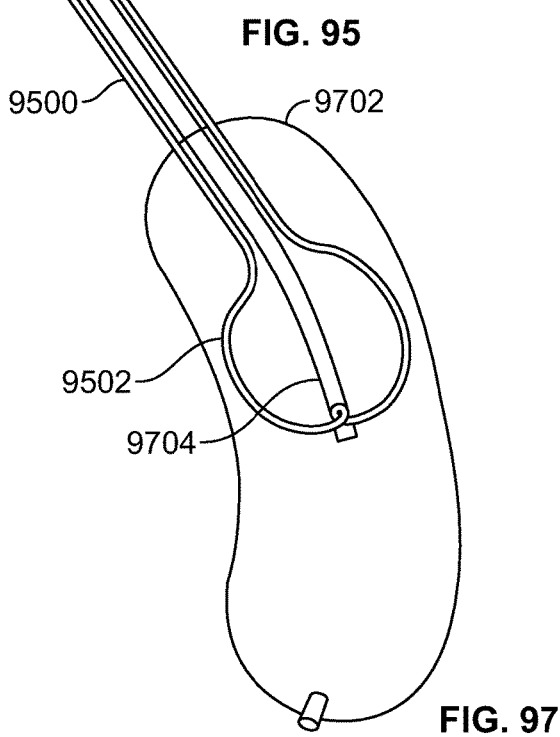
FIG. 97 shows illustrative apparatus in accordance with principles of the invention.

FIG. 97 shows illustrative curved path 9702 that may be made with a tool such as tool 9500. Broaching head 9704 may be flexible.

Path 9702 may be defined by an arc-shaped guide (not shown). The guide may be a trunnion-like mechanism, or flexible shaft, etc.) The cavity may be created by traveling distally or proximally along the trunnion. The cavity shape may be governed by deflection of broaching member 9502 from high density bone. For example, path 9702 may be defined by tissue density contours that may constrain the path of the rotating broaching member. High density tissue may resist advancement of the broaching member. Low density tissue may yield to, and thus be removed by, the broaching member. The cavity may be created by traveling distally or proximally along a path of low density tissue. The cavity may be created by traveling distally or proximally along the trunnion.

Figure 98:
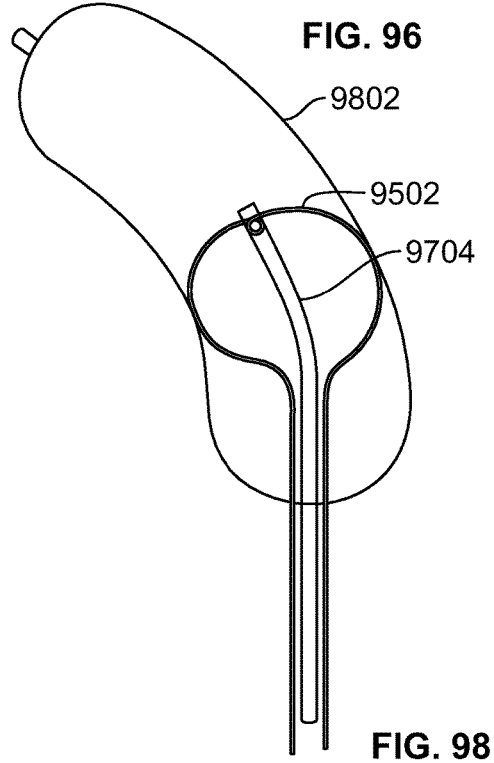
FIG. 98 shows illustrative apparatus in accordance with principles of the invention.

FIG. 98 shows illustrative path 9802. Path 9802 may have one or more features in common with path 9702 (shown in FIG. 97).

A broaching member form may involve 1, 2, 3, 4 or more hinge points, or as many as needed to facilitate a particular expanded shape. The distal segments may be supported. For example, a distal hinge point may be supported to provide distal strength. A hinge point may be stationary relative to the support. A hinge point may be movable relative to the support. A hinge point may be movable relative to the support. A hinge point may be movable relative to another hinge point.

The length of the broaching members between the hinge or control points may be variable or fixed. The length of the blades between the hinge or control points may be variable or fixed.

Figure 99:
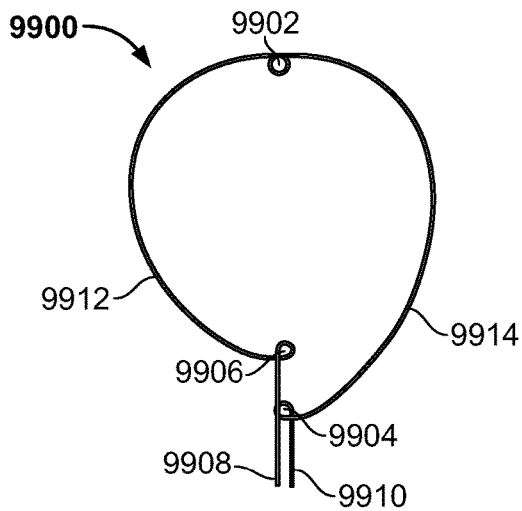
FIG. 99 shows illustrative apparatus in accordance with principles of the invention.

FIG. 99 shows illustrative broaching member 9900. Broaching member 9900 may include hinge point 9902. Broaching member 9900 may include hinge point 9904. Broaching member 9900 may include hinge point 9906. Broaching member 9900 may be one continuous member that is hinged at hinge points 9902, 9904 and 9906. Broaching member 9900 may include ends 9908 and 9910. One or both of ends 9908 and 9910 may be anchored to a broaching head (not shown) at a hinge. One or both of ends 9908 and 9910 may be anchored to a broaching head (not shown) by any suitable securement mechanism.

Broaching member 9900 may include segments such as segment 9912 and 9914. Segments 9912 and 9914 may be unequal in length. Segments 9912 and 9914 may be non-symmetrical to each other.

Control elements (not shown) may displace one or both of ends 9908 and 9910 to change the distances between hinge point 9906 and hinge point 9902. The control elements may displace one or both of ends 9908 and 9910 to change the distances between hinge point 9904 and hinge point 9902.

The control elements may displace one or both of hinge points 9904 and 9906 to change the distances between hinge point 9906 and hinge point 9902. The control elements may displace one or both of hinge points 9904 and 9906 to change the distances between hinge point 9904 and hinge point 9902.

Endpoints of different segments may be simultaneously acted upon to actuate the corresponding segments. The endpoints of different segments may be non-simultaneously acted upon to actuate the corresponding segments. The endpoints of different segments may be acted upon independently to actuate the corresponding segments. The endpoints of different segments may be acted upon in an interdependent manner to actuate the corresponding segments.

Figure 100:
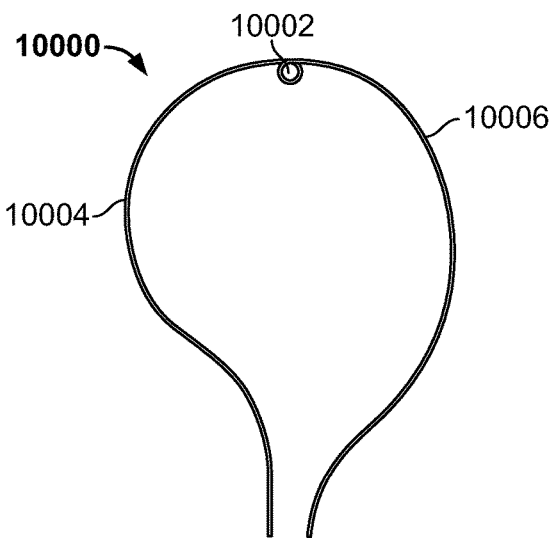
FIG. 100 shows illustrative apparatus in accordance with principles of the invention.

FIG. 100 shows illustrative broaching member 10000. Broaching member 10000 may include single hinge point 10002. Broaching member 10000 may include left segment 10004 and right segment 10006. Left segment 10004 and right segment 10006 may be preset to different shapes.

Figure 101:
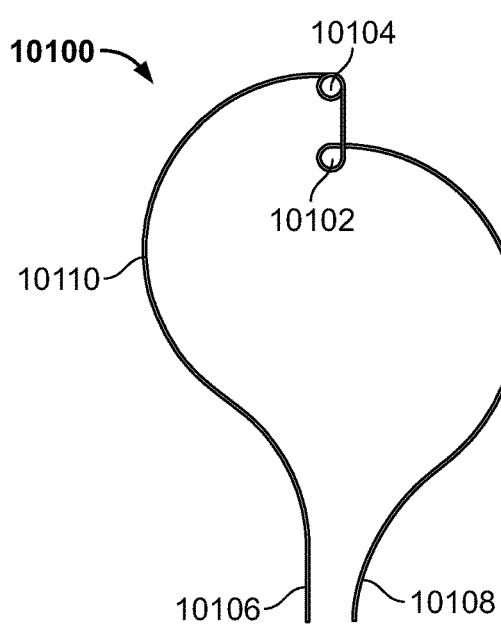
FIG. 101 shows illustrative apparatus in accordance with principles of the invention.

FIG. 101 shows illustrative broaching member 10100. Broaching member 10100 may include two hinge points— 10102 and 10104. Hinge point 10104 is a distal hinge point. Hinge point 10102 is distal relative to ends 10106 and 10108. Hinge point 10102 is proximal relative to hinge point 10104. The hinge points are at different longitudinal positions to provide distally offset cavity surfaces having different radii and contours. Segments 10110 and 10112 may be activated individually or in conjunction with each other.

Figure 102:
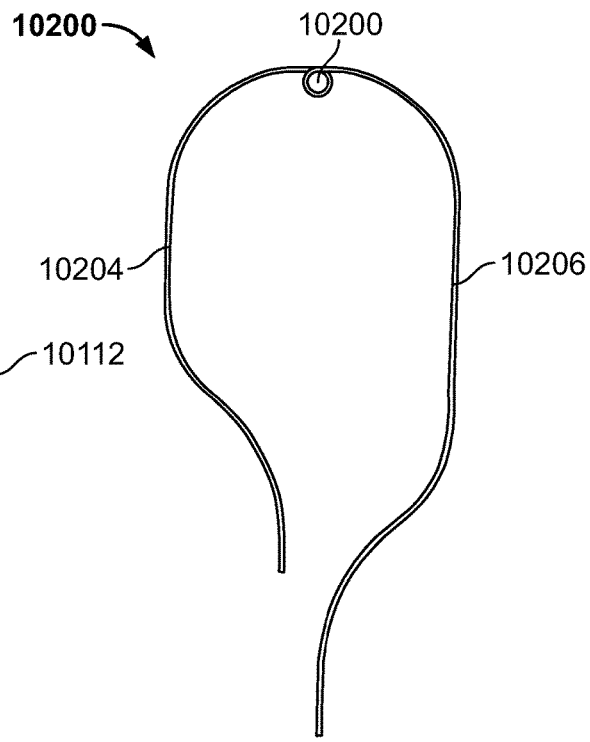
FIG. 102 shows illustrative apparatus in accordance with principles of the invention.

FIG. 102 shows illustrative non-symmetrical broaching member 10200. Broaching member 10200 may include single hinge point 10202. Broaching member 10200 may include left segment 10204 and right segment 10206. Left segment 10204 and right segment 10205 may be preset to different shapes. Proximal segments of the broaching member may be actuated in conjunction with each other. Proximal segments of the broaching member may be actuated independently of each other.

Figures 103, 104, 105:
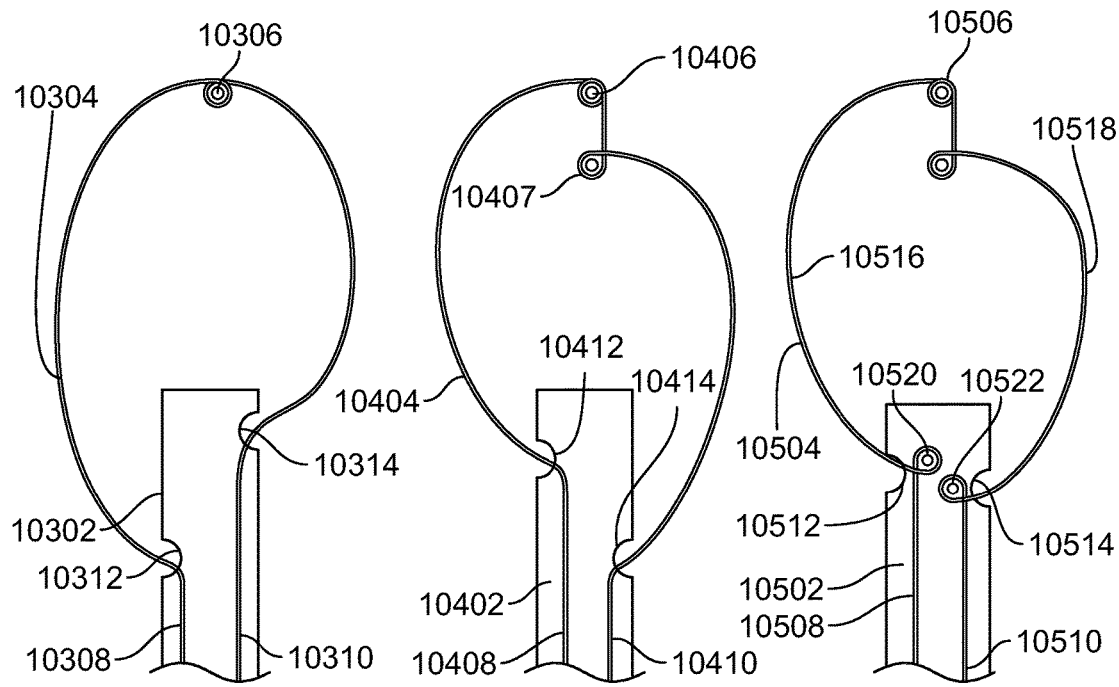
FIG. 103 shows illustrative apparatus in accordance with principles of the invention.

FIG. 103 shows illustrative support 10302. Support 10302 may support broaching member 10304. A broaching head (not shown) may support hinge point 10306. Broaching member ends 10308 and 10310 may be drawn, respectively, through apertures 10312 and 10314 in support 10302. Broaching member ends 10308 and 10310 may be secured independently or together within or proximal of support 10302.

FIG. 104 shows illustrative support 10402. Support 10402 may support broaching member 10404. A broaching head (not shown) may support hinge point 10406. The broaching head may support hinge point 10407. The broaching head may support any suitable number of hinge points. Broaching member ends 10408 and 10410 may be drawn, respectively, through apertures 10412 and 10414 in support 10402. Broaching member ends 10408 and 10410 may be secured independently or together within or proximal of support 10402.

FIG. 105 shows illustrative support 10502. Support 10502 may support broaching member 10504. A broaching head (not shown) may support hinge point 10506. The broaching head may support hinge point 10507. The broaching head may support any suitable number of hinge points. Broaching member ends 10508 and 10510 may be drawn, respectively, through apertures 10512 and 10514 in support 10502. Broaching member ends 10508 and 10510 may be secured independently or together within or proximal of support 10502. Segments 10516 and 10518 may be secured at hinge points 10520 and 10522, respectively, inside support 10502.

Figures 106, 107:
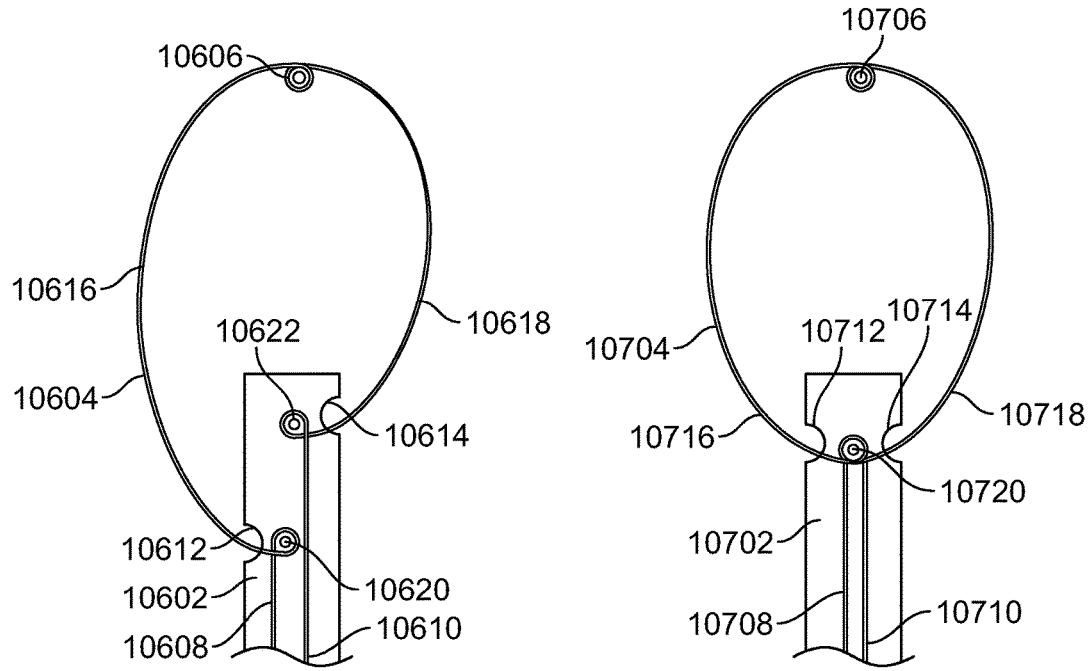

FIG. 106 shows illustrative support 10602. Support 10602 may support broaching member 10604. A broaching head (not shown) may support hinge point 10606. The broaching head may support any suitable number of hinge points. Broaching member ends 10608 and 10610 may be drawn, respectively, through apertures 10612 and 10614 in support 10602. Broaching member ends 10608 and 10610 may be secured independently or together within or proximal of support 10602. Segments 10616 and 10618 may be secured at hinge points 10620 and 10622, respectively, inside support 10602.

FIG. 107 shows illustrative support 10702. Support 10702 may support broaching member 10704. A broaching head (not shown) may support hinge point 10706. The broaching head may support any suitable number of hinge points. Broaching member ends 10708 and 10710 may be drawn, respectively, through apertures 10712 and 10714 in support 10702. Broaching member ends 10708 and 10710 may be secured independently or together within or proximal of support 10702. Segments 10716 and 10718 may be secured at hinge points 10720 and 10722 (not shown; disposed transversely "behind" hinge point 10720 in view shown), respectively, inside support 10702.

Support 10702 may have a diameter relatively larger than that of support 10602 (shown in FIG. 106), because of the transverse alignment of hinge points 10720 and 10722 in support 10702. In contrast, hinge points 10620 and 10622 in support 10602 are in longitudinal alignment along support 10602 and thus require a relatively smaller diameter to be accommodated within support 10602. The smaller diameter may provide for a smaller access hole into the intramedullary space. The smaller diameter may provide for a cavity shape that is different from that corresponding to the larger diameter support.

FIG. 108 shows illustrative tool 10800. Illustrative tool 10800 may have one or more features in common with tool 100 (shown in FIG. 1). Illustrative tool 10800 may include broaching member 10802. Broaching member 10802 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching member 10802 may include proximal ends 10804 and 10806. Rotator 10808 may support ends 10804 and 10806. A broaching head (not shown) may support loop 10812. The broaching head may support distal support 10810.

Broaching member 10802 is shown conforming to reference profile PR1. Based on reference profile PR1, broaching member 10802 may form a cavity having a surface that is oblong or near-oblong, ellipsoidal or near-ellipsoidal, oval or near-oval, or the like. The surface may include one or more reentrant portions such as reentrant portion 10812. Reentrant portion 10812 may form by deflection of broaching member 10802 from high density bone HD, which is surrounded by low density bone LD. Compliant broaching members may thus create key-hole cavities.

FIG. 109 shows illustrative tool 10800 rotated about longitudinal axis Z relative to reference profile PR1. Reentrant region 10812 is shown to be dome-like in perspective view. Broaching member 10801 is shown as deflecting from a surface defined by dense bone due to responsiveness of the broaching member to tissue density.

FIG. 110 shows illustrative tool 11000. Illustrative tool 11000 may have one or more features in common with tool 100 (shown in FIG. 1). Illustrative tool 11000 may include broaching member 11002. Broaching member may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching member 11002 may include proximal ends 11004 and 11006. Rotator 11008 may support ends 11004 and 11006. A broaching head (not shown) may support loop 11012. The broaching head may support distal support 11010.

Broaching member 11002 is shown conforming to reference profile PR2. Based on reference profile PR2, broaching member 11002 may form a cavity having a surface that is oblong or near-oblong, ellipsoidal or near-ellipsoidal, oval or near-oval, conical, cone-like, or the like.

FIG. 111 shows illustrative tool 11000 rotated about longitudinal axis Z relative to reference profile PR2.

Broaching member 11002 may be shaped along its length to provide a cavity shape. The broaching member may be supported at distal hinge 11012. The broaching member may be placed in position and shaped for creating the cavity by a change in length between the hinge and the captured free ends. The free ends may be engaged by an actuator. All or some of broaching member 11002 may be constrained for deployment, for example by a sheath, and then released inside the bone.

FIG. 112 shows illustrative tool 11200. Illustrative tool 11200 may have one or more features in common with tool 100 (shown in FIG. 1). Illustrative tool 11200 may include broaching member 11202. Broaching member 11202 may have one or more features in common with broaching member 102 (shown in FIG. 1), broaching member 1800 (shown in FIG. 18), broaching member 2600 (shown in FIG.

26), broaching member 3400 (shown in FIG. 34) and broaching member 3500 (shown in FIG. 35).

Broaching member 11202 may include proximal ends 11204 and 11206. Rotator 11208 may support ends 11204 and 11206. A broaching head (not shown) may support loop 11212. The broaching head may support distal support 11210.

Broaching member 11202 is shown conforming to reference profile PR3. Based on reference profile PR3, broaching member 11202 may form a cavity having a surface that is bulb- or near-bulb-shaped, or the like.

FIG. 113 shows illustrative tool 11200 rotated about longitudinal axis Z relative to reference profile PR3.

FIG. 114 shows illustrative tool 11400. Illustrative tool 11400 may have one or more features in common with tool 100 (shown in FIG. 1). Illustrative tool 11400 may include broaching member 11402. Broaching member 11402 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching member 11402 may include proximal ends 11404 and 11406. Rotator 11408 may support ends 11404 and 11406. A broaching head (not shown) may support loop 11412. The broaching head may support distal support 11410.

Broaching member 11402 is shown conforming to reference profile PR4. Based on reference profile PR4, broaching member 11402 may form a cavity having a surface that is oblong or near-oblong, ellipsoidal or near-ellipsoidal, oval or near-oval, conical, cone-like, or the like.

FIG. 115 shows illustrative tool 11400 rotated about longitudinal axis Z relative to reference profile PR4.

PR4 includes straight sections PR4*a* and PR4*b*. Straight sections PR4*a* and PR4*b* correspond to cylindrical surfaces to be made in the cavity. Some broaching member span segments, such as longer longitudinal span segments like span segments 11502 and 11503 may have reduced outward radial strength because of their length. Such segments may be constructed of stiffer material, thicker stock, or may be reinforced to increase outward radial strength. The increased outward radial strength may oppose inward radial bending forces.

Multiple offset segments, such as segments 10110 and 10112 of broaching member 10100 (shown in FIG. 101) may be shorter in the longitudinal direction than span segments 11502 and 11503 (shown in FIG. 115). Segments 10110 and 10112 have more curvature along a longitudinal stretch than segments 11502 and 11503 (shown in FIG. 115). This may give segments 10110 and 10112 (shown in FIG. 101) greater outward radial strength and provide the same cavity shape as segments 11502 and 11503 (shown in FIG. 115). Segments 10110 and 10112 may not require the stiffness that segments 11502 and 11503 (shown in FIG. 115) may require.

FIG. 116 shows illustrative tool 11600. Illustrative tool 11600 may have one or more features in common with tool 100 (shown in FIG. 1). Illustrative tool 11600 may include broaching member 11602. Broaching member 11602 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Illustrative tool 11600 may include broaching member 11603. Broaching member 11602 may include proximal end 11604. Broaching member 11603 may include proximal end 11606. Rotator 11608 may support ends 11604 and 11606. A broaching head (not shown) may support one or both of loops 11612 and 11614. The broaching head may support distal support 11610.

The broaching head may include a brace (not shown) to brace broaching member 11603 at knee 11616. The brace may brace knee 11616 against displacing forces during rotation against bone material. The brace may brace knee 11616 against torsional forces during rotation against bone material.

The broaching head may include a brace (not shown) to brace broaching member 11603 at knee 11618. The brace may brace knee 11618 against displacing forces during rotation against bone material. The brace may brace knee 11618 against torsional forces during rotation against bone material.

Broaching members 11602 and 11603 are shown conforming, when in rotation about axis Z, to reference profile PR5. Based on reference profile PR5, broaching members 11602 and 11603 may form a cavity having a surface that is oblong or near-oblong, ellipsoidal or near-ellipsoidal, oval or near-oval, conical, cone-like, or the like.

FIG. 117 shows illustrative tool 11600 rotated about longitudinal axis Z relative to reference profile PR5.

FIG. 118 shows illustrative tool 11800. Illustrative tool 11800 may have one or more features in common with tool 100 (shown in FIG. 1). Illustrative tool 11800 may include broaching member 11802. Broaching member 11802 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Illustrative tool 11800 may include broaching member 11803. Broaching member 11802 may include proximal end 11804. Broaching member 11803 may include proximal end 11806. Rotator 11808 may support ends 11804 and 11806. A broaching head (not shown) may support one or both of loops 11812 and 11814. The broaching head may support distal support 11810. The broaching head may support one or more of distal end 11815, knee 11816, span segment 11817, knee 11818 and any other suitable features of broaching members 11802 and 11803. The broaching head may include a brace (not shown) to brace one or more of distal end 11815, knee 11816, span segment 11817, knee 11818 and any other suitable features of broaching members 11802 and 11803 to the broaching head. The brace may brace the features against displacing forces during rotation against bone material. The brace may brace the features against torsional forces during rotation against bone material.

Broaching members 11802 and 11803 are shown conforming, when in rotation about axis Z, to reference profile PR6. PR6 includes waist 11820. Based on reference profile PR6, broaching members 11802 and 11803 may form a waisted cavity having a surface that is oblong or near-oblong, ellipsoidal or near-ellipsoidal, oval or near-oval, conical, cone-like, or the like.

FIG. 119 shows illustrative tool 11800 rotated about longitudinal axis Z relative to reference profile PR6.

FIG. 120 shows illustrative tool 12000. Illustrative tool 12000 may have one or more features in common with tool 100 (shown in FIG. 1). Illustrative tool 12000 may include broaching member 12002. Broaching member 12002 may have one or more features in common with broaching member 102 (shown in FIG. 1), broaching member 1800 (shown in FIG. 18), broaching member 2600 (shown in FIG.

26), broaching member 3400 (shown in FIG. 34) and broaching member 3500 (shown in FIG. 35).

Illustrative tool 12000 may include broaching member 12003. Broaching member 12002 may include proximal end 12004. Broaching member 12003 may include proximal end 12006. Rotator 12008 may support ends 12004 and 12006. A broaching head (not shown) may support one or both of loops 12012 and 12014. The broaching head may support distal support 12010. The broaching head may support one or more of knee 12016, span segment 12018 and any other suitable features of broaching members 12002 and 12003. The broaching head may include a brace (not shown) to brace one or more of knee 12016, span segment 12018 and any other suitable features of broaching members 12002 and 12003 to the broaching head. The brace may brace the features against displacing forces during rotation against bone material. The brace may brace the features against torsional forces during rotation against bone material.

Broaching members 12002 and 12003 are shown conforming, when in rotation about axis Z, to reference profile PR7. PR7 includes bulge 12020. Based on reference profile PR7, broaching members 12002 and 12003 may form a bulging cavity having a surface that is oblong or near-oblong, ellipsoidal or near-ellipsoidal, oval or near-oval, conical, cone-like, or the like. In other embodiments, profile PR7 may be provided by a single broaching member with a single blade. In other embodiments, profile PR7 may be provided by two symmetrical blades on separate broaching members.

FIG. 121 shows illustrative tool 12000 rotated about longitudinal axis Z relative to reference profile PR7.

Tool 12000 may be rotated at least one full revolution to provide a cavity with cylindrical symmetry. Tool 12000 may be rotated less than a full revolution to provide a cavity with a non-cylindrical symmetry.

FIG. 122 shows illustrative apparatus 12200. Apparatus 12200 may include expandable mesh cage 12207.

Cage 12207 may be a self expanding structure. Cage 12207 may be constructed from laser-cut tube stock that is expanded into a suitable shape, such as that shown. Cage 12207 may include a plurality of interconnected cells. Each of the interconnected cells may be defined by one or more cage segments. Cage 12207 may be a mesh cage. The cage segments may be mesh segments. The cage segments may be defined by one or more broaching members.

Some cage segments may be defined by structures other than broaching members. The interconnected cells may be arranged in a network. The cells may be linked such that when the structure is stressed (e.g., compressed) at a point the stress is distributed to nearby cells. Cage 12207 may thus rotate in a bone cavity that has an irregular shape, for example, nonround, oblong, or angular. The cavity may be smaller than a diameter of cage 12207, such as expanded diameter.

A proximal end of cage 12207 may be supported by a proximal end of support 12205. A distal end of cage 12207 may be supported by a distal end of support 12205. Support 12205 may be coupled to a rotator (not shown). Support 12205 may be decoupled from the rotator.

A proximal end of support 12205 may include holes 12209. Holes 12209 may be configured to receive a fixation device, such as a screw, for fixing cage 12207 to an intramedullary space. Cage 12207 may be fixed to an intramedullary space temporarily, and later withdrawn. Cage 12207 may be fixed to an intramedullary space permanently.

Cage 12200 may include broaching member 12201. Broaching member 12201 may be a cutting-ribbon that includes a cutting edge. The cutting ribbon may include any suitable material, such as any material that may be included in a broaching member. Broaching member 12201 may be broaching member, an elongated body, a wire, a ribbon, a cutting wire, a cutting ribbon, a braided wire, or any other suitable member. Broaching member 12201 may include one or more cutting edges. Broaching member 12201 may include a plurality of sections. Each of the sections may have a width and a length. A width and a length of a first section may be different from a width and a length of a second section.

Broaching member 12201 may be supported by cage 12207. Broaching member 12201 may be woven through cells of cage 12207. Broaching member 12201 may be mechanically engaged, without being woven, to outer portions of cage 12207. Broaching member 12201 may be integral to the structure of cage 12207. Broaching member 12201 may be connected to outer portions of cage 12207 by connectors. Broaching member 12201 or a blade on broaching member 12201 may be monolithic with cage 12207.

When broaching member 12201 is woven through the mesh, the section extending through the mesh may have a small cross-sectional diameter relative to a section that is not directly supported, because the mechanical load from tissue engagement is distributed to closely spaced multiple support points on the cage.

Broaching member 12201 may be one of 2, 3, 4, 5, 6, 10, 11-20, 21-50, 51-100 or more cutting ribbons on the cage. Broaching member 12201 may be fabricated as a separate element from the cage. Broaching member 12201 may be fabricated as an element that is integral to the cage.

Broaching member 12201 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching member 12201 may run along a proximal-distal "meridian" of cage 12207. Broaching member 12201 may run at an oblique angle to the meridian of cage 12207. Broaching member 12201 may run perpendicular to the meridian of cage 12207. Broaching member 12201 may include one or more blades. Cage 12207 may have an expanded state that corresponds to a desired cavity shape.

A first end of broaching member 12207 may be coupled to a distal end of support 12205. A second end of broaching member 12207 may be coupled to a distal end of support 12205. A portion of broaching member 12207 may pass over a distal end of support 12205. A portion of broaching member 12205 may pass under the distal end of support 12205.

Cage 12207 may be a bone implant that is rotatingly driven around its center axis as it is deployed. Cage 12207 may be a bone implant that is translatingly driven along its center axis as it is deployed. Cage 12207 may be a bone implant that is both rotatingly and translatingly driven around its axis as it is deployed. Rotation of cage 12207 around its center axis may engage the broaching member with tissue. The broaching member may displace the tissue. Displacement of the tissue may aid in creating a cavity for the implant as it is being deployed.

A cage segment may have one or more features in common with a segment of a broaching member. The cage segment may include a cutting edge. The cutting edge may be sharpened. The cage segment may be twisted to present the cutting edge to the tissue at a predetermined angle.

The cage segment may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Broaching member 12201 may include a T-termination that may be received by a slotted ring included in support 12205. The slotted ring may be included in a distal end of support 12205. The slotted ring may be included in a proximal end of support 12205. Support 12205 may include an expansion limited slot for receiving the T-termination. Support 12205 may include an expansion limited slot for receiving the T-termination in the distal end.

FIG. 122A shows a view of illustrative apparatus 12200 (shown in FIG. 122).

FIG. 123 shows illustrative cage 12300. Cage 12300 may include inner mesh 12301 and outer mesh 12303. Inner mesh 12301 and outer mesh 12303 may be connected to support 12305. Support 12305 may include holes 12309 for receiving a fixation device for fixing cage 12300 to an intramedullary space.

Inner mesh 12301 and outer mesh 12303 may have one or more properties similar to cage 12207 (shown in FIG. 122). Broaching member 12311 may be woven through outer mesh 12303. Broaching member 12311, and the engagement of broaching member 12311 with outer mesh 12303 may have one or more properties similar to broaching member 12201 (shown in FIG. 122) and the engagement of broaching member 12201 with cage 12207.

Inner mesh 12301 and outer mesh 12303 may be formed from laser cut tubes. Inner mesh 12301, when expanded, may be in physical contact with a portion of outer mesh 12303. A longitudinally intermediate region of inner mesh 12301 may be in physical contact with a portion of outer mesh 12303. One or more intermediate regions of inner mesh 12301 may be in physical contact with a one or more portions of outer mesh 12303.

The area of contact between inner mesh 12301 and outer mesh 12303 may give additional radial strength to outer mesh 12303. The additional radial strength may increase the efficiency of outer mesh 12303 at cutting tissue. The additional radial strength may increase the efficiency of broaching member 12311 at cutting tissue.

FIG. 123A shows a view of illustrative cage 12300 (shown in FIG. 123).

FIG. 123B shows a view of illustrative cage 12300. The view in FIG. 123B shows the top of cage 12300. The view also shows broaching member 12311 threaded through outer mesh 12303 and passing over a distal end of support 12305.

FIG. 124 shows a partial cross sectional view of illustrative cage 12300 taken along lines 124-124 (shown in FIG. 123). The view in FIG. 124 shows area 12401 where inner mesh 12301 supports outer mesh 12303. Area 12401 may provide outer mesh 12303 with greater radial strength then outer mesh 12303 would have without inner mesh 12301 support it along area 12401. Area 12401 may provide broaching member 12311 with greater cutting efficiency than broaching member 12311 would have without inner mesh 12301 supporting outer mesh 12303 along area 12401.

FIG. 124A shows a partial cross sectional view of illustrative cage 12207 taken along lines 124A-124A (shown in FIG. 122). The view in FIG. 124A shows broaching member 12201 interwoven through cage 12207. Cage 12207 may have less radial strength than cage 12300 (shown in FIG. 123) because cage 12207 does not have an inner mesh supporting segments of cage 12207.

FIG. 125 shows illustrative cage 12501 implanted into, and fixed to, bone B by screws 12511. Cage 12501 may include inner mesh 12505 and outer mesh 12503. Cage 12501 may include broaching member 12507. Broaching member may be woven though mess segments of outer mesh 12503.

Inner mesh 12505 may be in physical contact with outer mesh 12503. The areas of physical contact may provide cage 12501 with greater radial strength. This may increase the efficiency of cage 12501 for supporting a broken bone.

FIG. 126 shows a portion of an illustrative mesh cage. The cage may include segments 12603. The cage may include openings 12601. The cage may include broaching member 12605 woven through the openings. Broaching member 12605 may have one or more features in common with broaching member 12201 (shown in FIG. 122).

FIG. 127 shows illustrative broaching member 12703. Broaching member 12703 may be passed through openings 12701 in a mesh cage. Broaching member 12703 may include thinned segments to reduce radii of curvature where broaching member 12703 curves around portions of the mesh cage. The thinned segments may help broaching member 12703 conform to the outer boundary of the mesh cage. The thinned segments may facilitate placement of broaching member 12703 through the slots. Broaching member 12703 may have one or more features in common with broaching member 12201 (shown in FIG. 122).

FIG. 128 shows a portion of an illustrative mesh cage that includes barbs 12803 that project radially outward. The mesh cage may be defined by connecting mesh segments 12801. The connecting mesh segments 12801 may form node 12807. Some of nodes 12807 may include two barbs 12803. Some of nodes 12807 may include one barb 12803. All of nodes 12807 may include two barbs 12803.

The mesh cage may be rotated, like cage 12207 (shown in FIG. 122), around its center axis as it is deployed to create a cavity. Barbs 12803 may be aligned in the direction of a longitudinal axis of the mesh cage. Barbs 12803 may be monolithic with the mesh cage. Barbs 12803 may be built into the mesh at a node 12807. Barbs 12803 may be struts that are fixed to node 12807. The strut may angle radially outward to engage the tissue.

FIG. 129 illustrates illustrative tube 12900 with ninety degree cuts 12901 and angled cuts 12903.

FIG. 129A shows a cross sectional view of illustrative tube 12900 taken along lines 129A-129A. The cross sectional view in FIG. 129A shows the two-dimensional shape of members formed from ninety degree cuts 12901 and members formed from angled cuts 12903.

FIG. 130 shows illustrative tube 13000 with illustrative angled laser cut patterns 13001 for forming a cutting tool. Tube 13000 may be cut by a laser. A laser may perform an angled cut in a tube by a practitioner aligning a central axis of the tube orthogonal to, but offset from, the laser beam. The tube may then be cut by the laser beam in a direction parallel to the tube central axis. Additional cuts may be performed by rotating the tube about the tube central axis by an angular displacement, and then cutting the tube again in the aligned direction while maintaining the offset. An annular rim may be left at the first end. An annular rim may be left at the second end. An annular rim may be left at both ends.

The angled tube-cutting may provide shaping to elongated members included in the cutting tool. The shaping may be set to result in a desired rake angle. The shaping may be set to provide a desired relief angle. The shaping may be set to provide a desired rake angle and a desired relief angle. The elongated members may be shaped further by heat-setting of one or more of angles (e.g., such as one or both of rake and relief angles), twists (e.g., about a central axis such as S, shown in FIG. 27) and bends (e.g., such as about an axis such as M, shown in FIG. 34).

FIG. 130A shows a cross sectional view of illustrative tube 13000 taken along lines 130A-130A. The cross sectional view of tube 1300 shows a two-dimensional shape of members formed from angled cuts 13001.

FIG. 131 shows a partial cross-sectional view of illustrative tube 13000 taken along lines 130A-130A. The partial cross sectional view shows a portion of tube 13000 with angled cuts 13001.

FIG. 132 shows illustrative cutting tool 13200. Cutting tool 13200 may be formed from a tube with angular cuts. Cutting tool 13200 may be a tube, with angular cuts, in an expanded state. Cutting tool 13200 may include one or more twists. Cutting tool 13200 may include one more cut patterns. For example, cutting tool 13200 may include cut patterns such as those shown in FIG. 130.

Cutting tool 13200 may include elongated members 13203. Cutting tool 13200 may include annular rims 13201. Annular rims may be formed by cutting a tube at a length that is less than the length of the tube.

Elongated members 13203 may have a rake angle and a relief angle. The rake angle and the relief angle may be the result of the angled cutting of a tube and subsequent compression of a first end of the tube towards a second end of the tube.

Elongated members 13203 may be shaped further by heat-setting of one or more of angles (e.g., such as one or both of rake and relief angles), twists (e.g., about a central axis such as S, shown in FIG. 27) and bends (e.g., such as about an axis such as M, shown in FIG. 34).

Elongated members 13203 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

Elongated members may be machined to include an additional cutting edge, or a larger cutting edge, than created by the angled cuts.

FIG. 133 shows a view of illustrative apparatus 13200.

FIG. 134 shows a partial cross-sectional view of illustrative apparatus 13200 taken along the lines 134-134. Cross-section 134-134 shows the rake angles and relief angles of the elongated members.

FIG. 135 shows illustrative tube 13500 with angled laser cut patterns 13501 for forming a cutting tool. Tube 12900 may be cut by a laser. A laser may perform an angled cut in a tube by a practitioner aligning a central axis of the tube orthogonal to, but offset from, the laser beam. The tube may then be cut by the laser beam in a direction parallel to the tube central axis.

The cutting may commence at a first end of the tube. During the cutting, the tube may be rotated about a tube central axis by an increasing angular displacement. The tube may be rotated by the increasing angular displacement until the cutting reaches the middle of the tube. When the cutting reaches the middle of the tube, the tube may be counter rotated about the tube central axis by a decreasing angular displacement until the cutting reaches a second end of the tube.

Additional cuts may be performed by rotating the tube about the tube central axis by an angular displacement, and then cutting the tube again in the aligned direction while maintaining the offset. An annular rim may be left at the first end. An annular rim may be left at the second end. An annular rim may be left at both ends.

The angled tube-cutting may provide shaping to elongated members included in the cutting tool. The shaping may be set to result in a desired rake angle. The shaping may be set to provide a desired relief angle. The shaping may be set to provide a desired rake angle and a desired relief angle. The elongated members may be shaped further by heat-setting of one or more of angles (e.g., such as one or both of rake and relief angles), twists (e.g., about a central axis such as S, shown in FIG. 27) and bends (e.g., such as about an axis such as M, shown in FIG. 34).

FIG. 136 shows illustrative cutting tool 13600. Cutting tool 13600 may be formed by compressing a first end of tube 12900 towards a second end of tube 12900.

Cutting tool may include elongated members 13603. Cutting tube may include annular rimes 13601.

Elongated members 13603 may have a rake angle and a relief angle. The rake angle and the relief angle may be the result of the angled cutting of a tube and subsequent compression of a first end of the tube towards a second end of the tube.

Elongated members 13603 may be shaped further by heat-setting of one or more of angles (e.g., such as one or both of rake and relief angles), twists (e.g., about a central axis such as S, shown in FIG. 27) and bends (e.g., such as about an axis such as M, shown in FIG. 34).

Elongated members 13603 may have one or more features in common with broaching member 102 (shown in FIG. 1), broaching member 1800 (shown in FIG. 18), broaching member 2600 (shown in FIG. 26), broaching member 3400 (shown in FIG. 34) and broaching member 3500 (shown in FIG. 35).

FIG. 137 shows a partial cross sectional view of illustrative cutting tool 136 taken along lines 137-137.

FIG. 138 shows illustrative cavity preparation tool 13800. Cavity preparation tool 13800 may include one or more broaching members 13803 wrapped spirally about central support member 13802. Broaching members 13803 may have a base that is fixed to central support member 13802. Broaching members 13803 may have a free end including cutting edge 13804.

Broaching members 13803 may be biased outwardly. Broaching members 13803 may be constrained by an outer capture sheath. The sheath may have a release opening. When the sheath is rotated in a first direction about central support member 13802, broaching members 13803 may extend through the release opening and radiate from the central support member 13802 in a motion that is one or both of circumferential and radial. When the sheath is rotated in a second direction, opposite the first direction, about central support member 13802, broaching members 13803 may be captured in the sheath.

Broaching member 13803 may be integral to central support member 13802. Broaching member 13803 may be moved independently of central support member 13802. Central support member 13802 may or may not have a central support shaft.

Deployment and activation of broaching members 13804 may be rotational motion of the control or support member.

Different broaching members 13803 may have different lengths. Different broaching members 13803 may have different relaxed radii of curvature functions. A radius of curvature function may define the change in radius of curvature with distance along a broaching member 13803 from a central axis of the central support member. The radius of curvature function and the length of broaching member 13803 may determine the expanded-state radial offset of cutting edge 13804 at the end of broaching member 13803. Different radial offsets may be present to obtain a desired cavity shape.

Different broaching members 13803 may be of the same length.

One or more broaching members 13803 may have a cutting edge. Cutting edge 13804 may be disposed on an outer face of a broaching member 13803 that faces away from central support member 13802. Cutting edge may be square-shaped. Cutting edge may be rectangular-shaped. Cutting edge 13804 may be formed from an opening in the free end of broaching member 13803. Cutting edge 13804 may have a base that runs along a perimeter of cutting edge 13804 and is monolithic with broaching member 13803.

Cutting edge 13804 may be cut out of broaching member 13803. Cutting edge 13804 may be annealed out of a plane defined by the free end of broaching member 13803.

Cutting edge 13804 may define a rake angle and a relief angle.

Cutting edge 13804 may run in the tool longitudinal direction, transversely across the broaching member, at the radially outermost end of the broaching member. Cutting edge 13804 may run along all or some of a length of broaching member 13804.

FIG. 139 shows a view of illustrative broaching tool 13800 (shown in FIG. 138). Tool 13800 may include blades 1308. Blades 1308 may be on an outer face of broaching member 13803.

FIG. 140 shows another view of illustrative broaching member 13800 (shown in FIG. 138). The view in FIG. 140 shows broaching members 13803 expanded away from central support member 13802 with different radial offsets.

FIG. 141 shows a view of a distal end of illustrative central support member 13802. The view in FIG. 141 shows broaching members 13803 expanded away from central support member 13802 with different radial offsets.

FIG. 142 shows illustrative cavity preparation tool 14200. Tool 14200 may include rotator 14202. Tool 14200 may include broaching member 14204. Tool 14200 may include broaching member 14206. Tool 14200 may include collapsible support 14208. Collapsible support 14208 may support broaching member 14204. Collapsible support 14210 may support broaching member 14206. Tool 14200 may include end cap 14212 at the end of rotator 14202.

Collapsible support 14208 may include hinged spans such as 14214, 14216 and 14218. Spans such as 14214 and 14216 may be joined proximate rotator 14202 at joint 14220 which may include a hinge (shown), a pin, a living hinge, a bend in a monolithic span or any other suitable joint. Spans such as 14216 and 14218 may be joined radially away from rotator 14202 at joint 14222 which may include a hinge, a pin, a living hinge, a bend (shown) in a monolithic span or any other suitable joint.

Span 14224 may be fixed to rotator 14202 adjacent or by end cap 14212. Joints 14220 and 14226 may be slidable longitudinally along rotator 14202. Foot 14228 may be slidable longitudinally along rotator 14202. When joints 14220 and 14226 and foot 14228 are moved proximally, the hinged spans spread out and are drawn toward rotator 14202. When joints 14220 and 14226 and foot 14228 are moved distally, the hinged spans are drawn together, become more radially aligned with respect to rotator 14202, and activate broaching member 14204. Collapsible support 14208 may be actuated by a spring, a control rod, a control sheath or any other suitable mechanism for moving collapsible support 14208 longitudinally along rotator 14202.

Collapsible support 14208 may provide outward radial force to broaching member 14204. Collapsible support 14208 may provide torsional force, about the longitudinal axis of rotator 14202, to broaching member 14204.

Broaching member 14204 may include one continuous segment. Broaching member 14204 may include multiple segments.

Collapsible support 14210 may have features that correspond to those of collapsible support 14208.

FIG. 143 shows that illustrative rotator 14202 may include slide 14230. Joints 14232 and 14234 and foot 14236 may be configured to slidingly engage slide 14230 so that collapsible support 14208 can elongated and contract longitudinally along slide 14230.

FIG. 144 shows illustrative tool 100 (shown in FIG. 1A) in exploded view. Broaching member 14402 may include segments 112 and 114. Segments 112 and 114 may be activated by moving broach head 104 longitudinally relative to shaft assembly 110. Shaft assembly 110 may include sleeve 14404. Shaft assembly 110 may include sleeve 14406. Sleeve 14406 may be disposed within and fixed longitudinally and rotationally to sleeve 14404. Shaft assembly 110 may be fixed within fitting 14408 of handle 120. Shaft assembly 110 may be longitudinally and rotationally fixed to handle 120.

Broaching head 104 may be disposed within sleeve 14406. Proximal ends 14408 and 14410 of broaching member 14402 may be secured within distal end 14412 of sleeve 14406. Cut-out 14412 may accommodate shoulder segments 14414 and 14416 of broaching member 14402. A practitioner may rotate knob 14408 to draw broaching head 104 toward handle 120. This draws distal end, along with loop 14418, toward handle 120. This shortens the longitudinal distance between proximal ends 14408 and 14410 and causes segments 112 and 114 to push radially outward into an activated state. Loop 14418 may be pinned in distal end 106 by transverse pin 108. Bushing 14420 may support loop 14418 radially away from pin 108. The practitioner may reverse the rotation of knob 14408 to deactivate broaching member 14402. Broaching member 14402 may be delivered to the interior of the bone through an access hole when broaching member 14402 is in a deactivated state. Pin 14422 may limit axial movement of broaching head 104.

FIG. 145 shows illustrative tool control handle 14500. Handle 14500 may include mechanisms for operating control elements that activate and deactivate broaching members such as those shown or described herein. Handle 14500 may include activation knob 14502. Knob 14502 may advance and retract notched control rod 14504 within housing 14506. Rod 14504 may advance and retract within sleeve 14508. Distal from housing 14506, rod 14504 may advance and retract an end of a broaching member to activate or deactivate the broaching member. The notches may provide switchable settings for activation and deactivation of the broaching member. The notches may provide switchable settings or stages for activation and deactivation of the broaching member.

One skilled in the art will appreciate that one or more of a sliding, rotational, screwed, cammed, levered or other type of mechanism may be included for displacing or otherwise operating the control elements. The handle may provide multi-stage control. Multi-stage control may include 1 stage, 2 stages, three stages, four stages, five stages, 10 stages, 20 stages or more stages. For example, the tool may include a mechanism for separate activation of each of several different broaching members.

FIG. 146 shows illustrative cavity preparation tool 14600. Tool 14600 may have features in common with the tool shown in FIG. 1 and other apparatus shown or described herein.

Tool 14600 may provide for activation of broaching member 14602 by the rotation of broaching member 14602 inside tissue. A practitioner may rotate knob 146004. This rotates tool 14600 en toto, in particular broaching member 14602. Torsional resistance from the tissue on broaching member 14602, however, causes torque from knob 146004 to be transferred to splined shaft 14606. Shaft 14606 rotates nut 14608. Threads 14610 drives nut 14608 distally to compress spring 14612.

Spring 14612 may allow the broaching member to "give" and provide a buffered application of force to the tissue. The spring may buffer longitudinal force against the tissue. The spring may buffer rotational force against the tissue.

Spring 14612 may have a spring constant that may be selected to regulate the amount of torque that is transferred to shaft 14606. Nut projection 14614 pushes on tubular control element 14616, which drives proximal ends 14618 and 14620 of broaching member 14602 in the distal direction and causes broaching member 14602 to activate by urging radially away from broaching head 14622. Broaching head 14622 is fixed longitudinally to housing 14622. Splined shaft 14606 may rotate relative to broaching head 14622. Broaching member 14602 may thus be driven by the tool to displace radially away from the longitudinal axis of tool 14600 automatically as the tool rotates.

In some embodiments, a compression spring may be integral with segments of the broaching member.

FIG. 147 shows an illustrative portion of tool 14700. Tool 14700 may have one or more features in common with broaching tool 14600. Broaching head 14702 supports broaching member 14706. Broaching member 14706 includes proximal ends 14708 and 14710. Proximal ends 14708 and 14710 are fixed to spring 14712. Spring 14712 may be fixed to tubular control element 14714. Spring 14712 may perform the same or a similar role as that performed by spring 14612 in tool 14600.

FIG. 148A shows illustrative broaching member assembly 14800. Broaching member assembly 4800 may include broaching member 14802. Broaching member assembly 4800 may include spring element 14804. Spring element 14804 may include bushing 14805. Spring element 14804 may include spring 14806. Spring element 14804 may include bushing 14808. Bushings 14806 and 14808 may provide for sound mechanical coupling between broaching member 14802, spring 14805 and a tubular control element such as 14714 (shown in FIG. 47).

In some embodiments, the broaching member may be proximally elongated and extend through a spring element such as spring element 14804. The spring element may be fixed directly or indirectly to a housing such as 14624 (shown in FIG. 146). The spring element may thus act as a collar around the broaching member and resist broaching member expansion by urging against portions of the broaching member that angle radially outward. The spring element resistance may buffer broaching member expansion. The spring element resistance may attenuate the force or speed with which the broaching member may expand. The spring element may assist in the expansion of the members.

FIG. 148B shows illustrative broaching member assembly 14800 in perspective view.

FIG. 149 shows illustrative cavity preparation tool 14900. Tool 14900 may have features in common with the tool shown in FIG. 1 and other apparatus shown or described herein.

Tool 14900 may provide for activation of broaching member 14902 by the rotation of broaching member 14902 inside tissue. A practitioner may rotate knob 14904. This may rotate tool 14900 en toto, in particular broaching member 14902. Torsional resistance from the tissue on broaching member 14902, however, may cause torque from knob 149004 to be transferred to toothed shaft 14906. Toothed shaft 14906 may act as a sun gear. Shaft 14906 may rotate and orbit planetary gears 14907 mounted on linear screw carriers 14909. Planetary gears 14907 may be rotationally supported by ring gears 14909. Ring gears 14909 may be molded inside handle 14911.

Planetary gears 14907 may drive nut 14908. Threads 14910 may drive nut 14908 linearly in the distal direction to linearly advance tubular control element 14912. This may cause broaching member 14902 to activate by urging radially away from broaching head 14922. Guide 14924 may be provided to guide tubular control element 14912 relative to broaching head 14922.

Broaching head 14922 is fixed longitudinally to housing 14911. Toothed shaft 14906 may rotate relative to broaching head 14922. The coupling of shaft 14906 to nut 14908 via planetary gears 14907 may reduce the linear motion of nut 14908 per unit turn of knob 14909. The ratio of the coupling may be selected to regulate the amount of torque that is transferred to shaft 14906. Broaching member 14902 may thus be driven by the tool to displace radially away from the longitudinal axis of tool 14900 automatically as the tool rotates.

For contraction of the broaching member, the rotation may be reversed to draw the broaching member radially inward. The tool may include a quick-release that disengages threads that convert rotation into linear translation. The broaching member may then be quickly contracted without reversing the rotation.

Energy delivered through these mechanisms, into tissue, may be generated by a human hand, a power assisted device such as a drill, or any other suitable device. Displacing bone tissue through human hand motion may include an additional feature of enabling a more direct feedback loop of interaction with the tissue and the tool. The more direct feedback loop may be desirable for some therapies.

FIG. 150 shows illustrative anatomy in connection with the apparatus and methods may be used. FIG. 150 shows illustrative skeleton S. Skeleton S includes illustrative bones Si in which apparatus and methods in accordance with the principles of the invention may be used. The apparatus and methods may be used in connection with "hollow" bones. The hollow bones may include cortical tissue. The hollow bones may include cancellous tissue. Cortical tissue may be referred to as "tissue." Cancellous tissue may be referred to as "tissue." Other matter in the interior of a bone may be considered "tissue." The bone may be considered "tissue."

The apparatus and methods may be used to create a space inside a bone. The space may be a cavity. The tissue may be inside the bone. The space may be created by breaking up the tissue. The space may be created by removing the tissue from the bone. The space may be created as part of a therapeutic procedure. The apparatus and methods may displace tissue by imparting mechanical energy to the tissue, for example, through one or more of expanding motion, rotational motion, axial motion, compressive motion, cutting motion, and any other suitable motions.

Illustrative bones Si in which apparatus and methods in accordance with the principles of the invention may be used are included in Table 1 below. Table 1 includes a partial list of bones Si.

TABLE 1

Bones $S_i$.

| Bone | Reference numeral in FIG. 1 |
|---|---|
| Distal Radius | $S_0$ |
| Humerus | $S_1$ |
| Proximal Radius and Ulna (Elbow) | $S_2$ |
| Metacarpals | $S_3$ |
| Clavicle | $S_4$ |
| Ribs | $S_5$ |
| Vertebrae | $S_6$ |
| Ulna | $S_7$ |
| Hip | $S_8$ |
| Femur | $S_9$ |
| Tibia | $S_{10}$ |
| Fibula | $S_{11}$ |
| Metatarsals | $S_{12}$ |

FIG. 150A shows illustrative anatomical features of fractured bone B. Reference frame 200 shows that the view of bone B is substantially in anterior/posterior plane 200. Lateral plane 204 includes volar half-plane VOL and dorsal half-plane DOR.

Bone B is illustrated as a radius that is fractured at fractures Fh and Fa Bone B includes bone portions Pb, Ph and Pa in distal end D. Bone segment Pb is the largest portion of bone B. Bone segment Ph is a head portion of bone B. Bone segments Ph and Pa include articular surface AS. Bone portions Pb, Ph and Pa are separated or partially separated along fractures Fa and Fh. Fracture Fa transects articular surface AS. Fracture Fh transects head of bone B.

Bone B, shown in a cross section that includes approximate longitudinal axis $L_B$, includes cortical bone BCO and cancellous bone $B_{CA}$. Deployment of an implant into distal end D of bone B may require an access hole at site H'. Deployment of the implant may require displacement of cancellous bone $B_{CA}$. Illustrative contours $C_1$, $C_2$ and $C_3$ in cancellous bone $B_{CA}$ are different contours within which cancellous bone $B_{CA}$ may be displaced. Contour $C_4$, which is a projection of contour $C_3$ onto articular surface AS, shows that contour $C_4$, for example, may be asymmetric. For example, contour $C_4$ may have major axis $A_1$ and minor axis $A_2$ (shown in half). The other contours may also be asymmetric.

Apparatus and methods provided herein may provide an access hole H at site H'. An apparatus inserted at site H' through access hole H, may travel a distance $X_H$ through intermedullary space IS to reach a head portion of bone B. An apparatus inserted at site I' through access hole I may travel a distance $X_I$ through intermedullary space IS to reach a head portion of bone B. An apparatus inserted at H' may require a "bend" to travel through intermedullary space IS to reach a head portion of bone B. An apparatus inserted at I' may not require a "bend" to reach a head portion of bone B. Apparatus and methods provided herein may displace cancellous bone $B_{CA}$ within a contour such as $C_1$, $C_2$ or $C_3$.

FIG. 151 shows illustrative intramedullary broach 15100. Broach 15100 may include broach head 15102. Broach head 15102 may include illustrative broaching member 15104.

Broaching member 15104 may be sufficiently rigid to displace cancellous bone $B_{CA}$. Broaching member 15104 may be sufficiently flexible to be deformed by cortical bone $B_{CO}$. In some embodiments, broaching member 15104 may be expandable. Broach head 15102 may be supported by and rotated by shaft assembly 15114. Broach control 15106 may include drive handle 15108 for rotating and translating broach head 15102. Broach control 15106 may include expansion control hub 15110. Expansion control hub 15110 may be displaceable along control shaft 15112 to expand or contract broaching member 15104. Broach head 15102 may include distal end 15180. Expansion control hub 15110 is shown in the "contract" position.

FIG. 152 shows illustrative broach 15100 deployed in bone B through hole H. Broach 15100 may be deployed while broaching member 15104 is contracted.

Broach head 15102 may be advanced, through intramedullary space IS, into metaphyseal region M of bone B. Broach head 15102 may be disposed in any portion of intramedullary space IS, such as in the end-bone.

Access hole H may be sufficiently small that it reduces the occurrence of stress risers at site H'. Expansion control hub 15110 is shown in the "expand" position and broaching member 15104 is shown expanded in bone B. Broaching member 15104 may be expanded during or after deployment.

A standard orthopaedic drill instrument (not shown) may be used to open access hole H in cortical bone $B_{CO}$ (shown in FIG. 150A) at site H' on bone B. The drill instrument may be guided by apparatus such as a guide. Axis hole H may be drilled along broach axis $L_C$. Broach axis $L_C$ may form an angle β with bone axis $L_B$. Angle β may be an acute angle.

FIG. 153 shows a view of a distal portion of illustrative broach 15100 taken along lines 153-153 (shown in FIG. 151). Pin 15103 may be located near the distal end of bracket 15120. Pin 15103 may fix the position of the distal end of broaching member 15104. Pin 15103 may support cylindrical form 15105. Cylindrical form 15105 may be coaxially mounted on pin 15103. Cylindrical form 15105 may support a spiral segment of broaching member 15104. One or more distal portions of broaching member 15104 may be welded or otherwise suitably fixed to cylindrical form 15105.

Cylindrical form 15105 may constrain or partially constrain the orientation of distal portions of broaching member 15104. Cylindrical form 15105 may be fixed relative to bracket 15120. Cylindrical form 15105 may be rotatable relative to bracket 15120.

Broach head 15102 may include end cap 15101. Broaching member 15104 may remove tissue that is generally proximal end cap 15101. In some embodiments, member 15104 may expand in such a manner as to extend distally of end cap 15101. In such embodiments, the broaching member may remove tissue that is distal of end cap 15101.

Reducing or minimizing the distance between the distal end of broaching member 15104 and end cap 15101 may allow broaching member 15104 to remove tissue that is more immediately proximal end cap 15101. End cap 15101 may be positioned at the distal end of bracket 15120. End cap 15101 may be configured to have a smooth, atraumatic surface. Bracket 15120 may be attached to drive shaft 15130.

Shaft assembly 15114 may include drive shaft 15130. Drive shaft 15130 may support bracket 15120 at union 15132. Drive shaft 15130 may be secured to bracket 15120 by pin 15134. Drive shaft 15130 may provide rotation to broach head 15102.

Proximal ends 15136 and 15138 of broaching member 15104 may be fixed to slide 15140, which may be a tube. Proximal end 15138 may be threaded through or keyed into windows 15142 and 15144 in slide 15140. Proximal end 15136 may be threaded through or keyed into slots 15146 and 15148 in slide 15140. Slide 15140 may slide relative to drive shaft 15130 to expand and contract broaching member 15104. Slide 15140 is shown in the "contract" state, in which broaching member 15104 is drawn close to bracket 15120. Slide cover 15150 may slide with slide 15140. One or both of slide 15140 and slide cover 15150 may be translated along axis $L_C$ by control hub 15110 (shown in FIG. 151) or any other suitable position controller.

Slide cover 15150 may remain stationary relative to drive shaft 15130 when slide 15140 slides relative to drive shaft 15130. In embodiments in which slide cover 15150 remains stationary when slide 15140 moves, distal end 15152 of slide cover 15150 may limit the radial position of broaching member 15104 at a fixed distance along drive shaft 15130 and thus affect the deformation of broaching member 15104 in the expanded state.

Broaching member 15104 may undergo one or both of elastic and plastic deformation.

FIG. 154 shows a view of a distal portion of illustrative broach 15100 taken along lines 153-153 (shown in FIG. 151) when broaching member 15104 is in an expanded state. Broaching member 15104 is shown as mainly circular. However, any desired shape may be able to be imparted in the expanded state such as but not limited to: square, triangular, oval, ellipsoid, teardrop, football, or any other suitable shape.

Different shapes may be obtained using several methods, such as utilizing a pre-set shape in a shape memory alloy, modifying the geometry of the member cross-section (along the member length) such that it preferentially bends in a desired manner, constraining broaching member 15104 (e.g., in force, shear or moment) in a way that forces the expansion to take desired shape, having the final shape be that of the expanded geometry and the reduced or collapsed geometry be that of a higher strain configuration, and/or any other suitable method of forming a desired shape.

For example, largely or substantially preventing radial movement of broaching member proximal ends 15136 and 15138, and allowing movement of the distal end of broaching member 15104 generally about pin 15103 while elastically deforming broaching member proximal ends 15136 and 15138, due to reducing the distance between the distal end and proximal ends 15136 and 15138 of broaching member 15104, may modify the geometry of broaching member 15104 from a generally straight configuration to a generally eggbeater shape.

The deformation may relatively increase the distance between (a) sections 15160 and 15162 and (b) bracket 15120. As this distance is increased, the swept-out volume of broaching member 15104, as broaching member 15104 rotates generally about an axis such as $L_C$ (shown in FIG. 152), is increased.

In some embodiments, a broach may include a broaching member that includes one or more stiff tines (not shown) that is joined to a drive shaft. The drive shaft may have a longitudinal axis. The tine may be joined to the drive shaft radially close to the axis at a proximal end of the tine. The tine may have a distal end that is spaced radially apart from the axis. The distal end of the tine may be distal of the distal end of the drive shaft. There may be numerous tines on the drive shaft. Such embodiments may be appropriate for rotation in intramedullary space IS of bone B (shown in FIG. 150A) using high torque at low rotational speeds.

FIG. 155 shows a view of illustrative broach 15100 along lines 155-155 (shown in FIG. 153). Broach 15100 is in the contracted state. Slide cover 15150 has been removed. Slots 15146, 15148 and 15502 in slide 15140 may be configured to coincide with features on proximal end 15136 (shown in FIG. 153) of broaching member 15104. When proximal end 15136 is engaged with slots 15146, 15148 and 15502, slots 15146, 15148 and 15502 may restrict movement of proximal end 15136 in either direction generally along axis $L_C$. Slots 15146, 15148 and 15502 may have any suitable geometry that allows for the engagement and axial translation of proximal end 15136.

Slots 15146, 15148 and 15502 may be of sufficient depth that, when proximal end 15136 is engaged in slots 15146, 15148 and 15502, slide cover 15150 (shown in FIG. 153) has adequate radial clearance with respect to proximal end 15136 and slide 15140 to slide over slide 15140 and slots 15146, 15148 and 15502. An inner surface of slide cover 15150 may prevent movement of proximal end 15136 from moving in a direction generally away from axis $L_C$.

Slide 15140 may include slots (not shown) that correspond to proximal end 15138 (shown in FIG. 153) and have one or more features in common with, slots 15146, 15148 and 15502.

Broach head 15120 may include broaching member wrap section 15504. Pin 15103 may be integrated into wrap section 15504. Wrap section 15504 may be separate from pin 15103. Wrap section 15504 may be configured to allow wrapping of broaching member 15104 generally around wrap section 15504. Broaching member 15104 may be looped in wrap section 15504. Broaching member 15104 may be wrapped (as shown in FIG. 155) at least one full turn in wrap section 15504. Wrapping about wrap section 15504 may bias segments 15160 and 15162 (shown in FIG. 154) away from axis $L_C$.

FIG. 156 shows a cross section, viewed along lines 156-156 (shown in FIG. 152) of a portion of illustrative broach control 15106 (shown in FIG. 151). Expansion control hub 15110 is shown with base 15602 at position pe. This may correspond to the expanded state of broaching member 15104, as shown in FIG. 152. Base 15602 may be moved distally to position pc. This may correspond to the contracted state of broaching member 15104, as shown in FIG. 151. Expansion control hub 15110 may operate in connection with body 15608. Body 15608 may include control shaft 15112 and distal stop 15610. Control shaft 15112 may include threads 15618.

Expansion control hub 15110 may include outer member 15612 and inner member 15614. Outer member 15612 and inner member 15614 may be fixed to each other. Slide pin 15604 may be captured between outer member 15612 and inner member 15614. Inner member 15614 may include threads 15616 for engagement with threads 15618 on control shaft 15112. Slide pin 15604 may travel in slots 15605 and 15607 in body 15608.

Expansion control hub 15110 may be moved along axis $L_C$ by applying force to expansion control hub 15110. In some embodiments, expansion control hub 15110 may be advanced axial generally along axis $L_C$ by applying rotational force generally about axis $L_C$ to expansion control hub 15110 such that threads 15616 move advance or retreat through threads 15618.

Axial movement of expansion control hub 15110 relative to body 15608 may be transferred to slide 15140 and slide cover 15150 while drive shaft 15130 remains axially fixed to body 15608 by pin 15606. Slide 15140 may include cut-outs 15630 and 15632. Slide cover 15150 may include cut-outs 15634 and 15636. Cut-outs 15630, 15632, 15634 and 15636 may provide clearance of pin 15606 when slide 15140 and slide cover 15150 travel axially.

When expansion control hub 15110 is moved axially, proximal ends 15136 and 15138 (shown in FIG. 153) of broaching member 15104 thus move axially. Distal end 15180 (shown in FIG. 151) of broaching member 15104 may be axially fixed to drive shaft 15130, which may be fixed to body 15608. Thus, when expansion control hub 15110 moves distally, the distance between (a) proximal ends 15136 and 15138 and; (b) distal end 15180 decreases and broaching member 15104 expands. When expansion control hub 15110 moves proximally, the distance between (a) proximal ends 15136 and 15138; and (b) distal end 15180 increases and broaching member 15104 contracts.

Distal stop 15610 and proximal stop 15620 may limit axial movement of expansion control hub 15110. Although proximal stop 15620 is shown as being part of handle 15108, proximal stop 15620 may be separate from handle 15108.

Handle 15108 may transfer rotational motion generally about axis $L_C$ to control shaft 15112. Control shaft 15112 may transfer the rotation to slide pin 15604 and drive shaft pin 15606. Slide pin 15604 may transfer the rotation to slide 15140 and slide cover 15150. Drive shaft pin 15606 may transfer the rotation to drive shaft 15130, which may drive broaching member 15104 (shown in FIG. 153).

Distal stop 15610 is shown as being integral with body 15608, but distal stop may be a separate element that is attached to control shaft 15112 or a different part of body 15608.

Pin 15606 may extend into recess feature 15622. Recess feature 15622 may be a through-hole. Pin 15606 may extend through the through hole to a location external to body 15608.

Pin 15604 may extend into recess feature 15624. Recess feature 15624 may be a through-hole. Pin 15604 may extend through the through-hole to a location external to body outer member 15612. Recess feature may extend circumferentially about axis $L_C$. If recess feature 15624 extends circumferentially about axis $L_C$, expansion control hub 15110 may rotate about axis $L_C$ substantially without restricting, or being restricted by, pin 15604.

Body 15608 may include circumferential recess 15626. Recess 15626 may be sized to engage O-ring 15628. Recess 15626 may prevent axial movement between body 15608 and O-ring 15628 generally along axis $L_C$. O-ring 15628 may be sized to provide an interference fit with outer member 15612. The interference fit may produce friction between O-ring 15628 and expansion control hub 15110. The friction may allow expansion control hub 15110 to be lightly locked at any rotational position relative to body 15608, generally about axis $L_C$.

FIG. 157 shows illustrative cavity preparation apparatus 15700. Apparatus 15700 may include broach 15750. Broach 15750 may include one or more of broach head 15725, elevator ribbon 15752 and control body 15760. Apparatus 15700 may include guide 15702. Guide 15702 may guide broach 15750 or any other suitable apparatus through an access hole. Guide 15702 may retain soft tissue at a distance from the access hole to prevent engagement of the soft tissue by an instrument that is present in guide 15702.

FIG. 157A shows in partial cross section illustrative broach head 15725 and illustrative elevator ribbon 15752.

Broach head 15725 may be driven about axis $L_E$ by rotating drive shaft 15740. Broach head 15725 may include broaching member 15724, which may have one or more features in common with broaching member 15104 (shown in FIG. 151). Broach head 15725 may include distal hub 15726 and proximal hub 15728. One or both of distal hub 15726 and proximal hub 15728 may transfer rotation to broaching member 15724. One or both of distal hub 15726 and proximal hub 15728 may support broaching member 15724.

Drive shaft 15740 may extend within broach sheath 15727. Drive shaft 15740 may be supported in rotation by bushing 15730 at the end of broach sheath 15727.

Illustrative elevator ribbon 15752 may be anchored to broach sheath 15727 at fixation 15732. When axial compressive force, generally along axis $L_E$, is applied to elevator ribbon 15752, elevator ribbon 15752 may buckle along its length. For example, elevator ribbon 15752 may buckle at or near section 15734. Section 15736 may be used to support broach sheath 15727 at an elevation relative to cancellous bone $B_{CA}$ or cortical bone $B_{CO}$ in bone B (shown in FIG. 150A).

Portions of elevator ribbon 15752 may extend inside broach sheath 15727 and pass through slots 15742 and 15744 to section 15734. In some embodiments, there may be contact between drive shaft 15740 and elevator ribbon 15752. In some embodiments, there may be no contact between drive shaft 15740 and elevator ribbon 15752.

Elevator ribbon 15752, when compressed, may apply tension to adjacent portion 15738 of broach sheath 15727 and compression to opposite portion 15740 of broach sheath 15727. One or both of the tension of adjacent portion 15738 and the compression of opposite portion 15740 may cause broach sheath 15727 to curve generally about an axis such as $L_F$.

One or both of adjacent portion 15738 and opposite portion 15740 may include stress-relief features that allow bending under tension and compression. The stress-relief features may include slots or slot patterns. The stress-relief features may be provided using laser-cutting. The stress-relief may provide an equilibrium curvature such that broach sheath 15727 is curved at rest.

The stress-relief features may include sintered particles. The particles may include metal, polymer, composite or any other suitable material.

FIG. 158 shows illustrative broach 15800 inserted in bone B. Broach 15800 may include broaching head 15802. Flexible rotating drive shaft 15804 may drive broaching head 15802 in rotation in directions ρ' or −ρ'. Drive shaft 15804 may be driven by a rotation source such as handle 15806. In some embodiments, the rotation source may include a surgical hand drill, a dremel motor or any other suitable rotational power source.

Drive shaft 15804 may be sheathed in a flexible cannula (apart from broach sheath 15810, which is described below).

Control body 15808 may be used to insert broaching head 15802 through a hole at site H'. During insertion, broaching head 15802 may be withdrawn into flexible broach sheath 15810. Proximal end 15812 of flexible broach sheath 15810 may be fixed to distal end 15814 of control body 15808. Actuator 15816 may engage drive shaft 15804 and may slide relative to control body 15808. Actuator 15816 may thus translate drive shaft 15804 along axis LM within guide sheath 15810.

In some embodiments, broaching head 15802 may be compressible and expandable. Broaching head 15802 may be compressed within guide sheath 15810. Broaching head 15802 may be expanded outside of guide sheath 15810. In some embodiments, broaching head 15802 may self-expand in bone B after being pushed out of guide sheath 15810 by drive shaft 15804. In some embodiments, broaching head 15802 may be outside guide sheath 15810 when broaching head 15802 is delivered into bone B.

Broaching head 15802 may include one or more broaching members 15818 that have sufficient rigidity to displace cancellous bone, but sufficient resilience to deform when brought into contact with cortical bone and thus leave the cortical bone substantially in place.

Broaching members 15818 may be formed from loops. The loops may be fixed to distal hub 15820. The loops may be fixed to proximal hub 15822. One or both of distal hub 15820 and proximal hub 15822 maybe axially fixed to drive shaft 15804. One or both of distal hub 15820 and proximal hub 15822 maybe rotationally fixed to drive shaft 15804. Broaching head 15802 may include any suitable number of loops. Broaching members 15818 may have one or more features in common with broaching member 15104 (shown in FIG. 151) or any other broaching member described or shown herein.

FIG. 159 shows illustrative jig 15900 engaged with bone B. Bone fragments may be provisionally reduced by k-wires 15901 and 15903. Jig 15900 may be held in place over an implant target location by K-wire 15902 that may be placed under fluoroscopy. Base arm 15904 pivots about K-wire 15902 and articulates with guide arm 15906 to place guide end 15906 at an access hole location registered to the target location.

A practitioner places drill or k-wire 15908 in a guide slot (hidden from view) at guide end 15906. The practitioner initiates a hole with drill or k-wire 15908 approximately normal to the surface of bone B. The practitioner then backs off drill or k-wire 15908 in the direction of the arrow until drill or k-wire 15908 is angled at k-wire 15902. The practitioner then completes and enlarges the hole for insertion of a cavity preparation tool such as one of those discussed or illustrated herein.

Thus, apparatus and methods for tissue cavity preparation have been provided. Persons skilled in the art will appreciate that the present invention can be practiced by other than the described examples, which are presented for purposes of illustration rather than of limitation. The present invention is limited only by the claims that follow.

What is claimed is:

1. A tissue cavity preparation tool comprising an elongated rotator and a broaching member including a first elongated body and a second elongated body, the first body and the second body being configured to be coupled to the rotator, wherein:
   the first elongated body has a first sharp edge, a first trailing edge and a first face, wherein the first elongated body, in a state in which the first body is not coupled to the rotator, curves in a plane parallel to the first face when the first elongated body is in a planar configuration;
   the second elongated body has a second sharp edge, a second trailing edge and a second face, wherein the second elongated body, in a state in which the second body is not coupled to the rotator, curves in a plane parallel to the second face when the second elongated body is in a planar configuration; and
   the elongated rotator defines a longitudinal axis and is configured to:
      retain a first end of the first body and a second end of the first body such that the first end of the first body is spaced longitudinally apart from the second end of the first body and the first face forms a first cone-like surface when the first body is coupled to the rotator and in an expanded state; and
      retain a first end of the second body and a second end of the second body such that the first end of the second body is spaced longitudinally apart from the second end of the second body and the second face forms a second cone-like surface when the second body is in coupled to the rotator and in an expanded state.

2. The tool of claim 1 wherein the second cone-like surface is identical to the first cone-like surface.

3. The tool of claim 1 wherein the second cone-like surface is not identical to the first cone-like surface.

4. The tool of claim 3 wherein the second cone-like surface defines an apical angle that is greater than an apical angle defined by the first cone-like surface.

5. The tool of claim 1 wherein:
   the first elongated body is fixed to the rotator at a distal position and a first intermediate position; and
   the second elongated body is fixed to the rotator at a second intermediate position and a proximal position;
wherein the first and second intermediate positions are longitudinally between the distal position and the proximal position.

6. The tool of claim 1 wherein:
   the first elongated body defines a first central axis and the first elongated body has a first length along the first central axis;
   the second elongated body defines a second central axis and the second elongated body has a second length along the second central axis; and
   the second length is greater than the first length.

7. The tool of claim 1 wherein the first elongated body has a first heat-set shape and the second elongated body has a second heat-set shape that is different from the first heat-set shape.

8. The tool of claim 1 further comprising:
   a first elongated controller that is configured to change a longitudinal distance between the first end of the first elongated body and the second end of the first elongated body; and
   a second elongated controller that is configured to change a longitudinal distance between the first end of the second elongated body and the second end of the second elongated body.

9. The tool of claim 1 further comprising:
   a loop, the first and second elongated bodies extending therefrom; and
   a coupler that couples the loop to the rotator.

10. The tool of claim 9 wherein the coupler includes a transverse member that is transverse to the longitudinal axis, is supported by the rotator, and engages the loop by passing through the loop.

11. The tool of claim 9 wherein:
   the first elongated body, the second elongated body and the loop are of monolithic construction;
   the loop forms a spirally wound spring; and
   the loop absorbs strain from the elongated members when the elongated members are subjected to stress.

12. The tool of claim 11 wherein the stress is directed radially inward toward the rotator.

13. The tool of claim 11 wherein the stress is directed circumferentially about the rotator.

14. The tool of claim 1 further comprising an outer sleeve concentric with the rotator, the outer sleeve configured to slide axially along the longitudinal axis toward a distal end of the rotator.

15. The tool of claim 1 wherein the rotator is flexible.

16. The tool of claim 1 wherein the rotator is rigid.

17. The tool of claim 1 wherein:
the first elongated body defines a central axis and a span segment, the span segment including the first sharp edge, the first trailing edge and the first face;
the first end of the first elongated body is disposed at an angular displacement, about the central axis, from the first span segment, when the first elongated body, in a state in which the first body is not coupled to the rotator, is in a planar configuration; and
the rotator further defines a radial direction orthogonal to the longitudinal direction and is configured to retain the first end of the first elongated body in an orientation that is normal to the radial direction, wherein the retaining counter-rotates a surface normal of the first face in a direction opposite the angular displacement.

18. The tool of claim 17 wherein:
the angular displacement is a first angular displacement, the spam segment is a first span segment and the central axis is a first central axis;
the second elongated body defines a second central axis and a second span segment, the second span segment including the second sharp edge, the second trailing edge and the second face;
the first end of the second elongated body is disposed at a second angular displacement, about the second central axis, from the second span segment, when the second elongated body, in a state in which the second body is not coupled to the rotator, is in a planar configuration; and
the rotator is further configured to retain the first end of the second elongated body in an orientation that is normal to the radial direction, where the retaining counter-rotates a surface normal of the second face in a direction opposite the second angular displacement.

19. The tool of claim 18 wherein the second angular displacement is equal in magnitude to the first angular displacement.

20. The tool of claim 18 wherein the second angular displacement is greater than the first angular displacement.

21. The tool of claim 18 wherein the second angular displacement is opposite in direction from the first angular displacement.

22. The tool of claim 18 wherein the second angular displacement is in the same direction as the first angular displacement.

23. The tool of claim 1 when the first elongated body, in a state in which the first body is not coupled to the rotator, is in a planar configuration wherein the first elongated body defines a central axis that is curved.

24. The tool of claim 23 wherein the central axis curves about an axis perpendicular to a plane that is parallel to the first face.

25. The tool of claim 23 when the second elongated body, in a state in which the second body is not coupled to the rotator, is in a planar configuration wherein:
the central axis is a first central axis; and
the second elongated body defines a second central axis that is curved.

26. The tool of claim 25 when the second central axis curves about an axis perpendicular to a plane that is parallel to the second face.

27. The tool of claim 1 wherein:
the first elongated body includes:
a first span segment, the first span segment including the first face, the first sharp edge and the first trailing edge; and
a first twist positioned between the first span segment and the first end of the first elongated body; and
the second elongated body includes:
a second span segment, the second span segment including the second face, the second sharp edge and the second trailing edge; and
a second twist positioned between the second span segment and the first end of the second elongated body.

28. tool of claim 27 wherein:
the first elongated body defines a first central axis;
the second elongated body defines a second central axis;
the first twist is a twist in the first elongated body about the first central axis; and
the second twist is a twist in the second elongated body about the second central axis.

29. The tool of claim 28 in a state in which the first and second bodies are not coupled to the rotator wherein:
the first twist positions the first end of the first elongated body at a first angular displacement, about the first central axis, from the first span segment; and
the second twist positions the first end of the second elongated body at a second angular displacement, about the second central axis, from the second span segment.

30. The tool of claim 27 wherein:
the first twist provides strain relief to the first elongated body when the first elongated body is subjected to stress; and
the second twist provides strain relief to the second elongated body when the second elongated body is subjected to stress.

31. The tool of claim 1 wherein:
the first sharp edge has a first length and the first trailing edge has a second length; and.
the first length is greater than the second length.

32. The tool of claim 31 wherein:
the second sharp edge has a third length and the second trailing edge has a fourth length; and
the third length is greater than the fourth length.

33. The tool of claim 1 when the first and second elongated bodies are coupled to the rotator wherein the first elongated body is disposed on the rotator opposite the second elongated body.

34. The tool of claim 1 when the first elongated body is coupled to the rotator and in an expanded state wherein:
the first elongated body bends about an axis;
the first sharp edge lies at a first radius from the axis;
the first trailing edge lies at a second radius from the axis; and
the first radius is greater than the second radius.

35. The tool of claim 34 when the second elongated body is coupled to the rotator and in an expanded state wherein:
the axis is a first axis;
the second elongated body bends about a second axis;
the second sharp edge lies at a third radius from the second axis;
the second trailing edge lies at a fourth radius from the second axis; and
the third radius is greater than the fourth radius.

36. The tool of claim 1 when the first elongated body, in a state in which the first body is not coupled to the rotator, is in a planar configuration wherein:

the first elongated body includes a first curved section and a second curved section;

the first curved section defines a first radius of curvature;

the second curved section defines a second radius of curvature; and the first radius of curvature is different from the second radius of curvature.

37. The tool of claim 36 when the second elongated body, in a state in which the second body is not coupled to the rotator, is in a planar configuration wherein:

the second elongated body includes a third curved section and a fourth curved section;

the third curved section defines a third radius of curvature;

the fourth curved section defines a fourth radius of curvature; and the third radius of curvature is different from the fourth radius of curvature.

38. A tissue cavity preparation tool comprising an elongated rotator, a fastener and a broaching member including a first elongated body, a second elongated body and a loop, the first and second bodies and the loop being of monolithic construction, wherein:

the first elongated body defines a first central axis through the first body and includes a first twist, a first span segment extending between a first body first end and the first twist, and a first body second end extending away from the twist, the first span segment including a sharp convex first edge, a first face and a first trailing edge, wherein when the first elongated body, in a state in which the first body is not coupled to the rotator, is in a planar configuration:

the first span segment curves in a plane parallel to the first face; and the first body second end is positioned at an angular displacement, about the first central axis relative to the first span segment;

the second elongated body defines a second central axis through the second body and includes a second twist, a second span segment extending between a second body first end and the second twist, and a second body second end extending away from the twist, the second span segment including a sharp convex second edge, a second face and a second trailing edge, wherein when the second elongated body, in a state in which the second body is not coupled to the rotator, is in a planar configuration:

the second span segment curves in a plane parallel to the second face; and the second body second end is positioned at an angular displacement, about the second central axis relative to the second span segment;

the rotator defines a longitudinal axis, the rotator being configured to:

retain the first body second end such that the first body second end is spaced longitudinally apart from the first body first end and the first face forms a first cone-like surface when the first body is coupled to the rotator and in an expanded state; and retain the second body second end such that the second body second end is spaced longitudinally apart from the second body first end and the second face forms a first cone-like surface when the second body is coupled to the rotator and in an expanded state; and the fastener is coupled to the rotator and is configured to engage the loop, the first body first end and the second body first end together forming the loop.

39. The tool of claim 38 wherein the second cone-like surface is not identical to the first cone-like surface.

40. The tool of claim 39 wherein the second cone-like surface defines an apical angle that is greater than an apical angle defined by the first cone-like surface.

41. The tool of claim 38 wherein:

the first elongated body has a first length along the first central axis from the loop to the first body second end;

the second elongated body has a second length along the second central axis from the loop to the second body second end; and the second length is greater than the first length.

42. The tool of claim 38 further comprising:

a first elongated controller that is configured to translate in a direction parallel to the longitudinal axis to change a longitudinal distance between the first body first end and the first body second end; and a second elongated controller that is configured to translate in the direction to change a longitudinal distance between the second body first end and the second body second end.

43. The tool of claim 24 further comprising an outer sleeve that is concentric with the rotator and is configured to slide axially along the central axis toward a distal end of the rotator.

44. The tool of claim 38 wherein the second cone-like surface is identical to the first cone-like surface.

45. The tool of claim 38 wherein the first elongated body has a first heat-set shape and the second elongated body has a second heat-set shape that is different from the first heat-set shape.

46. The tool of claim 38 wherein the rotator is flexible.

47. The tool of claim 38 wherein the rotator is rigid.

48. The tool of claim 38 wherein the rotator further defines a radial direction orthogonal to the longitudinal axis and is configured to retain the first body second end in an orientation normal to the radial direction.

49. The tool of claim 48 wherein the rotator is further configured to retain the second body second end in an orientation normal to the radial direction.

50. The tool of claim 38 wherein:

the sharp convex first edge has a first length. and the first trailing edge has a second length; and the first length is greater than the second length.

51. The tool of claim 50 wherein:

the sharp convex second edge has a third length and the second trailing edge has a fourth length; and the third length is greater than the fourth length.

52. The tool of claim 38 when the first and second elongated bodies are coupled to the rotator wherein the first elongated body is disposed on the rotator opposite the second elongated body.

53. The tool of claim 38 when the first elongated body is coupled to the rotator and in an expanded state wherein:

the first elongated body bends about an axis;

the sharp convex first edge lies at a first radius from the axis;

the first trailing edge lies at a second radius from the axis; and the first radius is greater than the second radius.

54. The tool of claim 53 when the second elongated body is coupled to the rotator and in an expanded state wherein:

the axis is a first axis;

the second elongated body bends about a second axis:

the sharp convex second edge lies at a third radius from the second axis;

the second trailing edge lies at a fourth radius from the second axis; and the third radius is greater than the fourth radius.

55. The tool of claim 38 when the first elongated body, in a state in which the first body is not coupled to the rotator, is in a planar configuration wherein:

the first elongated body includes a first curved section and a second curved section;

the first curved section defines a first radius of curvature;

the second curved section defines a second radius of curvature; and the first radius of curvature is different from the second radius of curvature.

56. The tool of claim 55 when the second elongated body, in a state in which the second body is not coupled to the rotator, is in a planar configuration wherein:

the second elongated body includes a third curved section and a fourth curved section;

the third curved section defines a third radius of curvature;

the fourth curved section defines a fourth radius of curvature; and the third radius of curvature is different from the fourth radius of curvature.

\* \* \* \* \*